United States Patent
Sabzevari et al.

(10) Patent No.: US 11,319,380 B2
(45) Date of Patent: May 3, 2022

(54) MUC16 SPECIFIC CHIMERIC ANTIGEN RECEPTORS AND USES THEREOF

(71) Applicant: Precigen, Inc., Germantown, MD (US)

(72) Inventors: Helen Sabzevari, Germantown, MD (US); Rutul R. Shah, Germantown, MD (US)

(73) Assignee: PRECIGEN, INC., Germantown, MD (US)

( * ) Notice: Subject to any disclaimer, the term of this patent is extended or adjusted under 35 U.S.C. 154(b) by 0 days.

(21) Appl. No.: 16/431,193

(22) Filed: Jun. 4, 2019

(65) Prior Publication Data

US 2019/0375854 A1 Dec. 12, 2019

Related U.S. Application Data

(60) Provisional application No. 62/680,297, filed on Jun. 4, 2018.

(51) Int. Cl.

| | | |
|---|---|---|
| *C07K 16/30* | (2006.01) | |
| *C07K 14/705* | (2006.01) | |
| *C07K 14/725* | (2006.01) | |
| *C07K 14/71* | (2006.01) | |
| *C07K 14/54* | (2006.01) | |
| *C07K 14/005* | (2006.01) | |
| *C12N 7/00* | (2006.01) | |
| *C12N 5/0783* | (2010.01) | |
| *A61P 35/00* | (2006.01) | |
| *A61K 35/17* | (2015.01) | |
| *A61K 9/00* | (2006.01) | |
| *A61K 39/00* | (2006.01) | |
| *A61K 38/00* | (2006.01) | |

(52) U.S. Cl.
CPC ........ *C07K 16/3092* (2013.01); *A61K 9/0019* (2013.01); *A61K 35/17* (2013.01); *A61P 35/00* (2018.01); *C07K 14/005* (2013.01); *C07K 14/5434* (2013.01); *C07K 14/5443* (2013.01); *C07K 14/7051* (2013.01); *C07K 14/70521* (2013.01); *C07K 14/70578* (2013.01); *C07K 14/71* (2013.01); *C12N 5/0636* (2013.01); *C12N 7/00* (2013.01); *A61K 38/00* (2013.01); *A61K 2039/505* (2013.01); *A61K 2039/54* (2013.01); *A61K 2039/545* (2013.01); *C07K 2317/622* (2013.01); *C07K 2317/732* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2770/00033* (2013.01)

(58) Field of Classification Search
CPC .............. C07K 16/3092; C07K 14/005; C07K 14/5434; C07K 14/5443; C07K 14/7051; C07K 14/70521; C07K 14/70578; C07K 14/71; A61P 35/00; A61K 9/0019; A61K 35/17; C12N 5/0636; C12N 7/00

See application file for complete search history.

(56) References Cited

U.S. PATENT DOCUMENTS

| | | | |
|---|---|---|---|
| 7,202,346 B2 | 4/2007 | Payne et al. | |
| 7,723,485 B2 | 5/2010 | Junutula et al. | |
| 7,989,595 B2 | 8/2011 | Dennis et al. | |
| 8,802,374 B2 * | 8/2014 | Jensen ................. | C12N 5/0636 435/6.17 |
| 8,821,863 B2 | 9/2014 | Kumar et al. | |
| 9,169,328 B2 * | 10/2015 | Spriggs .............. | C07K 16/3092 |
| 9,629,877 B2 * | 4/2017 | Cooper .......... | A61K 39/001112 |
| 9,790,283 B2 | 10/2017 | Spriggs et al. | |
| 9,944,702 B2 * | 4/2018 | Galetto ............. | C07K 16/2803 |
| 2016/0009813 A1 | 1/2016 | Themeli et al. | |
| 2016/0296634 A1 | 10/2016 | Dennis et al. | |
| 2018/0002397 A1 | 1/2018 | Shah et al. | |

FOREIGN PATENT DOCUMENTS

| | | | |
|---|---|---|---|
| EP | | 2135881 B1 | 9/2011 |
| EP | | 2552959 B1 | 1/2017 |
| WO | WO-2007001851 A3 | | 3/2007 |
| WO | WO-2016160618 A3 | | 11/2016 |
| WO | WO-2017040945 A1 | | 3/2017 |
| WO | WO-2017172981 A2 * | | 10/2017 |
| WO | WO-2017172981 A3 | | 11/2017 |
| WO | WO-2018023093 A1 | | 2/2018 |

OTHER PUBLICATIONS

Attwood (Science 290: 471-473, 2000).*
Skolnick et al. (Trends in Biotech. 18: 34-39, 2000).*
Chekmasova, Alena A., et al., Successful Eradication of Established Peritoneal Ovarian Tumors in SCID-Beige Mice following Adoptive Transfer of T Cells Genetically Targeted to the MUC16 Antigen, ancer Therapy: Preclinical, Published online First Jul. 13, 2010; DOI: 10.1158/1078-0432.CCR-10-0192.
Koneru et al. IL-12 secreting tumor-targeted chimeric antigen receptor T cells eradicate ovarian tumors in vivo. OncoImmunology 4(3):e994446 (2015).
Koneru, Mythili et al., A phase I clinical trial of adoptive T cell therapy using IL-12 secreting MUC-16ecto directed chimeric antigen receptors for recurrent ovarian cancer, Journal of Translational Medicine, (2015) 13:102. DOI 10.1186/s12967-015-0460-x.
Pegu, A., et al., Synthetic construct immunoglobulin light chain simianized VRCO L/anti-rhesus CD3 scFv fusion protein gene, complete cds. Genbank Entry, national Center for Biotechnology Information. Oct. 19, 2015 (retrieved on Nov. 6, 2019); Retrieved from the Internet: ,URL: https://www.ncbi.nlm.nih.gov/nucleotide/KT365999.1>; pp. 1-2.

(Continued)

*Primary Examiner* — Sharon X Wen
*Assistant Examiner* — Peter Johansen
(74) *Attorney, Agent, or Firm* — Gene J. Yao; Barnes & Thornburg LLP

(57) ABSTRACT

Provided herein are chimeric antigen receptors (CARs) for cancer therapy, and more particularly, CARs containing a scFv from an anti-MUC16 monoclonal antibody. Provided are immune effector cells containing such CARs, and methods of treating proliferative disorders.

11 Claims, 22 Drawing Sheets

Specification includes a Sequence Listing.

(56) References Cited

OTHER PUBLICATIONS

Rao et al., Appl. Immunohistochem. Mol. Morphol., 18:462-472 (2010).
Huls et al., Journal of Visualized Experiments, 72:e50070 (2013).
Hurton et al., Proc. Natl Acad. Sci. USA, 113:E7788-E7797 (2016).

* cited by examiner

MUC16 SPECIFIC CHIMERIC ANTIGEN RECEPTORS AND USES THEREOF

CROSS-REFERENCE TO RELATED APPLICATION

The present application claims the benefit of U.S. Provisional Patent Application No. 62/680,297 filed Jun. 4, 2018, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 23, 2019, is named 50471-715_201_SL.txt and is 331,880 bytes in size.

BACKGROUND OF THE DISCLOSURE

Recombinant polypeptides such as chimeric polypeptides have been a valuable for research, diagnostic, manufacturing and therapeutic applications. Modified effector cells expressing antigen binding polypeptides such as CARs are useful in the treatment of diseases and disorders such as infectious disease, autoimmune disorders and cancers.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is an isolated nucleic acid encoding a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain. In some embodiments, the MUC16 antigen binding domain comprises at least one of: (a) a polypeptide having at least 90%, 91%, 92%, 93%, 94%, 95%, 96%, 97%, 98%, 99% or 100% identity with at least one of amino acid sequences as shown in SEQ ID NOs: 1, 3, 5, 7, 9, 12, and 14; (b) a polypeptide having at least 90%, 91%, 92%, 93%, 94%, 95%, 96%, 97%, 98%, 99% or 100% identity with at least one of amino acid sequences as shown in SEQ ID NOs: 2, 4, 6, 8, 10, 11, 13, and 15; and (c) a polypeptide having at least 90%, 91%, 92%, 93%, 94%, 95%, 96%, 97%, 98%, 99% or 100% identity with at least one of amino acid sequences as shown in SEQ ID NOs: 27-57.

In some embodiments, the MUC16 antigen binding domain is a polypeptide having at least 90%, 91%, 92%, 93%, 94%, 95%, 96%, 97%, 98%, 99% or 100% identity with at least one of amino acid sequences as shown in SEQ ID NOs: 27-57. In some embodiments, the stalk domain is a polypeptide having at least 90%, 91%, 92%, 93%, 94%, 95%, 96%, 97%, 98%, 99% or 100% identity with the amino acid sequence of SEQ ID NO: 16. In some embodiments, the costimulatory signaling domain comprises 4-1BB. In some embodiments, the costimulatory signaling domain of 4-1BB comprises a polypeptide having at least 90%, 91%, 92%, 93%, 94%, 95%, 96%, 97%, 98%, 99% or 100% identity with the amino acid sequence of SEQ ID NO: 22. In some embodiments, the costimulatory signaling domain comprises CD28. In some embodiments, the costimulatory signaling domain of CD28 comprises a polypeptide having at least 90%, 91%, 92%, 93%, 94%, 95%, 96%, 97%, 98%, 99% or 100% identity with the amino acid sequence of SEQ ID NO: 23.

In some embodiments, the CD3 zeta signaling domain comprises a polypeptide having at least 90%, 91%, 92%, 93%, 94%, 95%, 96%, 97%, 98%, 99% or 100% identity with the amino acid sequence of SEQ ID NO: 26. In some embodiments, the isolated nucleic acid as provided herein can further comprise a truncated epidermal growth factor receptor. In some embodiments, the truncated epidermal growth factor receptor is HER1t and comprises a polypeptide having at least 90%, 91%, 92%, 93%, 94%, 95%, 96%, 97%, 98%, 99% or 100% identity with the amino acid sequence of SEQ ID NO: 65. In some embodiments, the truncated epidermal growth factor receptor is HER1t−1 and comprises a polypeptide having at least 90%, 91%, 92%, 93%, 94%, 95%, 96%, 97%, 98%, 99% or 100% identity with the amino acid sequence of SEQ ID NO: 66.

In some embodiments, the CAR comprises a polypeptide having at least 90%, 91%, 92%, 93%, 94%, 95%, 96%, 97%, 98%, 99% or 100% identity with an amino acid sequence shown in SEQ ID NOs: 27-57.

Provided herein is a vector comprising a backbone and a nucleic acid sequence encoding: (1) a truncated epidermal growth factor receptor comprising at least one of HERR, HER1t−1 or a functional variant thereof; (2) a cytokine; and (3) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain.

In some embodiments, the cytokine is IL-15 or IL-12. In some embodiments, the vector is a lentivirus vector, a retroviral vector, or a non-viral vector. In some embodiments, the truncated epidermal growth factor receptor comprises a polypeptide having at least 90%, 91%, 92%, 93%, 94%, 95%, 96%, 97%, 98%, 99% or 100% identity with the amino acid sequence of SEQ ID NO: 65 or SEQ ID NO: 66. In some embodiments, the IL-15 is membrane bound IL-15. In some embodiments, membrane bound IL-15 comprises a nucleotide sequence encoding for SEQ ID NO: 161.

In some embodiments, any of the vectors provided herein can further comprise a nucleotide sequence encoding a self-cleaving Thosea asigna virus (T2A) peptide. In some embodiments, the backbone is Sleeping Beauty transposon DNA plasmid or pFUGW. In some embodiments, any of the vectors provided herein can further comprise a promoter. In some embodiments, the promoter is hEF1a1. In some embodiments, the MUC16 antigen binding domain comprises at least one of: (a) a polypeptide having at least 90%, 91%, 92%, 93%, 94%, 95%, 96%, 97%, 98%, 99% or 100% identity with at least one of amino acid sequences as shown in SEQ ID NO: 1, 3, 5, 7, 9, 12, and 14; (b) a polypeptide having at least 90%, 91%, 92%, 93%, 94%, 95%, 96%, 97%, 98%, 99% or 100% identity with at least one of amino acid sequences as shown in SEQ ID NOs: 2, 4, 6, 8, 10, 11, 13, and 15; and; (c) a polypeptide having at least 90%, 91%, 92%, 93%, 94%, 95%, 96%, 97%, 98%, 99% or 100% identity with at least one of amino acid sequences as shown in SEQ ID NOs: 27-57. In some embodiments, the MUC16 antigen binding domain is a polypeptide having at least 90%, 91%, 92%, 93%, 94%, 95%, 96%, 97%, 98%, 99% or 100% identity with at least one of amino acid sequences as shown in SEQ ID NO: 27-57. In some embodiments, the stalk domain comprises a polypeptide having at least 90%, 91%, 92%, 93%, 94%, 95%, 96%, 97%, 98%, 99% or 100% identity with the amino acid sequence of SEQ ID NO: 16. In some embodiments, the costimulatory signaling domain comprises 4-1BB. In some embodiments, the costimulatory signaling domain of 4-1BB comprises a nucleic acid sequence having at least 90%, 91%, 92%, 93%, 94%, 95%, 96%, 97%, 98%, 99% or 100% identity with the amino acid sequence of SEQ ID NO: 22.

In some embodiments, the costimulatory signaling domain comprises CD28. In some embodiments, the costimulatory signaling domain of CD28 comprises a nucleic acid sequence having at least 90%, 91%, 92%, 93%, 94%, 95%, 96%, 97%, 98%, 99% or 100% identity with the amino acid sequence of SEQ ID NO: 23. In some embodiments, the CD3 zeta signaling domain comprises a nucleic acid sequence having at least 90%, 91%, 92%, 93%, 94%, 95%, 96%, 97%, 98%, 99% or 100% identity with the amino acid sequence of SEQ ID NO: 26.

In some embodiments, the vector comprises a plasmid. In some embodiments, each the vector comprises an expression plasmid. In some embodiments, the non-viral vector is a Sleeping Beauty transposon.

Provided herein is an immune effector cell comprising any of nucleotides as provided herein. Provided herein is an immune effector cell comprising (1) a cell tag (2) IL-15 and (3) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain.

In some embodiments, the IL-15 is membrane bound IL-15. In some embodiments, the membrane bound IL-15 comprises the polypeptide sequence of SEQ ID NO: 161. In some embodiments, the cell tag comprises HER1t, and the HER1t comprises the polypeptide sequence of SEQ ID NO: 65. In some embodiments, the cell tag comprises HER1t-1, and the HER1t-1 comprises the polypeptide sequence of SEQ ID NO: 66.

Provided herein is an immune effector cell comprising any of the vectors as described herein. In some embodiments, the cell is a T cell, a Natural Killer (NK) cell, a cytotoxic T lymphocyte (CTL), or a regulatory T cell. In some embodiments, the CAR comprises at least one of amino acid sequences SEQ ID Nos: 27-57.

Provided herein is a method for stimulating a T cell-mediated immune response to a target cell population or tissue in a human subject in need thereof, comprising administering to the human subject an effective amount of a cell genetically modified to express a CAR, wherein the CAR comprises (a) a MUC16 antigen binding domain; (b) a stalk domain; (c) a transmembrane domain; (d) a costimulatory signaling domain comprising 4-1BB or CD28, or both; (e) a CD3 zeta signaling domain; and (f) a truncated epidermal growth factor receptor (HER1t). In some embodiments, the human has been diagnosed with at least one of ovarian and breast cancer. In some embodiments, the ovarian or breast cancer is relapsed or refractory ovarian or breast cancer.

Provided herein is an isolated nucleic acid encoding a chimeric antigen receptor (CAR), wherein the CAR comprises: (a) a MUC16 antigen binding domain with at least one of amino acid sequences of as shown in SEQ ID NO: 1-15 or 27-57; (b) a stalk domain with the amino acid sequence of SEQ ID NO: 16; (c) a costimulatory signaling domain comprising CD28 with the amino acid sequence of SEQ ID NO: 23; (d) a HER1 tag which comprises at least one of HER1t with the amino acid sequence of SEQ ID NO: 65 and HER1t-1 with the amino acid sequence of SEQ ID NO: 66; and (e) a CD3 zeta signaling domain with the amino acid sequence of SEQ ID NO: 26.

Provided herein is an isolated nucleic acid encoding a chimeric antigen receptor (CAR), wherein the CAR comprises: (a) a MUC16 antigen binding domain with at least one of amino acid sequences as shown in SEQ ID NO: 1-15 or 27-57; (b) a stalk domain with the amino acid sequence of SEQ ID NO: 16; (c) a costimulatory signaling domain comprising 4-1BB with the amino acid sequence of SEQ ID NO: 23; (d) a HER1 tag which comprises at least one of HER1t with the amino acid sequence of SEQ ID NO: 65 and HER1t-1 with the amino acid sequence of SEQ ID NO: 66; (e) a CD3 zeta signaling domain with the amino acid sequence of SEQ ID NO: 26.

Provided herein is a vector comprising any one or more of the polynucleotides as described herein. In some embodiments, the vector is a lentivirus vector, a retroviral vector, or a non-viral vector. In some embodiments, the non-viral vector is a Sleeping Beauty transposon. In some embodiments, the vector is a plurality of vectors.

Provided herein is a system for expressing a CAR in an immune effector cell, the system comprising one or more vectors encoding an isolated nucleic acid as provided herein. In some embodiments, the immune effector cell is a T cell or NK cell. In some embodiments, the system provided herein can further comprise a nucleic acid encoding at least one additional gene. In some embodiments, the additional gene comprises a cytokine. In some embodiments, the cytokine comprises at least one of IL-2, IL-15, IL-12, IL-21, and a fusion of IL-15 and IL-15Rα. In some embodiments, the cytokine is in secreted form. In some embodiments, the cytokine is in membrane bound form. In some embodiments, the system comprises one vector. In some embodiments, the one or more vectors is a lentivirus vector, a retroviral vector, or a non-viral vector. In some embodiments, the non-viral vector is a Sleeping Beauty transposon. In some embodiments, the system provided herein can further comprise a Sleeping Beauty transposase. In some embodiments, the Sleeping Beauty transposase is SB11, SB100X or SB110. In some embodiments, the immune effector cell is a mammalian cell.

Provided herein is a method of stimulating the proliferation and/ or survival of engineered T-cells comprising: (a) obtaining a sample of cells from a subject, the sample comprising T-cells or T-cell progenitors; (b) transfecting the cells with one or more vectors comprising a nucleic acid encoding a chimeric antigen receptor (CAR) comprising a MUC16 antigen binding domain, a stalk domain, a transmembrane domain, a costimulatogv signaling domain comprising 4-1BB andgor CD28, and a CD3 zeta signaling domain; and a vector encoding a transposase, to provide a population of engineered MUC16 CAR-expressing T-cells; (C) and optionally, culturing the population of MUC16 CAR T-cells ex vivo for 2 days or less. In certain embodiments, the vector further encodes a truncated epidermal growth factor receptor. In certain such embodiments. the vector also further encodes a cvtokine.

In some embodiments, the method of stimulating the proliferation and/or survival of engineered T-cells can further comprise transfecting the cells with a vector encoding a cytokine. In some embodiments, the cytokine is a fusion protein comprising IL-15 and IL-15Rα. In some embodiments, the one or more vectors is a lentivirus vector, a retroviral vector, or a non-viral vector. In some embodiments, the non-viral vector is a Sleeping Beauty transposon. In some embodiments, the method can further comprise a Sleeping Beauty transposase. In some embodiments, the Sleeping Beauty transposase is SB11, SB100X or SB110.

Provided herein is a method of treating cancer in a subject in need thereof comprising administering to the subject one or more doses of an effective amount of engineered T-cells, wherein the engineered T-cells comprise MUC16 CAR and membrane bound IL-15. In some embodiments, a first dose of an effective amount of engineered T-cells is administered intraperitoneally. In some embodiments, a second dose of an effective amount of engineered T-cells is administered intravenously. In some embodiments, the cancer is ovarian cancer. In some embodiments, the cancer is breast cancer. In some embodiments, the MUC16 CAR is encoded by any one of sequences as shown in SEQ ID NOs: 95-107, 119-149, or 194-195. In some embodiments, the membrane bound IL-15 is encoded by SEQ ID NO: 161. In some embodiments, an effective amount of engineered T-cells is at least $10^2$ cells/kg. In some embodiments, an effective amount of engineered T-cells is at least $10^4$ cells/kg. In some embodiments, an effective amount of engineered T-cells is at least $10^5$ cells/kg.

BRIEF DESCRIPTION OF THE FIGURES

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
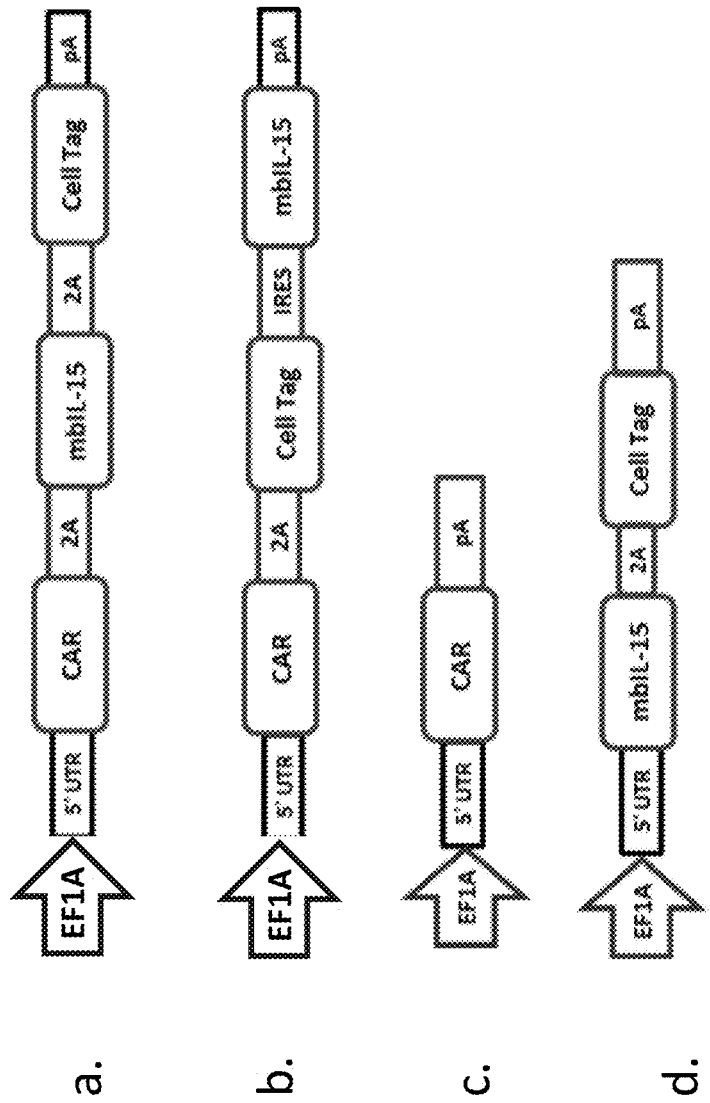
FIG. 1 is an exemplary schematic of Sleeping Beauty Transposon System. Sleeping Beauty derived DNA plasmids coding for MUC16 CAR and cytokine such as membrane bound IL15 (mbIL15) transposons and DNA plasmid coding for SB transposase are delivered into immune effector cells e.g. by electroporation. The engineered immune effector cells can be manufactured under point-of-care methods described herein. In certain cases, the MUC16 CAR and/or cytokine can be co-expressed with a cell or kill tag for conditional in vivo ablation.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention can be described in the context of a single embodiment, the features can also be provided separately or in any suitable combination. Conversely, although the invention can be described herein in the context of separate embodiments for clarity, the invention can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide" is used interchangeably with the terms "polypeptides" and "protein(s)," and refers to a polymer of amino acid residues. A "mature protein" is a protein which is full-length and which, optionally, includes glycosylation or other modifications typical for the protein in a given cellular environment.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology.

The terms "identical" or "sequence identity" in the context of two nucleic acid sequences or amino acid sequences of polypeptides refers to the residues in the two sequences which are the same when aligned for maximum correspondence over a specified comparison window. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is the to have certain percentage of sequence identity with a larger molecule, it means that when the two molecules are optimally aligned, the percentage of residues in the smaller molecule finds a match residue in the larger molecule in accordance with the order by which the two molecules are optimally aligned.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

The nucleic acid sequences and vectors disclosed or contemplated herein can be introduced into a cell by "transfection," "transformation," "nucleofection" or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)); and nucleofection (Trompeter et al., J. Immunol. Methods 274:245-256 (2003). Phage or viral vectors can be introduced into host cells, after growth of infectious particles in suitable packaging cells, many of which are commercially available.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch.

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

"Coding sequence" as used herein refers to a segment of a polynucleotide that codes for a polypeptide. The region or sequence is bounded nearer the 5' end by a start codon and nearer the 3' end with a stop codon. Coding sequences can also be referred to as open reading frames.

"Operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription, promoter activity and/or expression brought about by a transcriptional regulator, relative to some basal level of transcription.

A "target" gene or "heterologous" gene, or "gene of interest (GOI)" refers to a gene introduced into the host cell by gene transfer.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are large number of proteins that catalyze phage integration and excision (e.g., λ integrase, φC31), resolution of circular plasmids (e.g., Tn3, gamma delta, Cre, Flp), DNA inversion for expression of alternate genes (e.g., Hin, Gin, Pin), assembly of genes during development (e.g., Anabaena nitrogen fixation genes), and transposition (e.g., IS607 transposon). Most site-specific recombinases fall into one of the two families, based on evolutionary and mechanistic relatedness. These are λ integrase family or tyrosine recombinases (e.g., Cre, Flp, Xer D) and resolvase/integrase family or serine recombinase family (e.g., φC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes can have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POW, respectively. In some representations herein, the "O" is omitted and attB and attP, for example, are designated as BB' and PP', respectively.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic" cells (i.e., "hyperplastic" cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

MUC16

Also known as CA-125 (cancer antigen 125, carcinoma antigen 125, or carbohydrate antigen 125) or mucin 16, MUC16 is a member of the mucin family of glycoproteins. MUC16 has been shown to play a role in advancing tumorigenesis and tumor proliferation by several different mechanisms. Antibody based approaches against MUC16 have met with very little success. Accordingly, other treatment strategies are needed.

MUC16 is a large carbohydrate antigen, also known as CA-125. MUC16 is encoded by the MUC16 gene located on human chromosome 19. MUC16 is a highly glycosylated multi-domain type I transmembrane protein comprising 3 domains. The C-terminal domain contains multiple extracellular SEA (sea urchin sperm protein, enterokinase, and agrin) modules that have an autoproteolytic activity. SEA harbors two proteolytic sites proximal to the transmembrane (TM) domain. A large cleaved domain termed CA-125 is released into circulation at acidic pH. CA-125 is commonly used as disease biomarker for ovarian cancer. The highly conserved truncated extracellular membrane tethered protein domain called MUC16ecto domain. A MUC16 antibody was identified that specifically bound the ectodomain of MUC16 that is retained on the tumor cell surface. "Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

Chimeric Antigen Receptors

In embodiments described herein, a CAR can comprise an extracellular antibody-derived single-chain variable domain (scFv) for target recognition, wherein the scFv can be connected by a flexible linker to a transmembrane domain and/or an intracellular signaling domain(s) that includes, for instance, CD3 for T-cell activation. Normally when T cells are activated in vivo they receive a primary antigen induced TCR signal with secondary costimulatory signaling from CD28 that induces the production of cytokines (i.e., IL-2 and IL-21), which then feed back into the signaling loop in an autocrine/paracrine fashion. As such, CARs can include a signaling domain, for instance, a CD28 cytoplasmic signaling domain or other costimulatory molecule signaling domains such as 4-1BB signaling domain. Chimeric CD28 co-stimulation improves T-cell persistence by up-regulation of anti-apoptotic molecules and production of IL-2, as well as expanding T cells derived from peripheral blood mononuclear cells (PBMC).

In one embodiment, CARs are fusions of single-chain variable fragments (scFv) derived from monoclonal antibodies specific for various epitopes of MUC16 for example, fused to transmembrane domain and CD3-zeta endodomain. Such molecules result in the transmission of a zeta signal in response to recognition by the scFv of its target.

In an embodiment, a CAR can have an ectodomain (extracellular), a transmembrane domain and an endodomain (intracellular). In one embodiment of the CAR ectodomain, a signal peptide directs the nascent protein into the endoplasmic reticulum. This is if the receptor is to be glycosylated and anchored in the cell membrane for example. Any eukaryotic signal peptide sequence is envisaged to be functional. Generally, the signal peptide natively attached to the amino-terminal most component is used (e.g., in a scFv with orientation light chain-linker-heavy chain, the native signal of the light-chain is used). In embodiments, the signal peptide is GM-CSFRa (SEQ ID NO: 58) or IgK (SEQ ID NO: 59). Other signal peptides that can be used include signal peptides from CD8alpha and CD28.

The antigen recognition domain can be a scFv. There can however be alternatives. An antigen recognition domain from native T-cell receptor (TCR) alpha and beta single chains are envisaged, as they have simple ectodomains (e.g. CD4 ectodomain) and as well as other recognition components such as a linked e.g., cytokine (which leads to recognition of cells bearing the cytokine receptor). Almost anything that binds a given target, such as e.g., viral associated antigen, with high affinity can be used as an antigen recognition region.

In general, CARs exist in a dimerized form and are expressed as a fusion protein that links the extracellular scFv (VH linked to VL) region, a stalk domain, a transmembrane domain, and intracellular signaling motifs. The endodomain of the first generation CAR induces T cell activation solely through CD3-ζ signaling. The second generation CAR provides activation signaling through CD3-ζ and CD28, or other endodomains such as 4-1BB or OX40. The 3rd generation CAR activates T cells via a CD3-ζ-containing combination of three signaling motifs such as CD28, 4-1BB, or OX40.

In embodiments, the present invention provides chimeric antigen receptor (CAR) comprising an extracellular domain, a transmembrane domain and an intracellular signaling domain. In embodiments, the extracellular domain comprises a target-specific binding element otherwise referred to as an antigen binding moiety or scFv and a stalk domain. In embodiments, the intracellular signaling domain or otherwise the cytoplasmic signaling domain comprises, a costimulatory signaling region and a zeta chain portion.

The costimulatory signaling region refers to a portion of the CAR comprising the intracellular signaling domain of a costimulatory molecule. Costimulatory molecules are cell surface molecules other than antigens receptors or their ligands that are required for an efficient response of lymphocytes to antigen.

In embodiments, between the extracellular domain and the transmembrane domain of the CAR, there is incorporated a stalk domain or stalk region. As used herein, the term "stalk domain" or "stalk region" generally means any oligonucleotide- or polypeptide that functions to link the transmembrane domain to, either the scFv or, the cytoplasmic domain in the polypeptide chain. A stalk domain can include a flexible hinge such as a Fc hinge and optionally one or two constant domains of Fc. In some instances, the stalk region comprises the hinge region from IgG1. In alternative instances, the stalk region comprises the CH2CH3 region of immunoglobulin and optionally portions of CD3. In some cases, the stalk region comprises a CD8α hinge region, an IgG4-Fc 12 amino acid hinge region (ESKYGPPCPPCP) (SEQ ID NO: 196) or IgG4 hinge regions as described in WO/2016/073755.

Figure 3:
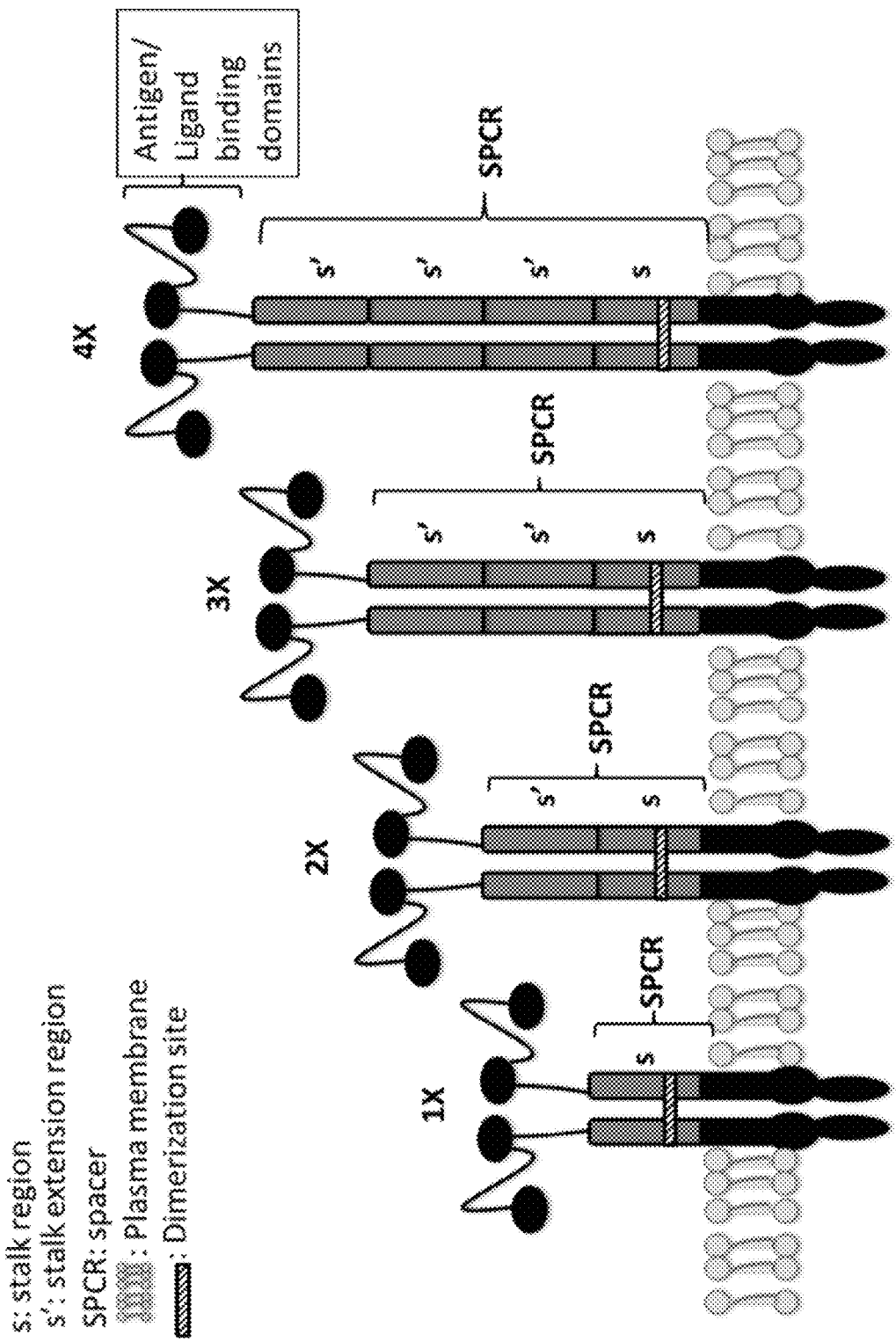
FIG. 3 depicts an illustration of MUC16 CARs with different stalk lengths.

In other embodiments, between the extracellular domain and the transmembrane domain of the CAR, there is incorporated a spacer. A spacer can comprise a stalk region and a stalk extension region as depicted in FIG. 3. In one embodiment, a spacer can include a single stalk region. In another embodiment, a spacer can comprise a stalk region (designated as "s") and stalk extension region(s), which is herein designated as "s-n'." For example, a spacer can comprise one (1) stalk region and s'-n, wherein n can be 0, 1, 2, 3, 4, 5, 6, 7, 8, 9, 10, 11, 12, 13, 14, 15, 16, 17, 18, 19, or 20. In further embodiments, the stalk region can be linked to stalk extension region s'-n via a linker.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length can form the linkage between the transmembrane domain and the cytoplasmic signaling domain of a CAR. In some embodiments, the linker is a glycine-serine linker. In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134), CD3-zeta or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), DAP10, DAP12 or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof. In some instances, a CAR described herein comprises at least one costimulatory domain DAP10 or a fragment thereof. In some instances, a CAR described herein comprises at least one costimulatory domain DAP12 or a fragment thereof.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In embodiments, provided herein is an isolated nucleic acid encoding a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; (e) a CD3 zeta signaling domain; and optionally (f) a truncated epidermal growth factor receptor (HER1t or HER1t1).

Included in the scope of the invention are nucleic acid sequences that encode functional portions of the CAR described herein. Functional portions encompass, for example, those parts of a CAR that retain the ability to recognize target cells, or detect, treat, or prevent a disease, to a similar extent, the same extent, or to a higher extent, as the parent CAR. In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

In embodiments, the CAR contains additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

Antigen Binding Moiety

In embodiments, a CAR described herein comprises a target-specific binding element otherwise referred to as an antigen-binding moiety. In embodiments, a CAR described herein engineered to target an antigen of interest by way of engineering a desired antigen-binding moiety that specifically binds to an antigen on a cell.

In embodiments, the antigen binding moiety of a CAR described herein is specific to MUC16 (MUC16 CAR). The MUC16-specific CAR, when expressed on the cell surface, redirects the specificity of T cells to human MUC16. In embodiments, the antigen binding domain comprises a single chain antibody fragment (scFv) comprising a variable domain light chain (VL) and variable domain heavy chain (VH) of a target antigen specific monoclonal anti-MUC16 antibody joined by a flexible linker, such as a glycine-serine linker or a Whitlow linker. In embodiments, the scFv are MUC16-1 scFv, MUC16-2 scFv, MUC16-3 scFv, MUC16-4 scFv, MUC16-5 scFv, MUC16-6 scFv or MUC16-7 scFv. In embodiments, the scFv is humanized. In some embodiments, the antigen binding moiety can comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with any one of amino acid sequences as shown in SEQ ID NOs: 1, 3, 5, 7, 9, 12, and 14 (MUC16 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with any one of amino acid sequences as shown in SEQ ID NOs: 2, 4, 6, 8, 10, 11, 13, and 15 (MUC16 VH).

In embodiments, a CAR described herein comprises antigen binding moieties VL (SEQ ID NOs: 1, 3, 5, 7, 9, 12, or 14) and VH (SEQ ID NOs: 2, 4, 6, 8, 10, 11, or 15) with Gly-Ser linker (SEQ ID NO: 83 or SEQ ID NO: 197) or functional variants of the linker.

In embodiments, a CAR described herein comprises a polypeptide having at least 90%, 91%, 92%, 93%, 94%, 95%, 96%, 97%, 98%, 99% or 100% identity with any one of amino acid sequences as shown in SEQ ID NOs: 27-57 (VH, VL and linker).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 2 (MUC16-1 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 1 (MUC16-1 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 4 (MUC16-2 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 3 (MUC16-2 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 6 (MUC16-3 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 5 (MUC16-3 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 8 (MUC16-4 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 7 (MUC16-4 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 10 (MUC16-5 VH-L).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 11 (MUC16-5 VH-F).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 9 (MUC16-5 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 13 (MUC16-6 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 12 (MUC16-6 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO: 15 (MUC16-7 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO: 14 (MUC16-7 VL).

In embodiments, the antigen binding moiety has GM-CSFRa signal peptide having at least 90%, 91%, 92%, 93%, 94%, 95%, 96%, 97%, 98%, 99% or 100% identity with the amino acid sequence of SEQ ID NO: 58.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 27. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 28. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 29.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 30.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 31. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 32. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 33.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 34. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 35. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 36.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 37. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 38. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 39.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 40. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 41. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 42.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 43. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 44. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 45.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 46. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 47. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 48.

In embodiments, a CAR described herein a polypeptide having at least 90%, 91%, 92%, 93%, 94%, 95%, 96%, 97%, 98%, 99% or 100% identity with the amino acid sequence of SEQ ID NO: 49. In embodiments, a CAR described herein comprises g a polypeptide having at least 90%, 91%, 92%, 93%, 94%, 95%, 96%, 97%, 98%, 99% or 100% identity with the amino acid sequence of SEQ ID NO: 50. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 51.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 52. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 53. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 54.

In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 55. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 56. In embodiments, a CAR described herein comprises a polypeptide having at least 90%, 91%, 92%, 93%, 94%, 95%, 96%, 97%, 98%, 99% or 100% identity with the amino acid sequence of SEQ ID NO: 57.

Stalk Domain

In embodiments, the MUC16 CAR of the invention comprises a stalk domain that provides a separation between the antigen binding moiety and the T cell membrane. In embodiments, the stalk domain establishes an optimal effector-target inter-membrane distance. In embodiments, the stalk domain provides flexibility for antigen binding domain to reach its target. In one embodiment, the stalk domain is a CD8alpha hinge domain.

In embodiments, the CD8alpha hinge domain comprises a polypeptide having at least 90%, 91%, 92%, 93%, 94%, 95%, 96%, 97%, 98%, 99% or 100% identity with the amino acid sequence of SEQ ID NO: 16.

Spacers

In other embodiments, between the extracellular domain and the transmembrane domain of the CAR, there is incorporated a spacer. As described herein, a spacer can comprise a stalk region and a stalk extension region as depicted in FIG. 3. In one embodiment, a spacer can include a single stalk region. In another embodiment, a spacer can comprise a stalk region (designated as "s") and stalk extension region(s), which is herein designated as "s-n'." For example, a spacer can comprise one (1) stalk region and s'-n, wherein n can be 0, 1, 2, 3, 4, 5, 6, 7, 8, 9, 10, 11, 12, 13, 14, 15, 16, 17, 18, 19, or 20. In further embodiments, the stalk region can be linked to stalk extension region s'-n via a linker. A linker as described herein can include for instance, a GSG linker (SEQ ID NO: 85), SGSG linker (SEQ ID NO: 86), (G4S)3 linker (SEQ ID NO: 83), (G4S)4 linker (SEQ ID NO: 200) and/or a Whitlow linker.

In one embodiment, stalk region and stalk extension region(s) can be derived or designed from a polypeptide of natural or of synthetic origin. The stalk region and/or stalk extension region(s) can comprise hinge domain(s) derived from a cell surface protein or derivatives or variants thereof. In some embodiments, the stalk region and/or stalk extension region(s) can comprise a hinge domain derived from CD28 or CD8alpha (CD8α). In some embodiments, each of the stalk region and stalk extension region(s) can be derived from at least one of a CD8alpha hinge domain, a CD28 hinge domain, a CTLA-4 hinge domain, a LNGFR extracellular domain, IgG1 hinge, IgG4 hinge and CH2-CH3 domain. The stalk and stalk extension region(s) can be separately derived from any combination of CD8alpha hinge domain, CD28 hinge domain, CTLA-4 hinge domain, LNGFR extracellular domain, IgG1 hinge, IgG4 hinge or CH2-CH3 domain. As an example, the stalk region can be derived from CD8alpha hinge domain and at least one stalk extension region can be derived from CD28 hinge domain thus creating a hybrid spacer. As another example, the stalk region can be derived from an IgG1 hinge or IgG4 hinge and at least one stalk extension region can be derived from a CH2-CH3 domain of IgG.

In certain embodiments, the stalk region can comprise one or more dimerization sites to form homo or hetero dimerized chimeric polypeptides. In other embodiments, the stalk region or one or more stalk extension regions can contain mutations that eliminate dimerization sites altogether. In some embodiments, a stalk extension region(s) can contain at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, the stalk extension region(s) lacks a dimerization site.

In some aspects of the embodiments disclosed herein, a stalk region of a subject antigen binding polypeptide comprises a sequence with at least about 65%, 70%, 75%, 80%, 85%, 90%, 95%, 99% or greater identity to a CD8alpha hinge domain. A CD8alpha hinge domain can comprise a polypeptide sequence with at least 65%, 70%, 75%, 80%, 85%, 90%, 95%, 99% or greater identity to the sequence shown in SEQ ID NO: 16. In some cases, a stalk extension region comprises a polypeptide sequence with at least 65%, 70%, 75%, 80%, 85%, 90%, 95%, or greater identity to the sequence shown in SEQ ID NO: 16. In some cases, a stalk extension region comprises a nucleotide sequence with at least 65%, 70%, 75%, 80%, 85%, 90%, 95%, or greater identity to the sequence shown in SEQ ID NO: 108. In some examples, a stalk region and stalk extension region can together comprise a polynucleotide sequence with at least 65%, 70%, 75%, 80%, 85%, 90%, 95%, or greater identity to the sequence shown in SEQ ID NO: 16.

Transmembrane Domain

In embodiments, the CAR comprises a transmembrane domain that is fused to the extracellular domain of the CAR stalk domain. In one embodiment, the transmembrane domain that naturally is associated with one of the domains in the CAR is used. In embodiments, the transmembrane domain is a hydrophobic alpha helix that spans the membrane.

The transmembrane domain can be derived from either a natural or a synthetic source. Where the source is natural, the domain can be derived from any membrane-bound or transmembrane protein. Transmembrane regions of particular use in this invention can be derived from (i.e. comprise at least the transmembrane region(s) of) the alpha, beta or zeta chain of the T-cell receptor, CD28, CD3 epsilon, CD45, CD4, CD5, CD8alpha, CD9, CD16, CD22, CD33, CD37, CD64, CD80, CD86, CD134, CD137, CD154. Alternatively the transmembrane domain can be synthetic, in which case it will comprise predominantly hydrophobic residues such as leucine and valine. In embodiments, a triplet of phenylalanine, tryptophan and valine will be found at each end of a synthetic transmembrane domain. Optionally, a short oligonucleotide or polypeptide linker, in embodiments, between 2 and 10 amino acids in length can form the linkage between the transmembrane domain and the cytoplasmic signaling domain of the CAR. In embodiments, the linker is a glycine-serine linker.

In embodiments, the transmembrane domain in a CAR described herein is the CD8alpha transmembrane domain. In embodiments, the CD8alpha transmembrane domain comprises a polypeptide having at least 90%, 91%, 92%, 93%, 94%, 95%, 96%, 97%, 98%, 99% or 100% identity with the amino acid sequence of SEQ ID NO: 20.

In embodiments, the transmembrane domain in a CAR described herein is the CD28 transmembrane domain. In embodiments, the CD28 transmembrane domain comprises a polypeptide having at least 90%, 91%, 92%, 93%, 94%, 95%, 96%, 97%, 98%, 99% or 100% identity with the amino acid sequence of SEQ ID NO: 21.

Cytoplasmic Domain (Co-Stimulatory Domain and Signaling Domain)

The cytoplasmic domain, also known as the intracellular signaling domain of a CAR described herein, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in a CAR described herein can include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone are generally insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner can contain signaling motifs which are known as immunoreceptor tyrosine-based activation motifs or ITAMs.

Examples of ITAM-containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In embodiments, the cytoplasmic signaling molecule in a CAR described herein comprises a cytoplasmic signaling sequence derived from CD3 zeta.

In embodiments, the cytoplasmic domain of the CAR can be designed to comprise the CD3-zeta signaling domain by itself or combined with any other desired cytoplasmic domain(s) useful in the context of a CAR described herein. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, DAP10, DAP12 and a ligand that specifically binds with CD83, and the like. In embodiments, costimulatory molecules can be used together, e.g., CD28 and 4-1BB or CD28 and OX40. Thus, while the invention in exemplified primarily with 4-1BB and CD28 as the co-stimulatory signaling element, other costimulatory elements are within the scope of the invention.

The cytoplasmic signaling sequences within the cytoplasmic signaling portion of a CAR described herein can be linked to each other in a random or specified order. Optionally, a short oligo- or polypeptide linker, between 2 and 10 amino acids in length can form the linkage. A glycine-serine doublet provides a particularly suitable linker.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB. In yet another embodiment, the cytoplasmic domain comprises the signaling domain of CD3-zeta and the signaling domains of CD28 and 4-1BB.

In one embodiment, the cytoplasmic domain in a CAR described herein comprises the signaling domain of 4-1BB and the signaling domain of CD3-zeta, wherein the signaling domain of 4-1BB comprises a polypeptide sequence having at least 90%, 91%, 92%, 93%, 94%, 95%, 96%, 97%, 98%, 99% or 100% identity with the polypeptide sequence of SEQ ID NO:22, and the signaling domain of CD3-zeta comprises a polypeptide sequence having at least 90%, 91%, 92%, 93%, 94%, 95%, 96%, 97%, 98%, 99% or 100% identity with the nucleic acid sequence of SEQ ID NO: 26.

In one embodiment, the cytoplasmic domain in a CAR described herein is designed to comprise the signaling domain of CD28 and the signaling domain of CD3-zeta, wherein the signaling domain of CD28 comprises a polypeptide sequence having at least 90%, 91%, 92%, 93%, 94%, 95%, 96%, 97%, 98%, 99% or 100% identity with the polypeptide sequence of SEQ ID NO: 23, and the signaling domain of CD3-zeta comprises a polypeptide sequence having at least 90%, 91%, 92%, 93%, 94%, 95%, 96%, 97%, 98%, 99% or 100% identity with the polypeptide sequence of SEQ ID NO: 26.

In one embodiment, the cytoplasmic domain in a CAR described herein comprises the signaling domain of 4-1BB and the signaling domain of CD3-zeta, wherein the signaling domain of 4-1BB comprises the amino acid sequence set forth in SEQ ID NO: 22 and the signaling domain of CD3-zeta comprises the amino acid sequence set forth in SEQ ID NO: 26.

Additional Genetic Elements

Although cellular therapies hold great promise for the treatment of human disease, significant toxicities from the cells themselves or from their transgene products have hampered clinical investigation. In embodiments described herein, immune effector cells comprising a CAR described herein that have been infused into a mammalian subject, e.g., a human, can be ablated in order to regulate the effect of such immune effector cells should toxicity arise from their use. Therefore, certain in embodiments, in addition to the therapeutic MUC16-specific chimeric antigen receptor described herein, a second gene is also introduced into an engineered immune effector cell described herein. The second gene is effectively a "kill switch" that allows for the depletion of MUC16 CAR or MUC16 CAR/mbIL-15 containing cells. In certain embodiments, the "kill switch" is a HER1 tag or a CD20 tag which comprise a HER1 polypeptide or a CD20 polypeptide which comprises at least an antibody binding epitope of HER1 or CD20 or functional fragment thereof, and optionally a signal polypeptide sequence or fragment thereof.

In certain embodiments, the second gene is a HER1 tag which is Epidermal Growth Factor Receptor (HER1) or a fragment or variant thereof. In embodiments, the second gene is a HER1 tag which is truncated human Epidermal Growth Factor Receptor 1 (for instance HER1t or HER1t1). In some cases, the second gene is a variant of a truncated human Epidermal Growth Factor Receptor 1. In embodiments, at least one of HER1, HER1t and HER1t1 provides a safety mechanism by allowing for depletion of infused CAR-T cells through administering FDA approved cetuximab or any antibody that recognizes HER1, HER1t and/or HER1t1. In embodiments, the HER1t gene comprises a nucleotide sequence having at least 90%, 91%, 92%, 93%, 94%, 95%, 96%, 97%, 98%, 99% or 100% identity with the nucleic acid sequence of SEQ ID NO: 65. In embodiments, the HER1t1 gene comprises a nucleotide sequence having at least 90%, 91%, 92%, 93%, 94%, 95%, 96%, 97%, 98%, 99% or 100% identity with the nucleic acid sequence of SEQ ID NO: 66. The truncated HER1 sequence, for instance HER1t and HER1t1 eliminate the potential for EGF ligand binding, homo- and hetero-dimerization of EGFR, and EGFR mediated signaling while keeping cetuximab binding to the receptor intact (Ferguson, K., 2008. A structure-based view of Epidermal Growth Factor Receptor regulation. *Annu Rev Biophys*, Volume 37, pp. 353-373).

In further embodiments, in addition to the therapeutic MUC16-specific chimeric antigen receptor of the invention the second gene introduced is a CD20 tag. In some cases, the CD20 tag is a full-length CD20 polypeptide, or a truncated CD20 polypeptide (CD20t-1). In some cases, the CD20 tag, for instance CD20 or CD20t-1 also provides a safety mechanism by allowing for depletion of infused CAR-T cells through administering FDA-approved rituximab therapy. In certain embodiments, the CD20 tag has a polypeptide sequence having at least 90%, 91%, 92%, 93%, 94%, 95%, 96%, 97%, 98%, 99% or 100% identity with the sequence of SEQ ID NO:36. In certain embodiments, the CD20 tag is a CD20t-1 tag and has a polypeptide sequence having at least 90%, 91%, 92%, 93%, 94%, 95%, 96%, 97%, 98%, 99% or 100% identity with the sequence of SEQ ID NO: 68. In some embodiments, the CD20 tag is encoded by a CD20 gene which comprises a nucleotide sequence having at least 90%, 91%, 92%, 93%, 94%, 95%, 96%, 97%, 98%, 99% or 100% identity with the nucleic acid sequence of SEQ ID NO: 160. In some embodiments, the CD20 tag is encoded by a CD20t-1 gene which comprises a nucleotide sequence having at least 90%, 91%, 92%, 93%, 94%, 95%, 96%, 97%, 98%, 99% or 100% identity with the nucleic acid sequence of SEQ ID NO: 160.

In embodiments, a CAR vector comprising a CAR described herein further comprises a full length CD20 tag comprising a nucleic acid sequence having at least 90%, 91%, 92%, 93%, 94%, 95%, 96%, 97%, 98%, 99% or 100% identity with the nucleic acid sequence of SEQ ID NO: 159.

In embodiments, the gene encoding the kill tag, for instance the HERR, HER1t-1, CD20 or CD20t-1 tag, is genetically fused to the MUC16 CAR at 3' end via in-frame with a self-cleaving peptide, for example but not restricted to Thosea asigna virus (T2A) peptide. In embodiments, the T2A peptide has an amino acid sequence having at least 90%, 91%, 92%, 93%, 94%, 95%, 96%, 97%, 98%, 99% or 100% identity with the amino acid sequence of SEQ ID NO: 72.

In embodiments, the kill tag gene is cloned into a lentiviral plasmid backbone in frame with the MUC16 CAR gene. In other embodiments, the kill tag is cloned into a separate lentiviral vector. In other embodiments, both genes are cloned into a Sleeping Beauty transposon vector. In yet other embodiments, the kill tag such as HER1t, HER1t-1, CD20 or CD20t-1 is cloned into a separate Sleeping Beauty transposon vector. In certain embodiments, the kill tags have a signal peptide, for instance, GM-CSFRa signal peptide wherein the GM-CSFRa signal peptide has at least 90%, 91%, 92%, 93%, 94%, 95%, 96%, 97%, 98%, 99% or 100% identity with the amino acid sequence of SEQ ID NO: 58. In certain embodiments, the signal peptide is IgK having a sequence at least 90%, 91%, 92%, 93%, 94%, 95%, 96%, 97%, 98%, 99% or 100% identity with the nucleic acid sequence of SEQ ID NO: 59. In some cases the signal peptide can be selected from IgE and CD8α variants and fragments thereof.

Figure 2:
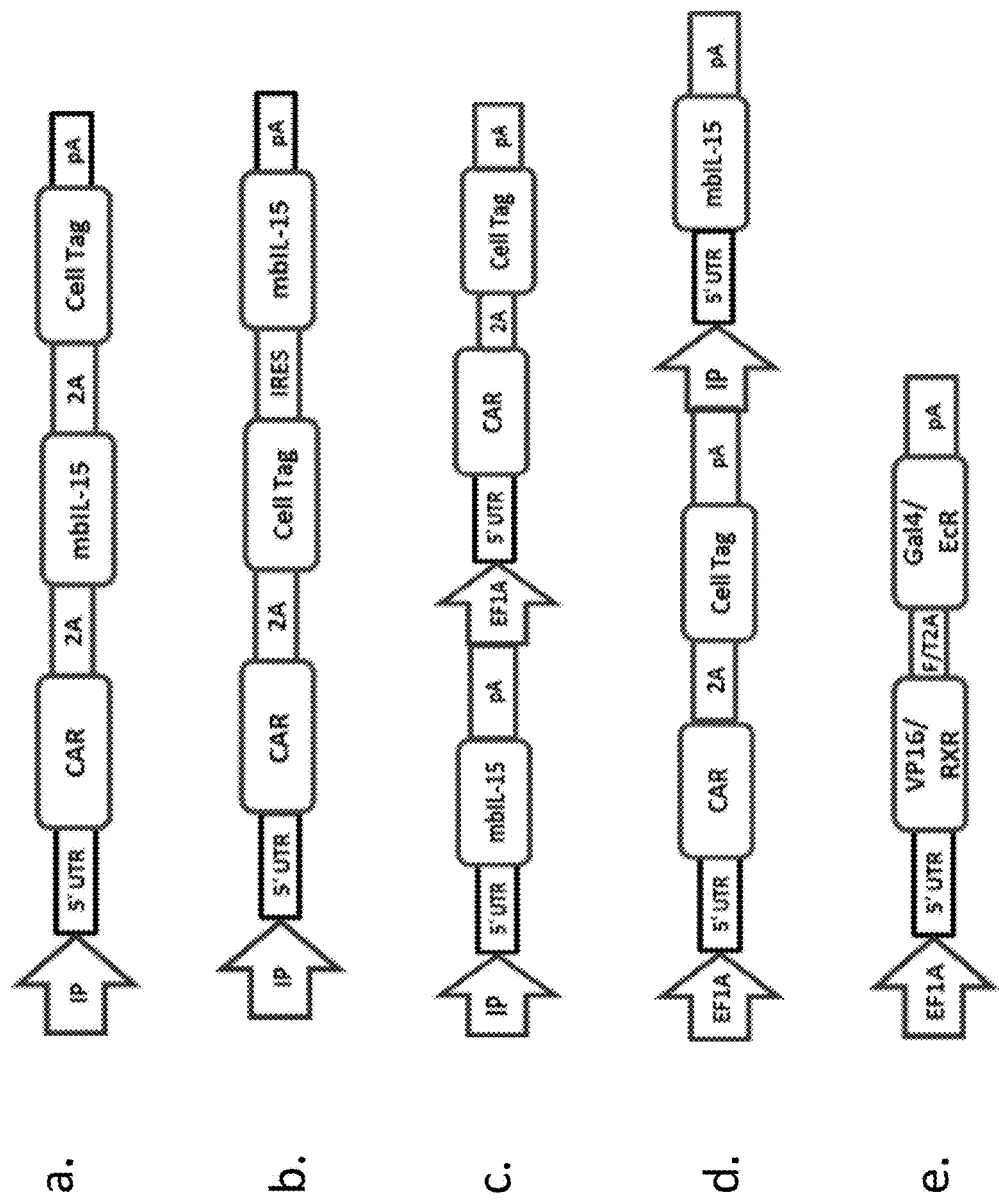
FIG. 2 depicts exemplary gene expression cassettes for MUC16 CARs and cytokines in different configurations with gene switch components.

Exemplary gene expression cassettes encoding a CAR and a kill tag as described herein are shown in FIGS. 1 and 2.

Exemplary CAR Open Reading Frames

Exemplary CAR and human MUC16 receptor open reading frames encompassed by methods and compositions described herein are in Table 1:

TABLE 1

| SEQ ID NO | CAR ORF |
|---|---|
| 27 | MUC16-2 scFv.CD8a.4-1BBz |
| 28 | MUC16-2 scFv.CD8a(2x).4-1BBz |
| 29 | MUC16-2 scFv.CD8a(3x).4-1BBz |
| 30 | SP-MUC16-3 scFv.CD8a.4-1BBz |
| 31 | MUC16-3 scFv.CD8a.4-1BBz |
| 32 | MUC16-3 scFv.CD8a(2x).4-1BBz |
| 33 | MUC16-3 scFv.CD8a(3x).4-1BBz |
| 34 | MUC16-2 (vh-vl)scFv.CD8a.CD28z |
| 35 | MUC16-2 (vh-vl)scFv.CD8a(2x).CD28z |
| 36 | MUC16-2 (vh-vl)scFv.CD8a(3x).CD28z |
| 37 | MUC16-2 (vh-vl)scFv.CD8a.CD28.4-1BB.z |
| 38 | MUC16-2 (vh-vl)scFv.CD8a(2x).CD28.4-1BBz |
| 39 | MUC 16-2 (vh-vl)scFv.CD8a(3x).CD28.4-1BBz |
| 40 | MUC16-2 (vl-vh)scFv.CD8a.CD28z |
| 41 | MUC16-2 (vl-vh)scFv.CD8a(2x).CD28z |
| 42 | MUC16-2 (vl-vh)scFv.CD8a(3x).CD28z |
| 43 | MUC16-2 (vl-vh)scFv.CD8a.CD28.4-1BBz |
| 44 | MUC16-2 (vl-vh)scFv.CD8a(2x).CD28.4-1BBz |
| 45 | MUC16-2 (vl-vh)scFv.CD8a(3x).CD28.4-1BBz |
| 46 | MUC16-3 (vh-vl)scFv.CD8a.CD28z |
| 47 | MUC16-3 (vh-vl)scFv.CD8a(2x).CD28z |
| 48 | MUC16-3 (vh-vl)scFv.CD8a(3x).CD28z |
| 49 | MUC16-3 (vh-vl)scFv.CD8a.CD28.4-1BBz |
| 50 | MUC16-3 (vh-vl)scFv.CD8a(2x).CD28.4-1BBz |
| 51 | MUC16-3 (vh-vl)scFv.CD8a(3x).CD28.4-1BBz |
| 52 | MUC16-3 (vl-vh)scFv.CD8a.CD28z |
| 53 | MUC16-3 (vl-vh)scFv.CD8a(2x).CD28z |
| 54 | MUC16-3 (vl-vh)scFv.CD8a(3x).CD28z |
| 55 | MUC16-3 (vl-vh)scFv.CD8a.CD28.4-1BBz |
| 56 | MUC16-3 (vl-vh)scFv.CD8a(2x).CD28.4-1BBz |
| 57 | MUC16-3 (vl-vh)scFv.CD8a(3x).CD28.4-1BBz |

In embodiments, provided herein is an isolated nucleic acid encoding a CAR, wherein the CAR comprises a polypeptide having at least 90%, 91%, 92%, 93%, 94%, 95%, 96%, 97%, 98%, 99% or 100% identity with an amino acid of SEQ ID NO: 3-4 or SEQ ID NO: 5-6.

In each of the embodiments listed in Table 1 with "MUC16-2 scFv," the CAR antigen binding moiety is MUC16-2 scFv comprising a polypeptide having at least 90%, 91%, 92%, 93%, 94%, 95%, 96%, 97%, 98%, 99% or 100% identity with the amino acid sequence of SEQ ID NO: 3-4. In embodiments, MUC16-3 scFv has GM-CSFRa signal peptide having at least 90%, 91%, 92%, 93%, 94%, 95%, 96%, 97%, 98%, 99% or 100% identity with the amino acid sequence of SEQ ID NO: 58.

In each of the embodiments in Table 1 with "CD8a," the transmembrane region of the CAR comprises CD8alpha transmembrane domain comprising a polypeptide having at least 90%, 91%, 92%, 93%, 94%, 95%, 96%, 97%, 98%, 99% or 100% identity with the amino acid sequence of SEQ ID NO: 20, and the stalk domain is CD8a comprising a polypeptide having at least 90%, 91%, 92%, 93%, 94%, 95%, 96%, 97%, 98%, 99% or 100% identity with the amino acid sequence of SEQ ID NO: 16.

In each of the embodiments in Table 1 with "CD28m," the intracellular domain of the CAR comprises CD28 with an amino acid sequence having at least 90%, 91%, 92%, 93%, 94%, 95%, 96%, 97%, 98%, 99% or 100% identity with the amino acid sequence of SEQ ID NO: 21.

In each of the embodiments in Table 1 with "T2A", the CAR ORF comprises a self-cleaving Thosea asigna virus (T2A) peptide, which enables the production of multiple gene products from a single vector. In embodiments, the T2A peptide has an amino acid sequence having at least 90%, 91%, 92%, 93%, 94%, 95%, 96%, 97%, 98%, 99% or 100% identity with the amino acid sequence of SEQ ID NO: 72.

In the embodiments in Table 1 with "HER1t," the CAR ORF comprises truncated human Epidermal Growth Factor Receptor 1 (HER1t), which provides a safety mechanism by allowing for depletion of infused CAR-T cells through administering FDA approved cetuximab therapy. The HER1t gene as described herein can comprise a polypeptide sequence having at least 90%, 91%, 92%, 93%, 94%, 95%, 96%, 97%, 98%, 99% or 100% identity with the amino acid sequence of SEQ ID NO: 65. Unless otherwise noted in Table 1, HER1t tags have GM-CSFRa signal peptide ("GM-CSFRsp") (SEQ ID NO: 58). In certain embodiments, the HER1t can be substituted with another tag, for instance, HER1t–1. The HER1t–1 gene as described herein can comprise a polypeptide sequence having at least 90%, 91%, 92%, 93%, 94%, 95%, 96%, 97%, 98%, 99% or 100% identity with the amino acid sequence of SEQ ID NO: 66. In the embodiments in Table 1 with "IgKsp," the signal peptide is IgK having an amino acid sequence at least 90%, 91%, 92%, 93%, 94%, 95%, 96%, 97%, 98%, 99% or 100% identity with the amino acid sequence of SEQ ID NO: 59.

In embodiments in Table 1 with "4-1BB," the CAR ORF comprises costimulatory molecule having a polypeptide sequence having at least 90%, 91%, 92%, 93%, 94%, 95%, 96%, 97%, 98%, 99% or 100% identity with the amino acid sequence of SEQ ID NO: 22.

In embodiments in Table 1 with "FL CD20," the CAR ORF comprises a full length CD20 tag comprising a polypeptide sequence having at least 90%, 91%, 92%, 93%, 94%, 95%, 96%, 97%, 98%, 99% or 100% identity with the amino acid sequence of SEQ ID NO: 67. CD20 provides a safety mechanism by allowing for depletion of infused CAR-T cells through administering FDA-approved rituximab therapy. In other embodiments, FL CD20 can be substituted with CD20t–1 comprising a polypeptide sequence having at least 90%, 91%, 92%, 93%, 94%, 95%, 96%, 97%, 98%, 99% or 100% identity with the amino acid sequence of SEQ ID NO: 68.

In certain embodiments in Table 1, the CAR ORF can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In some embodiments, the CAR ORF and gene switch components can be configured as depicted in FIGS. 1-2.

Cytokines

In some embodiments, a CAR described herein is administered to a subject with one or more additional therapeutic agents that include but are not limited to cytokines. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and functional variants and fragments thereof. In some embodiments, the cytokines can be membrane bound or secreted. In embodiments, the cytokine is soluble IL-15, soluble IL-15/IL-15Rα complex (e.g., ALT-803). In certain cases, the interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified immune effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," PNAS 2016. In some cases, the cytokine is expressed in the same immune effector cell as the CAR.

In further embodiments, an immune effector cell expressing a CAR described herein expresses membrane-bound IL-15 ("mIL-15 or mbIL-15"). In aspects of the invention, the mbIL-15 comprises a fusion protein between IL-15 and IL-15Rα. In further embodiments, the mbIL-15 comprises an amino acid sequence having at least 90%, 91%, 92%, 93%, 94%, 95%, 96%, 97%, 98%, 99% or 100% identity with the amino acid sequence of SEQ ID NO: 69. In certain cases, the CAR and the cytokine is expressed in separate vectors. In specific cases, the vectors can be lentiviral vectors, retroviral vectors or Sleeping Beauty transposons.

In some embodiments, the mbIL-15 is expressed with a cell tag such as HERR, HER-1t-1, CD20t-1 or CD20 as described herein. The mbIL-15 can be expressed in-frame with HERR, HER-1t-1, CD20t-1 or CD20.

In some embodiments, the mbIL-15 can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Gene Switch

Provided herein are gene switch polypeptides, polynucleotides encoding ligand-inducible gene switch polypeptides, and methods and systems incorporating these polypeptides and/or polynucleotides. The term "gene switch" refers to the combination of a response element associated with a promoter, and for instance, an ecdysone receptor (EcR) based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283, 173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter ("IP") can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/US2002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497, 093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919; each of which is incorporated by reference in its entirety.

Provided are systems for modulating the expression of a CAR and/or a cytokine in a host cell, comprising polynucleotides encoding for gene-switch polypeptides disclosed herein. Further provided herein are polynucleotides encoding gene switch polypeptides for ligand-inducible control of gene expression, wherein the gene switch polypeptides comprise (a) a first gene switch polypeptide comprising a DNA-binding domain (DBD) fused to a nuclear receptor ligand binding domain; and (b) a second gene switch polypeptide comprising a transactivation domain fused to a nuclear receptor ligand binding domain; wherein the first gene switch polypeptide and the second gene switch polypeptide are connected by a linker. In some embodiments, the linker is a cleavable or ribosome skipping linker sequence selected from the group consisting of 2A, GSG-2A, GSG linker (SEQ ID NO: 85), SGSG linker (SEQ ID NO: 86), furinlink variants and derivatives thereof. In certain embodiments, the 2A linker is a p2A linker, a T2A linker, F2A linker, or E2A linker.

In some embodiments, the DNA binding domain (DBD) comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In some cases, the transactivation domain comprises at least one of a VP16 transactivation domain, and a B42 acidic activator transactivation domain. In other cases, the nuclear receptor ligand binding domain comprises at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. In some embodiments, the nuclear receptor ligand binding domain is derived from the Ecdysone Receptor polypeptide sequence of SEQ ID NOs: 91 and 92.

In yet another embodiment, the first gene switch polypeptide comprises a GAL4 DBD fused to an EcR nuclear receptor ligand binding domain, and the second gene switch polypeptide comprises a VP16 transactivation domain fused to a retinoid receptor X (RXR) nuclear receptor ligand binding domain. In some cases, the first gene switch polypeptide and the second gene switch polypeptide are connected by a linker, which is selected from the group consisting of 2A, GSG-2A, GSG linker (SEQ ID NO: 85), SGSG linker (SEQ ID NO: 86), furinlink variants and derivatives thereof.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or more of: F/T2A, T2A, p2A, 2A, GSG-p2A, GSG linker (SEQ ID NO:

85), and furinlink variants. In certain embodiments, the linker polypeptide comprises SEQ ID NOs: 72-86 or 197-199.

In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro (SEQ ID NO: 201). A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston, Kallioinen et al. 2008). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG (SEQ ID NO: 85)) ahead of the 2A peptides. In some cases, constructs can combine a spacers, linkers, adaptors, promotors, or combinations thereof. For example, a construct can have a spacer (SGSG (SEQ ID NO: 86) or GSG (SEQ ID NO: 85)) and furin linker (R-A-K-R (SEQ ID NO: 81)) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described in SEQ ID NOs: 72-86 or 197-199.

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioester.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 197). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers does not have rigid structures in some cases, they can serve as a passive linker to keep a distance between functional domains. The length of a flexible linkers can be adjusted to allow for proper folding or to achieve optimal biological activity of the fusion proteins.

A linker described herein can further include a rigid linker in some cases. A rigid linker can be utilized to maintain a fixed distance between domains of a polypeptide. Examples of rigid linkers can be: Alpha helix-forming linkers, Pro-rich sequence, (XP)n, X-Pro backbone, A(EAAAK)nA (n=2-5) (SEQ ID NO: 202), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g., cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioester. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO: 82. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO: 173. In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO: 173.

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 75. In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO: 167. In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 167.

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 76. In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprises the sequence of SEQ ID NO: 168. In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 168.

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 77. In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 169.

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a sequence of SEQ ID NO: 72 to SEQ ID NO: 86 or SEQ ID NO: 197 to SEQ ID NO: 199. In other cases, multiple linkers can be used in a vector. For example, genes of interest, and one or more gene switch polypeptide sequences described herein can be separated by at least two linkers. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro)(P), phenylalanine (Phe)(F), methionine (Met)(M), tryptophan (Trp)(W). In some cases, a polypeptide linker can also include one or more GS linker sequences, for instance (GS)n (SEQ ID NO: 203), (SG)n (SEQ ID NO: 204), (GSG)n (SEQ ID NO: 198) and (SGSG)n (SEQ ID NO: 199) wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ (SEQ ID NO: 205); and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ (SEQ ID NO: 205).

In other instances, the linker can be an IRES. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

Exemplary IRES sequences can be found in SEQ ID NO: 192 and 193. In certain cases, a polynucleotide encoding 2×Rbm3 IRES a can be or can be about at least 45%, 50%, 55%, 60%, 65%, 70%, 75%, 80%, 85%, 90%, 95%, 97%, 98%, 99% or 100% identical to SEQ ID NO: 192. In certain cases, a polynucleotide encoding EMCV IRES a can be or can be about at least 45%, 50%, 55%, 60%, 65%, 70%, 75%, 80%, 85%, 90%, 95%, 97%, 98%, 99% or 100% identical to SEQ ID NO: 193.

In some embodiments are systems for modulating the expression of a CAR and a cytokine in a host cell, comprising a first gene expression cassette comprising a first polynucleotide encoding a first polypeptide; a second gene expression cassette comprising a second polynucleotide encoding a second polypeptide; and a ligand; wherein the first and second polypeptides comprise one or more of: (i) a transactivation domain; (ii) a DNA-binding domain; and (iii) a ligand binding domain; (iv) CAR; (vi) cytokine, and/or (vii) cell tag such that upon contacting the host cell with the first gene expression cassette and the second gene expression cassette in the presence of the ligand, the CAR and the cytokine are expressed in the host cell. In some cases, the CAR is a MUC16 CAR and the cytokine is mbIL-15. In some cases, MUC16CAR, mbIL-15 are co-expressed with one cell tag. In some cases, MUC16 CAR and mbIL-15 are each co-expressed with a cell tag. In other cases, MUC16 CAR is expressed with a cell tag and mbIL-15 is expressed with a second cell tag. Exemplary configurations of gene expression cassettes are depicted in FIGS. 1 and 2. In other cases, the CAR is a MUC16 CAR and the cytokine is IL-12. In some cases, MUC16CAR, IL-12 are co-expressed with one cell tag. In some cases, MUC16 CAR and IL-12 are each co-expressed with a cell tag. In other cases, MUC16 CAR is expressed with a cell tag and IL-12 is expressed with a second cell tag.

In some embodiments are systems for modulating the expression of a CAR and a cytokine in a host cell, comprising a first gene expression cassette comprising a first polynucleotide encoding a first polypeptide; a second gene expression cassette comprising a second polynucleotide encoding a second polypeptide; and a ligand; wherein the first polypeptide comprise one or more of: (i) a transactivation domain; (ii) a DNA-binding domain; and (iii) a ligand binding domain and the second polypeptide comprise one or more of (i) CAR; (ii) cytokine, and/or (iii) cell tag such that upon contacting the host cell with the first gene expression cassette and the second gene expression cassette in the presence of the ligand, the CAR and/or the cytokine are expressed in the host cell. In some cases, the CAR is a MUC16 CAR and the cytokine is mbIL-15. In some cases, MUC16 CAR and mbIL-15 are each co-expressed with a cell tag. In other cases, MUC16 CAR is expressed with a first cell tag and mbIL-15 is expressed with a second cell tag.

Exemplary configurations of systems for modulating the expression of a MUC16 CAR and a cytokine in a host cell are depicted in FIGS. 1-2. In some embodiments, the gene expression cassettes are introduced into an immune effector cell using viral or viral based systems. Examples of non-viral based delivery systems as described herein include SB11 transposon system, the SB100X transposon system, the SB110 transposon system, the piggyBac transposon system. In one embodiment, the gene expression cassettes are introduced into an immune effector cell in one or more Sleeping Beauty transposons.

Exemplary embodiments of gene expression cassettes that encode for constitutive expression of MUC16 CAR, cytokine (such as mbIL-15 or IL-12) and cell tag are depicted in FIG. 1. FIG. 1a-b depict exemplary gene expression cassette designs for MUC16 CAR, mbIL-15 and cell tag in various configurations. In this embodiment, the gene expression cassette is introduced into an immune effector cell in one Sleeping Beauty transposon. FIG. 1c-d depict gene expression cassette configurations where MUC16 CAR can be in one gene expression cassette and mbIL-15 and cell tag are in a second gene expression cassette. In this embodiment, the gene expression cassette is introduced into an immune effector cell in one or more Sleeping Beauty transposons.

Exemplary embodiments of gene expression cassettes that encode for inducible expression of MUC16 CAR, cytokine (such as mbIL-15) and/or cell tag are depicted in FIG. 2. FIG. 2a-d depict exemplary gene expression cassette designs for MUC16 CAR, mbIL-15 and cell tag in various configurations under the control of an inducible promoter. FIG. 2e is an exemplary embodiment of a gene expression cassette encoding gene-switch polypeptides as described herein. In this embodiment, the gene expression cassette(s) is introduced into an immune effector cell in one or more Sleeping Beauty transposons.

Ligands

In some embodiments, a ligand used for inducible gene switch regulation can be selected from any of, but without limitation to, following: N-[(1R)-1-(1,1-dimethylethyl)butyl]-N'-(2-ethyl-3-methoxybenzoyl)-3,5-dimethylbenzohydrazide (also referred to as veledimex), (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroyl-hydrazines such as those disclosed in U.S. Pat. No. 5,225, 443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxy-cholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Di-methyl-benzoic acid N-(1-tert-butyl-butyl)-N'-(2-ethyl-3-methoxy-benzoyl)-hydrazide), and RG-115830 (3,5-Dimethyl-b enzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Non-Viral Based Delivery Systems

A nucleic acid encoding a CAR described invention can also be introduced into immune effector cells using non-viral based delivery systems, such as the "Sleeping Beauty (SB) Transposon System," which refers a synthetic DNA transposon system for introducing DNA sequences into the chromosomes of vertebrates. An exemplary SB transposon system is described for example, in U.S. Pat. Nos. 6,489,458 and 8,227,432, and is illustrated in FIG. 3. The Sleeping Beauty transposon system comprises a Sleeping Beauty (SB) transposase and SB transposon(s). As used herein, the Sleeping Beauty transposon system can comprise Sleeping Beauty transposase polypeptides as well as derivatives, variants and/or fragments that retain activity, and Sleeping Beauty transposon polynucleotides, derivatives, variants, and/or fragments that retain activity. In certain embodiments, the Sleeping Beauty transposase is provided as an mRNA. In some aspects, the mRNA encodes for a SB10, SB11, SB100x or SB110 transposase. In some aspects, the mRNA comprises a cap and a poly-A tail.

DNA transposons translocate from one DNA site to another in a simple, cut-and-paste manner. Transposition is a precise process in which a defined DNA segment is excised from one DNA molecule and moved to another site in the same or different DNA molecule or genome. As with other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy. Briefly, the Sleeping Beauty (SB) system (Hackett et al., Mol Ther 18:674-83, (2010)) was adapted to genetically modify the immune effector cells (Cooper et al., Blood 105:1622-31, (2005)). In one embodiment, this involved two steps: (i) the electro-transfer of DNA plasmids expressing a SB transposon [i.e., chimeric antigen receptor (CAR) to redirect T-cell specificity (Jin et al., Gene Ther 18:849-56, (2011); Kebriaei et al., Hum Gene Ther 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In another, embodiment, the second step (ii) is eliminated and the genetically modified T cells are cryopreserved or immediately infused into a patient.

In one embodiment, the SB transposon systems are described for example in Hudecek et al., Critical Reviews in Biochemistry and Molecular Biology, 52:4, 355-380 (2017), Singh et al., Cancer Res (8):68 (2008). Apr. 15, 2008 and Maiti et al., J Immunother. 36(2): 112-123 (2013), incorporated herein by reference in their entireties.

In certain embodiments, a MUC16 CAR and mbIL-15 are encoded in a transposon DNA plasmid vector, and the SB transposase is encoded in a separate vector. In certain embodiments, a MUC16 CAR described herein is encoded in a transposon DNA plasmid vector, mb-IL15 is encoded in a second transposon DNA plasmid vector, and the SB transposase is encoded in a third DNA plasmid vector. In some embodiment, the CAR is encoded with a kill tag, for instance, HER1t, HER1t1, CD20 or CD20t-1. In some embodiments, the mbIL-15 is encoded with a kill tag, for instance, HERR, HER1t1, CD20 or CD20t-1.

In embodiments, the MUC16 CAR can be co-expressed with mbIL-15 and the cell tag from a transposon DNA plasmid vector. In further embodiments, the MUC16 CAR can be under the control of an inducible promoter. In another embodiment, the mbIL-15 can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In certain embodiments, the MUC16 CAR, mbIL-15 and kill tag can be configured in one, two or more transposons. Exemplary configurations of the MUC16 CAR or mbIL15 under the control of an inducible promoter are depicted in FIG. 2.

In embodiments, the MUC16 CARs and other genetic elements are delivered to a cell using the SB11 transposon system, the SB100X transposon system, the SB110 transposon system, the piggyBac transposon system (see, e.g., U.S. Pat. No. 9,228,180, Wilson et al, "PiggyBac Transposon-mediated Gene Transfer in Human Cells," Molecular Therapy 15:139-145 (2007), incorporated herein by reference in its entirety) and/or the piggyBat transposon system (see, e.g., Mitra et al., "Functional characterization of piggyBat from the bat *Myotis lucifugus* unveils an active mammalian DNA transposon," Proc. Natl. Acad. Sci USA 110:234-239 (2013). Additional transposases and transposon systems are provided in U.S. Pat. Nos. 7,148,203; 8,227, 432; U.S. Patent Publn. No. 2011/0117072; Mates et al., *Nat Genet,* 41(6):753-61 (2009). doi: 10.1038/ng.343. Epub 2009 May 3, *Gene Ther.,* 18(9):849-56 (2011). doi: 10.1038/gt.2011.40. Epub 2011 Mar. 31 and in Ivics et al., *Cell.* 91(4):501-10, (1997), each of which is incorporated herein by reference in their entirety.

In other embodiments, the MUC16 CAR and other genetic elements such as cytokines, mbIL-15 and/or HER1t/

HER1t1/CD20/CD20t-1 tag, can be integrated into the immune effector cell's DNA through a recombinase and integrating expression vectors. Such vectors can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

A recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (λ) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a φRv1 recombinase. Examples of serine recombinases are described in detail in U.S. Pat. No. 9,034,652, hereby incorporated by reference in its entirety.

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP)

or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ϕRv1 recombinase, and a Bxb1 recombinase. In one embodiment the recombination results in integration.

Regardless of the method used to introduce exogenous nucleic acids into a host cell, in order to confirm the presence of the recombinant DNA sequence in the host cell, a variety of assays can be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify peptides or proteins or nucleic acids falling within the scope of the invention.

Viral Based Delivery Systems

Also provided herein are viral-based delivery systems, in which a nucleic acid of the present invention is inserted. Representative viral expression vectors include, but are not limited to, the adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)) and retroviral vectors (e.g., the pFB-ERV plus pCFB-EGSH), herpes viruses. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In embodiments, provided is a lentiviral vector comprising a backbone and a nucleic acid sequence encoding a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; (e) a CD3 zeta signaling domain. Optionally, the vector further comprises a nucleic acid encoding a truncated epidermal growth factor receptor (HER1t or HER1t1), CD20t-1 or a full length CD20.

In some cases is provided a vector comprising a backbone and a nucleic acid sequence encoding (1) a truncated epidermal growth factor receptor for instance HER1t or HERt-1 or a functional variant thereof; and (2) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain.

In some cases is provided a vector comprising a backbone and a nucleic acid sequence encoding (1) full length CD20, truncated CD20 or functional variants thereof, and (2) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain.

In embodiments, the nucleic acid encoding the MUC16 specific CAR is cloned into a vector comprising lentiviral backbone components. Exemplary backbone components include, but are not limited to, pFUGW, and pSMPUW. The pFUGW lentiviral vector backbone is a self-inactivating (SIN) lentiviral vector backbone and has unnecessary HIV-1 viral sequences removed resulting in reduced potential for the development of neoplasia, harmful mutations, and regeneration of infectious particles. In embodiments, the vector encoding the MUC16 CAR also encodes mbIL-15 in a single construct. In embodiments, the MUC16 CAR and mbIL-15 are encoded on two separate lentiviral vectors. In some embodiments, the mbIL-15 is expressed with a truncated epidermal growth factor receptor tag. In embodiments, the MUC16 CAR can be co-expressed with mbIL-15 and the cell tag from a single lentiviral vector. In further embodiments, the MUC16 CAR can be under the control of an inducible promoter. In another embodiment, the mbIL-15 can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEO-SWITCH® gene switch.

In one embodiment, a MUC16 CAR described herein comprises anti-MUC16 scFv, human CD8 hinge and transmembrane domain, and human 4-1BB and CD3zeta signaling domains. In another embodiment, the MUC16 CAR of the invention comprises anti-MUC16 scFv, human CD8 hinge and transmembrane domain, human 4-1BB and CD3zeta signaling domains and optionally, a truncated epidermal growth factor receptor (HER1t or HER1t-1) tag. Other suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising a CAR described herein comprises hEF1a1 functional variants.

However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention as previously described. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In order to assess the expression of a CAR described herein or portions thereof, the expression vector to be introduced into a cell can also contain either a selectable marker gene or a reporter gene or both to facilitate identification and selection of expressing cells from the population of cells sought to be transfected or infected through viral vectors or non-viral vectors. In other aspects, the selectable marker can be carried on a separate piece of DNA and used in a co-transfection procedure. Both selectable markers and reporter genes can be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t or HER1t-1) tag can be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

In embodiments, a viral vector described herein can comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are well known. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell, for instance an immune effector cell, include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection. In some embodiments, a method for introduction of a polynucleotide into a host cell is electroporation.

Biological methods for introducing a polynucleotide of interest into a host cell, for instance an immune effector cell, include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. Lipid formulations can be used for the introduction of the nucleic acids into a host cell (in vitro, ex vivo, or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

Cells Comprising MUC16 CARs and Vectors

Provided herein are engineered cells expressing a CAR described herein. In certain embodiments, an engineered cell described herein is an immune effector cell. In embodiments, provided herein is an immune effector cell comprising a vector comprising a backbone and a nucleic acid sequence encoding (1) a truncated epidermal growth factor receptor (HER1t or HER1t1) and (2) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and e) a CD3 zeta signaling domain.

In certain embodiments is an immune effector cell comprising a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; e) a CD3 zeta signaling domain; and (f) a truncated epidermal growth factor receptor (HER1t or HER1t1).

In embodiments, provided herein is an immune effector cell comprising (1) a cell tag for use as a kill switch, selection marker, a biomarker, or a combination thereof, and (2) a chimeric antigen receptor (CAR), wherein the CAR comprises (a) a MUC16 antigen binding domain; (b) a stalk domain; (c) a transmembrane domain; (d) a costimulatory signaling domain comprising 4-1BB or CD28, or both; and (e) a CD3 zeta signaling domain. In embodiments, the cell tag is HERR, HER1t1, CD20t-1 or CD20.

In embodiments, an immune effector cell is a T cell, a Natural Killer (NK) cell, a cytotoxic T lymphocyte (CTL), and a regulatory T cell. In embodiments, the cell exhibits an anti-tumor activity when the MUC16 antigen binding domain binds to MUC16.

Modified Immune Effector Cells

Provided are immune effector cells modified to express one or more heterologous genes or polypeptides described herein. Provided are immune effector cells modified to express a MUC16 CAR described herein and at least one of a HER1t, HER1t1, CD20 and CD20t-1 tag. In some cases is provided an immune effector cell modified to express MUC16 CAR, mbIL-15 and at least one of a HER1t, HER1t1, CD20 and CD20t-1 tag disclosed herein.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

In some embodiments, modified immune effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells can be either CD4+ or CD8+. Memory T cells can express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Modified Immune Effector Cell Doses

In some embodiments, an amount of modified immune effector cells is administered to a subject in need thereof and the amount is determined based on the efficacy and the potential of inducing a cytokine-associated toxicity. In some cases, an amount of modified immune effector cells comprises about $10^2$ to about $10^9$ modified immune effector cells/kg. In some cases, an amount of modified immune effector cells comprises about $10^3$ to about $10^9$ modified immune effector cells/kg. In some cases, an amount of modified immune effector cells comprises about $10^4$ to about $10^9$ modified immune effector cells/kg. In some cases, an amount of modified immune effector cells comprises about $10^5$ to about $10^9$ modified immune effector cells/kg. In some cases, an amount of modified immune effector cells comprises about $10^5$ to about $10^8$ modified immune effector cells/kg. In some cases, an amount of modified immune effector cells comprises about $10^5$ to about $10^7$ modified immune effector cells/kg. In some cases, an amount of modified immune effector cells comprises about $10^6$ to about $10^9$ modified immune effector cells/kg. In some cases, an amount of modified immune effector cells comprises about $10^6$ to about $10^8$ modified immune effector cells/kg. In some cases, an amount of modified immune effector cells comprises about $10^7$ to about $10^9$ modified immune effector cells/kg. In some cases, an amount of modified immune effector cells comprises about $10^5$ to about $10^6$ modified immune effector cells/kg. In some cases, an amount of modified immune effector cells comprises about $10^6$ to about $10^7$ modified immune effector cells/kg. In some cases, an amount of modified immune effector cells comprises about $10^7$ to about $10^8$ modified immune effector cells/kg. In some cases, an amount of modified immune effector cells comprises about $10^8$ to about $10^9$ modified immune effector cells/kg. In some instances, an amount of modified immune effector cells comprises about $10^9$ modified immune effector cells/kg. In some instances, an amount of modified immune effector cells comprises about $10^8$ modified immune effector cells/kg. In some instances, an amount of modified immune effector cells comprises about $10^7$ modified immune effector cells/kg. In some instances, an amount of modified immune effector cells comprises about $10^6$ modified immune effector cells/kg. In some instances, an amount of modified immune effector cells comprises about $10^5$ modified immune effector cells/kg.

In some embodiments, are CAR-T cells which are MUC16-specific CAR-T cells. In some cases, an amount of MUC16-specific CAR-T cells comprises about $10^2$ to about $10^9$ CAR-T cells/kg. In some cases, an amount of MUC16-specific CAR-T cells comprises about $10^3$ to about $10^9$ CAR-T cells/kg. In some cases, an amount of MUC16-specific CAR-T cells comprises about $10^4$ to about $10^9$ CAR-T cells/kg. In some cases, an amount of MUC16-specific CAR-T cells comprises about $10^5$ to about $10^9$ CAR-T cells/kg. In some cases, an amount of MUC16-specific CAR-T cells comprises about $10^5$ to about $10^8$ CAR-T cells/kg. In some cases, an amount of MUC16-specific CAR-T cells comprises about $10^5$ to about $10^7$ CAR-T cells/kg. In some cases, an amount of MUC16-specific CAR-T cells comprises about $10^6$ to about $10^9$ CAR-T cells/kg. In some cases, an amount of MUC16-specific CAR-T cells comprises about $10^6$ to about $10^8$ CAR-T cells/kg. In some cases, an amount of MUC16-specific CAR-T cells comprises about $10^7$ to about $10^9$ CAR-T cells/kg. In some cases, an amount of MUC16-specific CAR-T cells comprises about $10^5$ to about $10^6$ CAR-T cells/kg. In some cases, an amount of MUC16-specific CAR-T cells comprises about $10^6$ to about $10^7$ CAR-T cells/kg. In some cases, an amount of MUC16-specific CAR-T cells comprises about $10^7$ to about $10^8$ CAR-T cells/kg. In some cases, an amount of MUC16-specific CAR-T cells comprises about $10^8$ to about $10^9$ CAR-T cells/kg. In some instances, an amount of MUC16-specific CAR-T cells comprises about $10^9$ CAR-T cells/kg. In some instances, an amount of MUC16-specific CAR-T cells comprises about $10^8$ CAR-T cells/kg. In some instances, an amount of MUC16-specific CAR-T cells comprises about $10^7$ CAR-T cells/kg. In some instances, an amount of MUC16-specific CAR-T cells comprises about $10^6$ CAR-T cells/kg. In some instances, an amount of MUC16-specific CAR-T cells comprises about $10^5$ CAR-T cells/kg. In some instances, an amount of MUC16-specific CAR-T cells comprises about $10^4$ CAR-T cells/kg. In some instances, an amount of MUC16-specific CAR-T cells comprises about $10^3$ CAR-T cells/kg. In some instances, an amount of MUC16-specific CAR-T cells comprises about $10^2$ CAR-T cells/kg.

Immune Effector Cell Sources

In certain aspects, the embodiments described herein include methods of making and/or expanding the antigen-specific redirected immune effector cells (e.g., T-cells, Tregs, NK-cell or NK T-cells) that comprises transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, iPS cell, T cell differentiated from iPS cell, immune effector cell or a precursor of these cells.

Sources of immune effector cells can include both allogeneic and autologous sources. In some cases immune effector cells can be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. In one aspect, the immune effector cells are Pan T cells. Following transfection or transduction (e.g., with a CAR expression construct), the cells can be immediately infused or can be cryopreserved. In certain aspects, following transfection or transduction, the cells can be preserved in a cytokine bath that can include IL-2 and/or IL-21 until ready for infusion. In certain aspects, following transfection, the cells can be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells can be expanded by stimulation with IL-2, or other cytokines that bind the common gamma-chain (e.g., IL-7, IL-12, IL-15, IL-21, and others). The recombinant T cells can be expanded by stimulation with artificial antigen presenting cells. The recombinant T cells can be expanded on artificial antigen presenting cell or with an antibody, such as OKT3, which cross links CD3 on the T cell surface. Subsets of the recombinant T cells can be further selected with the use of magnetic bead based isolation methods and/or fluorescence activated cell sorting technology and further cultured with the AaPCs. In a further aspect, the genetically modified cells can be cryopreserved.

T cells can also be obtained from a number of sources, including bone marrow, lymph node tissue, cord blood, thymus tissue, tissue from a site of infection, ascites, pleural effusion, spleen tissue, and tumors. In certain embodiments of the present invention, any number of T cell lines available in the art, can be used. In certain embodiments of the present invention, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. In another embodiment, CD14+ cells are depleted from the T-cell population. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it can be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc.). Such populations of cells can have therapeutic value and would be desirable to obtain. For example, using high concentration of cells allows more efficient selection of $CD8^+$ T cells that normally have weaker CD28 expression.

In a related embodiment, it can be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells can be incubated on a rotator for varying lengths of time at varying speeds at either 2-10° C. or at room temperature.

T cells for stimulation can also be frozen after a washing step. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing can be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also provided in certain embodiments is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells can be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, (1991); Henderson et al., *Immun* 73:316-321, (1991); Bierer et al., *Curr. Opin. Immun* 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells can be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after engineering of the T cells to express a CAR described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells described herein are expanded by contact with a surface having attached thereto an agent that stimulates a CD3/TCR complex associated signal and a ligand that stimulates a co-stimulatory molecule on the surface of the T cells. In particular, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, (1998); Haanen et al., *J. Exp. Med.* 190(9):13191328, (1999); Garland et al., *J. Immunol Meth.* 227(1-2):53-63, (1999)).

In certain embodiments, the primary stimulatory signal and the co-stimulatory signal for the T cell can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between can be used to stimulate T cells or other target cells. As those of ordinary skill in the art can readily appreciate, the ratio of particles to cells can depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios can be suitable for use in the present invention. In particular, ratios will vary depending on particle size and on cell size and type.

In further embodiments described herein, the immune effector cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins can be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1, or MACS® Micro-Beads from Miltenyi Biotec) are combined in a buffer, for example, PBS (without divalent cations such as, calcium and magnesium). Again, those of ordinary skill in the art can readily appreciate any cell concentration can be used. For example, the target cell can be very rare in the sample and comprise only 0.01% of the sample or the entire sample (i.e., 100%) can comprise the target cell of interest. Accordingly, any cell number is within the context of the present invention. In certain embodiments, it can be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells. Such populations of cells can have therapeutic value and would be desirable to obtain in certain embodiments. For example, using high concentration of cells allows more efficient selection of CD8+ T cells that normally have weaker CD28 expression.

In one embodiment described herein, the mixture can be cultured for several hours (about 3 hours) to about 14 days or any hourly integer value in between. In another embodiment, the mixture can be cultured for 21 days. In one embodiment of the invention the beads and the T cells are cultured together for about eight days. In another embodiment, the beads and T cells are cultured together for 2-3 days. Several cycles of stimulation can also be desired such that culture time of T cells can be 60 days or more. Conditions appropriate for T cell culture include an appropriate media (e.g., Minimal Essential Media or RPMI Media 1640 or, X-vivo 15, (Lonza)) that can contain factors necessary for proliferation and viability, including serum (e.g., fetal bovine or human serum), interleukin-2 (IL-2), insulin, IFN-$\gamma$., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times can exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells can be advantageous. Similarly, if an antigen-specific subset of $T_C$ cells has been isolated it can be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs can be genetically modified K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference. In yet a further aspect of the embodiments, culturing the genetically modified CAR cells comprises culturing the genetically modified CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs can comprise additional molecules that activate or co-stimulate T-cells in some cases. The additional molecules can, in some cases, comprise membrane-bound Cy cytokines. In yet still further aspects, the AaPCs are inactivated or irradiated, or have been tested for and confirmed to be free of infectious material. In still further aspects, culturing the genetically modified CAR cells in the presence of AaPCs comprises culturing the genetically modified CAR cells in a medium comprising soluble cytokines, such as IL-15, IL-21 and/or IL-2. The cells can be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs can express CD137L. In some aspects, the AaPCs can further express the antigen that is targeted by the CAR cell, for example MUC16 (full length, truncate or any variant thereof. In other aspects, the AaPCs can further express CD64, CD86, or mIL15. In certain aspects, the AaPCs can express at least one anti-CD3 antibody clone, such as, for example, OKT3 and/or UCHT1. In one aspect, the AaPCs can be inactivated (e.g., irradiated). In one aspect, the AaPCs can have been tested for and confirmed to be free of infectious material. Methods for producing such AaPCs are known in the art. In one aspect, culturing the CAR-modified T cell population with AaPCs can comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step can further comprise culturing with an aminobisphosphonate (e.g., zoledronic acid).

In one aspect, the population of genetically modified CAR cells is immediately infused into a subject or cryopreserved. In another aspect, the population of genetically modified CAR cells is placed in a cytokine bath prior to infusion into a subject. In a further aspect, the population of genetically modified CAR cells is cultured and/or stimulated for no more than 1, 2, 3, 4, 5, 6, 7, 14, 21, 28, 35, 42 days, 49, 56, 63 or 70 days. In an embodiment, a stimulation includes the co-culture of the genetically modified CAR T cells with AaPCs to promote the growth of CAR positive T cells. In another aspect, the population of genetically modified CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the genetically modified cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching can comprise fluorescence-activated cell sorting (FACS) to sort for CAR-expressing cells. In a further aspect, the sorting for CAR-expressing cells comprises use of a CAR-binding antibody. The enriching can also comprise depletion of CD56+ cells. In yet still a further aspect of the embodiment, the method further comprises cryopreserving a sample of the population of genetically modified CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems can also comprise at least one exogenous assisting molecule. Any suitable number and combination of assisting molecules can be employed. The assisting molecule can be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules can include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a Drosophila cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs can be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs can be frozen and stored for an extended period of time prior to thawing. Frozen AaPCs can also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, can be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells can be used, for example, as described above, to propagate immune effector cells ex vivo. In further aspects, engineered APCs can, themselves be administered to a patient and thereby stimulate expansion of immune effector cells in vivo. Engineered APCs of the embodiments can, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to cell(s) that comprises at least a first transgene, wherein the first transgene encodes a HLA. Such engineered APCs can further comprise a second transgene for expression of an antigen, such that the antigen is presented at the surface of the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments can further comprise at least a third transgene encoding co-stimulatory molecule. The co-stimulatory molecule can be a co-stimulatory cytokine that can be a membrane-bound Cγ cytokine. In certain aspects, the co-stimulatory cytokine is IL-15, such as membrane-bound IL-15. In some further aspects, an engineered APC can comprise an edited (or deleted) gene. For example, an inhibitory gene, such as PD-1, LIM-3, CTLA-4 or a TCR, can be edited to reduce or eliminate expression of the gene. An engineered APC of the embodiments can further comprise a transgene encoding any target antigen of interest.

Point-of-Care

In one embodiment of the present disclosure, the immune effector cells described herein are modified at a point-of-care site. In some cases, modified immune effector cells are also referred to as engineered T cells. In some cases, the point-of-care site is at a hospital or at a facility (e.g., a medical facility) near a subject in need of treatment. The subject undergoes apheresis and peripheral blood mononuclear cells (PBMCs) or a sub population of PBMC can be enriched for example, by elutriation or Ficoll separation. Enriched PBMC or a subpopulation of PBMC can be cryopreserved in any appropriate cryopreservation solution prior to further processing. In one instance, the elutriation process is performed using a buffer solution containing human serum albumin. Immune effector cells, such as T cells can be isolated by selection methods described herein. In one instance, the selection method for T cells includes beads specific for CD3 or beads specific for CD4 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours. 72 hours or 96 hours ahead of infusion. The thawed cells can be placed in cell culture buffer, for example in cell culture buffer (e.g. RPMI) supplemented with fetal bovine serum (FBS) or human serum AB or placed in a buffer that includes cytokines such as IL-2 and IL-21, prior to modification. In another aspect, the harvested immune effector cells can be modified immediately without the need for cryopreservation.

In some cases, the immune effector cells are modified by engineering/introducing a chimeric receptor, one or more cell tag(s), and/or cytokine(s) into the immune effector cells and then rapidly infused into a subject. In some cases, the sources of immune effector cells can include both allogeneic and autologous sources. In one case, the immune effector cells can be T cells or NK cells. In one case, the chimeric receptor can be a MUC16 CAR. In another case, the cytokine can be mbIL-15. In one case, the mbIL-15 is of SEQ ID NO: 69, or variant or fragment thereof. In yet another case, expression of mbIL-15 is modulated by ligand inducible gene-switch expression systems described herein. For example, a ligand such as veledimex can be delivered to the subject to modulate the expression of mbIL-15. In another case, the cytokine can be IL-12. In yet another case, expression of IL-12 is modulated by ligand inducible gene-switch expression systems described herein. For example, a ligand such as veledimex can be delivered to the subject to modulate the expression of IL-12.

In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags as described herein.

In some embodiments, such immune effectors cells are modified by the constructs as described in FIGS. 1-2 through electroporation. In one instance, electroporation is performed with electroporators such as Lonza's Nucleofector™ electroporators. In other embodiments, the vector comprising the above-mentioned constructs is a non-viral or viral vector. In one case, the non-viral vector includes a Sleeping Beauty transposon-transposase system. In one instance, the immune effector cells are electroporated using a specific sequence. For example, the immune effector cells can be electroporated with one transposon followed by the DNA encoding the transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells can be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In certain cases, the modified immune effector cells are placed in a buffer that includes IL-2 and IL21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in saline buffer in preparation for infusion into the subject.

In one instance, the subject has been lymphodepleted prior to infusion. In other instances, lymphodepletion is not required and the modified immune effector cells are rapidly infused into the subject. Exemplary lymphodepletion regimens are listed in Tables 2 and 3 below:

TABLE 2

Regimen 1

| | |
|---|---|
| D-6 | Admit/IV Hydration |
| D-5 | Fludarabine 25 mg/m2, Cyclophosphamide 250 mg/m2 |
| D-4 | Fludarabine 25 mg/m2, Cyclophosphamide 250 mg/m2 |
| D-3 | Fludarabine 25 mg/m2 IV, Cyclophosphamide 250 mg/m2 |
| D-2 | REST |
| D-1 | REST |
| D0 | T-cell infusion |

TABLE 3

Regimen 2

| | |
|---|---|
| D-6 | Admit/IV Hydration |
| D-5 | Fludarabine 30 mg/m2, Cyclophosphamide 500 mg/m2 |
| D-4 | Fludarabine 30 mg/m2, Cyclophosphamide 500 mg/m2 |
| D-3 | Fludarabine 30 mg/m2 IV, Cyclophosphamide 500 mg/m2 |
| D-2 | REST |
| D-1 | REST |
| D0 | T-cell infusion |

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepletion protocol can include a shortened period of lymphodepletion, for example 1 day or 2 days.

In one embodiment, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing a chimeric receptor and a cytokine into the immune effector cells and then infused in 0 days, <1 day, <2 days, <3 days, <4 days, <5 days, <6 days or <7 days into a subject.

In some embodiments, an amount of modified effector cells is administered to a subject in need thereof and the amount is determined based on the efficacy and the potential of inducing a cytokine-associated toxicity. In another embodiment, the modified effector cells are CAR$^+$ and CD3$^+$ cells. In some cases, an amount of modified effector cells comprises about $10^4$ to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises >$10^4$ but ≤$10^5$ modified effector cells/kg. In some cases, an amount of modified effector cells comprises >$10^5$ but ≤$10^6$ modified effector cells/kg. In some cases, an amount of modified effector cells comprises >$10^6$ but ≤$10^7$ modified effector cells/kg.

In one embodiment, the modified immune effector cells are targeted to the cancer via regional delivery directly to the tumor tissue. For example, in ovarian cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In another embodiment, a catheter can be placed at the tumor or metastasis site for further administration of 1, 2, 3, 4, 5, 6, 7, 8, 9, 10 doses of modified immune effector cells. In some cases, doses of modified effector cells can comprise about $10^2$ to about $10^9$ modified effector cells/kg. In cases where toxicity is observed, doses of modified effector cells can comprise about $10^2$ to about $10^5$ modified effector cells/kg. In some cases, doses of modified effector cells can start at about $10^2$ modified effector cells/kg and subsequent doses can be increased to about: $10^4$, $10^5$, $10^6$, $10^7$, $10^8$ or $10^9$ modified effector cells/kg.

In other embodiments, a method of stimulating the proliferation and/or survival of engineered cells comprises obtaining a sample of cells from a subject, and transfecting cells of the sample of cells with one or more polynucleotides that comprise one or more transposons. In one embodiment, the transposons encode a chimeric antigen receptor (CAR), a cytokine, one or more cell tags, and a transposase effective to integrate said one or more polynucleotides into the genome of said cells, to provide a population of engineered cells. In an embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo propagation of engineered cells comprises obtaining a sample of cells from a subject, and transfecting cells of the sample of cells with one or more polynucleotides that comprise one or more transposons. In one embodiment, the transposons encode a chimeric antigen receptor (CAR), a cytokine, one or more cell tags, and a transposase effective to integrate said one or more polynucleotides into the genome of said cells, to provide a population of engineered cells. In an embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons. In some cases, one or more transposons encode a chimeric antigen receptor (CAR), a cytokine, one or more cell tags, and a transposase effective to integrate the DNA into the genome of said cells, to provide a population of engineered cells. In some cases, one or more transposons encode a chimeric antigen receptor (CAR), a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

In another embodiment, a method of treating a subject with a solid tumor comprises obtaining a sample of cells from a subject, transfecting cells of the sample with one or more polynucleotides that comprise one or more transposons, and administering the population of engineered cells to the subject. In one instance, lymphodepletion is not required prior to administration of the engineered cells to a subject. In some cases, the one or more transposons encode a chimeric antigen receptor (CAR), a cytokine, one or more cell tags, and a transposase effective to integrate the DNA into the genome of the cells. In some cases, the one or more transposons encode a chimeric antigen receptor (CAR), a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15R or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the CAR is capable of binding at least MUC-16. In some cases, the transposase is salmonid-type Tc1-like transposase. In some cases, the transposase is SB11 or SB100x transposase. In other cases, the transposase is PiggyBac. In some cases, the cell tag comprises at least one of a HER1 truncated variant or a CD20 truncated variant.

Therapeutic Applications

In embodiments described herein, is an immune effector cell (e.g., T cell) transduced with Sleeping Beauty transposon(s) and Sleeping Beauty transposase. For example, the Sleeping Beauty transposon or transposons can include a CAR that combines an antigen recognition domain of MUC16 with a stalk domain of CD8 alpha hinge and variants thereof, an intracellular domain of CD3-zeta, CD28, 4-1BB, or any combinations thereof and the intracellular domain CD3zeta, one or more cell tags, one or more cytokines and optionally, components of the gene switch system as described herein. Therefore, in some instances, the transduced T cell can elicit a CAR-mediated T-cell response.

In embodiments described herein, is provided the use of a CAR to redirect the specificity of a primary T cell to a MUC16 surface antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with MUC16, a stalk domain, a zeta chain portion comprising for example the intracellular domain of human CD3zeta, and a costimulatory signaling region.

In one embodiment, the present disclosure includes a cellular therapy where T cells are genetically modified to express the MUC16-specific CARs of the invention and the CART cell is infused to a recipient in need thereof. The infused cell is able to kill cells overexpressing MUC16 in the recipient. Unlike antibody therapies, CART cells as described herein are able to replicate in vivo resulting in long-term persistence that can lead to sustained effect on tumor cells.

The invention additionally provides a method for detecting a disease that comprises overexpression of MUC16 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of MUC16, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

In one embodiment, the MUC16 CART cells described herein can undergo robust in vivo T cell expansion and can persist for an extended amount of time. In another embodiment, the CAR T cells described herein can evolve into specific memory T cells that can be reactivated.

The CAR-modified T cells described herein can also serve as a type of vaccine for ex vivo immunization and/or in vivo therapy in a mammal. In embodiments, the mammal is a human. With respect to ex vivo immunization, at least one of the following occurs in vitro prior to administering the immune effector cell into a mammal: i) expansion of the cells, ii) introducing a nucleic acid encoding a CAR to the cells, and/or iii) cryopreservation of the cells.

Ex vivo procedures are well known and are discussed more fully below. Briefly, cells are isolated from a mammal (for example, a human) and genetically modified (i.e., transduced or transfected in vitro) with a vector expressing a CAR disclosed herein. The CAR-modified cell can be administered to a mammalian recipient to provide a therapeutic benefit. The mammalian recipient can be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein can be utilized in the treatment and prevention of diseases that arise in individuals who are immunocompromised. In particular, the CAR-modified T cells of the invention are used in the treatment of MUC16 malignancies, such as for example, MUC16. In certain embodiments, the cells of the invention are used in the treatment of patients at risk for developing MUC16. Thus, the methods for the treatment or prevention of MUC16 comprising administering to a subject in need thereof, a therapeutically effective amount of the CAR-modified T cells of the invention. In embodiments, the cells activated and expanded as described herein can be utilized in the treatment of MUC16.

Briefly, pharmaceutical compositions described herein can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In embodiments, compositions of the present invention are formulated for intravenous administration.

Pharmaceutical compositions described herein can be administered in a manner appropriate to the disease to be treated (or prevented). The quantity and frequency of administration will be determined by such factors as the condition of the patient, and the type and severity of the patient's disease, although appropriate dosages can be determined by clinical trials.

When "an immunologically effective amount", or "therapeutic amount" is indicated, the precise amount of the compositions described herein to be administered can be determined by a physician with consideration of individual differences in age, weight, and condition of the patient (subject). It can generally be stated that a pharmaceutical composition comprising the T cells described herein can be administered at a dosage of $10^4$ to $10^9$ cells/kg body weight, $10^5$ to $10^6$ cells/kg body weight, including all integer values within those ranges. T cell compositions can also be administered multiple times at these dosages. The cells can be administered by using infusion techniques that are commonly known in immunotherapy (see, e.g., Rosenberg et al., New Eng. J. of Med. 319:1676, (1988)). The optimal dosage and treatment regime for a particular patient can readily be determined by one skilled in the art of medicine by monitoring the patient for signs of disease and adjusting the treatment accordingly.

In certain embodiments, it can be desired to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol can serve to select out certain populations of T cells. In another embodiment, it can be desired to administer activated T cells of the subject composition following lymphodepletion of the patient, either via radiation or chemotherapy.

The administration of compositions described herein can be carried out in any convenient manner, including by aerosol inhalation, injection, ingestion, transfusion, implantation or transplantation. The compositions described herein can be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the MUC16 CAR-T cell compositions of the present invention are administered by i.v. injection. The compositions of T cells can be injected directly into a lymph node, or site of primary tumor or metastasis.

The dosage of the above treatments to be administered to a patient will vary with the precise nature of the condition being treated and the recipient of the treatment. The scaling of dosages for human administration can be performed according to art-accepted practices. For example, the dose of the above treatment can be in the range of $1\times10^4$ CAR+ cells/kg to $5\times10^6$ CAR+ cells/kg. Exemplary doses can be $1\times10^2$ CAR+ cells/kg, $1\times10^3$ CAR+ cells/kg, $1\times10^4$ CAR+ cells/kg, $1\times10^5$ CAR+ cells/kg, $3\times10^5$ CAR+ cells/kg, $1\times10^6$ CAR+ cells/kg, $5\times10^6$ CAR+ cells/kg, $1\times10^7$ CAR+ cells/kg, $1\times10^8$ CAR+ cells/kg or $1\times10^9$ CAR+ cells/kg. The appropriate dose can be adjusted accordingly for an adult or a pediatric patient.

Alternatively, a typical amount of immune effector cells administered to a mammal (e.g., a human) can be, for example, in the range of one hundred, one thousand, ten thousand, one million to 100 billion cells; however, amounts below or above this exemplary range are within the scope of the invention. For example, the dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens can be useful and are within the scope of the invention. The desired dosage can be delivered by a single bolus administration of the composition, by multiple bolus administrations of the composition, or by continuous infusion administration of the composition.

The composition comprising the immune effector cells expressing the disclosed nucleic acid sequences, or a vector comprising the those nucleic acid sequences, can be administered with one or more additional therapeutic agents, which can be co-administered to the mammal. By "co-administering" is meant administering one or more additional therapeutic agents and the composition comprising the inventive host cells or the inventive vector sufficiently close in time to enhance the effect of one or more additional therapeutic agents, or vice versa. In this regard, the composition comprising the immune effector cells described herein or a vector described herein can be administered simultaneously with one or more additional therapeutic agents, or first, and the one or more additional therapeutic agents can be administered second, or vice versa. Alternatively, the composition comprising the disclosed immune effector cells or the vectors described herein and the one or more additional therapeutic agents can be administered simultaneously.

An example of a therapeutic agents that can be included in or co-administered with the composition (or included in kits) comprising the inventive host cells and/or the inventive vectors are interleukins, cytokines, interferons, adjuvants and chemotherapeutic agents. In embodiments, the additional therapeutic agents are IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, and TLR10.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits and Compositions

One aspect of the disclosure relates to kits and compositions including a first vector including coding regions that encode the MUC16-specific CARs of the invention and optionally genes included for safety reasons, e.g., HER1t or HER1t-1 and functional variants thereof, or CD20 or CD20t-1, and functional variants thereof. The kits and compositions can further include cytokines. In another aspect, the kits and compositions can include RHEOSWITCH® gene switch components. These kits and compositions can include multiple vectors each encoding different proteins or subsets of proteins. These vectors can be viral, non-viral, episomal, or integrating. In some embodiments, the vectors are transposons, e.g., Sleeping Beauty transposons.

In some embodiments, the kits and compositions include not only vectors but also cells and agents such as interleukins, cytokines, interleukins and chemotherapeutics, adjuvants, wetting agents, or emulsifying agents. In one embodiment the cells are T cells. In one embodiment the kits and composition includes IL-2. In one embodiment, the kits and compositions include IL-21. In one embodiment, the kits and compositions include Bcl-2, STAT3 or STAT5 inhibitors. In embodiments, the kit includes IL-15, or mbIL-15.

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., MUC16-specific CAR-T cells described herein), and optionally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1. Nucleofection of T Cells with Sleeping Beauty System

To generate the genetically modified T cells, cryopreserved pan T cells were thawed, washed and resuspended with pre-warmed Phenol Red free RPMI 1640 media supplemented with FBS and Glutamax (R20 media) and placed in in a humidified incubator at 37° C. with 5% CO2. Cells were counted and centrifuged and resuspended in nucleofection buffer. To generate CAR-T cells, a total of 15 μg of the transposon plasmid(s) comprising CAR constructs were combined with 5 μg of plasmid encoding SB transposase for each nucleofection cuvette containing a specified number of T cells (typically ranging from $5$-$40 \times 10^6$ per cuvette) reaction. Electroporation of the T cells was achieved using the Amaxa 2b Nucleofection device or 4D Nucleofector (Lonza, Walkersville, Md.). Following electroporation, the contents from each cuvette were transferred to pre-warmed R20 media and placed in incubator at 37° C. A sample of each T cell culture was taken for flow cytometric analysis to characterize CAR, HER1t and mbIL-15 expression where applicable at specified time point. For certain experiments, CAR$^+$ T cells were numerically expanded ex vivo for further characterization. For ex vivo numerical expansion of the generated CAR$^+$ T cells, the T cells were further co-cultured with activating and propagating cells (AaPCs). Briefly, irradiated AaPCs derived from K562 cell line engineered to express CD86, 41BBL, mbIL15 along with truncated MUC16 (MUC16t) antigen were co-cultured with CAR$^+$ T cells in complete media with IL-21 and IL-2 for subsequent weekly AaPC additions.

Flow cytometric analysis for CAR, HER1t1 and mbIL15 expression was performed at Day 1 after electroporation and prior to each AaPC stimulation using HiLyte™ Fluor 647-conjugated recombinant MUC16t-Fc fusion protein or Protein-L labelled with AF647, Phycoerythrin (PE)-conjugated Cetuximab and Fluorescein isothiocyanate (FITC) conjugated anti-IL-15 and anti-IL-15RA antibodies respectively.

Example 2. Generation of MUC16 CAR-T Cells

CAR-T cells expressing MUC16-2 CAR were generated by electroporation of SB system plasmids as described in Example 1. MUC16-2 CAR-HER1t1 T cells were generated by electroporation of a SB transposon plasmid encoding MUC16-2 CAR and HER1t1 and SB11 transposase plasmid in to human T cells. MUC16-2 CAR-mbIL15-HER1t1 T cells were generated by electroporation of (1) a SB transposon plasmid encoding MUC16-2 CAR, mbIL15 and HER1t1, and (2) a SB11 transposase plasmid in to human T cells. Expression of CAR, mbIL15 and HER1t1 was quantified using multi parameter flow cytometry at Day 1 post nucleofection.

Table 4 shows transfection efficiency as measured by % of cells expressing transgenes in different donor T cells after nucleofection of SB system plasmids using transposons expressing MUC16-2 CAR and HER1t1 genes (MUC16-2 CAR-HER1t1 T cells) or MUC16-2 CAR, mbIL15 and HER1t1 (MUC16-2 CAR-mbIL15-HER1t1 T cells) at Day 1 post nucleofection. Cells were gated on live CD3+ population.

TABLE 4

Transfection efficiency as measured by CAR expression.

| Sample # | Donor ID # | | | | | |
|---|---|---|---|---|---|---|
| | D327320 | D326782 | D128090 | D326636 | D246366 | B001000226 |
| MUC16-2 CAR-HER1t1 | 33.4 | 38.6 | 20 | 33.3 | 31.4 | 47.9 |
| MUC16-2 CAR-mbIL15-HER1t1 | 35.3 | 35.2 | 17.7 | 32.2 | 20.1 | 41.8 |

CAR-T cells expressing MUC16-3 CAR were generated by electroporation of SB system plasmids as shown in Example 1. MUC16-3 CAR-HER1t1 T cells were generated by electroporation of a SB transposon plasmid encoding MUC16-3 CAR and HERR' and SB11 transposase plasmid in to human T cells. MUC16-3 CAR-mbIL15-HER1t1 T cells were generated by electroporation of a SB transposon plasmid encoding MUC16-3 CAR, mbIL15 and HER1t1 and SB11 transposase plasmid in to human T cells. Expression of CAR, mbIL15 and HER1t1 was quantified using multi parameter flow cytometry at Day 1 post nucleofection.

Figure 4:
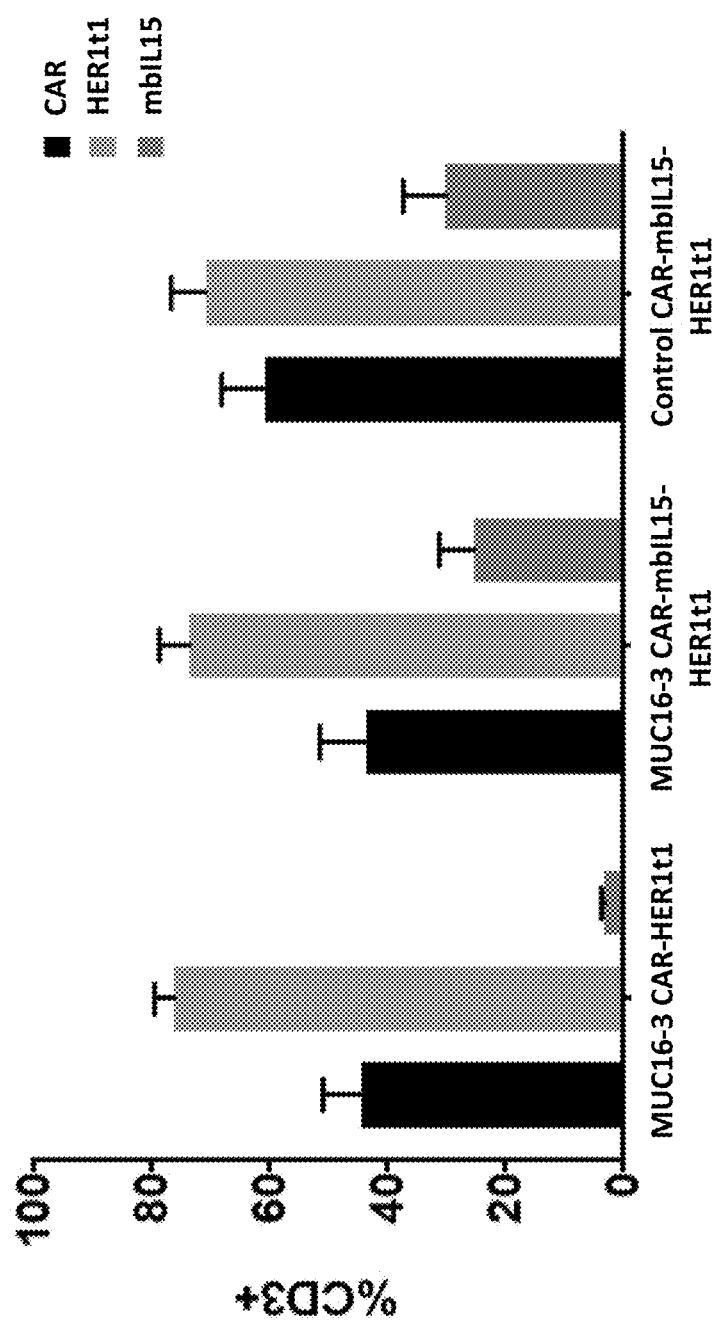
FIG. 4 shows expression of CAR, mbIL15 and HER1t1 transgenes. T cells were nucleofected with MUC16-3 CAR-HER1t1 or MUC16-3 CAR-mbIL15-HER1t1 transposon and SB transposase. Expression of transgenes was measured at Day 1 post nucleofection. Cells were gated as live CD3+ cells. Data shown is mean±SEM from three healthy donors.

As evident in FIG. 4, T cells nucleofected with either the MUC16-3-HER1t1 or the MUC16-3-mbIL15-HER1t1 plasmids express transgenes as confirmed by HER1t1 expression following overnight incubation post nucleofection. Individual data points from each donor are shown in Table 5.

TABLE 5

Transfection efficiency as measured by HER1t1 expression

| Sample # | Donor ID# | | |
|---|---|---|---|
| | D327172 | D137592 | D305620 |
| MUC16-3 CAR-HER1t1 | 47 | 41 | 43 |
| MUC16-3 CAR-mbIL15-HER1t1 | 55 | 47 | 45 |

Example 3. MUC16 CAR with Different Spacer Lengths

Figure 5:
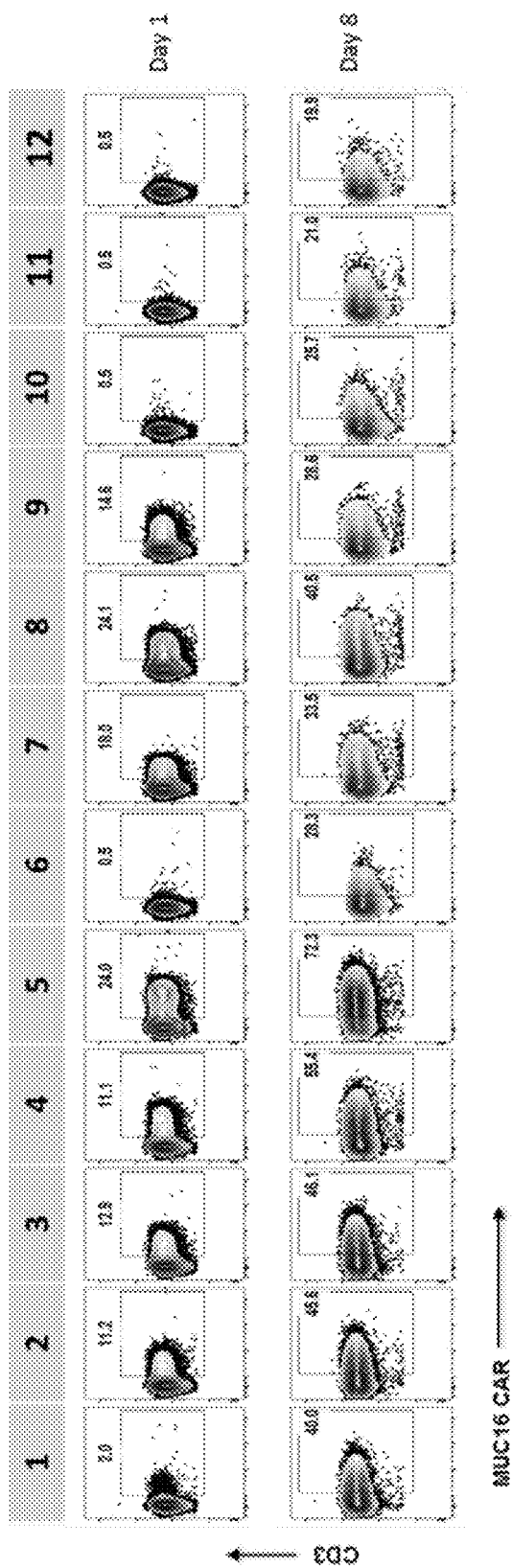
FIG. 5 shows expression of MUC16 CARs of different spacer lengths derived from CD8 alpha hinge regions in CAR-T cells. MUC16 CAR-T cells were generated by electroporation of SB system plasmids in healthy donor T cells (donor # D133098). CAR-T cells were numerically expanded ex vivo by co-culture with MUC16t expressing AaPC by once weekly stimulation. Expression of CAR was measured by multi parameter flow cytometry at Day 1 and Day 8 post nucleofection. Test articles are listed in Table 6.

CAR-T cells expressing MUC16 CARs of different spacer lengths derived from CD8 alpha hinge regions were generated by electroporation of SB system plasmids in healthy donor T cells (donor # D133098) as described in Example 1. CAR-T cells were numerically expanded ex vivo by co-culture with MUC16t expressing AaPC by once weekly stimulation as described in Example 1. Expression of CAR was measured by multi parameter flowcytometry at Day 1 and Day 8 post nucleofection. CAR-T test articles evaluated are listed in Table 6. FIG. 5 shows flow cytometry data on MUC16 CAR expression of different MUC16 CAR-T cells. Cells were gated on live CD3+ cells. As shown in FIG. 5, varying degrees of MUC16 CAR expression was observed one day post gene transfer depending on MUC16 scFv and the spacer utilized for construction of CAR molecule. Enrichment of CAR+ T cells was observed upon co-culture of CAR+ T cells with MUC16t+ AaPC line in vitro. For MUC16 CAR-T cells derived from donor # D133098, better enrichment of CAR+ T cells was observed from Day 1 to Day 8 post electroporation using CD8a(3×) spacer for MUC16-2 CAR and using CD8a(2×) spacer for MUC16-7 CAR.

TABLE 6

MUC16 CAR constructs as utilized in FIG. 5

| No. | Description of CAR constructs |
|---|---|
| 1 | MUC16-1 CD8a.CD28ζ CAR-HER1t1 |
| 2 | MUC16-1 CD8a.4-1BBζ CAR-HER1t1 |
| 3 | MUC16-2 CD8a.4-1BBζ CAR-HER1t1 |
| 4 | MUC16-2 CD8a(2x).4-1BBζ CAR-HER1t1 |
| 5 | MUC16-2 CD8a(3x).4-1BBζ CAR-HER1t1 |
| 6 | MUC16-6 CD8a.4-1BBζ CAR-HER1t1 |
| 7 | MUC16-7 CD8a.4-1BBζ CAR-HER1t1 |
| 8 | MUC16-7 CD8a(2x).4-1BBζ CAR-HER1t1 |
| 9 | MUC16-7 CD8a(3x).4-1BBζ CAR-HER1t1 |
| 10 | MUC16-4 CD8a.4-1BBζ CAR-HER1t1 |
| 11 | MUC16-4 CD8a(2x).4-1BBζ CAR-HER1t1 |
| 12 | MUC16-4 CD8a(3x).4-1BBζ CAR-HER1t1 |

Figure 6:
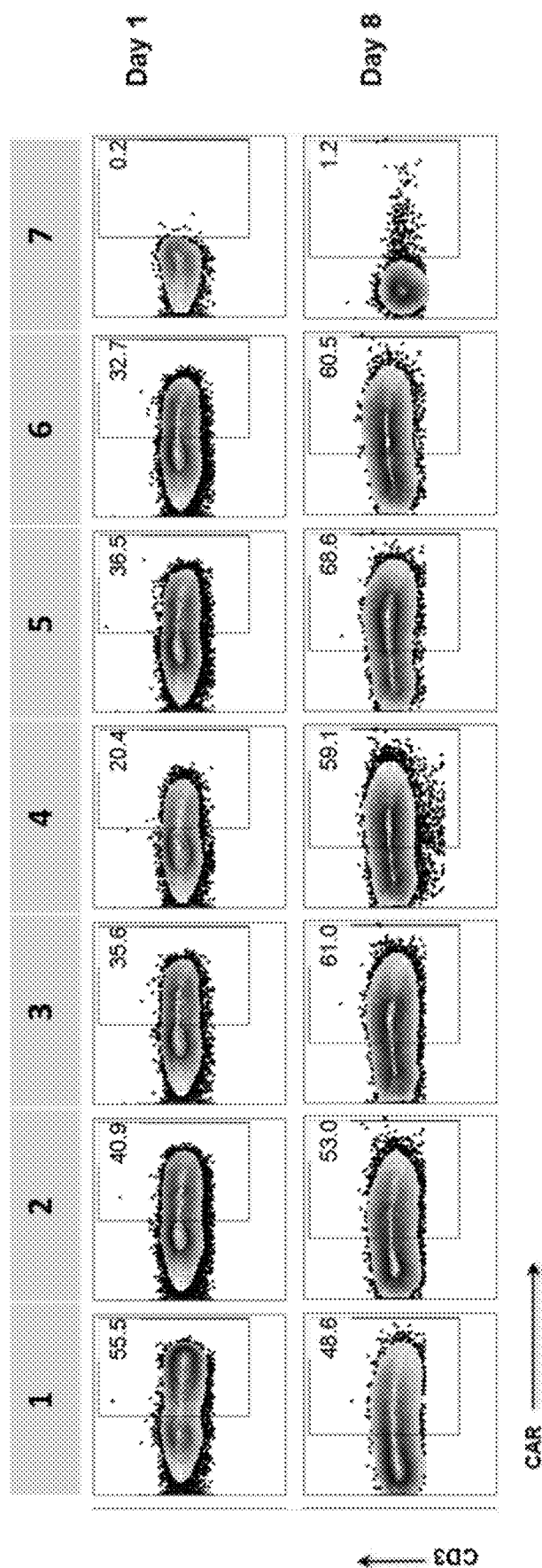
FIG. 6 shows CAR-T cells expressing MUC16 CARs of different spacer lengths derived from CD8 alpha hinge regions. CAR-T cells were generated by electroporation of SB system plasmids in healthy donor T cells (donor # D132552). CAR-T cells were numerically expanded ex vivo by co-culture with MUC16t expressing AaPC by once weekly stimulation. Expression of CAR was measured by multi parameter flow cytometry at Day 1 and Day 8 post nucleofection. Test articles are listed in Table 7.

MUC16-3 CAR-HER1t1 and MUC16-3-mbIL15-HER1t1 T cells expressing MUC16-3 CARS of with different spacers derived from CD8 alpha hinge regions were generated by electroporation of SB system plasmids in healthy donor T cells (donor # D132552). CAR+ T cells were numerically expanded ex vivo by co-culture with MUC16t expressing AaPC by once weekly stimulation as previously described. Expression of MUC16-3 CAR was measured by MUC16-Fc protein staining using multi parameter flow cytometry at Day 1 and Day 8 post nucleofection. CAR-T constructs that were evaluated are listed in Table 7. FIG. 6 shows flow cytometry data on MUC16-3 CAR expression of different MUC16-3 CAR-T cells. As shown in FIG. 6, varying degree of MUC16 CAR expression one day after gene transfer was observed depending on spacer utilized for construction of CAR molecule. Varying degree of enrichment of CAR$^+$ T cells eight days post gene transfer was observed upon co-culture of CAR$^+$ T cells with MUC16t$^+$ AaPC line in vitro depending on the spacer utilized for construction of CAR molecule.

TABLE 7

MUC16 CAR constructs as utilized in FIG. 6

| No. | Description of CAR constructs |
|---|---|
| 1 | MUC16-3 CD8a.4-1BBζ CAR-HER1t1 |
| 2 | MUC16-3 CD8a(2x).4-1BBζ CAR-HER1t1 |
| 3 | MUC16-3 CD8a(3x).4-1BBζ CAR-HER1t1 |
| 4 | MUC16-3 CD8a.4-1BBζ CAR-mbIL15-HER1t1 |
| 5 | MUC16-3 CD8a(2x).4-1BBζ CAR-mbIL15-HER1t1 |
| 6 | MUC16-3 CD8a(3x).4-1BBζ CAR-mbIL15-HER1t1 |
| 7 | Mock transfected T cells |

Example 4. Western Blot

T cell lysates were generated by resuspending cell pellets in radio-immunoprecipitation assay containing protease inhibitors. The cleared lysate was separated from the cellular extract and stored cryopreserved. A bicinchoninic acid (BCA) assay was performed to determine the total protein concentration and for normalization across samples. A total of 10 μg of protein sample was analyzed by electrophoresis under reducing conditions. Protein material from the gel was transferred to polyvinylidene fluoride (PVDF) membranes. Transferred protein membranes were blocked and then incubated with the primary antibody, mouse anti-human CD3ζ or anti-IL-15 antibody on a rocking platform. The membrane was washed prior to adding the appropriate horse-radish peroxidase (HRP)-labeled secondary antibody. Blots were prepared using chemiluminescence (ECL) detection. Images of the western blot were captured on the FluorChem™ E Imager system.

For the detection of HER1t1, an immunoprecipitation method was performed followed by western blot. Additional controls were analyzed that include A431 cell lysate (positive control) and an immunoprecipitation control (immunoprecipitation with no lysate; negative control). Protein material from the gel was transferred to PVDF membranes. Transferred protein membranes were blocked and then incubated with the primary antibody, mouse anti-human EGFR antibody. The membrane was washed prior to adding the horse-radish peroxidase (HRP)-labeled goat anti-mouse antibody. Images of the western blot were captured on the FluorChem™ E Imager.

Figure 7:
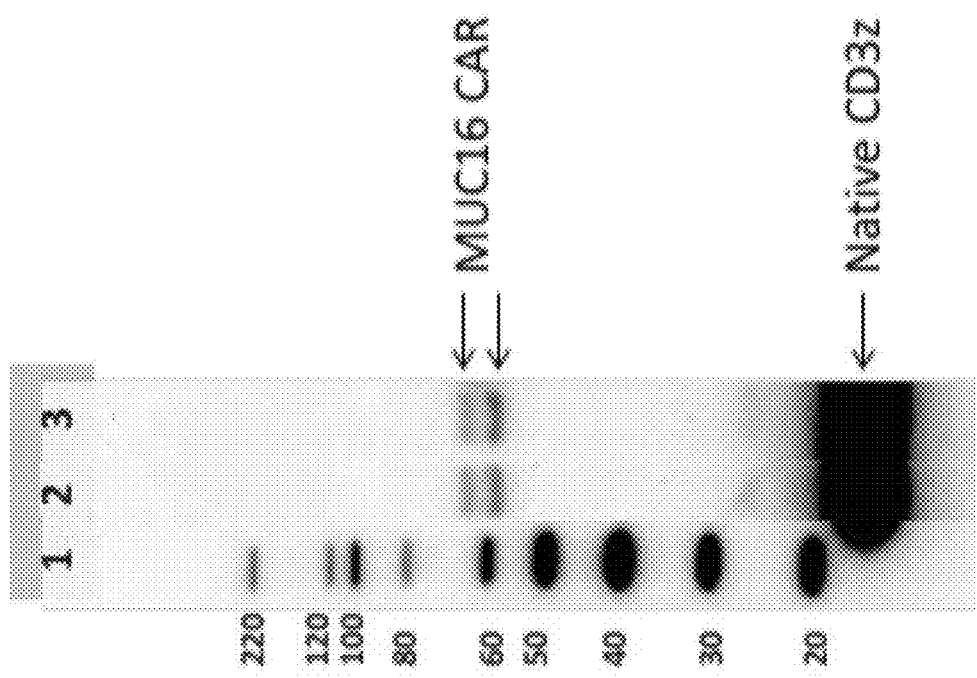
FIG. 7 shows Western blot analysis of MUC16 CAR expression. MUC16 CAR expression was measured by staining with mouse anti-human CD3ζ antibody. Lane 1: Protein Marker; Lane 2: MUC16-3 CAR-HER1t1 T cells; and 3: MUC16-3 CAR-mbIL15-HER1t1 T cells.
Figure 8:
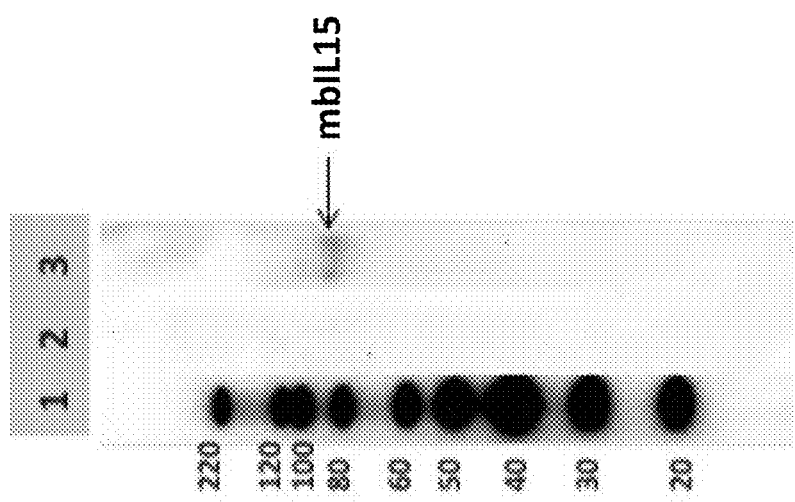
FIG. 8 shows Western blot analysis of mbIL15 expression. mbIL15 expression was measured by staining with anti-IL-15 antibody. Lane 1: Protein Marker; Lanes 2: MUC16-3 CAR-HER1t1 T cells and Lane 3: MUC16-3 CAR-mbIL15-HER1t1 T cells.
Figure 9:
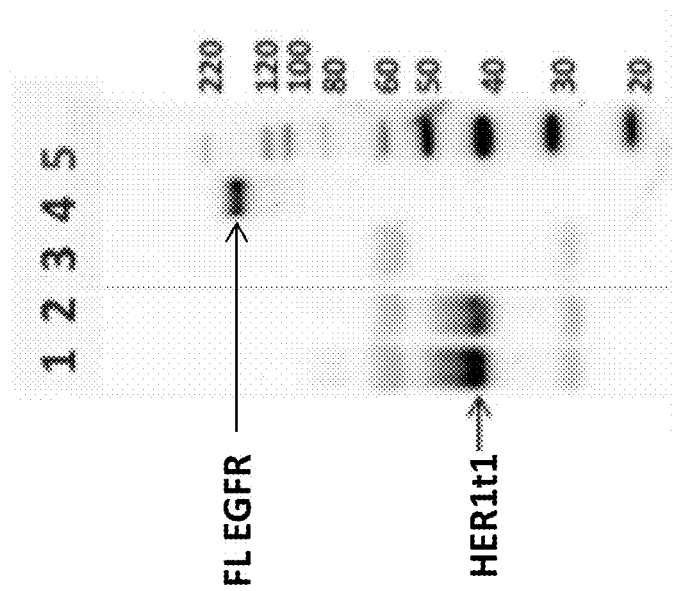
FIG. 9 shows Western blot analysis of HER1t1 expression. HER1t1 expression was measured by immunoprecipitation method followed by western blot. Lane 1: MUC16-3 CAR-HER1t1 T cells; Lane 2: MUC16-3 CAR-mbIL15-HER1t1 T cells; Lane 3: No lysate immunoprecipitation control; Lane 4: A431 cell line lysate; and Lane 5: Protein Marker.

FIGS. 7-9 show images of Western Blots using MUC16-3 CAR-HER1t1 T cells and MUC16-3 CAR-mbIL15-HER1t1 T cell lysates. As shown in FIG. 7, MUC16-3 CAR bands were detected in both MUC16-3 CAR-HER1t1 T cell and MUC16-3 CAR-mbIL15-HER1t1 T cell lysates. Native CD3ζ bands of lower molecular weight were also detected as expected form CAR-T cell lysates. As shown in FIG. 8, mbIL15 protein expression was detected only in lysate from MUC16-3 CAR-mbIL15-HER1t1 T cells that co-express mbIL15 (FIG. 8). FIG. 9 shows expression of HER1t1, of expected molecular weight of approximately 40 kDa, in MUC16-3 CAR-HER1t1 T cells and MUC16-3 CAR-mbIL15-HER1t1 T cells. In summary, these data demonstrate T cells expressing MUC16 CAR, mbIL15, and HER1t can be generated using SB system.

Example 5. Cytotoxicity of MUC16-3 CAR-T Cells

T cell cytotoxic activity was determined using a luminescent cell viability assay. The specific cytotoxicity of the MUC16-3 CAR-mbIL15-HER1t1 cells was assessed using CAR$^+$ T cells generated as described above. MUC16-3 CAR-mbIL15-HER1t1, the control MUC16-3 CAR-HER1t1 T cells, and non-MUC16 control CAR-mbIL15-HER1t1 T cells were assessed for expression of MUC16 CAR, HER1t1 and mbIL-15. Effector CAR-T cells were identified by the expression of HER1t1. Different Effector: Target (E:T) ratios were evaluated with ovarian cell line, SKVO3 with ectopic expression of MUC16t (SKOV3-MUC16t), the SKVO3 parental line that does not express MUC16, OVCAR3 with natural expression of MUC16, and the MUC16 negative cell line, A549. The supernatants from the cell culture were stored at −80° C. until cytokine analyses. The percent cytotoxicity was determined using the formula below:

$$\text{Specific Cytotoxicity (\%)} = 100 \times \left(1 - \frac{\text{Test - Average Background}}{\text{Average Target Only - Average Background}}\right).$$

Figure 10A:
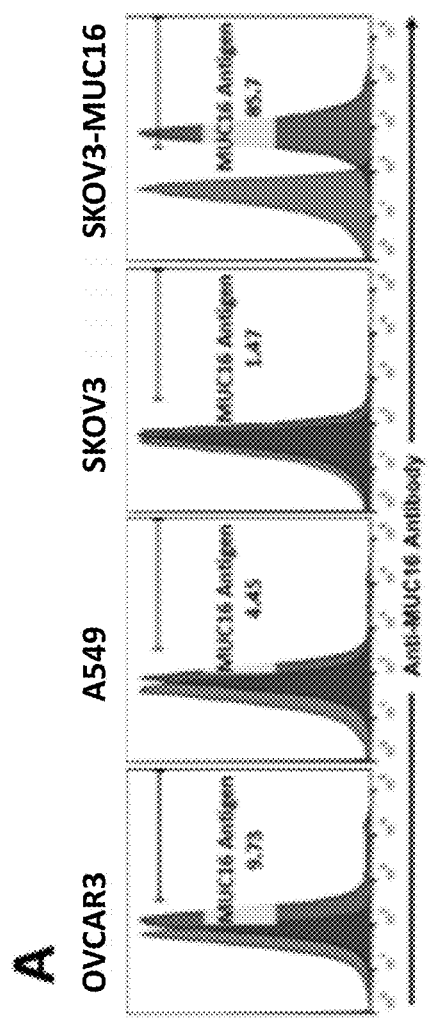
FIG. 10A shows flow cytometry analysis of MUC16 expression in various tumor cell lines tested.
Figure 10B:
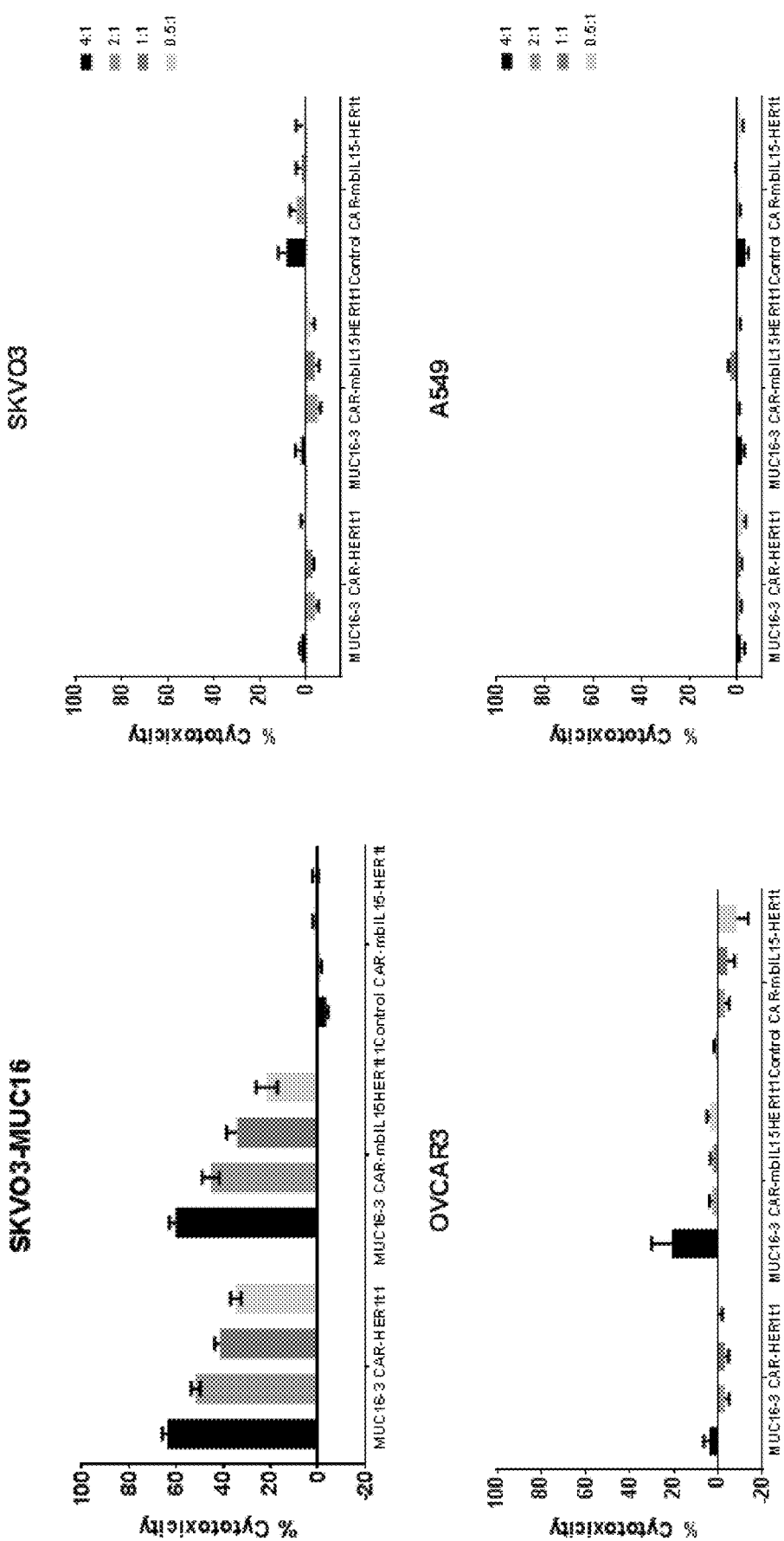
FIG. 10B shows specific cytotoxicity of MUC16 CAR-T cells. Cytotoxicity of MUC16-3 CAR-HER1t1 T cells and MUC16-3 CAR-mbIL15-HER1t1 T cells towards various tumor cell lines at varying E:T ratios. Control CAR-mbIL15-HER1t1 T cells were utilized as negative control. Mean±SEM from triplicate wells from 3 donors is shown.

The specific cytotoxicity of MUC16-3 CAR-T cells generated from three healthy donor T cells towards MUC16-expressing tumor targets was demonstrated by comparing the cytotoxic activity various tumor cell lines at varying E:T ratios. CAR-T cells expressing control CAR were used as negative control. FIG. 10A shows that MUC16t is expressed only by SKOV3-MUC16t tumor cells. Effector CAR-T cells (normalized based on HER1t1 cell expression) were co-cultured with target tumor cells at varying E:T ratios. As shown in FIG. 10B, both the MUC16-3 CAR-HER1t1 T cells (lacking mbIL15) and MUC16-3 CAR-mbIL15-HER1t1 demonstrated similar dose-dependent cytotoxicity against SKOV3-MUC16t and OVCAR3 tumor cell lines. However, only MUC16-3 CAR-mbIL15-HER1t1 killed OVCAR3 at the higher E:T ratio. The selective killing of OVCAR3 cells by MUC16-3 CAR-mbIL15-HER1t1 suggests the enhanced activation of T cells in the modified T cells. No background signal was detected from culture of labelled target cells alone. Furthermore, MUC16-specific CAR-T cells did not kill MUC16t$^{neg}$ tumor cell lines (SKOV3 and A549) and no killing of any tumor cell line was observed with control CAR-mbIL15-HER1t T cells. Taken together, these results demonstrate that MUC16-3 CAR-mbIL15-HER1t1 specifically mediated killing of MUC16-expressing tumor cell lines.

Example 6. Cytokine Production by MUC16-3 CAR-T Cells

Culture supernatants from cytotoxicity assay from Example 5 were screened using custom multi-analyte kits for cytokine production including IFNγ and Granzyme B.

Figure 11:
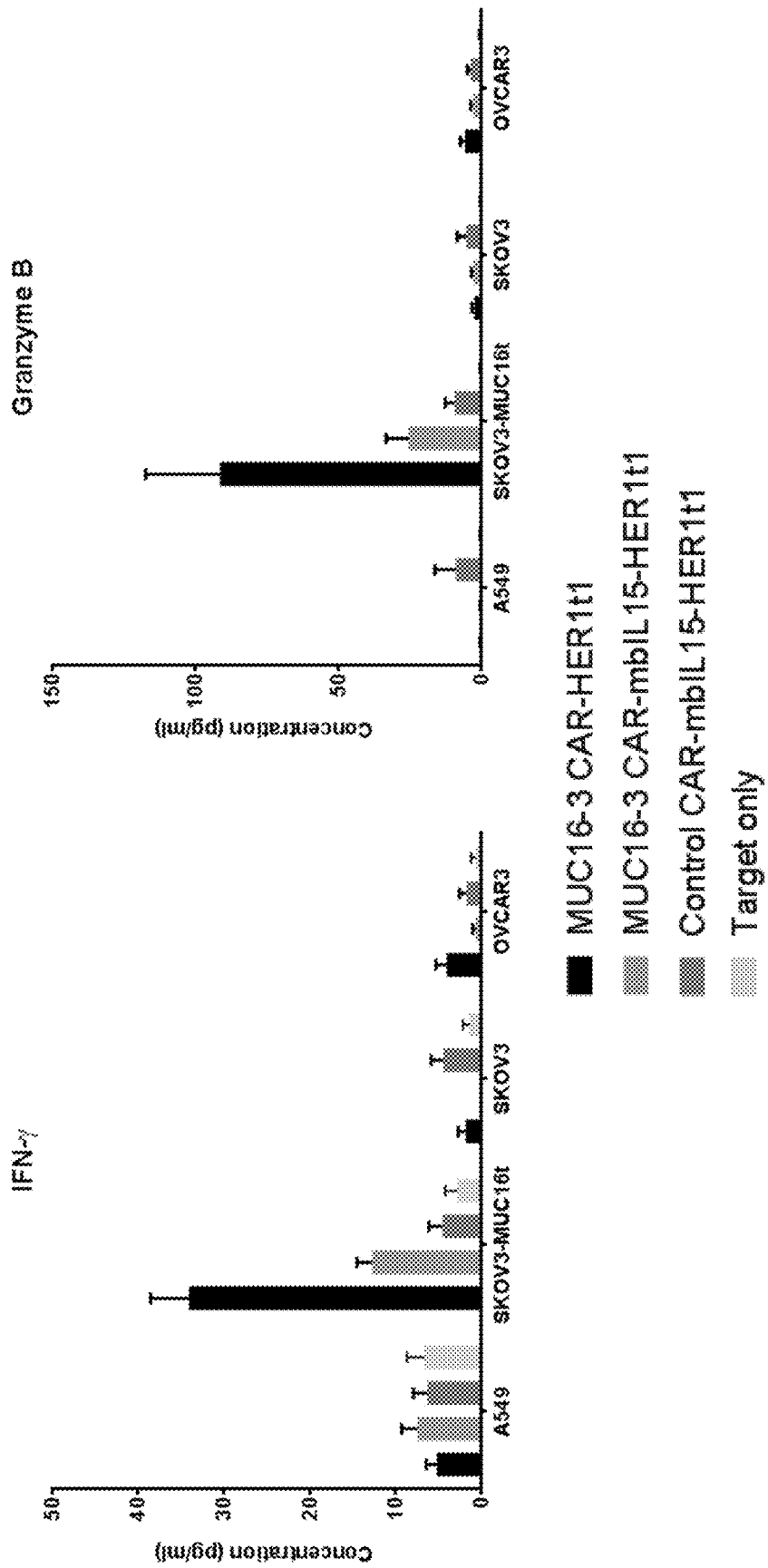
FIG. 11 shows cytokine production by MUC16 CAR-T cells upon co-culture with various tumor cell lines. CAR-T cells generated using three healthy donor T cells were co-cultured with specified tumor cells lines at E:T ratio of 1:1 for seven days. Mean±SEM from triplicate wells from 3 donors is shown.

Redirected specificity of MUC16-3 CAR-HER1t1 T cells (lacking mbIL15) and MUC16-3 CAR-mbIL15-HER1t1 T cells towards MUC16 expressing tumor cells was further studied by examining cytokine secretion upon co-culture with the MUC16- and non-expressing and MUC16-expressing tumor cell lines. In these studies, cytokine production by MUC16-3 CAR-mbIL15-HER1t1 T cells from 3 different donors was assessed at an E:T cell ratio of 1:1 after co-culture with tumor cell lines. As shown in FIG. 11, elevated levels of proinflammatory cytokines were observed only with tumor cell lines expressing MUC16t. Further, expression of mbIL15 in MUC16-3 CAR-mbIL15-HER1t1 T resulted in low cytokine production compared to levels observed following testing of MUC16-3 CAR-HER1t1 T cells without mbIL15. These data demonstrated that MUC16-3 CAR-mbIL15-HER1t1 T cells exhibit specific cytotoxic function towards MUC16-expressing tumor cells and showed that co-expression of mbIL15 can reduce production of proinflammatory cytokines, without compromising the cytotoxic effects of MUC16-3 CAR-mbIL15-HER1t1.

Example 7. Specificity of MUC16 CAR-T Cells

T cell cytotoxic activity was determined using a luciferase assay. MUC16 CAR-T cells (Table 8) along with control CAR-T cells were generated by electroporation of SB system plasmids into two healthy donor T cells (D326782 and D132552) and numerically expanded by ex vivo co-culture with AaPCs as described in Example 1. Cytotoxicity was evaluated at different E:T ratios using SKOV3-MUC16t, OVCAR3, and MUC16$^{neg}$ A549 cell lines as target cells in triplicate wells. The percent cytotoxicity was determined using the formula as previously described above.

TABLE 8

Figure 12:
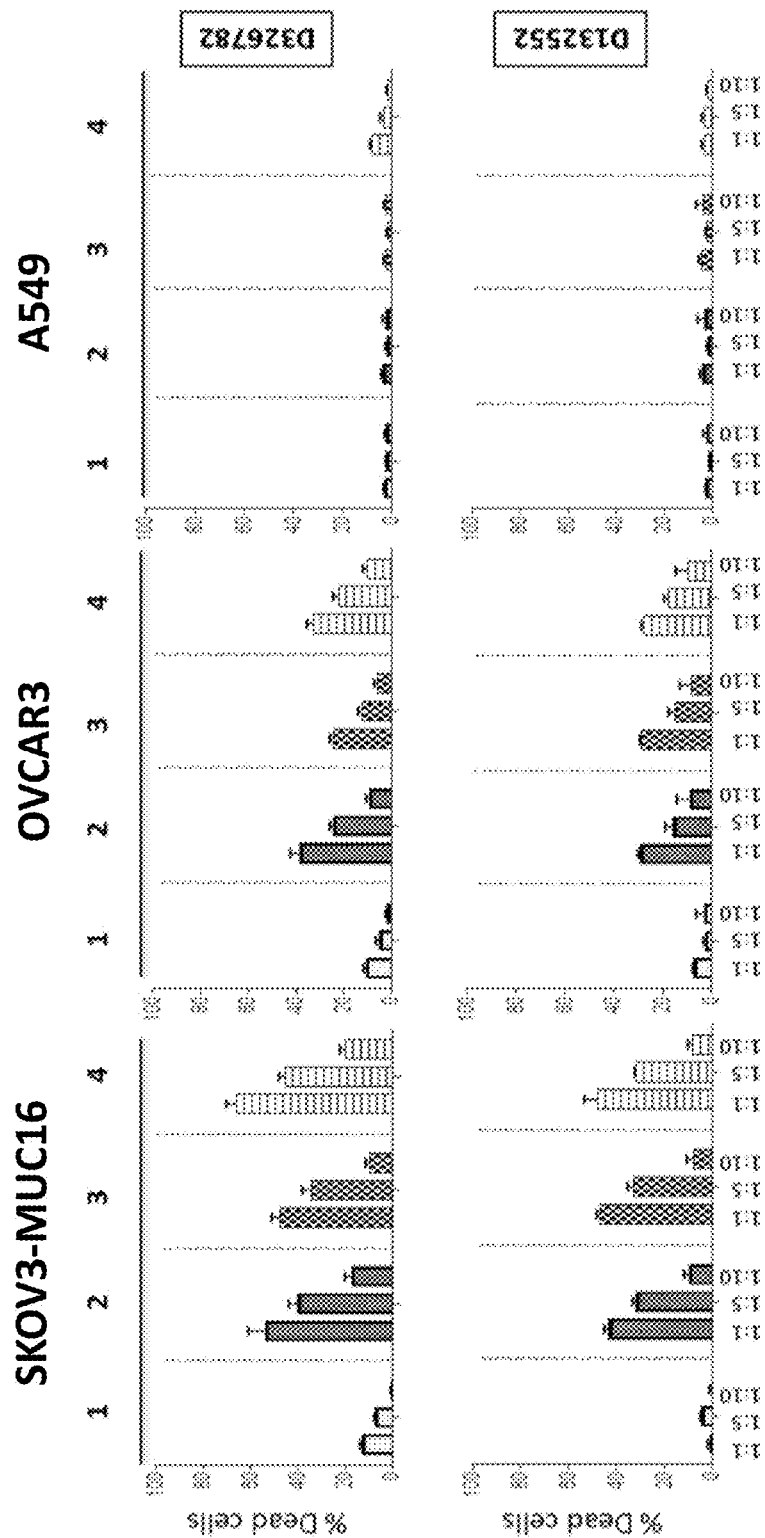
FIG. 12 shows cytotoxicity of MUC16 CAR-T cells in a luciferase assay. CAR-T cells generated from two healthy donor T cells were cultured with tumor cell lines. Test articles are listed in Table 8.

MUC16 CAR constructs as utilized in FIG. 12

| No. | Description of CAR constructs |
|---|---|
| 1 | Control CAR-mbIL15-HER1t1 (Control) |
| 2 | MUC16-2 CD8a.4-1BBζ CAR-mbIL15-HER1t1 |
| 3 | MUC16-3 CD8a.4-1BBζ CAR-mbIL15-HER1t1 |
| 4 | MUC16-3 CD8a(2x).4-1BBζ CAR-mbIL15-HER1t1 |

As shown in FIG. 12, MUC16 CAR-T cells co-expressing mbIL15 and HER1t1 exhibited specific cytotoxicity of MUC16$^+$ tumor cells lines in concentration dependent manner. None of the MUC16 CAR-T cells tested exhibited significant cytotoxicity of MUC16$^{neg}$ tumor cell line A549. MUC16-3 CAR-mbIL15-HER1t1 cells with CD8a(2x) spacer exhibited higher specific cytotoxicity of MUC16$^+$ tumor cells lines compared to CD8a spacer in the CAR-T cells generated from healthy donor T cells shown.

Example 8. Persistence and Lack of Autonomous Proliferation of MUC16 CAR-T Cells Expressing mbIL15

To assess the impact of mbIL15 on persistence of the CAR-T cells, MUC16-3 CAR-HER1t1 T and MUC16-3 CAR-mbIL15-HER1t1 T cells were labeled with Cell-Trace™ Violet and co-cultured with autologous PBMCs. Co-cultures were maintained at for 14 days. During cell culture, a cell samples were evaluated to measure viability and stained for flow cytometry for the assessment of CAR T cells and memory phenotype. The proliferation was determined by dilution of the dye.

Figures 13A, 13B:
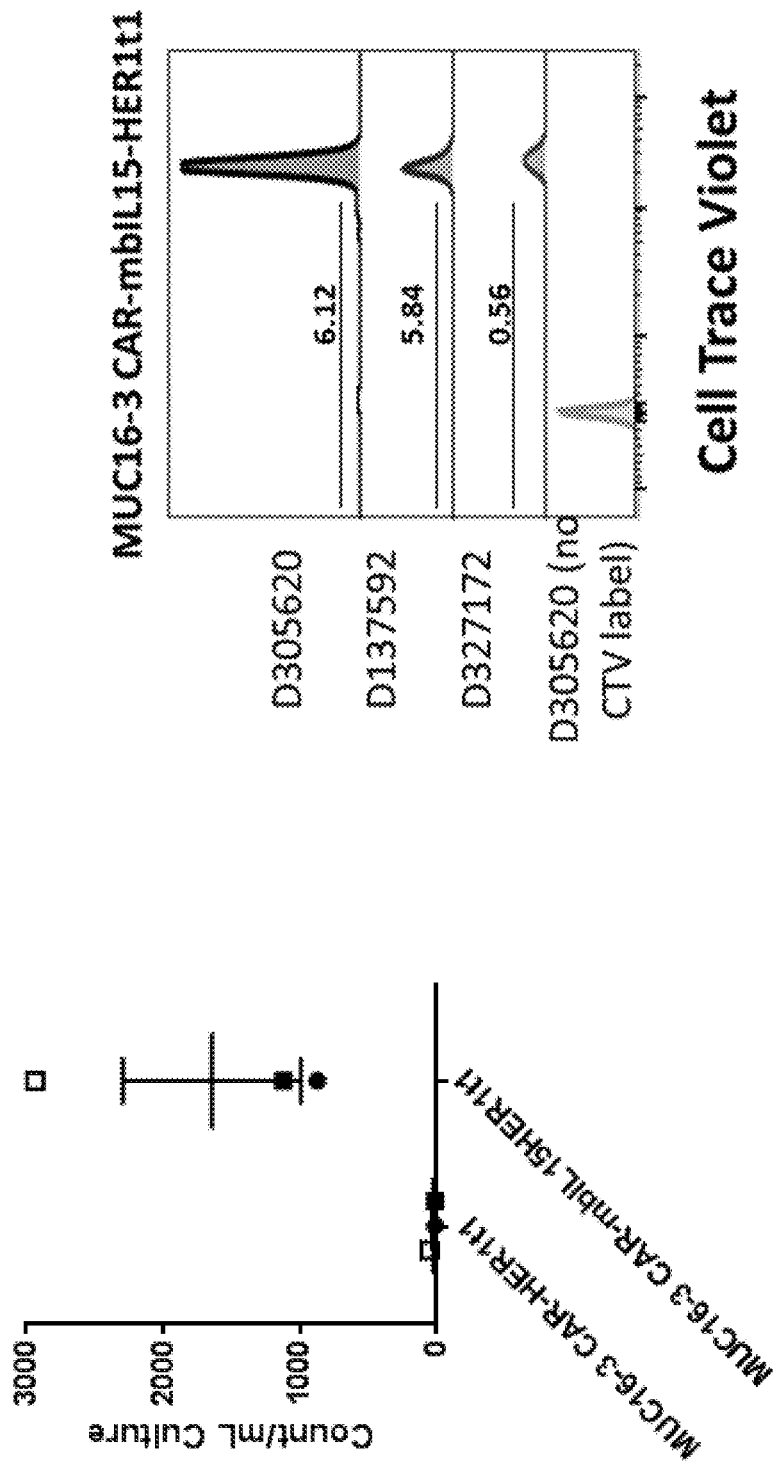
FIG. 13A shows biological function of mbIL15 in MUC16 CAR-T cells. CAR-T cells were generated from three healthy donor T cells. Persistence of MUC16-3 CAR-HER1t1 T cells and MUC16-3 CAR-mbIL15-HER1t1 T cells in in vitro culture in absence of antigen and exogenous cytokines. Each symbol represents individual donor CAR-T cells. Mean±SEM from three donors is shown.
FIG. 13B shows biological function of mbIL15 in MUC16 CAR-T cells. CAR-T cells were generated from three healthy donor T cells. Proliferation of CAR-T cells is shown. Each symbol represents individual donor CAR-T cells. Mean±SEM from three donors is shown.
Figure 13C:
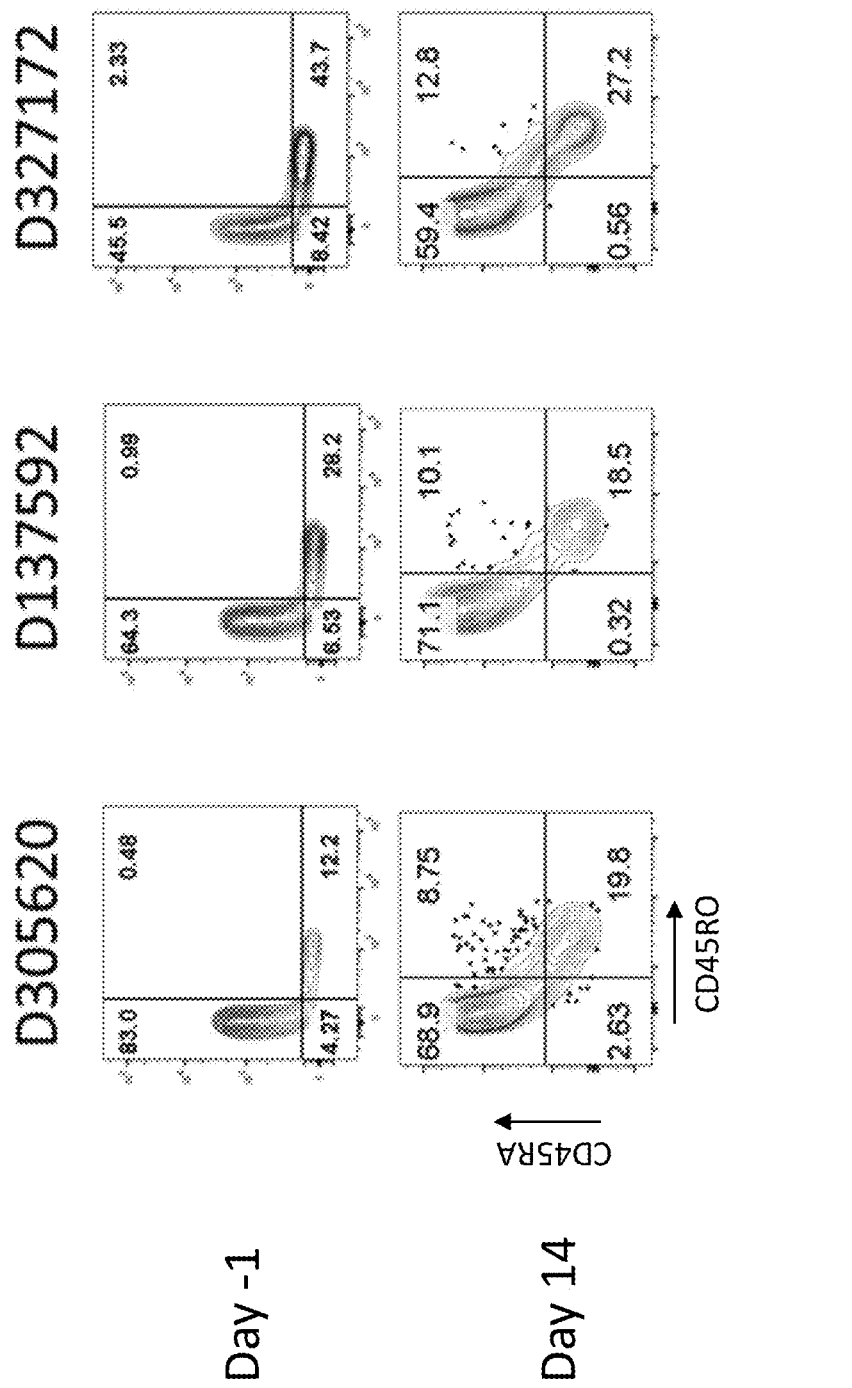
FIG. 13C shows biological function of mbIL15 in MUC16 CAR-T cells. CAR-T cells were generated from three healthy donor T cells. Memory marker analysis of MUC16-3 CAR-mbIL15-HER1t1 T cells is shown. Each symbol represents individual donor CAR-T cells. Mean±SEM from three donors is shown.

Cell persistence assessments showed that MUC16-3 CAR-HER1t (lacking mbIL15) did not persist in culture after two weeks and only MUC16-3 CAR-mbIL15-HER1t1 T cells were detected in culture lacking cytokines at day 14 (FIG. 13A) demonstrating role of mbIL15 in improved persistence of CAR-T cells. Assessment of the potential for autonomous proliferation showed that although MUC16-3 CAR-mbIL15-HER1t1 T cells are detected at day 14, they failed to undergo proliferation, demonstrated by the absence of daughter cells (FIG. 13B). Furthermore, at day 14, persistent MUC16-3 CAR-mbIL15-HER1t1 T cells showed an enrichment of memory-like or quiescent state-like T cell population as determined by higher levels of CD45RA$^+$/CD45RO$^+$ cells compared to Day −1 (FIG. 13C).

MUC16-2 CAR-HER1t1 T cells (lacking mbIL15 expression) and MUC16-2 CAR-mbIL15-HER1t1 T cells were generated by electroporation to SB system plasmids into three healthy donor T cells. CAR-T cells were numerically expanded ex vivo by weekly stimulations with AaPC. CAR-T cells were cultured in medium without exogenous cytokines for 2 weeks. Viable T cells in culture as a fraction of starting cell numbers were calculated to show persistence.

Figure 14:
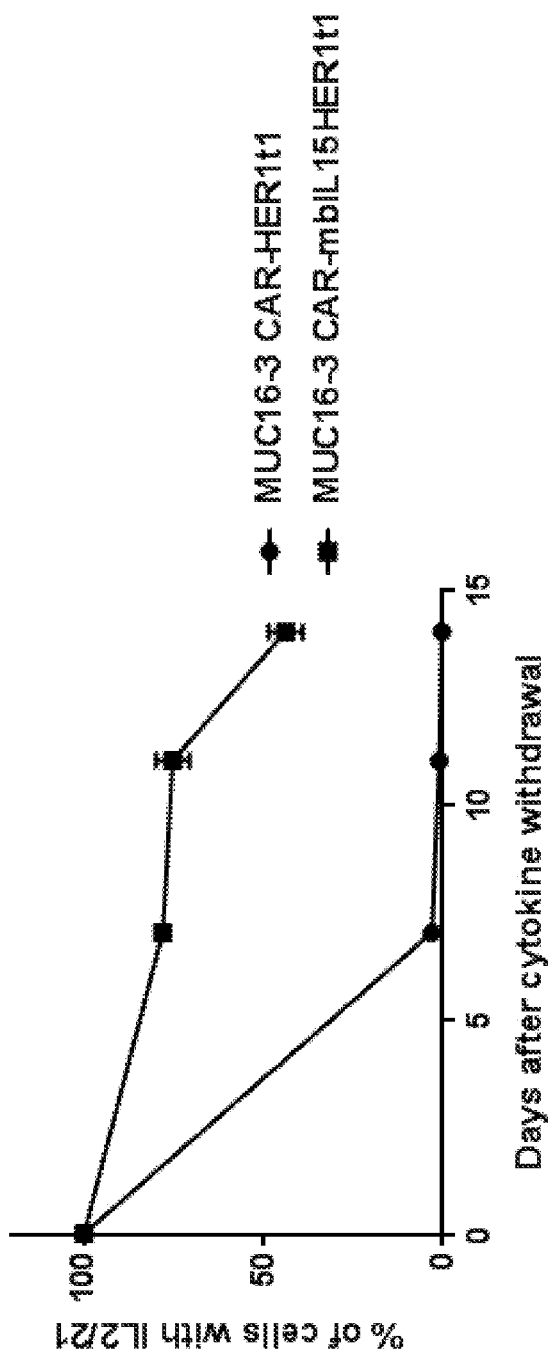
FIG. 14 shows in vitro persistence of MUC16 CAR-T cells in absence of exogenous cytokines. MUC16-2 CAR-HER1t1 T cells and MUC16-2 CAR-mbIL15-HER1t1 T cells from three healthy donor T cells were cultured in presence or absence of exogenous cytokines for 2 weeks. Viable T cells in culture without cytokine as a fraction of T cells in culture with cytokines were graphed. Data shown is mean±SEM from three donors.

As shown in FIG. 14, MUC16-2 CAR-mbIL15-HER1t1 T cells expressing mbIL15 could be maintained in ex vivo culture at Day 15 post withdrawal of cytokines, while MUC16-2 CAR-HER1t1 T cells lacking mbIL15 expression did not survive beyond 7 days in the absence of cytokines.

These data shows improved persistence of MUC16 CAR-T cells when mbIL15 is co-expressed with CAR.

Example 9. ADCC Assay

Autologous Natural killer (NK) cells were used as effector cells in ADCC assay. Ex vivo expanded MUC16-2 CAR-mbIL15-HER1t1 cells were used as the target cells in this assay. Effector and target cell co-cultures were set up at a 10:1 E:T ratio in the presence of 10 μg/mL cetuximab or rituximab or without an antibody. Viability was assessed following the co-culture using flow cytometry. In order to determine % ADCC, of CAR$^+$ T cells, the fractional loss of labelled CD3$^+$ cells was determined by comparison with the starting CAR$^+$ T cell population.

Figure 15:
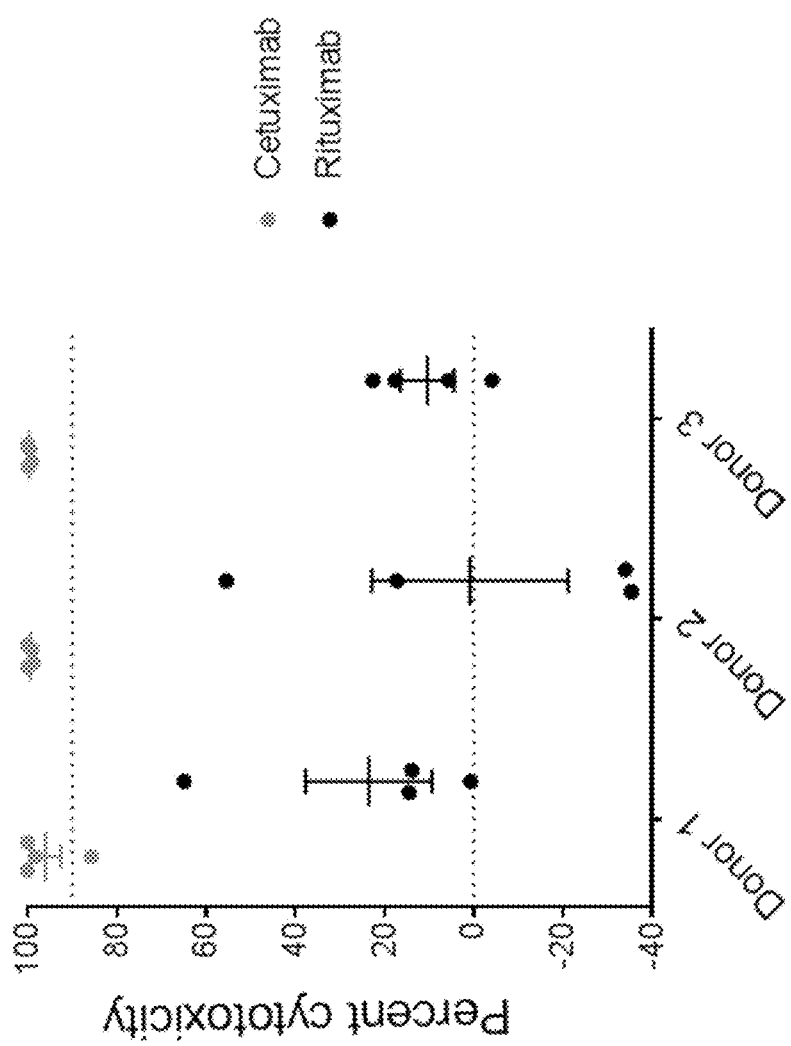
FIG. 15 shows cetuximab-mediated ADCC activity (expressed as % cytotoxicity; y-axis) of MUC16 CAR-T cells co-expressing HER1t1. Allogeneic NK cells were used as effector cells at 10:1 E:T ratio. Cetuximab showed specific cytotoxicity towards HER1t1 expressing MUC16 CAR-T cells. Data shown are mean±SEM.

FIG. 15 demonstrates that MUC16-2 CAR-mbIL15-HER1t1 T cells generated from three different healthy donor T cells were efficiently eliminated via ADCC when cetuximab was added to the culture. Addition of anti-CD20 rituximab (non-specific control) to the culture showed low background levels of cytotoxicity proving specificity of cetuximab mediated ADCC of CAR-T cells. Data shown are mean+/−SEM.

Example 10. Functional Evaluation of MUC16-2 CAR-T Cells in an In Vivo Model of Ovarian Cancer SKOV3-fLUC-MUC16 were administered IP into NSG mice (Day 0). On Day 6, mice with established tumor burden confirmed by IVIS imaging were randomized (n=5-7 mice per group) to receive a single IP injection with either: Saline (HBSS), MUC16-2 CAR-HER1t1 T cells (2×10$^6$ cells/mouse), MUC16-2 CAR-mbIL15-HER1t1 T cells (2×10$^6$ cells/mouse) or single IV injection with MUC16-2 CAR-mbIL15-HER1t1 T cells (2×10$^6$ cells/mouse). Effectiveness against tumor growth was evaluated by in vivo bioluminescence (IVIS) imaging performed every 3-4 days post CAR-T cell dosing to assess tumor burden. General safety was evaluated by assessment of body weight and clinical observations performed throughout the study at a minimum of 2-3 per week post CAR T cell administration.

Figure 16:
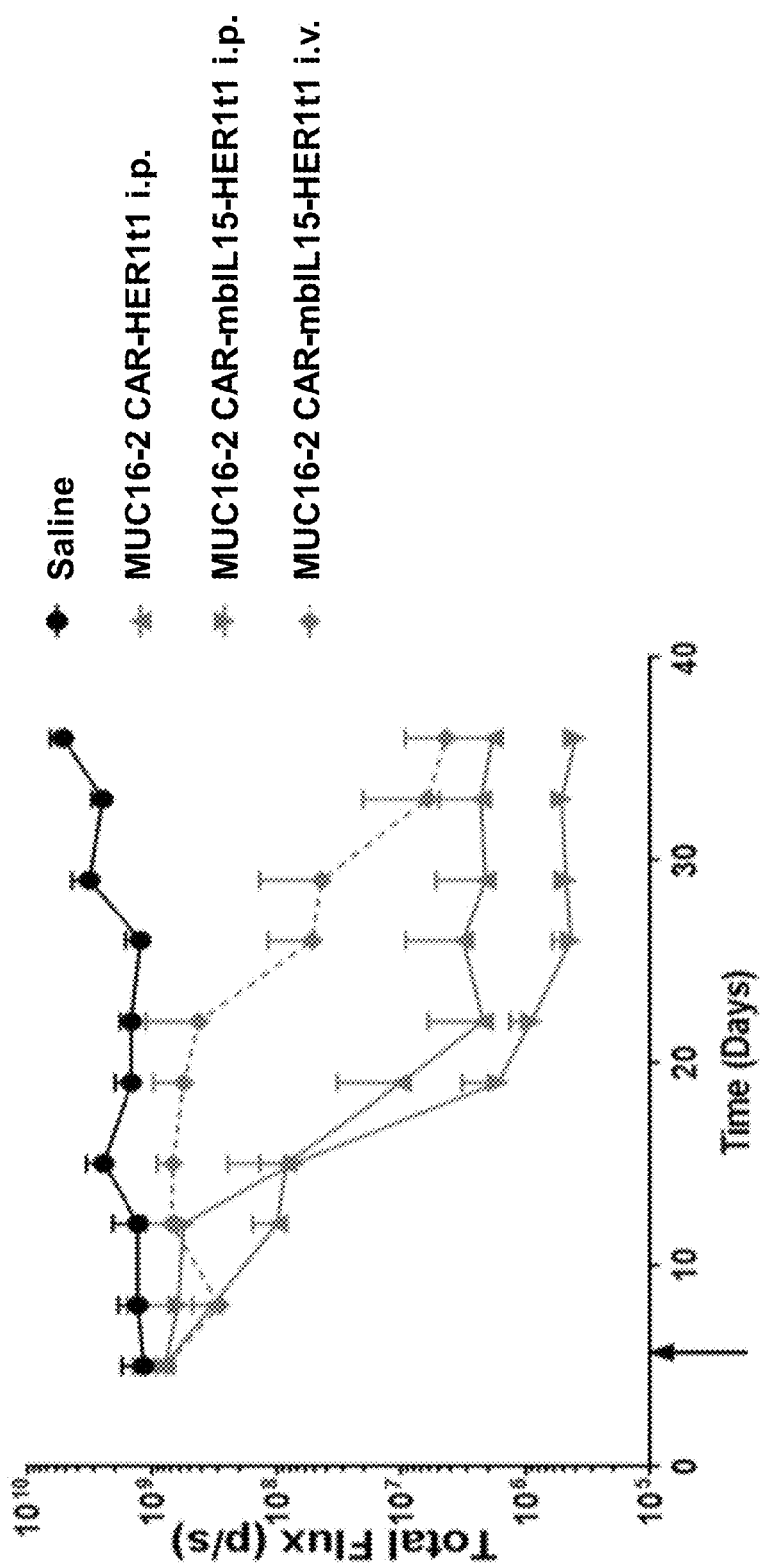
FIG. 16 shows quantitative analysis of SKOV3-fLUC-MUC16 tumor burden as measured by in vivo bioluminescence (IVIS) imaging. NSG mice (N=5-7 mice per group) were administered with SKOV3-fLUC-MUC16 tumor cell line via i.p. injection on Day 0. Tumor bearing mice were treated with different MUC16 CAR-T treatment via single i.p. or i.v. injection and tumor burden was quantified via IVIS through the course of treatment. Data shown are mean±SEM. Arrow represents the day of CAR-T administration.

As shown in FIG. 16, single IP or IV injection of MUC16-2 CAR-T cells was effective at eliminating SKOV3-fLUC-MUC16 tumor in mice. Anti-tumor response of CAR-T cells injected vial IV injection was delayed in comparison to IP infusion.

Example 11. Functional Evaluation of MUC16-3 CAR-T Cells in an In Vivo Model of Ovarian Cancer SKOV3-fLUC-MUC16 tumor cells were administered IP into NSG mice on Day 0. On Day 5, mice with established tumor burden (as confirmed by IVIS imaging) were randomized (n=5-7 mice per group) to receive a single IP injection with either: Saline (HBSS), MUC16-3 CAR-HER1t1 T cells ($2\times10^6$ cells/mouse), or MUC16-3 CAR-mbIL15-HER1t1 T cells ($2\times10^6$ cells/mouse). Effectiveness against tumor growth was evaluated by in vivo bioluminescence (IVIS) imaging performed every 3-4 days post CAR-T cell dosing to assess tumor burden. Whole blood samples in EDTA were collected once per week and subjected to multi-parameter flow cytometry for evaluation of MUC16 CART cell persistence, expansion and determination of the different T cell subsets. Plasma samples were analyzed for human cytokine as an index of T cell activity. General safety was evaluated by assessment of body weight and clinical observations performed throughout the study at a minimum of 2-3 per week post CAR T cell administration.

Figure 17:
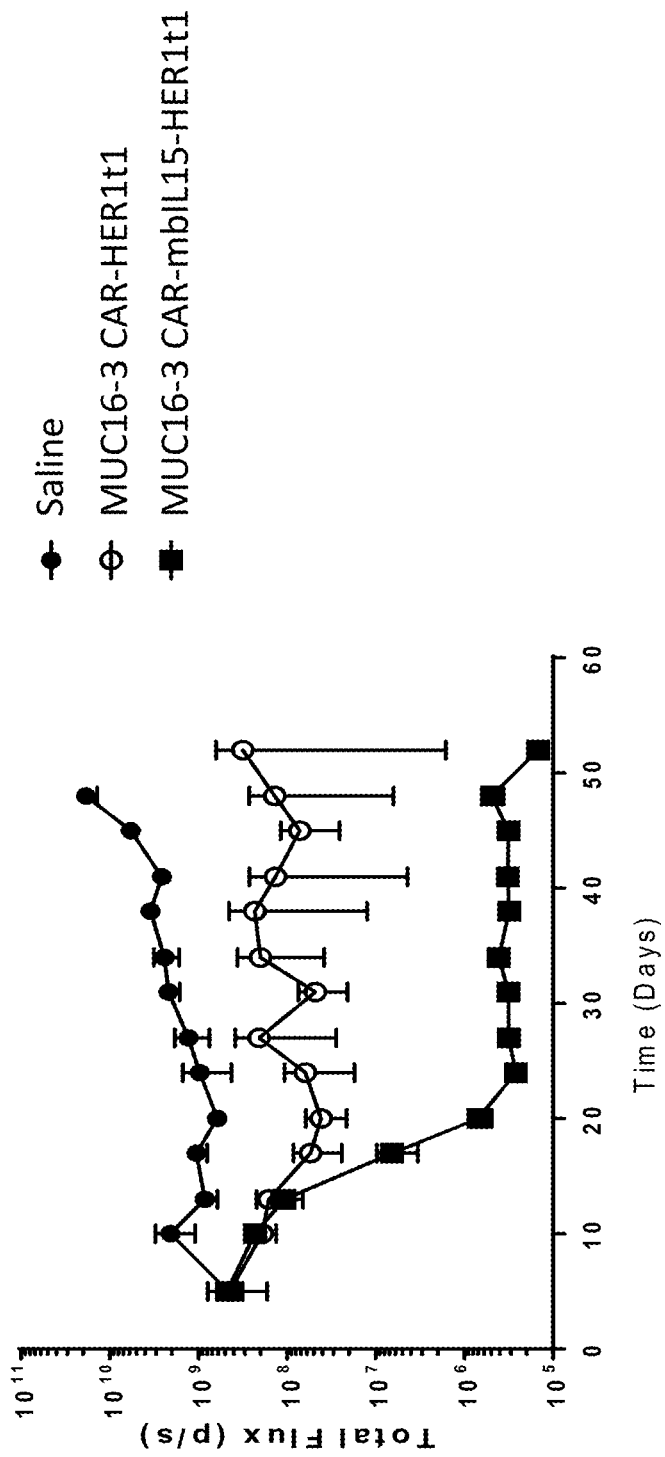
FIG. 17 shows quantitative analysis of SKOV3-fLUC-MUC16 tumor burden as measured by in vivo bioluminescence (IVIS) imaging. NSG mice (N=5-7 mice per group) were administered with SKOV3-fLUC-MUC16 tumor cell line via i.p. injection on Day 0. Tumor bearing mice were treated with different MUC16 CAR-T treatment via single i.p. injection five days after tumor cell administration and tumor burden was quantified via IVIS through the course of treatment. Data shown are mean±SEM.

As shown in FIG. 17, IP administration of MUC16-3 CAR-mbIL15-HER1t1 T cells to NSG mice bearing MUC16 expressing SKOV-3 tumors resulted in significant reduction (>3 log decrease in total flux value) in tumor burden when compared to the saline control-treated group. Co-expression of mbIL15 in the MUC16-3 CAR-mbIL15-HER1t1 T cells was associated with significantly greater reductions in tumor burden compared to MUC16-3 CAR-HER1t1 T cells lacking mbIL15 expression.

Figure 18A:
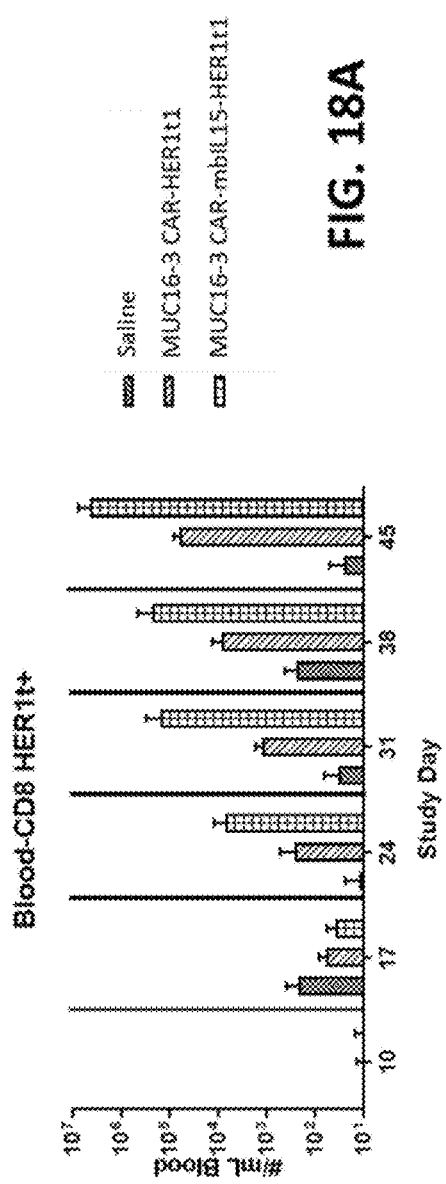
FIG. 18A and FIG. 18B show quantification of MUC16 CAR-T cells in the blood of treated tumor bearing NSG mice. NSG mice (N=5-7 mice per group) were administered with SKOV3-fLUC-MUC16 tumor cell line via i.p. injection. Tumor bearing mice were treated with different MUC16 CAR-T treatment via single i.p. injection five days after tumor cell administration and CAR-T cells were quantified (number of CAR-T cells per mL of blood; y-axis) via measurement of $CD8^+$ $HER1t1^+$ (FIG. 18A) and $CD4^+$ $HER1t1^+$ (FIG. 18B) T cells in mouse blood samples. Data shown are mean±SEM; n=5-7 mice at each time point.
Figure 18B:
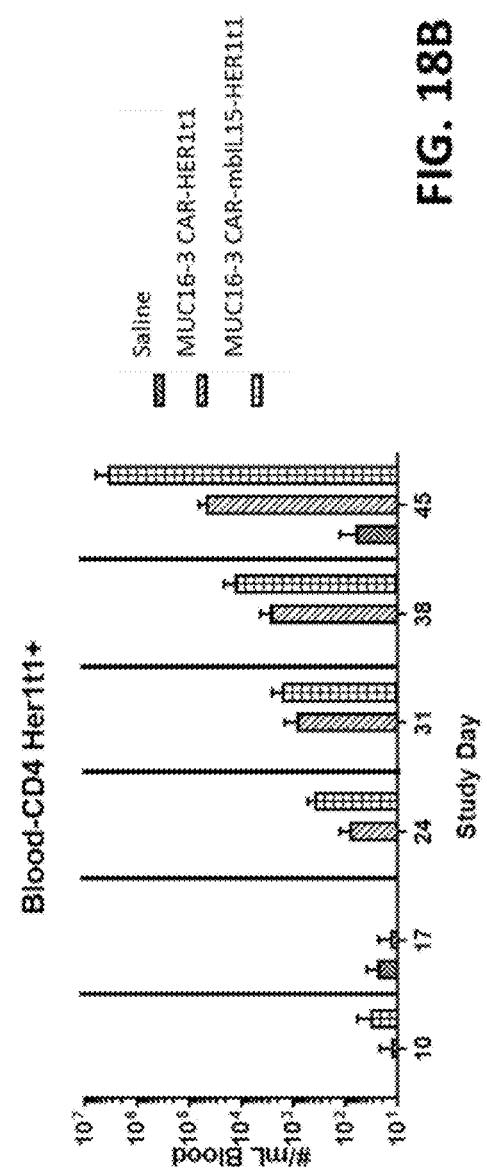

MUC16-3 CAR-mbIL15-HER1t1 T cells showed enhanced persistence and expansion in vivo, as was demonstrated by increased numbers of T cells expressing HER1t1 in the blood compared to MUC16-3 CAR-mbIL15-HER1t1 T cells. Furthermore, both $CD4^+$ and $CD8^+$ CAR-T cells showed in vivo expansion and persistence. See FIGS. 18A-B.

Example 12. Dose Response of MUC16 CAR-T Cells in an In Vivo Model of Ovarian Cancer SKOV3-fLUC-MUC16 were administered IP into NSG mice on Day 0. On Day 6, mice with established tumor burden (as confirmed by IVIS imaging) were randomized (n=5 mice per group) to receive a single IP injection with either: Saline (HBSS), three different doses of MUC16-2 CAR-mbIL15-HER1t1 T cells ($1\times10^5$, $5\times10^5$, or $1\times10^6$ cells/mouse), and MUC16-3 CAR-mbIL15-HER1t1 T cells ($1\times10^5$, $5\times10^5$, or $1\times10^6$ cells/mouse) or single dose of MUC16-3 CAR-HER1t1 T cells ($1\times10^6$ cells/mouse). MUC16-2 CAR-mbIL15-HER1t1 T cells, MUC16-3 CAR-HER1t1 T cells and MUC16-3 CAR-mbIL15-HER1t1 T cells were all derived from a single donor and manufactured in <2 days. Effectiveness against tumor growth was evaluated by in vivo bioluminescence (IVIS) imaging performed every 3-4 days post CAR-T cell dosing to assess tumor burden.

Figure 19:
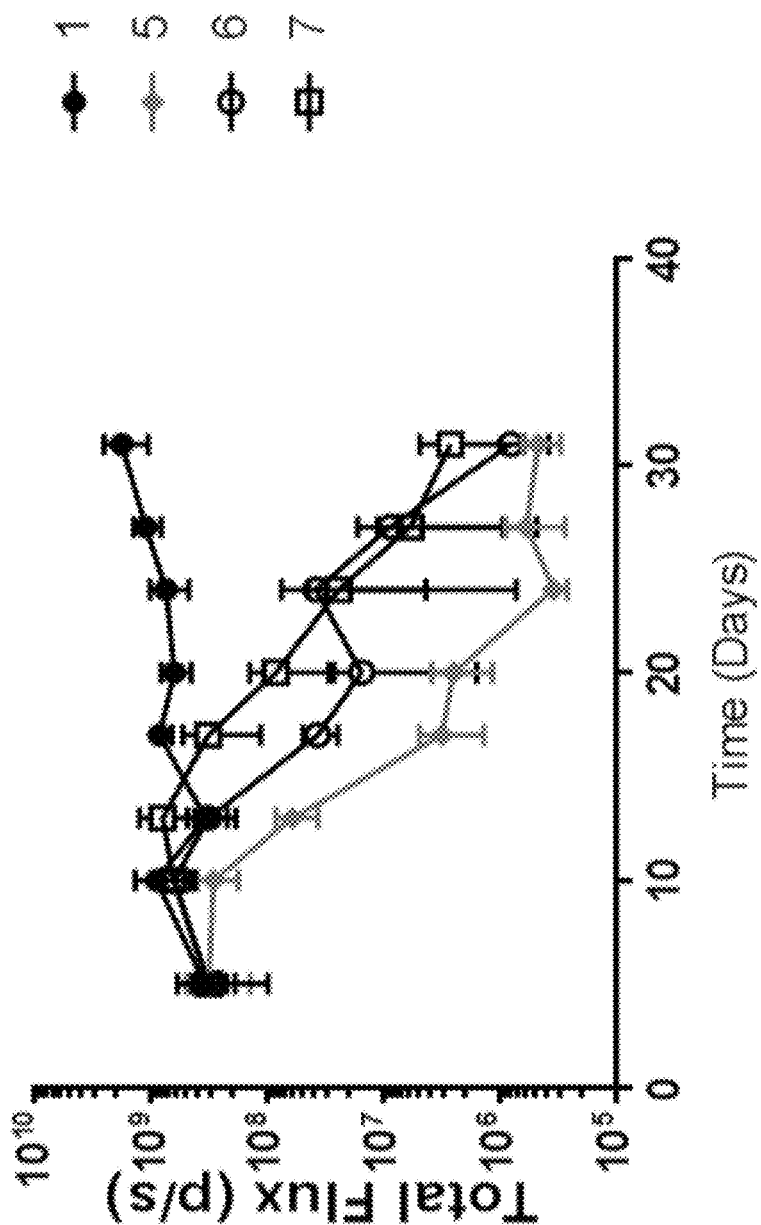
FIG. 19 shows quantitative analysis of SKOV3-fLUC-MUC16 tumor burden as measured by in vivo bioluminescence (IVIS) imaging. NSG mice (N=5 mice per group) were administered with SKOV3-fLUC-MUC16 tumor cell line via i.p. injection on Day 0. Tumor bearing mice were treated with one of the three different doses of MUC16-2 CAR-T cells via single i.p. injection five days after tumor cell administration and tumor burden was quantified via IVIS through the course of treatment. Test articles are listed in Table 9. Data shown are mean±SEM.
Figure 20:
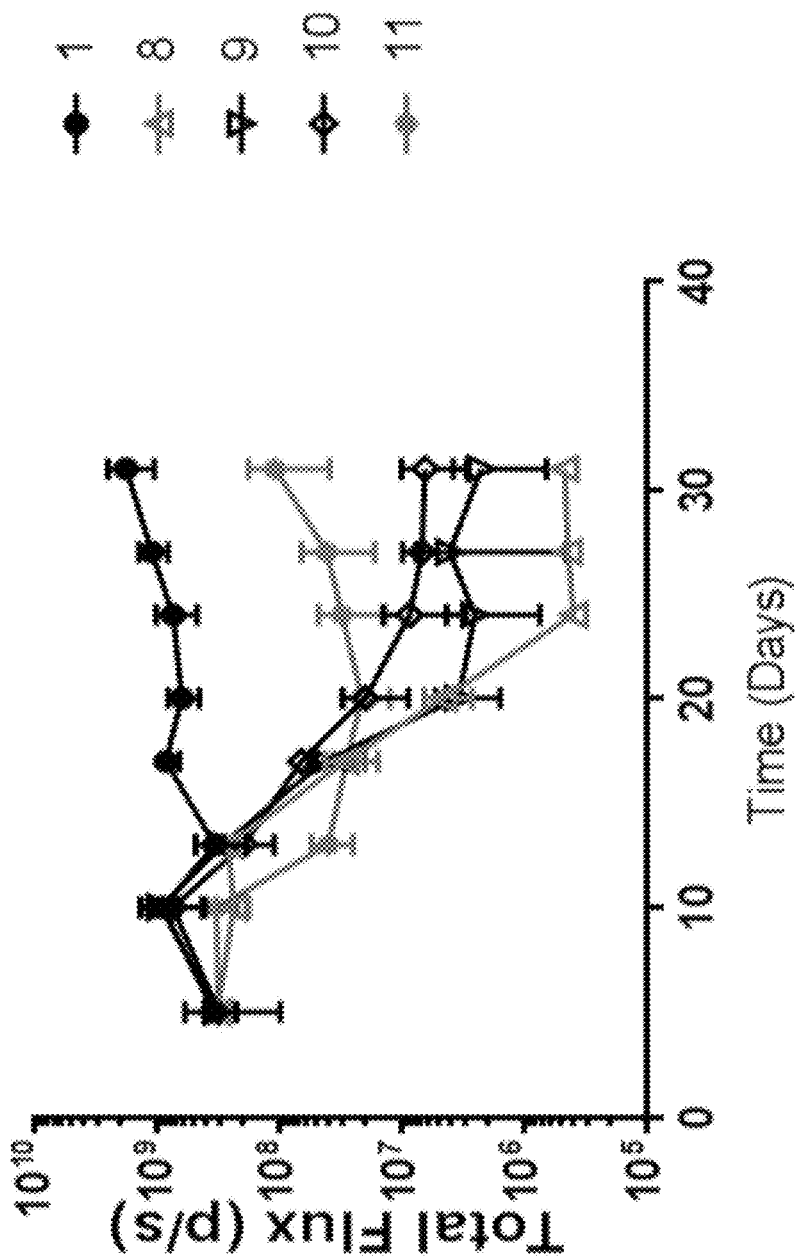
FIG. 20 shows quantitative analysis of SKOV3-fLUC-MUC16 tumor burden as measured by in vivo bioluminescence (IVIS) imaging. NSG mice (N=5 mice per group) were administered with SKOV3-fLUC-MUC16 tumor cell line via i.p. injection on Day 0. Tumor bearing mice were treated with one of the three different doses of MUC16-3 CAR-T cells via single i.p. injection five days after tumor cell administration and tumor burden was quantified via IVIS through the course of treatment. Test articles are listed in Table 9. Data shown are mean±SEM.

As shown in FIGS. 19-20, both MUC16-2 CAR-mbIL15-HER1t1 T cells and MUC16-3 CAR-mbIL15-HER1t1 T cells exhibited CAR-T dose dependent elimination of SKOV3-fLUC-MUC16 tumor cells in mice. MUC16-3 CAR-mbIL15-HER1t1 T cells exhibited potent anti-tumor response even at $1\times10^5$ CAR-T cells/mouse dose compared to MUC16-3 CAR-HER1t1 T cells lacking mbIL15 at $1\times10^6$ CAR-T cell/mouse dose.

TABLE 9

Description of Test Articles as utilized in FIGS. 19 and 20

| Group # | Test article |
|---|---|
| 1 | Saline (HBSS) |
| 5 | MUC16-2 CAR-mbIL15-HER1t1 (1E05 CAR-T/mouse) |
| 6 | MUC16-2 CAR-mbIL15-HER1t1 (5E05 CAR-T/mouse) |
| 7 | MUC16-2 CAR-mbIL15-HER1t1 (1E06 CAR-T/mouse) |
| 8 | MUC16-3 CAR-mbIL15-HER1t1 (1E05 CAR-T/mouse) |
| 9 | MUC16-3 CAR-mbIL15-HER1t1 (5E05 CAR-T/mouse) |
| 10 | MUC16-3 CAR-mbIL15-HER1t1 (1E06 CAR-T/mouse) |
| 11 | MUC16-3 CAR-HER1t1 (1E06 CAR-T/mouse) |

Example 13. Binding Affinity of Anti-MUC16 Monoclonal Antibodies

Binding affinity of various anti-MUC16 monoclonal antibodies (mAbs) were assessed by surface plasmon resonance (SPR) assay using Biacore 3000. Anti-MUC16 mAbs were generated via transient transfection of respective light and heavy chain plasmids into HEK-293 cells. Variable regions of anti-MUC16 mAbs were fused to mouse constant chain regions to generate chimeric mouse IgG1 mAbs. Truncated MUC16 fused to human Fc region was immobilized on sensor chip CM5. Different concentrations of mAbs were injected in solution phase and data was analyzed using BIAevaluation to calculate KD of mAbs.

TABLE 10

Affinity of three anti-MUC16 mAbs.

| Antibody | Binding affinity to MUC16-Fc antigen ($K_D$, M) |
|---|---|
| MUC16-1 mAb (mIgG1) | 1.02e−10 |
| MUC16-2 mAb (mIgG1) | 1.4e−11 |
| MUC16-3 mAb (mIgG1) | 4.24e−9 |

Unless defined otherwise, all technical and scientific terms and any acronyms used herein have the same meanings as commonly understood by one of ordinary skill in the art in the field of this invention.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein can be employed in practicing the present disclosure. It is intended that the following claims define the scope of the present disclosure and that methods and structures within the scope of these claims and their equivalents be covered thereby.

Sequences

Provided in Table 11 is a representative list of certain sequences included in embodiments provided herein.

TABLE 11

| Name | SEQ ID NO | Amino Acid Sequence | SEQ ID NO | Nucleotide Sequence |
|---|---|---|---|---|
| CAR Sequences | | | | |
| MUC16-1 VL | 1 | DIELTQSPSSLAVSAGEKVTMSCKSSQSLLNSRTRKNQLAWYQQKPGQSPELLIYWASTRQSGVPDRFTGSGSGTDFTLTISSVQAEDLAVYYCQQSYNLLTFGPGTKLEVKR | 95 | GACATCGAGCTGACACAGAGCCCATCTAGCCTGGCTGTGTCTGCCGGCGAGAAAGTGACCATGAGCTGCAAGAGCAGCCAGAGCCTGCTGAACAGCCGGACCAGAAAGAATCAGCTGGCCTGGTATCAGCAGAAGCCCGGCCAATCTCCTGAGCTGCTGATCTACTGGGCCAGCACAAGACAGAGCGGCGTGCCCGATAGATTCACAGGATCTGGCAGCGGCACCGACTTCACCCTGACAATCAGTTCTGTGCAGGCCGAGGACCTGGCCGTGTACTACTGTCAGCAGAGCTACAACCTGCTGACCTTCGGACCCGGCACCAAGCTGGAAGTGAAGAGA |
| MUC16-1 VH | 2 | VKLQESGGGFVKPGGSLKVSCAASGFTFSSYAMSWVRLSPEMRLEWVATISSAGGYIFYSDSVQGRFTISRDNAKNTLHLQMGSLRSGDTAMYYCARQGFGNYGDYYAMDYWGQGTTVTVSS | 96 | GTGAAGCTGCAAGAGTCCGGCGGAGGCTTTGTGAAGCCTGGCGGCTCTCTGAAAGTGTCCTGTGCCGCCAGCGGCTTCACCTTTAGCAGCTACGCCATGAGCTGGGTCCGACTGAGCCCTGAGATGAGACTGGAATGGGTCGCCACCATCAGTAGCGCAGGCGGCTACATCTTCTACAGCGACTCTGTGCAGGGCAGATTCACCATCAGCCGGGACAACGCCAAGAACACCCTGCACCTCCAGATGGGCAGTCTGAGAAGCGGCGATACCGCCATGTACTACTGCGCCAGACAAGGCTTCGGCAACTACGGCGACTACTATGCCATGGATTACTGGGGCCAGGGCACCACCGTGACAGTCTCTTCT |
| MUC16-2 VL | 3 | DIELTQSPSSLAVSAGEKVTMSCKSSQSLLNSRTRKNQLAWYQQKTGQSPELLIYWASTRQSGVPDRFTGSGSGTDFTLTISSVQAEDLAVYYCQQSYNLLTFGPGTKLEIKR | 97 | GACATCGAGCTGACACAGAGCCCATCTAGCCTGGCTGTGTCTGCCGGCGAGAAAGTGACCATGAGCTGCAAGAGCAGCCAGAGCCTGCTGAACAGCCGGACCAGAAAGAATCAGCTGGCCTGGTATCAGCAGAAAACCGGACAGAGCCCCGAGCTGCTGATCTACTGGGCCAGCACAAGACAGAGCGGCGTGCCCGATAGATTCACAGGATCTGGCAGCGGCACCGACTTCACCCTGACAATCAGTTCTGTGCAGGCCGAGGACCTGGCCGTGTACTACTGTCAGCAGAGCTACAACCTGCTGACCTTCGGACCCGGCACCAAGCTGGAAATCAAGAGA |
| MUC16-2 VH | 4 | VKLEESGGGFVKPGGSLKISCAASGFTFRNYAMSWVRLSPEMRLEWVATISSAGGYIFYSDSVQGRFTISRDNAKNTHLQMGSLRSGDTAMYYCARQGFGNYGDYYAMDYWGQGTTVTVSS | 98 | GTGAAGCTGGAAGAGTCCGGCGGAGGCTTTGTGAAGCCTGGCGGAAGCCTGAAGATCAGCTGTGCCGCCAGCGGCTTCACCTTCAGAAACTACGCCATGAGCTGGGTCCGACTGAGCCCCGAGATGAGACTGGAATGGGTCGCCACAATCAGCAGCGCAGGCGGCTACATCTTCTACAGCGATAGCGTGCAGGGCAGATTCACCATCAGCCGGGACAACGCCAAGAACACCCTGCACCTCCAGATGGGCAGTCTGAGATCTGGCGACACCGCCATGTACTACTGCGCCAGACAAGGCTTCGGCAACTACGGCGACTACTATGCCATGGATTACTGGGGCCAGGGCACCACCGTGACAGTCTCTTCT |
| MUC16-3 VL | 5 | DIKMAQSPSSVNASLGERVTITCKASRDINNFLSWFHQKPGKSPKTLIYRANRLVDGVPS | 99 | GACATCAAGATGGCTCAGTCCCCTTCTAGCGTGAATGCTTCGCTAGGGGAGCGTGTGACCATCACATGTAAAGCATCACGCGACATAAATAATTTCCTTTC |

TABLE 11-continued

Exemplary Sequences

|   |   |   |
|---|---|---|
| | RFSGSGSGQDYSFTIS<br>SLEYEDVGIYYCLQY<br>GDLYTFGGGTKLEIK | CTGGTTTCATCAGAAACCGGGCAAG<br>TCGCCTAAGACGCTGATTTACAGAG<br>CAAATCGGTTGGTAGATGGAGTGCC<br>AAGCAGATTCAGCGGGAGCGGAAG<br>TGGACAGGATTATAGCTTCACTATT<br>TCATCCCTGGAATACGAGGACGTAG<br>GTATCTATTATTGCCTCCAGTATGGC<br>GATCTTTACACATTTGGTGGGGGA<br>CTAAGCTGGAGATTAAG |
| MUC16-<br>3 VH | 6 DVQLLESGPGLVRPS<br>QSLSLTCSVTGYSIVS<br>HYYWNWIRQFPGNK<br>LEWMGYISSDGSNEY<br>NPSLKNRISISLDTSK<br>NQFFLKFDFVTTADT<br>ATYFCVRGVDYWGQ<br>GTTLTVSS | 100 GACGTGCAACTTCTGGAGAGCGGGC<br>CAGGGCTAGTCAGGCCCTCCCAGTC<br>GCTTTCACTGACTTGCAGTGTGACC<br>GGTTACTCTATTGTGAGTCACTACTA<br>TTGGAACTGGATTCGGCAGTTCCCA<br>GGCAACAAACTGGAATGGATGGGG<br>TACATATCTTCCGATGGCTCGAATG<br>AATATAACCCATCATTGAAAAATCG<br>TATTTCCATCAGTCTGGATACGAGT<br>AAAAACCAGTTTTTCCTCAAATTCG<br>ATTTCGTGACTACAGCAGATACTGC<br>CACATACTTCTGTGTACGAGGTGTC<br>GATTATTGGGGACAGGGCACAACGC<br>TGACCGTAAGTTCT |
| MUC16-<br>4 VL | 7 DIQMTQSSSFLSVSLG<br>GRVTITCKASDLIHN<br>WLAWYQQKPGNAPR<br>LLISGATSLETVPSR<br>FSGSGSGNDYTLSIAS<br>LQTEDAATYYCQQY<br>WTTPFTFGSGTKLEIK | 101 GACATCCAGATGACCCAGAGCAGCA<br>GCTTCCTGAGCGTGTCCCTTGGCG<br>CAGAGTGACCATCACCTGTAAAGCC<br>AGCGACCTGATCCACAACTGGCTGG<br>CCTGGTATCAGCAGAAGCCTGGCAA<br>CGCTCCCAGACTGCTGATTAGCGGC<br>GCCACCTCTCTGGAAACAGGCGTGC<br>CAAGCAGATTTTCCGGCAGCGGCTC<br>CGGCAACGACTACACACTGTCTATT<br>GCCAGCCTGCAGACCGAGGATGCCG<br>CCACCTATTACTGCCAGCAGTACTG<br>GACCACACCTTTCACCTTTGGCAGC<br>GGCACCAAGCTGGAAATCAAG |
| MUC16-<br>4 VH | 8 DVQLQESGPGLVNPS<br>QSLSLTCTVTGYSITN<br>DYAWNWIRQFPGNK<br>LEWMGYINYSGYTT<br>YNPSLKSRISITRDTS<br>KNQFFLHLNSVTTED<br>TATYYCARWDGGLT<br>YWGQGTLVTVSA | 102 GACGTTCAGCTGCAAGAGTCTGGCC<br>CTGGCCTGGTCAATCCTAGCCAGAG<br>CCTGAGCCTGACATGTACCGTGACC<br>GGCTACAGCATCACCAACGACTACG<br>CCTGGAACTGGATCAGACAGTTCCC<br>CGGCAACAAGCTGGAATGGATGGG<br>CTACATCAACTACAGCGGCTACACC<br>ACCTACAATCCCAGCCTGAAGTCCC<br>GGATCTCCATCACCAGAGACACCAG<br>CAAGAACCAGTTCTTCCTGCACCTG<br>AACAGCGTGACCACCGAGGATACCG<br>CCACCTACTACTGCGCTAGATGGGA<br>TGGCGGCCTGACATATTGGGGCCAG<br>GGAACACTGGTCACCGTGTCTGCT |
| MUC16-<br>5 VL | 9 DIQMTQSPSSLSASV<br>GDRVTITCKASDLIH<br>NWLAWYQQKPGKA<br>PKLLISGATSLETVP<br>SRFSGSGSGTDFTLTI<br>SSLQPEDFATYYCQQ<br>YWTTPFTFGQGTKVE<br>IKR | 103 GACATCCAGATGACCCAGAGCCCCA<br>GCAGCCTGAGCGCCAGCGTGGGCGA<br>CAGGGTGACCATCACCTGCAAGGCC<br>AGCGACCTGATCCACAACTGGCTGG<br>CCTGGTACCAGCAGAAGCCCGGCAA<br>GGCCCCCAAGCTGCTGATCAGCGGC<br>GCCACCAGCCTGGAGACCGGCGTGC<br>CCAGCAGGTTCAGCGGCAGCGGCAG<br>CGGCACCGACTTCACCCTGACCATC<br>AGCAGCCTGCAGCCCGAGGACTTCG<br>CCACCTACTACTGCCAGCAGTACTG<br>GACCACCCCCTTCACCTTCGGCCAG<br>GGCACCAAGGTGGAGATCAAGAGG |
| MUC16-<br>5 VH-L | 10 EVQLVESGGGLVQPG<br>GSLRLSCAASGYSITN<br>DYAWNWVRQAPGK<br>GLEWVGYINYSGYTT<br>YNPSLKSRFTISRDNS<br>KNTLYLQMNSLRAE<br>DTAVYYCARWDGGL<br>TYWGQGTLVTVSS | 194 GAGGTGCAGCTGGTGGAGAGCGGC<br>GGCGGCCTGGTGCAGCCCGGCGGCA<br>GCCTGAGGCTGAGCTGCGCCGCCAG<br>CGGCTACAGCATCACCAACGACTAC<br>GCCTGGAACTGGGTGAGGCAGGCC<br>CCGGCAAGGGCCTGGAGTGGGTGG<br>GCTACATCAACTACAGCGGCTACAC<br>CACCTACAACCCCAGCCTGAAGAGC<br>AGGTTCACCATCAGCAGGGACAACA<br>GCAAGAACACCCTGTACCTGCAGAT |

| | | | |
|---|---|---|---|
| | | | GAACAGCCTGAGGGCCGAGGACAC CGCCGTGTACTACTGCGCCAGGTGG GACGGCGGCCTGACCTACTGGGGCC AGGGCACCCTGGTGACCGTGAGCAG C |
| MUC16-5 VH-F | 11 | EVQLVESGGGLVQPG GSLRLSCAASGYSITN DYAWNWVRQAPGK GLEWVGYINYSGYTT YNPSLKSRFTISRDNS KNTFYLQMNSLRAE DTAVYYCARWDGGL TYWGQGTLVTVSS | 195 GAGGTGCAGCTGGTGGAGAGCGGC GGCGGCCTGGTGCAGCCCGGCGGCA GCCTGAGGCTGAGCTGCGCCGCCAG CGGCTACAGCATCACCAACGACTAC GCCTGGAACTGGGTGAGGCAGGCCC CCGGCAAGGGCCTGGAGTGGGTGG GCTACATCAACTACAGCGGCTACAC CACCTACAACCCCAGCCTGAAGAGC AGGTTCACCATCAGCAGGGACAACA GCAAGAACACCTTCTACCTGCAGAT GAACAGCCTGAGGGCCGAGGACAC CGCCGTGTACTACTGCGCCAGGTGG GACGGCGGCCTGACCTACTGGGGCC AGGGCACCCTGGTGACCGTGAGCAG C |
| MUC16-6 VL | 12 | DIVLTQSPAIMSASLG ERVTMTCTASSSVSS SYLHWYQQKPGSSP KLWIYSTSNLASGVP GRFSGSGSGTSYSLTI SSMEAEDAATYYCH QYHRSPYTFGGGTKV EIKR | 104 GACATCGTGCTGACACAGAGCCCTG CCATCATGTCTGCCAGCCTCGGCGA GCGAGTGACCATGACATGTACAGCC AGCAGCAGCGTGTCCAGCAGCTACC TGCATTGGTATCAGCAGAAGCCCGG CAGCAGCCCCAAGCTGTGGATCTAC AGCACAAGCAATCTGGCCAGCGGCG TGCCAGGCAGATTTTCTGGTTCTGG CAGCGGCACCAGCTACAGCCTGACA ATCAGCAGCATGGAAGCCGAGGAT GCCGCCACCTACTACTGCCACCAGT ACCACAGAAGCCCCTACACCTTTGG CGGAGGCACCAAGGTGGAAATCAA GCGG |
| MUC16-6 VH | 13 | EVQLQQSGAELVKPG ASVKLSCTASGFNIK DTYMHWVKQRPEQG LEWIGRVDPANGNT KYDPKFQGKATLTA DTSSNTAYLQLSSLTS EDTAVYFCVRDYYG HTYGFAFCDQGTTLT VSA | 105 GAGGTTCAGCTGCAGCAGTCTGGCG CCGAACTTGTGAAACCTGGCGCCTC TGTGAAGCTGAGCTGTACCGCCAGC GGCTTCAACATCAAGGACACCTACA TGCACTGGGTCAAGCAGAGGCCTGA GCAGGGCCTCGAATGGATCGGAAG AGTGGATCCCGCCAACGGCAACACC AAATACGACCCCAAGTTCCAGGGCA AAGCCACACTGACCGCCGACACCTC TAGCAACACAGCCTACCTGCAGCTG TCCAGCCTGACCTCTGAAGATACCG CCGTGTACTTCTGCGTGCGGGACTA CTACGGCCATACCTACGGCTTCGCC TTCTGCGACCAAGGCACAACCCTGA CAGTGTCTGCT |
| MUC16-7 VL | 14 | DIQMTQSPSSLSASV GDRVTITCTASSSVSS SYLHWYQQKPGKAP KLLIYSTSNLASGVPS RFSGSGSGTDFTLTIS SLQPEDFATYYCHQY HRSPYTFGQGTKVEI KR | 106 GACATCCAGATGACACAGAGCCCTA GCAGCCTGTCTGCCAGCGTGGGAGA CAGAGTGACCATCACCTGTACAGCC AGCAGCAGCGTGTCCAGCAGCTACC TGCATTGGTATCAGCAGAAGCCCGG CAAGGCCCCTAAGCTGCTGATCTAC AGCACCAGCAATCTGGCCAGCGGCG TGCCAAGCAGATTTTCTGGCTCTGG CAGCGGCACCGACTTCACCCTGACC ATATCTAGCCTGCAGCCTGAGGACT TCGCCACCTACTACTGCCACCAGTA CCACAGAAGCCCCTACACCTTTGGC CAGGGCACCAAGGTGGAAATCAAG CGG |
| MUC16-7 VH | 15 | EVQLVESGGGLVQPG GSLRLSCAASGFNIK DTYMHWVRQAPGK GLEWVGRVDPANGN TKYDPKFQGRFTISA DTSKNTAYLQMNSL RAEDTAVYYCVRDY YGHTYGFAFWGQGT LVTVSS | 107 GAGGTGCAGCTGGTTGAATCTGGCG GAGGACTGGTTCAGCCTGGCGGATC TCTGAGACTGTCTTGTGCCGCCAGC GGCTTCAACATCAAGGACACCTACA TGCACTGGGTCCGACAGGCCCCTGG CAAAGGACTTGAGTGGGTTGGAAGA GTGGACCCCGCCAACGGCAACACCA AATACGACCCCAAGTTCCAGGGCAG ATTCACCATCAGCGCCGACACCAGC AAGAACACCGCCTACCTGCAGATGA |

TABLE 11-continued

Exemplary Sequences

|  |  |  |
|---|---|---|
| | | ACAGCCTGAGAGCCGAGGACACCG<br>CCGTGTACTATTGCGTGCGGGATTA<br>CTACGGCCATACCTACGGCTTCGCC<br>TTTTGGGGCCAGGGCACACTGGTTA<br>CCGTTAGCTCT |
| CD8alpha<br>hinge | 16 KPTTTPAPRPPTPAPTIA<br>SQPLSLRPEACRPAAGG<br>AVHTRGLDFACD | 108 AAGCCCACCACCACCCCTGCCCCTAGAC<br>CTCCAACCCCAGCCCCTACAATCGCCAG<br>CCAGCCCCTGAGCCTGAGGCCCGAAGC<br>CTGTAGACCTGCCGCTGGCGGAGCCGTG<br>CACACCAGAGGCCTGGATTTCGCCTGCG<br>AC |
| CD8alpha<br>2x | 17 KPTTTPAPRPPTPAPT<br>IASQPLSLRPEASRPA<br>AGGAVHTRGLDFAS<br>DKPTTTPAPRPPTPAP<br>TIASQPLSLRPEACRP<br>AAGGAVHTRGLDFA<br>CD | 109 AAACCTACTACAACTCCTGCCCCCC<br>GGCCTCCTACACCAGCTCCTACTAT<br>CGCCTCCCAGCCACTCAGTCTCAGA<br>CCCGAGGCTTCTAGGCCAGCGGCCG<br>GAGGCGCGGTCCACACCCGCGGGCT<br>GGACTTTGCATCCGATAAGCCCACC<br>ACCACCCCTGCCCCTAGACCTCCAA<br>CCCCAGCCCCTACAATCGCCAGCCA<br>GCCCCTGAGCCTGAGGCCCGAAGCC<br>TGTAGACCTGCCGCTGGCGGAGCCG<br>TGCACACCAGAGGCCTGGATTTCGC<br>CTGCGAC |
| CD8alpha<br>3x | 18 KPTTTPAPRPPTPAPT<br>IASQPLSLRPEASRPA<br>AGGAVHTRGLDFAS<br>DKPTTTPAPRPPTPAP<br>TIASQPLSLRPEASRP<br>AAGGAVHTRGLDFA<br>SDKPTTTPAPRPPTPA<br>PTIASQPLSLRPEACR<br>PAAGGAVHTRGLDF<br>ACD | 110 AAGCCTACCACCACCCCCGCACCTC<br>GTCCTCCAACCCCTGCACCTACGAT<br>TGCCAGTCAGCCTCTTTCACTGCGG<br>CCTGAGGCCAGCAGACCAGCTGCCG<br>GCGGTGCCGTCCATACAAGAGGACT<br>GGACTTCGCGTCCGATAAACCTACT<br>ACCACTCCAGCCCCAAGGCCCCCAA<br>CCCCAGCACCGACTATCGCATCACA<br>GCCTTTGTCACTGCGTCCTGAAGCC<br>AGCCGGCCAGCTGCAGGGGGGGCC<br>GTCCACACAAGGGGACTCGACTTTG<br>CGAGTGATAAGCCCACCACCACCCC<br>TGCCCCTAGACCTCCAACCCCAGCC<br>CCTACAATCGCCAGCCAGCCCCTGA<br>GCCTGAGGCCCGAAGCCTGTAGACC<br>TGCCGCTGGCGGAGCCGTGCACACC<br>AGAGGCCTGGATTTCGCCTGCGAC |
| CD8alpha<br>4x | 19 TTPAPRPPTPAPTIAS<br>QPLSLRPEASRPAAG<br>GAVHTRGLDFASDKP<br>TTTPAPRPPTPAPTIA<br>SQPLSLRPEASRPAA<br>GGAVHTRGLDFASD<br>KPTTTPAPRPPTPAPT<br>IASQPLSLRPEASRPA<br>AGGAVHTRGLDFAS<br>DKPTTTPAPRPPTPAP<br>TIASQPLSLRPEACRP<br>AAGGAVHTRGLDFA<br>CD | 111 AAGCCTACCACCACCCCCGCACCTC<br>GTCCTCCAACCCCTGCACCTACGAT<br>TGCCAGTCAGCCTCTTTCACTGCGG<br>CCTGAGGCCAGCAGACCAGCTGCCG<br>GCGGTGCCGTCCATACAAGAGGACT<br>GGACTTCGCGTCCGATAAACCTACT<br>ACCACTCCAGCCCCAAGGCCCCCAA<br>CCCCAGCACCGACTATCGCATCACA<br>GCCTTTGTCACTGCGTCCTGAAGCC<br>AGCCGGCCAGCTGCAGGGGGGGCC<br>GTCCACACAAGGGGACTCGACTTTG<br>CGAGTGATAAACCTACTACAACTCC<br>TGCCCCCCGGCCTCCTACACCAGCT<br>CCTACTATCGCCTCCCAGCCACTCA<br>GTCTCAGACCCGAGGCTTCTAGGCC<br>AGCGGCCGGAGGCGCGGTCCACACC<br>CGCGGGCTGGACTTTGCATCCGATA<br>AGCCCACCACCACCCCTGCCCCTAG<br>ACCTCCAACCCCAGCCCCTACAATC<br>GCCAGCCAGCCCCTGAGCCTGAGGC<br>CCGAAGCCTGTAGACCTGCCGCTGG<br>CGGAGCCGTGCACACCAGAGGCCTG<br>GATTTCGCCTGCGAC |
| CD8alpha<br>TM | 20 IYIWAPLAGTCGVLLLS<br>LVITLYCNHRN | 112 ATCTACATCTGGGCCCCTCTGGCCGGCA<br>CCTGTGGCGTGCTGCTGCTGAGCCTGGT<br>CATCACCCTGTACTGCAACCACCGGAAT |
| CD28 TM | 21 FWVLVVVGGVLACYSL<br>LVTVAFIIFWV | 113 TTTTGGGTGCTGGTGGTGGTTGGTGGAG<br>TCCTGGCTTGCTATAGCTTGCTAGTAAC<br>AGTGGCCTTTATTATTTTCTGGGTG |

TABLE 11-continued

Exemplary Sequences

| | | | |
|---|---|---|---|
| 4-1BB signaling domain | 22 | KRGRKKLLYIFKQPFM RPVQTTQEEDGCSCRFP EEEEGGCEL | 114 | AAGAGAGGCCGGAAGAAACTGCTGTAC ATCTTCAAGCAGCCCTTCATGCGGCCCG TGCAGACCACCCAGGAAGAGGACGGCT GCAGCTGCCGGTTCCCCGAGGAAGAGG AAGGCGGCTGCGAACTG |
| CD28 signaling domain | 23 | RSKRSRGGHSDYMNM TPRRPGPTRKHYQPYAP PRDFAAYRS | 115 | AGGAGCAAGCGGAGCAGAGGCGGCCAC AGCGACTACATGAACATGACCCCCCGG AGGCCTGGCCCCACCCGGAAGCACTAC CAGCCCTACGCCCCTCCCAGGGACTTCG CCGCCTACCGGAGC |
| DNAX-activation protein 10 (DAP 10) Signaling Domain | 24 | LCARPRRSPAQEDGK VYINMPGRG | 116 | CTGTGCGCACGCCCACGCCGCAGCC CCGCCCAAGAAGATGGCAAAGTCTA CATCAACATGCCAGGCAGGGGC |
| DNAX-activation protein 12 (DAP12) Signaling Domain | 25 | YFLGRLVPRGRGAAE AATRKQRITETESPY QELQGQRSDVYSDL NTQRPYYK | 117 | TACTTCCTGGGCCGGCTGGTCCCCTC GGGGGCGAGGGGCTGCGGAGGCAG CGACCCGGAAACAGCGTATCACTGA GACCGAGTCGCCTTATCAGGAGCTC CAGGGTCAGAGGTCGGATGTCTACA GCGACCTCAACACACAGAGGCCGTA TTACAAA |
| CD3ζ signaling domain | 26 | RVKFSRSADAPAYQQG QNQLYNELNLGRREEY DVLDKRRGRDPEMGG KPRRKNPQEGLYNELQ KDKMAEAYSEIGMKGE RRRGKGHDGLYQGLST ATKDTYDALHMQALPP R | 118 | CGGGTGAAGTTCAGCCGGAGCGCCGAC GCCCCTGCCTACCAGCAGGGCCAGAAC CAGCTGTACAACGAGCTGAACCTGGGC CGGAGGGAGGAGTACGACGTGCTGGAC AAGCGGAGAGGCCGGGACCCTGAGATG GGCGGCAAGCCCCGGAGAAAGAACCCT CAGGAGGGCCTGTATAACGAACTGCAG AAAGACAAGATGGCCGAGGCCTACAGC GAGATCGGCATGAAGGGCGAGCGGCGG AGGGGCAAGGGCCACGACGGCCTGTAC CAGGGCCTGAGCACCGCCACCAAGGAT ACCTACGACGCCCTGCACATGCAGGCCC TGCCCCCCAGA |
| MUC16-2 scFv. CD8a. 4-1BBz | 27 | VKLEESGGGFVKPGG SLKISCAASGFTFRNY AMSWVRLSPEMRLE WVATISSAGGYIFYS DSVQGRFTISRDNAK NTLHLQMGSLRSGDT AMYYCARQGFGNYG DYYAMDYWGQGTT VTVSSGGGGSGGGGS GGGGSDIELTQSPSSL AVSAGEKVTMSCKSS QSLLNSRTRKNQLA WYQQKTGQSPELLIY WASTRQSGVPDRFTG SGSGTDFTLTISSVQA EDLAVYYCQQSYNL LTFGPGTKLEIKRKPT TTPAPRPPTPAPTIAS QPLSLRPEACRPAAG GAVHTRGLDFACDIY IWAPLAGTCGVLLLS LVITLYCNHRNKRGR KKLLYIFKQPFMRPV QTTQEEDGCSCRFPE EEEGGCELRVKFSRS ADAPAYQQGQNQLY NELNLGRREEYDVLD KRRGRDPEMGGKPR RKNPQEGLYNELQK DKMAEAYSEIGMKG ERRRGKGHDGLYQG LSTATKDTYDALHM QALPPR | 119 | GTGAAGCTGGAAGAGTCCGGCGGA GGCTTTGTGAAGCCTGGCGGAAGCC TGAAGATCAGCTGTGCCGCCAGCGG CTTCACCTTCAGAAACTACGCCATG AGCTGGGTCCGACTGAGCCCCGAGA TGAGACTGGAATGGGTCGCCACAAT CAGCAGCGCAGGCGGCTACATCTTC TACAGCGATAGCGTGCAGGGCAGAT TCACCATCAGCCGGGACAACGCCAA GAACACCCTGCACCTCCAGATGGGC AGTCTGAGATCTGGCGACACCGCCA TGTACTACTGCGCCAGACAAGGCTT CGGCAACTACGGCGACTACTATGCC ATGGATTACTGGGGCCAGGGCACCA CCGTGACAGTCTCTTCTGGTGGCGG AGGCGGATCTGACATCGAGCTGA CACAGAGCCCATCTAGCCTGGCTGT GTCTGCCGGCGAGAAAGTGACCATG AGCTGCAAGAGCAGCCAGAGCCTGC TGAACAGCCGGACCAGAAAGAATC AGCTGGCCTGGTATCAGCAGAAAAC CGGACAGAGCCCCGAGCTGCTGATC TACTGGGCCAGCACAAGACAGAGC GGCGTGCCCGATAGATTCACAGGAT CTGGCAGCGGCACCGACTTCACCCT GACAATCAGTTCTGTGCAGGCCGAG GACCTGGCCGTGTACTACTGTCAGC AGAGCTACAACCTGCTGACCTTCGG ACCCGGCACCAAGCTGGAAATCAAG AGAAAGCCCACCACCACCCCTGCCC CTAGACCTCCAACCCCAGCCCCTAC AATCGCCAGCCAGCCCCTGAGCCTG AGGCCCGAAGCCTGTAGACCTGCCG CTGGCGGAGCCGTGCACACCAGAGG CCTGGATTTCGCCTGCGACATCTAC ATCTGGGCCCCTCTGGCCGGCACCT |

TABLE 11-continued

Exemplary Sequences

|  |  |  |
|---|---|---|
|  |  | GTGGCGTGCTGCTGCTGAGCCTGGT |
|  |  | CATCACCCTGTACTGCAACCACCGG |
|  |  | AATAAGAGAGGCCGGAAGAAACTG |
|  |  | CTGTACATCTTCAAGCAGCCCTTCAT |
|  |  | GCGGCCCGTGCAGACCACCCAGGAA |
|  |  | GAGGACGGCTGCAGCTGCCGGTTCC |
|  |  | CCGAGGAAGAGGAAGGCGGCTGCG |
|  |  | AACTGCGGGTGAAGTTCAGCCGGAG |
|  |  | CGCCGACGCCCCTGCCTACCAGCAG |
|  |  | GGCCAGAACCAGCTGTACAACGAGC |
|  |  | TGAACCTGGGCCGGAGGGAGGAGT |
|  |  | ACGACGTGCTGGACAAGCGGAGAG |
|  |  | GCCGGGACCCTGAGATGGGCGGCA |
|  |  | AGCCCCGGAGAAAGAACCCTCAGG |
|  |  | AGGGCCTGTATAACGAACTGCAGAA |
|  |  | AGACAAGATGGCCGAGGCCTACAG |
|  |  | CGAGATCGGCATGAAGGGCGAGCG |
|  |  | GCGGAGGGGCAAGGGCCACGACGG |
|  |  | CCTGTACCAGGGCCTGAGCACCGCC |
|  |  | ACCAAGGATACCTACGACGCCCTGC |
|  |  | ACATGCAGGCCCTGCCCCCCAGA |
| MUC16-<br>2 scFv.<br>CD8a<br>(2x).4-<br>1BBz | 28 VKLEESGGGFVKPGG<br>SLKISCAASGFTFRNY<br>AMSWVRLSPEMRLE<br>WVATISSAGGYIFYS<br>DSVQGRFTISRDNAK<br>NTLHLQMGSLRSGDT<br>AMYYCARQGFGNYG<br>DYYAMDYWGQGTT<br>VTVSSGGGGSGGGGS<br>GGGGSDIELTQSPSSL<br>AVSAGEKVTMSCKSS<br>QSLLNSRTRKNQLA<br>WYQQKTGQSPELLIY<br>WASTRQSGVPDRFTG<br>SGSGTDFTLTISSVQA<br>EDLAVYYCQQSYNL<br>LTFGPGTKLEIKRKPT<br>TTPAPRPPTPAPTIAS<br>QPLSLRPEASRPAAG<br>GAVHTRGLDFASDKP<br>TTTPAPRPPTPAPTIA<br>SQPLSLRPEACRPAA<br>GGAVHTRGLDFACDI<br>YIWAPLAGTCGVLLL<br>SLVITLYCNHRNKRG<br>RKKLLYIFKQPFMRP<br>VQTTQEEDGCSCRFP<br>EEEEGGCELRVKFSR<br>SADAPAYQQGQNQL<br>YNELNLGRREEYDVL<br>DKRRGRDPEMGGKP<br>RRKNPQEGLYNELQ<br>KDKMAEAYSEIGMK<br>GERRRGKGHDGLYQ<br>GLSTATKDTYDALH<br>MQALPPR | 120 GTGAAGCTGGAAGAGTCCGGCGGA<br>GGCTTTGTGAAGCCTGGCGGAAGCC<br>TGAAGATCAGCTGTGCCGCCAGCGG<br>CTTCACCTTCAGAAACTACGCCATG<br>AGCTGGGTCCGACTGAGCCCCGAGA<br>TGAGACTGGAATGGGTCGCCACAAT<br>CAGCAGCGCAGGCGGCTACATCTTC<br>TACAGCGATAGCGTGCAGGGCAGAT<br>TCACCATCAGCCGGGACAACGCCAA<br>GAACACCCTGCACCTCCAGATGGGC<br>AGTCTGAGATCGGCGACACCGCCA<br>TGTACTACTGCGCCAGACAAGGCTT<br>CGGCAACTACGGCGACTACTATGCC<br>ATGGATTACTGGGGCCAGGGCACCA<br>CCGTGACAGTCTCTTCTGGTGGCGG<br>TGGCTCGGGCGGTGGTGGGTCGGGT<br>GGCGGCGGATCTGACATCGAGCTGA<br>CACAGAGCCCATCTAGCCTGGCTGT<br>GTCTGCCGGCGAGAAAGTGACCATG<br>AGCTGCAAGAGCAGCCAGAGCCTGC<br>TGAACAGCCGGACCAGAAAGAATC<br>AGCTGGCCTGGTATCAGCAGAAAAC<br>CGGACAGAGCCCCGAGCTGCTGATC<br>TACTGGGCCAGCACAAGACAGAGC<br>GGCGTGCCCGATAGATTCACAGGAT<br>CTGGCAGCGGCACCGACTTCACCCT<br>GACAATCAGTTCTGTGCAGGCCGAG<br>GACCTGGCCGTGTACTACTGTCAGC<br>AGAGCTACAACCTGCTGACCTTCGG<br>ACCCGGCACCAAGCTGGAAATCAAG<br>AGAAAACCTACTACAACTCCTGCCC<br>CCCGGCCTCCTACACCAGCTCCTAC<br>TATCGCCTCCCAGCCACTCAGTCTC<br>AGACCCGAGGCTTCTAGGCCAGCGG<br>CCGGAGGCGCGGTCCACACCCGCGG<br>GCTGGACTTTGCATCCGATAAGCCC<br>ACCACCACCCCTGCCCCTAGACCTC<br>CAACCCCAGCCCCTACAATCGCCAG<br>CCAGCCCCTGAGCCTGAGGCCCGAA<br>GCCTGTAGACCTGCCGCTGGCGGAG<br>CCGTGCACACCAGAGGCCTGGATTT<br>CGCCTGCGACATCTACATCTGGGCC<br>CCTCTGGCCGGCACCTGTGGCGTGC<br>TGCTGCTGAGCCTGGTCATCACCCT<br>GTACTGCAACCACCGGAATAAGAGA<br>GGCCGGAAGAAACTGCTGTACATCT<br>TCAAGCAGCCCTTCATGCGGCCCGT<br>GCAGACCACCCAGGAAGAGGACGG<br>CTGCAGCTGCCGGTTCCCCGAGGAA<br>GAGGAAGGCGGCTGCGAACTGCGG<br>GTGAAGTTCAGCCGGAGCGCCGACG<br>CCCCTGCCTACCAGCAGGGCCAGAA<br>CCAGCTGTACAACGAGCTGAACCTG<br>GGCCGGAGGGAGGAGTACGACGTG<br>CTGGACAAGCGGAGAGGCCGGGAC<br>CCTGAGATGGGCGGCAAGCCCCGGA |

TABLE 11-continued

Exemplary Sequences

| | | |
|---|---|---|
| | | GAAAGAACCCTCAGGAGGGCCTGTA |
| | | TAACGAACTGCAGAAAGACAAGAT |
| | | GGCCGAGGCCTACAGCGAGATCGGC |
| | | ATGAAGGGCGAGCGGCGGAGGGGC |
| | | AAGGGCCACGACGGCCTGTACCAGG |
| | | GCCTGAGCACCGCCACCAAGGATAC |
| | | CTACGACGCCCTGCACATGCAGGCC |
| | | CTGCCCCCCAGA |
| MUC16-<br>2 scFv.<br>CD8a<br>(3x).4-<br>1BBz | 29 VKLEESGGGFVKPGG<br>SLKISCAASGFTFRNY<br>AMSWVRLSPEMRLE<br>WVATISSAGGYIFYS<br>DSVQGRFTISRDNAK<br>NTLHLQMGSLRSGDT<br>AMYYCARQGFGNYG<br>DYYAMDYWGQGTT<br>VTVSSGGGGSGGGGS<br>GGGGSDIELTQSPSSL<br>AVSAGEKVTMSCKSS<br>QSLLNSRTRKNQLA<br>WYQQKTGQSPELLIY<br>WASTRQSGVPDRFTG<br>SGSGTDFTLTISSVQA<br>EDLAVYYCQQSYNL<br>LTFGPGTKLEIKRKPT<br>TTPAPRPPTPAPTIAS<br>QPLSLRPEASRPAAG<br>GAVHTRGLDFASDKP<br>TTTPAPRPPTPAPTIA<br>SQPLSLRPEASRPAA<br>GGAVHTRGLDFASD<br>KPTTTPAPRPPTPAPT<br>IASQPLSLRPEACRPA<br>AGGAVHTRGLDFAC<br>DIYIWAPLAGTCGVL<br>LLSLVITLYCNHRNK<br>RGRKKLLYIFKQPFM<br>RPVQTTQEEDGCSCR<br>FPEEEEGGCELRVKF<br>SRSADAPAYQQGQN<br>QLYNELNLGRREEYD<br>VLDKRRGRDPEMGG<br>KPRRKNPQEGLYNEL<br>QKDKMAEAYSEIGM<br>KGERRRGKGHDGLY<br>QGLSTATKDTYDAL<br>HMQALPPR | 121 GTGAAGCTGGAAGAGTCCGGCGGA<br>GGCTTTGTGAAGCTGGCGGAAGCC<br>TGAAGATCAGCTGTGCCGCCAGCGG<br>CTTCACCTTCAGAAACTACGCCATG<br>AGCTGGGTCCGACTGAGCCCCGAGA<br>TGAGACTGGAATGGGTCGCCACAAT<br>CAGCAGCGCAGGCGGCTACATCTTC<br>TACAGCGATAGCGTGCAGGGCAGAT<br>TCACCATCAGCCGGGACAACGCCAA<br>GAACACCCTGCACCTCCAGATGGGC<br>AGTCTGAGATCTGGCGACACCGCCA<br>TGTACTACTGCGCCAGACAAGGCTT<br>CGGCAACTACGGCGACTACTATGCC<br>ATGGATTACTGGGGCCAGGGCACCA<br>CCGTGACAGTCTCTTCTGGTGGCGG<br>TGGCTCGGGCGGTGGTGGGTCGGGT<br>GGCGGCGGATCTGACATCGAGCTGA<br>CACAGAGCCCATCTAGCCTGGCTGT<br>GTCTGCCGGCGAGAAAGTGACCATG<br>AGCTGCAAGAGCAGCCAGAGCCTGC<br>TGAACAGCCGGACCAGAAAGAATC<br>AGCTGGCCTGGTATCAGCAGAAAAC<br>CGGACAGAGCCCCGAGCTGCTGATC<br>TACTGGGCCAGCACAAGACAGAGC<br>GGCGTGCCCGATAGATTCACAGGAT<br>CTGGCAGCGGCACCGACTTCACCCT<br>GACAATCAGTTCTGTGCAGGCCGAG<br>GACCTGGCCGTGTACTACTGTCAGC<br>AGAGCTACAACCTGCTGACCTTCGG<br>ACCCGGCACCAAGCTGGAAATCAAG<br>AGAAAGCCTACCACCACCCCCGCAC<br>CTCGTCCTCCAACCCCTGCACCTAC<br>GATTGCCAGTCAGCCTCTTTCACTGC<br>GGCCTGAGGCCAGCAGACCAGCTGC<br>CGGCGGTGCCGTCCATACAAGAGGA<br>CTGGACTTCGCGTCCGATAAACCTA<br>CTACCACTCCAGCCCCAAGGCCCCC<br>AACCCCAGCACCGACTATCGCATCA<br>CAGCCTTTGTCACTGCGTCCTGAAG<br>CCAGCCGGCCAGCTGCAGGGGGGG<br>CCGTCCACACAAGGGGACTCGACTT<br>TGCGAGTGATAAGCCCACCACCACC<br>CCTGCCCCTAGACCTCCAACCCCAG<br>CCCCTACAATCGCCAGCCAGCCCCT<br>GAGCCTGAGGCCCGAAGCCTGTAGA<br>CCTGCCGCTGGCGGAGCCGTGCACA<br>CCAGAGGCCTGGATTTCGCCTGCGA<br>CATCTACATCTGGGCCCCTCTGGCC<br>GGCACCTGTGGCGTGCTGCTGCTGA<br>GCCTGGTCATCACCCTGTACTGCAA<br>CCACCGGAATAAGAGAGGCCGGAA<br>GAAACTGCTGTACATCTTCAAGCAG<br>CCCTTCATGCGGCCCGTGCAGACCA<br>CCCAGGAAGAGGACGGCTGCAGCT<br>GCCGGTTCCCCGAGGAAGAGGAAG<br>GCGGCTGCGAACTGCGGGTGAAGTT<br>CAGCCGGAGCGCCGACGCCCCTGCC<br>TACCAGCAGGGCCAGAACCAGCTGT<br>ACAACGAGCTGAACCTGGGCCGGA<br>GGGAGGAGTACGACGTGCTGGACA<br>AGCGGAGAGGCCGGGACCCTGAGA<br>TGGGCGGCAAGCCCCGGAGAAAGA<br>ACCCTCAGGAGGGCCTGTATAACGA<br>ACTGCAGAAAGACAAGATGGCCGA<br>GGCCTACAGCGAGATCGGCATGAAG<br>GGCGAGCGGCGGAGGGGCAAGGGC<br>CACGACGGCCTGTACCAGGGCCTGA |

TABLE 11-continued

Exemplary Sequences

|  |  |  |
|---|---|---|
|  |  | GCACCGCCACCAAGGATACCTACGA CGCCCTGCACATGCAGGCCCTGCCC CCCAGA |
| SP-MUC16-3 scFv. CD8a. 4-1BBz | 30 MLLLVTSLLLCELPH PAFLLIPDIKMAQSPS SVNASLGERVTITCK ASRDINNFLSWFHQK PGKSPKTLIYRANRL VDGVPSRFSGSGSGQ DYSFTISSLEYEDVGI YYCLQYGDLYTFGG GTKLEIKGGGGSGGG GSGGGGSDVQLLESG PGLVRPSQSLSLTCSV TGYSIVSHYYWNWIR QFPGNKLEWMGYISS DGSNEYNPSLKNRISI SLDTSKNQFFLKFDF VTTADTATYFCVRG VDYWGQGTTLTVSS KPTTTPAPRPPTPAPT IASQPLSLRPEACRPA AGGAVHTRGLDFAC DIYIWAPLAGTCGVL LLSLVITLYCNHRNK RGRKKLLYIFKQPFM RPVQTTQEEDGCSCR FPEEEEGGCELRVKF SRSADAPAYQQGQN QLYNELNLGRREEYD VLDKRRGRDPEMGG KPRRKNPQEGLYNEL QKDKMAEAYSEIGM KGERRRGKGHDGLY QGLSTATKDTYDAL HMQALPPR | 122 ATGCTGCTGCTGGTGACCAGCCTGC TGCTGTGTGAGCTGCCCCACCCCGC CTTTCTGCTGATCCCCGACATCAAG ATGGCTCAGTCCCCTTCTAGCGTGA ATGCTTCGCTAGGGGAGCGTGTGAC CATCACATGTAAAGCATCACGCGAC ATAAATAATTTCCTTTCCTGGTTTCA TCAGAAACCGGGCAAGTCGCCTAAG ACGCTGATTTACAGAGCAAATCGGT TGGTAGATGGAGTGCCAAGCAGATT CAGCGGGAGCGGAAGTGGACAGGA TTATAGCTTCACTATTTCATCCCTGG AATACGAGGACGTAGGTATCTATTA TTGCCTCCAGTATGGCGATCTTTACA CATTTGGTGGGGGACTAAGCTGGA GATTAAGGGCGGAGGCGGAAGCGG AGGCGGAGGCTCCGGCGGAGGCGG AAGCGACGTGCAACTTCTGGAGAGC GGGCCAGGGCTAGTCAGGCCCTCCC AGTCGCTTTCACTGACTTGCAGTGT GACCGGTTACTCTATTGTGAGTCAC TACTATTGGAACTGGATTCGGCAGT TCCCAGGCAACAAACTGGAATGGAT GGGGTACATATCTTCCGATGGCTCG AATGAATATAACCCCATCATTGAAAA ATCGTATTTCCATCAGTCTGGATAC GAGTAAAAACCAGTTTTTCCTCAAA TTCGATTTCGTGACTACAGCAGATA CTGCCACATACTTCTGTGTACGAGG TGTCGATTATTGGGACAGGGCACA ACGCTGACCGTAAGTTCTAAGCCCA CCACCACCCCTGCCCCTAGACCTCC AACCCCAGCCCCTACAATCGCCAGC CAGCCCCTGAGCCTGAGGCCCGAAG CCTGTAGACCTGCCGCTGGCGGAGC CGTGCACACCAGAGGCCTGGATTTC GCCTGCGACATCTACATCTGGGCCC CTCTGGCCGGCACCTGTGGCGTGCT GCTGCTGAGCCTGGTCATCACCCTG TACTGCAACCACCGGAATAAGAGAG GCCGGAAGAAACTGCTGTACATCTT CAAGCAGCCCTTCATGCGGCCCGTG CAGACCACCCAGGAAGAGGACGGC TGCAGCTGCCGGTTCCCCGAGGAAG AGGAAGGCGGCTGCGAACTGCGGG TGAAGTTCAGCCGGAGCGCCGACGC CCCTGCCTACCAGCAGGGCCAGAAC CAGCTGTACAACGAGCTGAACCTGG GCCGGAGGGAGGAGTACGACGTGC TGGACAAGCGGAGAGGCCGGGACC CTGAGATGGGCGGCAAGCCCCGGA GAAAGAACCCTCAGGAGGGCCTGTA TAACGAACTGCAGAAAGACAAGAT GGCCGAGGCCTACAGCGAGATCGGC ATGAAGGGCGAGCGGCGGAGGGGC AAGGGCCACGACGGCCTGTACCAGG GCCTGAGCACCGCCACCAAGGATAC CTACGACGCCCTGCACATGCAGGCC CTGCCCCCCAGA |
| MUC16-3 scFv. CD8a. 4-1BBz | 31 DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE YNPSLKNRISISLDTS KNQFFLKFDFVTTAD | 123 GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGA CTAAGCTGGAGATTAAGGGCGGAG GCGGAAGCGGAGGCGGAGGCTCCG |

TABLE 11-continued

Exemplary Sequences

| | | | |
|---|---|---|---|
| | | TATYFCVRGVDYWG<br>QGTTLTVSSKPTTTP<br>APRPPTPAPTIASQPL<br>SLRPEACRPAAGGAV<br>HTRGLDFACDIYIWA<br>PLAGTCGVLLLSLVIT<br>LYCNHRNKRGRKKL<br>LYIFKQPFMRPVQTT<br>QEEDGCSCRFPEEEE<br>GGCELRVKFSRSADA<br>PAYQQGQNQLYNEL<br>NLGRREEYDVLDKR<br>RGRDPEMGGKPRRK<br>NPQEGLYNELQKDK<br>MAEAYSEIGMKGER<br>RRGKGHDGLYQGLS<br>TATKDTYDALHMQA<br>LPPR | | GCGGAGGCGGAAGCGACGTGCAAC<br>TTCTGGAGAGCGGGCCAGGGCTAGT<br>CAGGCCCTCCCAGTCGCTTTCACTG<br>ACTTGCAGTGTGACCGGTTACTCTA<br>TTGTGAGTCACTACTATTGGAACTG<br>GATTCGGCAGTTCCCAGGCAACAAA<br>CTGGAATGGATGGGTACATATCTT<br>CCGATGGCTCGAATGAATATAACCC<br>ATCATTGAAAAATCGTATTTCCATC<br>AGTCTGGATACGAGTAAAAACCAGT<br>TTTTCCTCAAATTCGATTTCGTGACT<br>ACAGCAGATACTGCCACATACTTCT<br>GTGTACGAGGTGTCGATTATTGGGG<br>ACAGGGCACAACGCTGACCGTAAGT<br>TCTAAGCCCACCACCACCCCTGCCC<br>CTAGACCTCCAACCCCAGCCCCTAC<br>AATCGCCAGCCAGCCCCTGAGCCTG<br>AGGCCCGAAGCCTGTAGACCTGCCG<br>CTGGCGGAGCCGTGCACACCAGAGG<br>CCTGGATTTCGCCTGCGACATCTAC<br>ATCTGGGCCCCTCTGGCCGGCACCT<br>GTGGCGTGCTGCTGCTGAGCCTGGT<br>CATCACCCTGTACTGCAACCACCGG<br>AATAAGAGAGGCCGGAAGAAACTG<br>CTGTACATCTTCAAGCAGCCCTTCAT<br>GCGGCCCGTGCAGACCACCCAGGAA<br>GAGGACGGCTGCAGCTGCCGGTTCC<br>CCGAGGAAGAGGAAGGCGGCTGCG<br>AACTGCGGGTGAAGTTCAGCCGGAG<br>CGCCGACGCCCCTGCCTACCAGCAG<br>GGCCAGAACCAGCTGTACAACGAGC<br>TGAACCTGGGCCGGAGGGAGGAGT<br>ACGACGTGCTGGACAAGCGGGAGAG<br>GCCGGGACCCTGAGATGGGCGGCA<br>AGCCCCGGAGAAAGAACCCTCAGG<br>AGGGCCTGTATAACGAACTGCAGAA<br>AGACAAGATGGCCGAGGCCTACAG<br>CGAGATCGGCATGAAGGGCGAGCG<br>GCGGAGGGGCAAGGGCCACGACGG<br>CCTGTACCAGGGCCTGAGCACCGCC<br>ACCAAGGATACCTACGACGCCCTGC<br>ACATGCAGGCCCTGCCCCCAGA |
| MUC16-<br>3 scFv.<br>CD8a<br>(2x).<br>4-1BBz | 32 | DIKMAQSPSSVNASL<br>GERVTITCKASRDIN<br>NFLSWFHQKPGKSPK<br>TLIYRANRLVDGVPS<br>RFSGSGSGQDYSFTIS<br>SLEYEDVGIYYCLQY<br>GDLYTFGGGTKLEIK<br>GGGGSGGGGSGGGG<br>SDVQLLESGPGLVRP<br>SQSLSLTCSVTGYSIV<br>SHYYWNWIRQFPGN<br>KLEWMGYISSDGSNE<br>YNPSLKNRISISLDTS<br>KNQFFLKFDFVTTAD<br>TATYFCVRGVDYWG<br>QGTTLTVSSKPTTTP<br>APRPPTPAPTIASQPL<br>SLRPEASRPAAGGAV<br>HTRGLDFASDKPTTT<br>PAPRPPTPAPTIASQP<br>LSLRPEACRPAAGGA<br>VHTRGLDFACDIYIW<br>APLAGTCGVLLLSLV<br>ITLYCNHRNKRGRKK<br>LLYIFKQPFMRPVQT<br>TQEEDGCSCRFPEEE<br>EGGCELRVKFSRSAD<br>APAYQQGQNQLYNE<br>LNLGRREEYDVLDK<br>RRGRDPEMGGKPRR<br>KNPQEGLYNELQKD<br>KMAEAYSEIGMKGE<br>RRRGKGHDGLYQGL<br>STATKDTYDALHMQ<br>ALPPR | 124 | GACATCAAGATGGCTCAGTCCCCTT<br>CTAGCGTGAATGCTTCGCTAGGGGA<br>GCGTGTGACCATCACATGTAAAGCA<br>TCACGCGACATAAATAATTTCCTTTC<br>CTGGTTTCATCAGAAACCGGGCAAG<br>TCGCCTAAGACGCTGATTTACAGAG<br>CAAATCGGTTGGTAGATGGAGTGCC<br>AAGCAGATTCAGCGGGAGCGGAAG<br>TGGACAGGATTATAGCTTCACTATT<br>TCATCCCTGGAATACGAGGACGTAG<br>GTATCTATTATTGCCTCCAGTATGGC<br>GATCTTTACACATTTGGTGGGGGGA<br>CTAAGCTGGAGATTAAGGGCGAG<br>GCGGAAGCGGAGGCGGAGGCTCCG<br>GCGGAGGCGGAAGCGACGTGCAAC<br>TTCTGGAGAGCGGGCCAGGGCTAGT<br>CAGGCCCTCCCAGTCGCTTTCACTG<br>ACTTGCAGTGTGACCGGTTACTCTA<br>TTGTGAGTCACTACTATTGGAACTG<br>GATTCGGCAGTTCCCAGGCAACAAA<br>CTGGAATGGATGGGTACATATCTT<br>CCGATGGCTCGAATGAATATAACCC<br>AGTCTGGATACGAGTAAAAACCAGT<br>TTTTCCTCAAATTCGATTTCGTGACT<br>ACAGCAGATACTGCCACATACTTCT<br>GTGTACGAGGTGTCGATTATTGGGG<br>ACAGGGCACAACGCTGACCGTAAGT<br>TCTAAACCTACTACAACTCCTGCCC<br>CCCGGCCTCCTACACCAGCTCCTAC<br>TATCGCCTCCCAGCCACTCAGTCTC<br>AGACCCGAGGCTTCTAGGCCAGCGG<br>CCGGAGGCGCGGTCCACACCCGCGG<br>GCTGGACTTTGCATCCGATAAGCCC<br>ACCACCACCCCTGCCCCTAGACCTC |

TABLE 11-continued

Exemplary Sequences

| | | | |
|---|---|---|---|
| | | | CAACCCCAGCCCCTACAATCGCCAG |
| | | | CCAGCCCCTGAGCCTGAGGCCCGAA |
| | | | GCCTGTAGACCTGCCGCTGGCGGAG |
| | | | CCGTGCACACCAGAGGCCTGGATTT |
| | | | CGCCTGCGACATCTACATCTGGGCC |
| | | | CCTCTGGCCGGCACCTGTGGCGTGC |
| | | | TGCTGCTGAGCCTGGTCATCACCCT |
| | | | GTACTGCAACCACCGGAATAAGAGA |
| | | | GGCCGGAAGAAACTGCTGTACATCT |
| | | | TCAAGCAGCCCTTCATGCGGCCCGT |
| | | | GCAGACCACCCAGGAAGAGGACGG |
| | | | CTGCAGCTGCCGGTTCCCCGAGGAA |
| | | | GAGGAAGGCGGCTGCGAACTGCGG |
| | | | GTGAAGTTCAGCCGGAGCGCCGACG |
| | | | CCCCTGCCTACCAGCAGGGCCAGAA |
| | | | CCAGCTGTACAACGAGCTGAACCTG |
| | | | GGCCGGAGGGAGGAGTACGACGTG |
| | | | CTGGACAAGCGGAGAGGCCGGGAC |
| | | | CCTGAGATGGGCGGCAAGCCCCGGA |
| | | | GAAAGAACCCTCAGGAGGGCCTGTA |
| | | | TAACGAACTGCAGAAAGACAAGAT |
| | | | GGCCGAGGCCTACAGCGAGATCGGC |
| | | | ATGAAGGGCGAGCGGCGGAGGGGC |
| | | | AAGGGCCACGACGGCCTGTACCAGG |
| | | | GCCTGAGCACCGCCACCAAGGATAC |
| | | | CTACGACGCCCTGCACATGCAGGCC |
| | | | CTGCCCCCCAGA |
| MUC16-<br>3 scFv.<br>CD8a<br>(3x).4-<br>1BBz | 33 | DIKMAQSPSSVNASL<br>GERVTITCKASRDIN<br>NFLSWFHQKPGKSPK<br>TLIYRANRLVDGVPS<br>RFSGSGSGQDYSFTIS<br>SLEYEDVGIYYCLQY<br>GDLYTFGGGTKLEIK<br>GGGGSGGGGSGGGG<br>SDVQLLESGPGLVRP<br>SQSLSLTCSVTGYSIV<br>SHYYWNWIRQFPGN<br>KLEWMGYISSDGSNE<br>YNPSLKNRISISLDTS<br>KNQFFLKFDFVTTAD<br>TATTFCVRGVDTWG<br>QGTTLTVSSKPTTTP<br>APRPPTPAPTIASQPL<br>SLRPEASRPAAGGAV<br>HTRGLDFASDKPTTT<br>PAPRPPTPAPTIASQP<br>LSLRPEASRPAAGGA<br>VHTRGLDFASDKPTT<br>TPAPRPPTPAPTIASQ<br>PLSLRPEACRPAAGG<br>AVHTRGLDFACDIYI<br>WAPLAGTCGVLLLSL<br>VITLYCNHRNKRGRK<br>KLLYIFKQPFMRPVQ<br>TTQEEDGCSCRFPEE<br>EEGGCELRVKFSRSA<br>DAPAYQQGQNQLYN<br>ELNLGRREEYDVLDK<br>RRGRDPEMGGKPRR<br>KNPQEGLYNELQKD<br>KMAEAYSEIGMKGE<br>RRRGKGHDGLYQGL<br>STATKDTYDALHMQ<br>ALPPR | 125 | GACATCAAGATGGCTCAGTCCCCTT<br>CTAGCGTGAATGCTTCGCTAGGGGA<br>GCGTGTGACCATCACATGTAAAGCA<br>TCACGCGACATAAATAATTTCCTTTC<br>CTGGTTTCATCAGAAACCGGGCAAG<br>TCGCCTAAGACGCTGATTTACAGAG<br>CAAATCGGTTGGTAGATGGAGTGCC<br>AAGCAGATTCAGCGGGAGCGGAAG<br>TGGACAGGATTATAGCTTCACTATT<br>TCATCCCTGGAATACGAGGACGTAG<br>GTATCTATTATTGCCTCCAGTATGGC<br>GATCTTTACACATTTGGTGGGGAA<br>CTAAGCTGGAGATTAAGGGCGGAG<br>GCGGAAGCGGAGGCGGAGGCTCCG<br>GCGGAGGCGGAAGCGACGTGCAAC<br>TTCTGGAGAGCGGGCCAGGGCTAGT<br>CAGGCCCTCCCAGTCGCTTTCACTG<br>ACTTGCAGTGTGACCGGTTACTCTA<br>TTGTGAGTCACTACTATTGGAACTG<br>GATTCGGCAGTTCCCAGGCAACAAA<br>CTGGAATGGATGGGGTACATATCTT<br>CCGATGGCTCGAATGAATATAACCC<br>ATCATTGAAAAATCGTATTTCCATC<br>AGTCTGGATACGAGTAAAAACCAGT<br>TTTTCCTCAAATTCGATTTCGTGACT<br>ACAGCAGATACTGCCACATACTTCT<br>GTGTACGAGGTGTCGATTATTGGGG<br>ACAGGGCACAACGCTGACCGTAAGT<br>TCTAAGCCTACCACCACCCCCGCAC<br>CTCGTCCTCCAACCCCTGCACCTAC<br>GATTGCCAGTCAGCCTCTTTCACTGC<br>GGCCTGAGGCCAGCAGACCAGCTGC<br>CGGCGGTGCCGTCCATACAAGAGGA<br>CTGGACTTCGCGTCCGATAAACCTA<br>CTACCACTCCAGCCCCAAGGCCCCC<br>AACCCCAGCACCGACTATCGCATCA<br>CAGCCTTTGTCACTGCGTCCTGAAG<br>CCAGCCGGCCAGCTGCAGGGGGG<br>CCGTCCACACAAGGGGACTCGACTT<br>TGCGAGTGATAAGCCCACCACCACC<br>CCTGCCCCTAGACCTCCAACCCCAG<br>CCCCTACAATCGCCAGCCAGCCCCT<br>GAGCCTGAGGCCCGAAGCCTGTAGA<br>CCTGCCGCTGGCGGAGCCGTGCACA<br>CCAGAGGCCTGGATTTCGCCTGCGA<br>CATCTACATCTGGGCCCCTCTGGCC<br>GGCACCTGTGGCGTGCTGCTGCTGA<br>GCCTGGTCATCACCCTGTACTGCAA<br>CCACCGGAATAAGAGAGGCCGGAA<br>GAAACTGCTGTACATCTTCAAGCAG |

TABLE 11-continued

Exemplary Sequences

| | | | |
|---|---|---|---|
| | | | CCCTTCATGCGGCCCGTGCAGACCA<br>CCCAGGAAGAGGACGGCTGCAGCT<br>GCCGGTTCCCCGAGGAAGAGGAAG<br>GCGGCTGCGAACTGCGGGTGAAGTT<br>CAGCCGGAGCGCCGACGCCCCTGCC<br>TACCAGCAGGGCCAGAACCAGCTGT<br>ACAACGAGCTGAACCTGGGCCGGA<br>GGGAGGAGTACGACGTGCTGGACA<br>AGCGGAGAGGCCGGGACCCTGAGA<br>TGGGCGGCAAGCCCCGGAGAAAGA<br>ACCCTCAGGAGGGCCTGTATAACGA<br>ACTGCAGAAAGACAAGATGGCCGA<br>GGCCTACAGCGAGATCGGCATGAAG<br>GGCGAGCGGCGGAGGGGCAAGGGC<br>CACGACGGCCTGTACCAGGGCCTGA<br>GCACCGCCACCAAGGATACCTACGA<br>CGCCCTGCACATGCAGGCCCTGCCC<br>CCCAGA |
| MUC16-<br>2 (vh-vl)<br>scFv.<br>CD8a.<br>CD28z | 34 | VKLEESGGGFVKPGG<br>SLKISCAASGFTFRNY<br>AMSWVRLSPEMRLE<br>WVATISSAGGYIFYS<br>DSVQGRFTISRDNAK<br>NTLHLQMGSLRSGDT<br>AMYYCARQGFGNYG<br>DYYAMDYWGQGTT<br>VTVSSGGGGSGGGGS<br>GGGGSDIELTQSPSSL<br>AVSAGEKVTMSCKSS<br>QSLLNSRTRKNQLA<br>WYQQKTGQSPELLIY<br>WASTRQSGVPDRFTG<br>SGSGTDFTLTISSVQA<br>EDLAVYYCQQSYNL<br>LTFGPGTKLEIKRKPT<br>TTPAPRPPTPAPTIAS<br>QPLSLRPEACRPAAG<br>GAVHTRGLDFACDIY<br>IWAPLAGTCGVLLLS<br>LVITLYCNHRNRSKR<br>SRGGHSDYMNMTPR<br>RPGPTRKHYQPYAPP<br>RDFAAYRSRVKFSRS<br>ADAPAYQQGQNQLY<br>NELNLGRREEYDVLD<br>KRRGRDPEMGGKPR<br>RKNPQEGLYNELQK<br>DKMAEAYSEIGMKG<br>ERRRGKGHDGLYQG<br>LSTATKDTYDALHM<br>QALPPR | 126 | GTGAAGCTGGAAGAGTCCGGCGGA<br>GGCTTTGTGAAGCCTGGCGGAAGCC<br>TGAAGATCAGCTGTGCCGCCAGCGG<br>CTTCACCTTCAGAAACTACGCCATG<br>AGCTGGGTCCGACTGAGCCCCGAGA<br>TGAGACTGGAATGGGTCGCCACAAT<br>CAGCAGCGCAGGCGGCTACATCTTC<br>TACAGCGATAGCGTGCAGGGCAGAT<br>TCACCATCAGCCGGGACAACGCCAA<br>GAACACCCTGCACCTCCAGATGGGC<br>AGTCTGAGATCTGGCGACACCGCCA<br>TGTACTACTGCGCCAGACAAGGCTT<br>CGGCAACTACGGCGACTACTATGCC<br>ATGGATTACTGGGGCCAGGGCACCA<br>CCGTGACAGTCTCTTCTGGTGGCGG<br>TGGCTCGGGCGGTGGTGGGTCGGGT<br>GGCGGCGGATCTGACATCGAGCTGA<br>CACAGAGCCCATCTAGCCTGGCTGT<br>GTCTGCCGGCGAGAAAGTGACCATG<br>AGCTGCAAGAGCAGCCAGAGCCTGC<br>TGAACAGCCGGACCAGAAAGAATC<br>AGCTGGCCTGGTATCAGCAGAAAAC<br>CGGACAGAGCCCCGAGCTGCTGATC<br>TACTGGGCCAGCACAAGACAGAGC<br>GGCGTGCCCGATAGATTCACAGGAT<br>CTGGCAGCGGCACCGACTTCACCCT<br>GACAATCAGTTCTGTGCAGGCCGAG<br>GACCTGGCCGTGTACTACTGTCAGC<br>AGAGCTACAACCTGCTGACCTTCGG<br>ACCCGGCACCAAGCTGGAAATCAAG<br>AGAAAGCCCACCACCACCCCTGCCC<br>CTAGACCTCCAACCCCAGCCCCTAC<br>AATCGCCAGCCAGCCCCTGAGCCTG<br>AGGCCCGAAGCCTGTAGACCTGCCG<br>CTGGCGGAGCCGTGCACACCAGAGG<br>CCTGGATTTCGCCTGCGACATCTAC<br>ATCTGGGCCCCTCTGGCCGGCACCT<br>GTGGCGTGCTGCTGCTGAGCCTGGT<br>CATCACCCTGTACTGCAACCACCGG<br>AATAGGAGCAAGCGGAGCAGAGGC<br>GGCCACAGCGACTACATGAACATGA<br>CCCCCCGGAGGCCTGGCCCCACCCG<br>GAAGCACTACCAGCCCTACGCCCCT<br>CCCAGGGACTTCGCCGCCTACCGGA<br>GCCGGGTGAAGTTCAGCCGGAGCGC<br>CGACGCCCCTGCCTACCAGCAGGGC<br>CAGAACCAGCTGTACAACGAGCTGA<br>ACCTGGGCCGGAGGGAGGAGTACG<br>ACGTGCTGGACAAGCGGAGAGGCC<br>GGGACCCTGAGATGGGCGGCAAGC<br>CCCGGAGAAAGAACCCTCAGGAGG<br>GCCTGTATAACGAACTGCAGAAAGA<br>CAAGATGGCCGAGGCCTACAGCGA<br>GAGGGGCAAGGGCCACGACGGCCT<br>GTACCAGGGCCTGAGCACCGCCACC<br>AAGGATACCTACGACGCCCTGCACA<br>TGCAGGCCCTGCCCCCAGA |

TABLE 11-continued

Exemplary Sequences

| | | | |
|---|---|---|---|
| MUC16-2 (vh-vl) scFv. CD8a (2x). CD28z | 35 | VKLEESGGGFVKPGG SLKISCAASGFTFRNY AMSWVRLSPEMRLE WVATISSAGGYIFYS DSVQGRFTISRDNAK NTLHLQMGSLRSGDT AMYYCARQGFGNYG DYYAMDYWGQGTT VTVSSGGGGSGGGGS GGGGSDIELTQSPSSL AVSAGEKVTMSCKSS QSLLNSRTRKNQLA WYQQKTGQSPELLIY WASTRQSGVPDRFTG SGSGTDFTLTISSVQA EDLAVYYCQQSYNL LTFGPGTKLEIKRKPT TTPAPRPPTPAPTIAS QPLSLRPEASRPAAG GAVHTRGLDFASDKP TTTPAPRPPTPAPTIA SQPLSLRPEACRPAA GGAVHTRGLDFACDI YIWAPLAGTCGVLLL SLVITLYCNHRNRSK RSRGGHSDYMNMTP RRPGPTRKHYQPYAP PRDFAAYRSRVKFSR SADAPAYQQGQNQL YNELNLGRREEYDVL DKRRGRDPEMGGKP RRKNPQEGLYNELQ KDKMAEAYSEIGMK GERRRGKGHDGLYQ GLSTATKDTYDALH MQALPPR | 127 | GTGAAGCTGGAAGAGTCCGGCGGA GGCTTTGTGAAGCCTGGCGGAAGCC TGAAGATCAGCTGTGCCGCCAGCGG CTTCACCTTCAGAAACTACGCCATG AGCTGGGTCCGACTGAGCCCCGAGA TGAGACTGGAATGGGTCGCCACAAT CAGCAGCGCAGGCGGCTACATCTTC TACAGCGATAGCGTGCAGGGCAGAT TCACCATCAGCCGGGACAACGCCAA GAACACCCTGCACCTCCAGATGGGC AGTCTGAGATCTGGCGACACCGCCA TGTACTACTGCGCCAGACAAGGCTT CGGCAACTACGGCGACTACTATGCC ATGGATTACTGGGGCCAGGGCACCA CCGTGACAGTCTCTTCTGGTGGCGG TGGCTCGGGCGGTGGTGGGTCGGGT GGCGGCGGATCTGACATCGAGCTGA CACAGAGCCCATCTAGCCTGGCTGT GTCTGCCGGCGAGAAAGTGACCATG AGCTGCAAGAGCAGCCAGAGCCTGC TGAACAGCCGGACCAGAAAGAATC AGCTGGCCTGGTATCAGCAGAAAAC CGGACAGAGCCCCGAGCTGCTGATC TACTGGGCCAGCACAAGACAGAGC GGCGTGCCCGATAGATTCACAGGAT CTGGCAGCGGCACCGACTTCACCCT GACAATCAGTTCTGTGCAGGCCGAG GACCTGGCCGTGTACTACTGTCAGC AGAGCTACAACCTGCTGACCTTCGG ACCCGGCACCAAGCTGGAAATCAAG AGAAAACCTACTACAACTCCTGCCC CCCGGCCTCCTACACCAGCTCCTAC TATCGCCTCCCAGCCACTCAGTCTC AGACCCGAGGCTTCTAGGCCAGCGG CCGGAGGCGCGGTCCACACCCGCGG GCTGGACTTTGCATCCGATAAGCCC ACCACCACCCCTGCCCCTAGACCTC CAACCCCAGCCCCTACAATCGCCAG CCAGCCCCTGAGCCTGAGGCCCGAA GCCTGTAGACCTGCCGCTGGCGGAG CCGTGCACACCAGAGGCCTGGATTT CGCCTGCGACATCTACATCTGGGCC CCTCTGGCCGGCACCTGTGGCGTGC TGCTGCTGAGCCTGGTCATCACCCT GTACTGCAACCACCGGAATAGGAGC AAGCGGAGCAGAGGCGGCCACAGC GACTACATGAACATGACCCCCCGGA GGCCTGGCCCCACCCGGAAGCACTA CCAGCCCTACGCCCCTCCCAGGGAC TTCGCCGCCTACCGGAGCCGGGTGA AGTTCAGCCGGAGCGCCGACGCCCC TGCCTACCAGCAGGGCCAGAACCAG CTGTACAACGAGCTGAACCTGGGCC GGAGGGAGGAGTACGACGTGCTGG ACAAGCGGAGAGGCCGGGACCCTG AGATGGGCGGCAAGCCCCGGAGAA AGAACCCTCAGGAGGGCCTGTATAA CGAACTGCAGAAAGACAAGATGGC CGAGGCCTACAGCGAGATCGGCATG AAGGGCGAGCGGCGGAGGGGCAAG GGCCACGACGGCCTGTACCAGGGCC TGAGCACCGCCACCAAGGATACCTA CGACGCCCTGCACATGCAGGCCCTG CCCCCCAGA |
| MUC16-2 (vh-vl) scFv. CD8a (3x). CD28z | 36 | VKLEESGGGFVKPGG SLKISCAASGFTFRNY AMSWVRLSPEMRLE WVATISSAGGYIFYS DSVQGRFTISRDNAK NTLHLQMGSLRSGDT AMYYCARQGFGNYG DYYAMDYWGQGTT VTVSSGGGGSGGGGS GGGGSDIELTQSPSSL AVSAGEKVTMSCKSS QSLLNSRTRKNQLA WYQQKTGQSPELLIY | 128 | GTGAAGCTGGAAGAGTCCGGCGGA GGCTTTGTGAAGCCTGGCGGAAGCC TGAAGATCAGCTGTGCCGCCAGCGG CTTCACCTTCAGAAACTACGCCATG AGCTGGGTCCGACTGAGCCCCGAGA TGAGACTGGAATGGGTCGCCACAAT CAGCAGCGCAGGCGGCTACATCTTC TACAGCGATAGCGTGCAGGGCAGAT TCACCATCAGCCGGGACAACGCCAA GAACACCCTGCACCTCCAGATGGGC AGTCTGAGATCTGGCGACACCGCCA TGTACTACTGCGCCAGACAAGGCTT CGGCAACTACGGCGACTACTATGCC |

TABLE 11-continued

Exemplary Sequences

| | | | |
|---|---|---|---|
| | | WASTRQSGVPDRFTG | ATGGATTACTGGGGCCAGGGCACCA |
| | | SGSGTDFTLTISSVQA | CCGTGACAGTCTCTTCTGGTGGCGG |
| | | EDLAVYYCQQSYNL | TGGCTCGGGCGGTGGTGGGTCGGGT |
| | | LTFGPGTKLEIKRKPT | GGCGGCGGATCTGACATCGAGCTGA |
| | | TTPAPRPPTPAPTIAS | CACAGAGCCCATCTAGCCTGGCTGT |
| | | QPLSLRPEASRPAAG | GTCTGCCGGCGAGAAAGTGACCATG |
| | | GAVHTRGLDFASDKP | AGCTGCAAGAGCAGCCAGAGCCTGC |
| | | TTTPAPRPPTPAPTIA | TGAACAGCCGGACCAGAAAGAATC |
| | | SQPLSLRPEASRPAA | AGCTGGCCTGGTATCAGCAGAAAAC |
| | | GGAVHTRGLDFASD | CGGACAGAGCCCCGAGCTGCTGATC |
| | | KPTTTPAPRPPTPAPT | TACTGGGCCAGCACAAGACAGAGC |
| | | IASQPLSLRPEACRPA | GGCGTGCCCGATAGATTCACAGGAT |
| | | AGGAVHTRGLDFAC | CTGGCAGCGGCACCGACTTCACCCT |
| | | DIYIWAPLAGTCGVL | GACAATCAGTTCTGTGCAGGCCGAG |
| | | LLSLVITLYCNHRNR | GACCTGGCCGTGTACTACTGTCAGC |
| | | SKRSRGGHSDYMNM | AGAGCTACAACCTGCTGACCTTCGG |
| | | TPRRPGPTRKHYQPY | ACCCGGCACCAAGCTGGAAATCAAG |
| | | APPRDFAAYRSRVKF | AGAAAGCCTACCACCACCCCCGCAC |
| | | SRSADAPAYQQGQN | CTCGTCCTCCAACCCCTGCACCTAC |
| | | QLYNELNLGRREEYD | GATTGCCAGTCAGCCTCTTTCACTGC |
| | | VLDKRRGRDPEMGG | GGCCTGAGGCCAGCAGACCAGCTGC |
| | | KPRRKNPQEGLYNEL | CGGCGGTGCCGTCCATACAAGAGGA |
| | | QKDKMAEAYSEIGM | CTGGACTTCGCGTCCGATAAACCTA |
| | | KGERRRGKGHDGLY | CTACCACTCCAGCCCCAAGGCCCCC |
| | | QGLSTATKDTYDAL | AACCCCAGCACCGACTATCGCATCA |
| | | HMQALPPR | CAGCCTTTGTCACTGCGTCCTGAAG |
| | | | CCAGCCGGCCAGCTGCAGGGGGGG |
| | | | CCGTCCACACAAGGGGACTCGACTT |
| | | | TGCGAGTGATAAGCCCACCACCACC |
| | | | CCTGCCCCTAGACCTCCAACCCCAG |
| | | | CCCCTACAATCGCCAGCCAGCCCCT |
| | | | GAGCCTGAGGCCCGAAGCCTGTAGA |
| | | | CCTGCCGCTGGCGGAGCCGTGCACA |
| | | | CCAGAGGCCTGGATTTCGCCTGCGA |
| | | | CATCTACATCTGGGCCCCTCTGGCC |
| | | | GGCACCTGTGGCGTGCTGCTGCTGA |
| | | | GCCTGGTCATCACCCTGTACTGCAA |
| | | | CCACCGGAATAGGAGCAAGCGGAG |
| | | | CAGAGGCGGCCACAGCGACTACATG |
| | | | AACATGACCCCCGGAGGCCTGGCC |
| | | | CCACCCGGAAGCACTACCAGCCCTA |
| | | | CGCCCCTCCCAGGGACTTCGCCGCC |
| | | | TACCGGAGCCGGGTGAAGTTCAGCC |
| | | | GGAGCGCCGACGCCCCTGCCTACCA |
| | | | GCAGGGCCAGAACCAGCTGTACAAC |
| | | | GAGCTGAACCTGGGCCGGAGGGAG |
| | | | GAGTACGACGTGCTGGACAAGCGG |
| | | | AGAGGCCGGGACCCTGAGATGGGC |
| | | | GGCAAGCCCCGGAGAAAGAACCCT |
| | | | CAGGAGGGCCTGTATAACGAACTGC |
| | | | AGAAAGACAAGATGGCCGAGGCCT |
| | | | ACAGCGAGATCGGCATGAAGGGCG |
| | | | AGCGGCGGAGGGGCAAGGGCCACG |
| | | | ACGGCCTGTACCAGGGCCTGAGCAC |
| | | | CGCCACCAAGGATACCTACGACGCC |
| | | | CTGCACATGCAGGCCCTGCCCCCCA |
| | | | GA |
| MUC16-2 (vh-vl) scFv. CD8a. CD28. 4-1BB.z | 37 | VKLEESGGGFVKPGG SLKISCAASGFTFRNY AMSWVRLSPEMRLE WVATISSAGGYIFYS DSVQGRFTISRDNAK NTLHLQMGSLRSGDT AMYYCARQGFGNYG DYYAMDYWGQGTT VTVSSGGGGSGGGGS GGGGSDIELTQSPSSL AVSAGEKVTMSCKSS QSLLNSRTRKNQLA WYQQKTGQSPELLIY WASTRQSGVPDRFTG SGSGTDFTLTISSVQA EDLAVYYCQQSYNL LTFGPGTKLEIKRKPT TTPAPRPPTPAPTIAS QPLSLRPEACRPAAG GAVHTRGLDFACDIY | 129 | GTGAAGCTGGAAGAGTCCGGCGGA GGCTTTGTGAAGCCTGGCGGAAGCC TGAAGATCAGCTGTGCCGCCAGCGG CTTCACCTTCAGAAACTACGCCATG AGCTGGGTCCGACTGAGCCCCGAGA TGAGACTGGAATGGGTCGCCACAAT CAGCAGCGCAGGCGGCTACATCTTC TACAGCGATAGCGTGCAGGGCAGAT TCACCATCAGCCGGGACAACGCCAA GAACACCCTGCACCTCCAGATGGGC AGTCTGAGATCTGGCGACACCGCCA TGTACTACTGCGCCAGACAAGGCTT CGGCAACTACGGCGACTACTATGCC ATGGATTACTGGGGCCAGGGCACCA CCGTGACAGTCTCTTCTGGTGGCGG TGGCTCGGGCGGTGGTGGGTCGGGT GGCGGCGGATCTGACATCGAGCTGA CACAGAGCCCATCTAGCCTGGCTGT GTCTGCCGGCGAGAAAGTGACCATG AGCTGCAAGAGCAGCCAGAGCCTGC |

TABLE 11-continued

Exemplary Sequences

| | | | |
|---|---|---|---|
| | IWAPLAGTGCVLLLS | | TGAACAGCCGGACCAGAAAGAATC |
| | LVITLYCNHRNRSKR | | AGCTGGCCTGGTATCAGCAGAAAAC |
| | SRGGHSDYMNMTPR | | CGGACAGAGCCCCGAGCTGCTGATC |
| | RPGPTRKHYQPYAPP | | TACTGGGCCAGCACAAGACAGAGC |
| | RDFAAYRSKRGRKK | | GGCGTGCCCGATAGATTCACAGGAT |
| | LLYIFKQPFMRPVQT | | CTGGCAGCGGCACCGACTTCACCCT |
| | TQEEDGCSCRFPEEE | | GACAATCAGTTCTGTGCAGGCCGAG |
| | EGGCELRVKFSRSAD | | GACCTGGCCGTGTACTACTGTCAGC |
| | APAYQQGQNQLYNE | | AGAGCTACAACCTGCTGACCTTCGG |
| | LNLGRREEYDVLDK | | ACCCGGCACCAAGCTGGAAATCAAG |
| | RRGRDPEMGGKPRR | | AGAAAGCCCACCACCACCCCTGCCC |
| | KNPQEGLYNELQKD | | CTAGACCTCCAACCCCAGCCCCTAC |
| | KMAEAYSEIGMKGE | | AATCGCCAGCCAGCCCCTGAGCCTG |
| | RRRGKGHDGLYQGL | | AGGCCCGAAGCCTGTAGACCTGCCG |
| | STATKDTYDALHMQ | | CTGGCGGAGCCGTGCACACCAGAGG |
| | ALPPR | | CCTGGATTTCGCCTGCGACATCTAC |
| | | | ATCTGGGCCCCTCTGGCCGGCACCT |
| | | | GTGGCGTGCTGCTGCTGAGCCTGGT |
| | | | CATCACCCTGTACTGCAACCACCGG |
| | | | AATAGGAGCAAGCGGAGCAGAGGC |
| | | | GGCCACAGCGACTACATGAACATGA |
| | | | CCCCCCGGAGGCCTGGCCCCACCCG |
| | | | GAAGCACTACCAGCCCTACGCCCCT |
| | | | CCCAGGGACTTCGCCGCCTACCGGA |
| | | | GCAAGAGAGGCCGGAAGAAACTGC |
| | | | TGTACATCTTCAAGCAGCCCTTCAT |
| | | | GCGGCCCGTGCAGACCACCCAGGAA |
| | | | GAGGACGGCTGCAGCTGCCGGTTCC |
| | | | CCGAGGAAGAGGAAGGCGGCTGCG |
| | | | AACTGCGGGTGAAGTTCAGCCGGAG |
| | | | CGCCGACGCCCCTGCCTACCAGCAG |
| | | | GGCCAGAACCAGCTGTACAACGAGC |
| | | | TGAACCTGGGCCGGAGGGAGGAGT |
| | | | ACGACGTGCTGGACAAGCGGAGAG |
| | | | GCCGGGACCCTGAGATGGGCGGCA |
| | | | AGCCCCGGAGAAAGAACCCTCAGG |
| | | | AGGGCCTGTATAACGAACTGCAGAA |
| | | | AGACAAGATGGCCGAGGCCTACAG |
| | | | CGAGATCGGCATGAAGGGCGAGCG |
| | | | GCGGAGGGGCAAGGGCCACGACGG |
| | | | CCTGTACCAGGGCCTGAGCACCGCC |
| | | | ACCAAGGATACCTACGACGCCCTGC |
| | | | ACATGCAGGCCCTGCCCCCAGA |
| MUC16-<br>2 (vh-vl)<br>scFv.<br>CD8a<br>(2x).<br>CD28.<br>4-1BB.z | 38 | VKLEESGGGFVKPGG<br>SLKISCAASGFTFRNY<br>AMSWVRLSPEMRLE<br>WVATISSAGGYIFYS<br>DSVQGRFTISRDNAK<br>NTLHLQMGSLRSGDT<br>AMYYCARQGFGNYG<br>DYYAMDYWGQGTT<br>VTVSSGGGGSGGGGS<br>GGGGSDIELTQSPSSL<br>AVSAGEKVTMSCKSS<br>QSLLNSRTRKNQLA<br>WYQQKTGQSPELLIY<br>WASTRQSGVPDRFTG<br>SGSGTDFTLTISSVQA<br>EDLAVYYCQQSYNL<br>LTFGPGTKLEIKRKPT<br>TTPAPRPPTPAPTIAS<br>QPLSLRPEASRPAAG<br>GAVHTRGLDFASDKP<br>TTTPAPRPPTPAPTIA<br>SQPLSLRPEACRPAA<br>GGAVHTRGLDFACDI<br>YIWAPLAGTCGVLLL<br>SLVITLYCNHRNRSK<br>RSRGGHSDYMNMTP<br>RRPGPTRKHYQPYAP<br>PRDFAAYRSKRGRK<br>KLLYIFKQPFMRPVQ<br>TTQEEDGCSCRFPEE<br>EEGGCELRVKFSRSA<br>DAPAYQQGQNQLYN<br>ELNLGRREEYDVLDK<br>RRGRDPEMGGKPRR | 130 | GTGAAGCTGGAAGAGTCCGGCGGA<br>GGCTTTGTGAAGCCTGGCGGAAGCC<br>TGAAGATCAGCTGTGCCGCCAGCGG<br>CTTCACCTTCAGAAACTACGCCATG<br>AGCTGGGTCCGACTGAGCCCCGAGA<br>TGAGACTGGAATGGGTCGCCACAAT<br>CAGCAGCGCAGGCGGCTACATCTTC<br>TACAGCGATAGCGTGCAGGGCAGAT<br>TCACCATCAGCCGGGACAACGCCAA<br>GAACACCCTGCACCTCCAGATGGGC<br>AGTCTGAGATCTGGCGACACCGCCA<br>TGTACTACTGCGCCAGACAAGGCTT<br>CGGCAACTACGGCGACTACTATGCC<br>ATGGATTACTGGGGCCAGGGCACCA<br>CCGTGACAGTCTCTTCTGGTGGCGG<br>TGGCTCGGGCGGTGGTGGGTCGGGT<br>GGCGGCGGATCTGACATCGAGCTGA<br>CACAGAGCCCATCTAGCCTGGCTGT<br>GTCTGCCGGCGAGAAAGTGACCATG<br>AGCTGCAAGAGCAGCCAGAGCCTGC<br>TGAACAGCCGGACCAGAAAGAATC<br>AGCTGGCCTGGTATCAGCAGAAAAC<br>CGGACAGAGCCCCGAGCTGCTGATC<br>TACTGGGCCAGCACAAGACAGAGC<br>GGCGTGCCCGATAGATTCACAGGAT<br>CTGGCAGCGGCACCGACTTCACCCT<br>GACAATCAGTTCTGTGCAGGCCGAG<br>GACCTGGCCGTGTACTACTGTCAGC<br>AGAGCTACAACCTGCTGACCTTCGG<br>ACCCGGCACCAAGCTGGAAATCAAG<br>AGAAAACCTACTACAACCTCCTGCCC<br>CCCGGCCTCCTACACCAGCTCCTAC<br>TATGCCTCCCAGCCACTCAGTCTC<br>AGACCCGAGGCTTCTAGGCCAGCGG |

TABLE 11-continued

Exemplary Sequences

| | | |
|---|---|---|
| | KNPQEGLYNELQKD<br>KMAEAYSEIGMKGE<br>RRRGKGHDGLYQGL<br>STATKDTYDALHMQ<br>ALPPR | CCGGAGGCGCGGTCCACACCCGCGG<br>GCTGGACTTTGCATCCGATAAGGAG<br>ACCACCACCCCTGCCCCTAGACCTC<br>CAACCCCAGCCCCTACAATCGCCAG<br>CCAGCCCCTGAGCCTGAGGCCCGAA<br>GCCTGTAGACCTGCCGCTGGCGGAG<br>CCGTGCACACCAGAGGCCTGGATTT<br>CGCCTGCGACATCTACATCTGGGCC<br>CCTCTGGCCGGCACCTGTGGCGTGC<br>TGCTGCTGAGCCTGGTCATCACCCT<br>GTACTGCAACCACCGGAATAGGAGC<br>AAGCGGAGCAGAGGCGGCCACAGC<br>GACTACATGAACATGACCCCCCGGA<br>GGCCTGGCCCCACCCGGAAGCACTA<br>CCAGCCCTACGCCCCTCCCAGGGAC<br>TTCGCCGCCTACCGGAGCAAGAGAG<br>GCCGGAAGAAACTGCTGTACATCTT<br>CAAGCAGCCCTTCATGCGGCCCGTG<br>CAGACCACCCAGGAAGAGGACGGC<br>TGCAGCTGCCGGTTCCCCGAGGAAG<br>AGGAAGGCGGCTGCGAACTGCGGG<br>TGAAGTTCAGCCGGAGCGCCGACGC<br>CCCTGCCTACCAGCAGGGCCAGAAC<br>CAGCTGTACAACGAGCTGAACCTGG<br>GCCGAGGGAGGAGTACGACGTGC<br>TGGACAAGCGGAGAGGCCGGGACC<br>CTGAGATGGGCGGCAAGCCCCGGA<br>GAAAGAACCCTCAGGAGGGCCTGTA<br>TAACGAACTGCAGAAAGACAAGAT<br>GGCCGAGGCCTACAGCGAGATCGGC<br>ATGAAGGGCGAGCGGCGGAGGGGC<br>AAGGGCCACGACGGCCTGTACCAGG<br>GCCTGAGCACCGCCACCAAGGATAC<br>CTACGACGCCCTGCACATGCAGGCC<br>CTGCCCCCCAGA |
| MUC16-<br>2 (vh-vl)<br>scFv.<br>CD8a<br>(3x).<br>CD28.<br>4-1BB.z | 39 VKLEESGGGFVKPGG<br>SLKISCAASGFTFRNY<br>AMSWVRLSPEMRLE<br>WVATISSAGGYIFYS<br>DSVQGRFTISRDNAK<br>NTLHLQMGSLRSGDT<br>AMYYCARQGFGNYG<br>DYYAMDYWGQGTT<br>VTVSSGGGGSGGGGS<br>GGGGSDIELTQSPSSL<br>AVSAGEKVTMSCKSS<br>QSLLNSRTRKNQLA<br>WYQQKTGQSPELLIY<br>WASTRQSGVPDRFTG<br>SGSGTDFTLTISSVQA<br>EDLAVYYCQQSYNL<br>LTFGPGTKLEIKRKPT<br>TTPAPRPPTPAPTIAS<br>QPLSLRPEASRPAAG<br>GAVHTRGLDFASDKP<br>TTTPAPRPPTPAPTIA<br>SQPLSLRPEASRPAA<br>GGAVHTRGLDFASD<br>KPTTTPAPRPPTPAPT<br>IASQPLSLRPEACRPA<br>AGGAVHTRGLDFAC<br>DIYIWAPLAGTCGVL<br>LLSLVITLYCNHRNR<br>SKRSRGGHSDYMNM<br>TPRRPGPTRKHYQPY<br>APPRDFAAYRSKRGR<br>KKLLYIFKQPFMRPV<br>QTTQEEDGCSCRFPE<br>EEEGGCELRVKFSRS<br>ADAPAYQQGQNQLY<br>NELNLGRREEYDVLD<br>KRRGRDPEMGGKPR<br>RKNPQEGLYNELQK<br>DKMAEAYSEIGMKG<br>ERRRGKGHDGLYQG<br>LSTATKDTYDALHM<br>QALPPR | 131 GTGAAGCTGGAAGAGTCCGGCGGA<br>GGCTTTGTGAAGCCTGGCGGAAGCC<br>TGAAGATCAGCTGTGCCGCCAGCGG<br>CTTCACCTTCAGAAACTACGCCATG<br>AGCTGGGTCCGACTGAGCCCCGAGA<br>TGAGACTGGAATGGGTCGCCACAAT<br>CAGCAGCGCAGGCGGCTACATCTTC<br>TACAGCGATAGCGTGCAGGGCAGAT<br>TCACCATCAGCCGGGACAACGCCAA<br>GAACACCCTGCACCTCCAGATGGGC<br>AGTCTGAGATCTGGCGACACCGCCA<br>TGTACTACTGCGCCAGACAAGGCTT<br>CGGCAACTACGGCGACTACTATGCC<br>ATGGATTACTGGGGCCAGGGCACCA<br>CCGTGACAGTCTCTTCTGGTGGCGG<br>TGGCTCGGGCGGTGGTGGGTCGGGT<br>GGCGGCGGATCTGACATCGAGCTGA<br>CACAGAGCCCATCTAGCCTGGCTGT<br>GTCTGCCGGCGAGAAAGTGACCATG<br>AGCTGCAAGAGCAGCCAGAGCCTGC<br>TGAACAGCCGGACCAGAAAGAATC<br>AGCTGGCCTGGTATCAGCAGAAAAC<br>CGGACAGAGCCCCGAGCTGCTGATC<br>TACTGGGCCAGCACAAGACAGAGC<br>GGCGTGCCCGATAGATTCACAGGAT<br>CTGGCAGCGGCACCGACTTCACCCT<br>GACAATCAGTTCTGTGCAGGCCGAG<br>GACCTGGCCGTGTACTACTGTCAGC<br>AGAGCTACAACCTGCTGACCTTCGG<br>ACCCGGCACCAAGCTGGAAATCAAG<br>AGAAAGCCTACCACCACCCCCGCAC<br>CTCGTCCTCCAACCCCTGCACCTAC<br>GATTGCCAGTCAGCCTCTTTCACTGC<br>GGCCTGAGGCCAGCAGACCAGCTGC<br>CGGCGGTGCCGTCCATACAAGGAGA<br>CTGGACTTCGCGTCCGATAAACCTA<br>CTACCACTCCAGCCCCAAGGCCCCC<br>AACCCCAGCACCGACTATCGCATCA<br>CAGCTTTGTCACTGCGTCCTGAAG<br>CCAGCCGGCCAGCTGCAGGGGGGG<br>CCGTCCACACAAGGGGACTCGACTT<br>TGCGAGTGATAAGCCCACCACCACC |

TABLE 11-continued

Exemplary Sequences

|  |  |  |
|---|---|---|
|  |  | CCTGCCCCTAGACCTCCAACCCCAG<br>CCCCTACAATCGCCAGCCAGCCCCT<br>GAGCCTGAGGCCCGAAGCCTGTAGA<br>CCTGCCGCTGGCGGAGCCGTGCACA<br>CCAGAGGCCTGGATTTCGCCTGCGA<br>CATCTACATCTGGGCCCCTCTGGCC<br>GGCACCTGTGGCGTGCTGCTGCTGA<br>GCCTGGTCATCACCCTGTACTGCAA<br>CCACCGGAATAGGAGCAAGCGGAG<br>CAGAGGCGGCCACAGCGACTACATG<br>AACATGACCCCCCGGAGGCCTGGCC<br>CCACCCGGAAGCACTACCAGCCCTA<br>CGCCCCTCCCAGGGACTTCGCCGCC<br>TACCGGAGCAAGAGAGGCCGGAAG<br>AAACTGCTGTACATCTTCAAGCAGC<br>CCTTCATGCGGCCCGTGCAGACCAC<br>CCAGGAAGAGGACGGCTGCAGCTG<br>CCGGTTCCCCGAGGAAGAGGAAGG<br>CGGCTGCGAACTGCGGGTGAAGTTC<br>AGCCGGAGCGCCGACGCCCCTGCCT<br>ACCAGCAGGGCCAGAACCAGCTGTA<br>CAACGAGCTGAACCTGGGCCGGAG<br>GGAGGAGTACGACGTGCTGGACAA<br>GCGGAGAGGCCGGGACCCTGAGAT<br>GGGCGGCAAGCCCCGGAGAAAGAA<br>CCCTCAGGAGGGCCTGTATAACGAA<br>CTGCAGAAAGACAAGATGGCCGAG<br>GCCTACAGCGAGATCGGCATGAAGG<br>GCGAGCGGCGGAGGGGCAAGGGCC<br>ACGACGGCCTGTACCAGGGCCTGAG<br>CACCGCCACCAAGGATACCTACGAC<br>GCCCTGCACATGCAGGCCCTGCCCC<br>CAGA |
| MUC16-<br>2 (vl-vh)<br>scFv.<br>CD8a.<br>CD28z | 40 DIELTQSPSSLAVSAG<br>EKVTMSCKSSQSLLN<br>SRTRKNQLAWYQQK<br>TGQSPELLIYWASTR<br>QSGVPDRFTGSGSGT<br>DFTLTISSVQAEDLA<br>VYYCQQSYNLLTFGP<br>GTKLEIKRGGGGSGG<br>GGSGGGGSVKLEESG<br>GGFVKPGGSLKISCA<br>ASGFTFRNYAMSWV<br>RLSPEMRLEWVATIS<br>SAGGYIFYSDSVQGR<br>FTISRDNAKNTLHLQ<br>MGSLRSGDTAMYYC<br>ARQGFGNYGDYYAM<br>DYWGQGTTVTVSSK<br>PTTTPAPRPPTPAPTI<br>ASQPLSLRPEACRPA<br>AGGAVHTRGLDFAC<br>DIYIWAPLAGTCGVL<br>LLSLVITLYCNHRNR<br>SKRSRGGHSDYMNM<br>TPRRPGPTRKHYQPY<br>APPRDFAAYRSRVKF<br>SRSADAPAYQQGQN<br>QLYNELNLGRREEYD<br>VLDKRRGRDPEMGG<br>KPRRKNPQEGLYNEL<br>QKDKMAEAYSEIGM<br>KGERRRGKGHDGLY<br>QGLSTATKDTYDAL<br>HMQALPPR | 132 GACATCGAGCTGACACAGAGCCCAT<br>CTAGCCTGGCTGTGTCTGCCGGCGA<br>GAAAGTGACCATGAGCTGCAAGAG<br>CAGCCAGAGCCTGCTGAACAGCCGG<br>ACCAGAAAGAATCAGCTGGCCTGGT<br>ATCAGCAGAAAACCGGACAGAGCC<br>CCGAGCTGCTGATCTACTGGGCCAG<br>CACAAGACAGAGCGGCGTGCCCGAT<br>AGATTCACAGGATCTGGCAGCGGCA<br>CCGACTTCACCCTGACAATCAGTTC<br>TGTGCAGGCCGAGGACCTGGCCGTG<br>TACTACTGTCAGCAGAGCTACAACC<br>TGCTGACCTTCGGACCCGGCACCAA<br>GCTGGAAATCAAGAGAGGTGGCGG<br>TGGCTCGGGCGGTGGTGGGTCGGGT<br>GGCGGCGGATCTGTGAAGCTGGAAG<br>AGTCCGGCGGAGGCTTTGTGAAGCC<br>TGGCGGAAGCCTGAAGATCAGCTGT<br>GCCGCCAGCGGCTTCACCTTCAGAA<br>ACTACGCCATGAGCTGGGTCCGACT<br>GAGCCCCGAGATGAGACTGGAATG<br>GGTCGCCACAATCAGCAGCGCAGGC<br>GGCTACATCTTCTACAGCGATAGCG<br>TGCAGGGCAGATTCACCATCAGCCG<br>GGACAACGCCAAGAACACCCTGCAC<br>CTCCAGATGGGCAGTCTGAGATCTG<br>GCGACACCGCCATGTACTACTGCGC<br>CAGACAAGGCTTCGGCAACTACGGC<br>GACTACTATGCCATGGATTACTGGG<br>GCCAGGGCACCACCGTGACAGTCTC<br>TTCTAAGCCCACCACCACCCCTGCC<br>CCTAGACCTCCAACCCCAGCCCCTA<br>CAATCGCCAGCCAGCCCCTGAGCCT<br>GAGGCCCGAAGCCTGTGACCTGCC<br>GCTGGCGGAGCCGTGCACACCAGAG<br>GCCTGGATTTCGCCTGCGACATCTA<br>CATCTGGGCCCCTCTGGCCGGCACC<br>TGTGGCGTGCTGCTGCTGAGCCTGG<br>TCATCACCCTGTACTGCAACCACCG<br>GAATAGGAGCAAGCGGAGCAGAGG<br>CGGCCACAGCGACTACATGAACATG<br>ACCCCCCGGAGGCCTGGCCCCACCC<br>GGAAGCACTACCAGCCCTACGCCCC<br>TCCCAGGGACTTCGCCGCCTACCGG |

TABLE 11-continued

Exemplary Sequences

| | | |
|---|---|---|
| | | AGCCGGGTGAAGTTCAGCCGGAGCG
CCGACGCCCCTGCCTACCAGCAGGG
CCAGAACCAGCTGTACAACGAGCTG
AACCTGGGCCGGAGGGAGGAGTAC
GACGTGCTGGACAAGCGGAGAGGC
CGGGACCCTGAGATGGGCGGCAAG
CCCCGGAGAAAGAACCCTCAGGAG
GGCCTGTATAACGAACTGCAGAAAG
ACAAGATGGCCGAGGCCTACAGCG
AGATCGGCATGAAGGGCGAGCGGC
GGAGGGGCAAGGGCCACGACGGCC
TGTACCAGGGCCTGAGCACCGCCAC
CAAGGATACCTACGACGCCCTGCAC
ATGCAGGCCCTGCCCCCCAGA |
| MUC16-
2 (vl-vh)
scFv.
CD8a
(2x).
CD28z | 41 DIELTQSPSSLAVSAG
EKVTMSCKSSQSLLN
SRTRKNQLAWYQQK
TGQSPELLIYWASTR
QSGVPDRFTGSGSGT
DFTLTISSVQAEDLA
VYYCQQSYNLLTFGP
GTKLEIKRGGGGSGG
GGSGGGGSVKLEESG
GGFVKPGGSLKISCA
ASGFTFRNYAMSWV
RLSPEMRLEWVATIS
SAGGYIFYSDSVQGR
FTISRDNAKNTLHLQ
MGSLRSGDTAMYYC
ARQGFGNYGDYYAM
DYWGQGTTVTVSSK
PTTTPAPRPPTPAPTI
ASQPLSLRPEASRPA
AGGAVHTRGLDFAS
DKPTTTPAPRPPTPAP
TIASQPLSLRPEACRP
AAGGAVHTRGLDFA
CDIYIWAPLAGTCGV
LLLSLVITLYCNHRN
RSKRSGGHSDYMN
MTPRRPGPTRKHYQP
YAPPRDFAAYRSRVK
FSRSADAPAYQQGQ
NQLYNELNLGRREEY
DVLDKRRGRDPEMG
GKPRRKNPQEGLYNE
LQKDKMAEAYSEIG
MKGERRRGKGHDGL
YQGLSTATKDTYDA
LHMQALPPR | 133 GACATCGAGCTGACACAGAGCCCAT
CTAGCCTGGCTGTGTCTGCCGGCGA
GAAAGTGACCATGAGCTGCAAGAG
CAGCCAGAGCCTGCTGAACAGCCGG
ACCAGAAAGAATCAGCTGGCCTGGT
ATCAGCAGAAAACCGGACAGAGCC
CCGAGCTGCTGATCTACTGGGCCAG
CACAAGACAGAGCGGCGTGCCCGAT
AGATTCACAGGATCTGGCAGCGGCA
CCGACTTCACCCTGACAATCAGTTC
TGTGCAGGCCGAGGACCTGGCCGTG
TACTACTGTCAGCAGAGCTACAACC
TGCTGACCTTCGGACCCGGCACCAA
GCTGGAAATCAAGAGAGGTGGCGG
TGGCTCGGGCGGTGGTGGGTCGGGT
GGCGGCGGATCTGTGAAGCTGGAAG
AGTCCGGCGGAGGCTTTGTGAAGCC
TGGCGGAAGCCTGAAGATCAGCTGT
GCCGCCAGCGGCTTCACCTTCAGAA
ACTACGCCATGAGCTGGGTCCGACT
GAGCCCCGAGATGAGACTGGAATG
GGTCGCCACAATCAGCAGCGCAGGC
GGCTACATCTTCTACAGCGATAGCG
TGCAGGGCAGATTCACCATCAGCCG
GGACAACGCCAAGAACACCCTGCAC
CTCCAGATGGGCAGTCTGAGATCTG
GCGACACCGCCATGTACTACTGCGC
CAGACAAGGCTTCGGCAACTACGGC
GACTACTATGCCATGGATTACTGGG
GCCAGGGCACCACCGTGACAGTCTC
TTCTAAACCTACTACAACTCCTGCCC
CCCGGCCTCCTACACCAGCTCCTAC
TATCGCCTCCCAGCCACTCAGTCTC
AGACCCGAGGCTTCTAGGCCAGCGG
CCGGAGGCGCGGTCCACACCCGCGG
GCTGGACTTTGCATCCGATAAGCCC
ACCACCACCCCTGCCCCTAGACCTC
CAACCCCAGCCCCTACAATCGCCAG
CCAGCCCCTGAGCCTGAGGCCCGAA
GCCTGTAGACCTGCCGCTGGCGGAG
CCGTGCACACCAGAGGCCTGGATTT
CGCCTGCGACATCTACATCTGGGCC
CCTCTGGCCGGCACCTGTGGCGTGC
TGCTGCTGAGCCTGGTCATCACCCT
GTACTGCAACCACCGGAATAGGAGC
AAGCGGAGCAGAGGCGGCCACAGC
GACTACATGAACATGACCCCCCGGA
GGCCTGGCCCCACCCGGAAGCACTA
CCAGCCCTACGCCCCTCCCAGGGAC
TTCGCCGCCTACCGGAGCCGGGTGA
AGTTCAGCCGGAGCGCCGACGCCCC
TGCCTACCAGCAGGGCCAGAACCAG
CTGTACAACGAGCTGAACCTGGGCC
GGAGGGAGGAGTACGACGTGCTGG
ACAAGCGGAGAGGCCGGGACCCTG
AGATGGGCGGCAAGCCCCGGAGAA
AGAACCCTCAGGAGGGCCTGTATAA
CGAACTGCAGAAAGACAAGATGGC
CGAGGCCTACAGCGAGATCGGCATG
AAGGGCGAGCGGCGGAGGGGCAAG
GGCCACGACGGCCTGTACCAGGGCC |

TABLE 11-continued

Exemplary Sequences

|  |  |  |
|---|---|---|
|  |  | TGAGCACCGCCACCAAGGATACCTA CGACGCCCTGCACATGCAGGCCCTG CCCCCCAGA |
| MUC16-2 (vl-vh) scFv. CD8a (3x). CD28z | 42 DIELTQSPSSLAVSAG EKVTMSCKSSQSLLN SRTRKNQLAWYQQK TGQSPELLIYWASTR QSGVPDRFTGSGSGT DFTLTISSVQAEDLA VYYCQQSYNLLTFGP GTKLEIKRGGGGSGG GGSGGGGSVKLEESG GGFVKPGGSLKISCA ASGFTFRNYAMSWV RLSPEMRLEWVATIS SAGGYIFYSDSVQGR FTISRDNAKNTLHLQ MGSLRSGDTAMYYC ARQGFGNYGDYYAM DYWGQGTTVTVSSR SKRSGGHSDYMNM TPRRPGPTRKHYQPY APPRDFAAYRSRVKF SRSADAPAYQQGQN QLYNELNLGRREEYD VLDKRRGRDPEMGG KPRRKNPQEGLYNEL QKDKMAEAYSEIGM KGERRRGKGHDGLY QGLSTATKDTYDAL HMQALPPR | 134 GACATCGAGCTGACACAGAGCCCAT CTAGCCTGGCTGTGTCTGCCGGCGA GAAAGTGACCATGAGCTGCAAGAG CAGCCAGAGCCTGCTGAACAGCCGG ACCAGAAAGAATCAGCTGGCCTGGT ATCAGCAGAAAACCGGACAGAGCC CCGAGCTGCTGATCTACTGGGCCAG CACAAGACAGAGCGGCGTGCCCGAT AGATTCACAGGATCTGGCAGCGGCA CCGACTTCACCCTGACAATCAGTTC TGTGCAGGCCGAGGACCTGGCCGTG TACTACTGTCAGCAGAGCTACAACC TGCTGACCTTCGGACCCGGCACCAA GCTGGAAATCAAGAGAGGTGGCGG TGGCTCGGGCGGTGGTGGGTCGGGT GGCGGCGGATCTGTGAAGCTGGAAG AGTCCGGCGGAGGCTTTGTGAAGCC TGGCGGAAGCCTGAAGATCAGCTGT GCCGCCAGCGGCTTCACCTTCAGAA ACTACGCCATGAGCTGGGTCCGACT GAGCCCCGAGATGAGACTGGAATG GGTCGCCACAATCAGCAGCGCAGGC GGCTACATCTTCTACAGCGATAGCG TGCAGGGCAGATTCACCATCAGCCG GGACAACGCCAAGAACACCCTGCAC CTCCAGATGGGCAGTCTGAGATCTG GCGACACCGCCATGTACTACTGCGC CAGACAAGGCTTCGGCAACTACGGC GACTACTATGCCATGGATTACTGGG GCCAGGGCACCACCGTGACAGTCTC TTCTAGGAGCAAGCGGAGCAGAGG CGGCCACAGCGACTACATGAACATG ACCCCCCGGAGGCCTGGCCCCACCC GGAAGCACTACCAGCCCTACGCCCC TCCCAGGGACTTCGCCGCCTACCGG AGCCGGGTGAAGTTCAGCCGGAGCG CCGACGCCCCTGCCTACCAGCAGGG CCAGAACCAGCTGTACAACGAGCTG AACCTGGGCCGGAGGGAGGAGTAC GACGTGCTGGACAAGCGGAGAGGC CGGGACCCTGAGATGGGCGGCAAG CCCCGGAGAAAGAACCCTCAGGAG GGCCTGTATAACGAACTGCAGAAAG ACAAGATGGCCGAGGCCTACAGCG AGATCGGCATGAAGGGCGAGCGGC GGAGGGGCAAGGGCCACGACGGCC TGTACCAGGGCCTGAGCACCGCCAC CAAGGATACCTACGACGCCCTGCAC ATGCAGGCCCTGCCCCCCAGA |
| MUC16-2 (vl-vh) scFv. CD8a. cd28. 4-1bb.z | 43 DIELTQSPSSLAVSAG EKVTMSCKSSQSLLN SRTRKNQLAWYQQK TGQSPELLIYWASTR QSGVPDRFTGSGSGT DFTLTISSVQAEDLA VYYCQQSYNLLTFGP GTKLEIKRGGGGSGG GGSGGGGSVKLEESG GGFVKPGGSLKISCA ASGFTFRNYAMSWV RLSPEMRLEWVATIS SAGGYIFYSDSVQGR FTISRDNAKNTLHLQ MGSLRSGDTAMYYC ARQGFGNYGDYYAM DYWGQGTTVTVSSR SKRSGGHSDYMNM TPRRPGPTRKHYQPY APPRDFAAYRSKRGR KKLLYIFKQPFMRPV QTTQEEDGCSCRFPE EEEGGCELRVKFSRS ADAPAYQQGQNQLY | 135 GACATCGAGCTGACACAGAGCCCAT CTAGCCTGGCTGTGTCTGCCGGCGA GAAAGTGACCATGAGCTGCAAGAG CAGCCAGAGCCTGCTGAACAGCCGG ACCAGAAAGAATCAGCTGGCCTGGT ATCAGCAGAAAACCGGACAGAGCC CCGAGCTGCTGATCTACTGGGCCAG CACAAGACAGAGCGGCGTGCCCGAT AGATTCACAGGATCTGGCAGCGGCA CCGACTTCACCCTGACAATCAGTTC TGTGCAGGCCGAGGACCTGGCCGTG TACTACTGTCAGCAGAGCTACAACC TGCTGACCTTCGGACCCGGCACCAA GCTGGAAATCAAGAGAGGTGGCGG TGGCTCGGGCGGTGGTGGGTCGGGT GGCGGCGGATCTGTGAAGCTGGAAG AGTCCGGCGGAGGCTTTGTGAAGCC TGGCGGAAGCCTGAAGATCAGCTGT GCCGCCAGCGGCTTCACCTTCAGAA ACTACGCCATGAGCTGGGTCCGACT GAGCCCCGAGATGAGACTGGAATG GGTCGCCACAATCAGCAGCGCAGGC GGCTACATCTTCTACAGCGATAGCG TGCAGGGCAGATTCACCATCAGCCG |

TABLE 11-continued

Exemplary Sequences

| | | | |
|---|---|---|---|
| | | NELNLGRREEYDVLD<br>KRRGRDPEMGGKPR<br>RKNPQEGLYNELQK<br>DKMAEAYSEIGMKG<br>ERRRGKGHDGLYQG<br>LSTATKDTYDALHM<br>QALPPR | GGACAACGCCAAGAACACCCTGCAC<br>CTCCAGATGGGCAGTCTGAGATCTG<br>GCGACACCGCCATGTACTACTGCGC<br>CAGACAAGGCTTCGGCAACTACGGC<br>GACTACTATGCCATGGATTACTGGG<br>GCCAGGGCACCACCGTGACAGTCTC<br>TTCTAGGAGCAAGCGGAGCAGAGG<br>CGGCCACAGCGACTACATGAACATG<br>ACCCCCCGGAGGCCTGGCCCCACCC<br>GGAAGCACTACCAGCCCTACGCCCC<br>TCCCAGGGACTTCGCCGCCTACCGG<br>AGCAAGAGAGGCCGGAAGAAACTG<br>CTGTACATCTTCAAGCAGCCCTTCAT<br>GCGGCCCGTGCAGACCACCCAGGAA<br>GAGGACGGCTGCAGCTGCCGGTTCC<br>CCGAGGAAGAGGAAGGCGGCTGCG<br>AACTGCGGGTGAAGTTCAGCCGGAG<br>CGCCGACGCCCCTGCCTACCAGCAG<br>GGCCAGAACCAGCTGTACAACGAGC<br>TGAACCTGGGCCGGAGGGAGGAGT<br>ACGACGTGCTGGACAAGCGGAGAG<br>GCCGGGACCCTGAGATGGGCGGCA<br>AGCCCCGGAGAAAGAACCCTCAGG<br>AGGGCCTGTATAACGAACTGCAGAA<br>AGACAAGATGGCCGAGGCCTACAG<br>CGAGATCGGCATGAAGGGCGAGCG<br>GCGGAGGGGCAAGGGCCACGACGG<br>CCTGTACCAGGGCCTGAGCACCGCC<br>ACCAAGGATACCTACGACGCCCTGC<br>ACATGCAGGCCCTGCCCCCAGA |
| MUC16-<br>2 (vl-vh)<br>scFv.<br>CD8a<br>(2x).<br>CD28.<br>4-1bb.z | 44 | DIELTQSPSSLAVSAG<br>EKVTMSCKSSQSLLN<br>SRTRKNQLAWYQQK<br>TGQSPELLIYWASTR<br>QSGVPDRFTGSGSGT<br>DFTLTISSVQAEDLA<br>VYYCQQSYNLLTFGP<br>GTKLEIKRGGGGSGG<br>GGSGGGGSVKLEESG<br>GGFVKPGGSLKISCA<br>ASGFTFRNYAMSWV<br>RLSPEMRLEWVATIS<br>SAGGYIFYSDSVQGR<br>FTISRDNAKNTLHLQ<br>MGSLRSGDTAMYYC<br>ARQGFGNYGDYYAM<br>DYWGQGTTVTVSSK<br>PTTTPAPRPPTPAPTI<br>ASQPLSLRPEASRPA<br>AGGAVHTRGLDFAS<br>DKPTTTPAPRPPTPAP<br>TIASQPLSLRPEACRP<br>AAGGAVHTRGLDFA<br>CDIYIWAPLAGTCGV<br>LLLSLVITLYCNHRN<br>RSKRSRGGHSDYMN<br>MTPRRPGPTRKHYQP<br>YAPPRDFAAYRSKRG<br>RKKLLYIFKQPFMRP<br>VQTTQEEDGCSCRFP<br>EEEEGGCELRVKFSR<br>SADAPAYQQGQNQL<br>YNELNLGRREEYDVL<br>DKRRGRDPEMGGKP<br>RRKNPQEGLYNELQ<br>KDKMAEAYSEIGMK<br>GERRRGKGHDGLYQ<br>GLSTATKDTYDALH<br>MQALPPR | 136 | GACATCGAGCTGACACAGAGCCCAT<br>CTAGCCTGGCTGTGTCTGCCGGCGA<br>GAAAGTGACCATGAGCTGCAAGAG<br>CAGCCAGAGCCTGCTGAACAGCCGG<br>ACCAGAAAGAATCAGCTGGCCTGGT<br>ATCAGCAGAAAACCGGACAGAGCC<br>CCGAGCTGCTGATCTACTGGGCCAG<br>CACAAGACAGAGCGGCGTGCCCGAT<br>AGATTCACAGGATCTGGCGGCA<br>CCGACTTCACCCTGACAATCAGTTC<br>TGTGCAGGCCGAGGACCTGGCCGTG<br>TACTACTGTCAGCAGAGCTACAACC<br>TGCTGACCTTCGGACCCGGCACCAA<br>GCTGGAAATCAAGAGAGGTGGCGG<br>TGGCTCGGGCGGTGGTGGGTCGGGT<br>GGCGGCGGATCTGTGAAGCTGGAAG<br>AGTCCGGCGGAGGCTTTGTGAAGCC<br>TGGCGGAAGCCTGAAGATCAGCTGT<br>GCCGCCAGCGGCTTCACCTTCAGAA<br>ACTACGCCATGAGCTGGGTCCGACT<br>GAGCCCCGAGATGAGACTGGAATG<br>GGTCGCCACAATCAGCAGCGCAGGC<br>GGCTACATCTTCTACAGCGATAGCG<br>TGCAGGGCAGATTCACCATCAGCCG<br>GGACAACGCCAAGAACACCCTGCAC<br>CTCCAGATGGGCAGTCTGAGATCTG<br>GCGACACCGCCATGTACTACTGCGC<br>CAGACAAGGCTTCGGCAACTACGGC<br>GACTACTATGCCATGGATTACTGGG<br>GCCAGGGCACCACCGTGACAGTCTC<br>TTCTAAACCTACTACAACTCCTGCCC<br>CCCGGCCTCCTACACCAGCTCCTAC<br>TATCGCCTCCCAGCCACTCAGTCTC<br>AGACCCGAGGCTTCTAGGCCAGCGG<br>CCGGAGGCGCGGTCCACACCCGCGG<br>GCTGGACTTTGCATCCGATAAGCCC<br>ACCACCACCCCTGCCCCTAGACCTC<br>CAACCCCAGCCCCTACAATCGCCAG<br>CCAGCCCCTGAGCCTGAGGCCCGAA<br>GCCTGTAGACCTGCCGCTGGCGGAG<br>CCGTGCACACCAGAGGCCTGGATTT<br>CGCCTGCGACATCTACATCTGGGCC<br>CCTCTGGCCGGCACCTGTGGCGTGC<br>TGCTGCTGAGCCTGGTCATCACCCT<br>GTACTGCAACCACCGGAATAGGAGC<br>AAGCGGAGCAGAGGCGGCCACAGC<br>GACTACATGAACATGACCCCCCGGA |

TABLE 11-continued

Exemplary Sequences

|  |  |  |
|---|---|---|
|  |  | GGCCTGGCCCCACCCGGAAGCACTA |
|  |  | CCAGCCCTACGCCCCTCCCAGGGAC |
|  |  | TTCGCCGCCTACCGGAGCAAGAGAG |
|  |  | GCCGGAAGAAACTGCTGTACATCTT |
|  |  | CAAGCAGCCCTTCATGCGGCCCGTG |
|  |  | CAGACCACCCAGGAAGAGGACGGC |
|  |  | TGCAGCTGCCGGTTCCCCGAGGAAG |
|  |  | AGGAAGGCGGCTGCGAACTGCGGG |
|  |  | TGAAGTTCAGCCGGAGCGCCGACGC |
|  |  | CCCTGCCTACCAGCAGGGCCAGAAC |
|  |  | CAGCTGTACAACGAGCTGAACCTGG |
|  |  | GCCGAGGGAGGAGTACGACGTGC |
|  |  | TGGACAAGCGGAGAGGCCGGGACC |
|  |  | CTGAGATGGGCGGCAAGCCCCGGA |
|  |  | GAAAGAACCCTCAGGAGGGCCTGTA |
|  |  | TAACGAACTGCAGAAAGACAAGAT |
|  |  | GGCCGAGGCCTACAGCGAGATCGGC |
|  |  | ATGAAGGGCGAGCGGCGGAGGGGC |
|  |  | AAGGGCCACGACGGCCTGTACCAGG |
|  |  | GCCTGAGCACCGCCACCAAGGATAC |
|  |  | CTACGACGCCCTGCACATGCAGGCC |
|  |  | CTGCCCCCCAGA |
| MUC16-2 (vl-vh) scFv. CD8a (3x). CD28. 4-1bb.z | 45 DIELTQSPSSLAVSAG EKVTMSCKSSQSLLN SRTRKNQLAWYQQK TGQSPELLIYWASTR QSGVPDRFTGSGSGT DFTLTISSVQAEDLA VYYCQQSYNLLTFGP GTKLEIKRGGGGSGG GGSGGGGSVKLEESG GGFVKPGGSLKISCA ASGFTFRNYAMSWV RLSPEMRLEWVATIS SAGGYIFYSDSVQGR FTISRDNAKNTLHLQ MGSLRSGDTAMYYC ARQGFGNYGDYYAM DYWGQGTTVTVSSK PTTTPAPRPPTPAPTI ASQPLSLRPEASRPA AGGAVHTRGLDFAS DKPTTTPAPRPPTPAP TIASQPLSLRPEASRP AAGGAVHTRGLDFA SDKPTTTPAPRPPTPA PTIASQPLSLRPEACR PAAGGAVHTRGLDF ACDIYIWAPLAGTCG VLLLSLVITLYCNHR NRSKRSRGGHSDYM NMTPRRPGPTRKHY QPYAPPRDFAAYRSK RGRKKLLYIFKQPFM RPVQTTQEEDGCSCR FPEEEEGGCELRVKF SRSADAPAYQQGQN QLYNELNLGRREEYD VLDKRRGRDPEMGG KPRRKNPQEGLYNEL QKDKMAEAYSEIGM KGERRRGKGHDGLY QGLSTATKDTYDAL HMQALPPR | 137 GACATCGAGCTGACACAGAGCCCAT CTAGCCTGGCTGTGTCTGCCGGCGA GAAAGTGACCATGAGCTGCAAGAG CAGCCAGAGCCTGCTGAACAGCCGG ACCAGAAAGAATCAGCTGGCCTGGT ATCAGCAGAAACCGGACAGAGCC CCGAGCTGCTGATCTACTGGGCCAG CACAAGACAGAGCGGCGTGCCCGAT AGATTCACAGGATCTGGCAGCGGCA CCGACTTCACCCTGACAATCAGTTC TGTGCAGGCCGAGGACCTGGCCGTG TACTACTGTCAGCAGAGCTACAACC TGCTGACCTTCGGACCCGGCACCAA GCTGGAAATCAAGAGAGGTGGCGG TGGCTCGGGCGGTGGTGGGTCGGGT GGCGGCGGATCTGTGAAGCTGGAAG AGTCCGGCGAGGCTTTGTGAAGCC TGGCGGAAGCCTGAAGATCAGCTGT GCCGCCAGCGGCTTCACCTTCAGAA ACTACGCCATGAGCTGGGTCCGACT GAGCCCCGAGATGAGACTGGAATG GGTCGCCACAATCAGCAGCGCAGGC GGCTACATCTTCTACAGCGATAGCG TGCAGGGCAGATTCACCATCAGCCG GGACAACGCCAAGAACACCCTGCAC CTCCAGATGGGCAGTCTGAGATCTG GCGACACCGCCATGTACTACTGCGC CAGACAAGGCTTCGGCAACTACGGC GACTACTATGCCATGGATTACTGGG GCCAGGGCACCACCGTGACAGTCTC TTCTAAGCCTACCACCACCCCCGCA CCTCGTCCTCCAACCCCTGCACCTAC GATTGCCAGTCAGCCTCTTTCACTGC GGCCTGAGGCCAGCAGACCAGCTGC CGGCGGTGCCGTCCATACAAGAGGA CTGGACTTCGCGTCCGATAAACCTA CTACCACTCCAGCCCCAAGGCCCCC AACCCCAGCACCGACTATCGCATCA CAGCCTTTGTCACTGCGTCCTGAAG CCAGCCGGCCAGCTGCAGGGGGG CCGTCCACACAAGGGGACTCGACTT TGCGAGTGATAAGCCCACCACCACC CCTGCCCCTAGACCTCCAACCCCAG CCCCTACAATCGCCAGCCAGCCCCT GAGCCTGAGGCCCGAAGCCTGTAGA CCTGCCGCTGGCGGAGCCGTGCACA CCAGAGGCCTGGATTTCGCCTGCGA CATCTACATCTGGGCCCCTCTGGCC GGCACCTGTGGCGTGCTGCTGCTGA GCCTGGTCATCACCCTGTACTGCAA CCACCGGAATAGGAGCAAGCGGAG CAGAGGCGGCCACAGCGACTACATG AACATGACCCCCGGAGGCCTGGCC CCACCCGGAAGCACTACCAGCCCTA CGCCCCTCCCAGGGACTTCGCCGCC |

TABLE 11-continued

Exemplary Sequences

|  |  |  |
|---|---|---|
|  |  | TACCGGAGCAAGAGAGGCCGGAAG |
|  |  | AAACTGCTGTACATCTTCAAGCAGC |
|  |  | CCTTCATGCGGCCCGTGCAGACCAC |
|  |  | CCAGGAAGAGGACGGCTGCAGCTG |
|  |  | CCGGTTCCCCGAGGAAGAGGAAGG |
|  |  | CGGCTGCGAACTGCGGGTGAAGTTC |
|  |  | AGCCGGAGCGCCGACGCCCCTGCCT |
|  |  | ACCAGCAGGGCCAGAACCAGCTGTA |
|  |  | CAACGAGCTGAACCTGGGCCGGAG |
|  |  | GGAGGAGTACGACGTGCTGGACAA |
|  |  | GCGGAGAGGCCGGGACCCTGAGAT |
|  |  | GGGCGGCAAGCCCCGGAGAAAGAA |
|  |  | CCCTCAGGAGGGCCTGTATAACGAA |
|  |  | CTGCAGAAAGACAAGATGGCCGAG |
|  |  | GCCTACAGCGAGATCGGCATGAAGG |
|  |  | GCGAGCGGCGGAGGGGCAAGGGCC |
|  |  | ACGACGGCCTGTACCAGGGCCTGAG |
|  |  | CACCGCCACCAAGGATACCTACGAC |
|  |  | GCCCTGCACATGCAGGCCCTGCCCC |
|  |  | CCAGA |
| MUC16-<br>3 (vh-vl)<br>scFv.<br>CD8a.<br>CD28z | 46 DVQLLESGPGLVRPS<br>QSLSLTCSVTGYSIVS<br>HYYWNWIRQFPGNK<br>LEWMGYISSDGSNEY<br>NPSLKNRISISLDTSK<br>NQFFLKFDFVTTADT<br>ATYFCVRGVDYWGQ<br>GTTLTVSSGGGGSGG<br>GGSGGGGSDIKMAQ<br>SPSSVNASLGERVTIT<br>CKASRDINNFLSWFH<br>QKPGKSPKTLIYRAN<br>RLVDGVPSRFSGSGS<br>GQDYSFTISSLEYEDV<br>GIYYCLQYGDLYTFG<br>GGTKLEIKKPTTTPAP<br>RPPTPAPTIASQPLSL<br>RPEACRPAAGGAVH<br>TRGLDFACDIYIWAP<br>LAGTCGVLLLSLVITL<br>YCNHRNRSKRSRGG<br>HSDYMNMTPRRPGP<br>TRKHYQPYAPPRDFA<br>AYRSRVKFSRSADAP<br>AYQQGQNQLYNELN<br>LGRREEYDVLDKRR<br>GRDPEMGGKPRRKN<br>PQEGLYNELQKDKM<br>AEAYSEIGMKGERRR<br>GKGHDGLYQGLSTA<br>TKDTYDALHMQALP<br>PR | 138 GACGTGCAACTTCTGGAGAGCGGGC<br>CAGGGCTAGTCAGGCCCTCCCAGTC<br>GCTTTCACTGACTTGCAGTGTGACC<br>GGTTACTCTATTGTGAGTCACTACTA<br>TTGGAACTGGATTCGGCAGTTCCCA<br>GGCAACAAACTGGAATGGATGGGG<br>TACATATCTTCCGATGGCTCGAATG<br>AATATAACCCATCATTGAAAAATCG<br>TATTTCCATCAGTCTGGATACGAGT<br>AAAAACCAGTTTTTCCTCAAATTCG<br>ATTTCGTGACTACAGCAGATACTGC<br>CACATACTTCTGTGTACGAGGTGTC<br>GATTATTGGGGACAGGGCACAACGC<br>TGACCGTAAGTTCTGGCGGAGGCGG<br>AAGCGGAGGCGGAGGCTCCGGCGG<br>AGGCGGAAGCGACATCAAGATGGC<br>TCAGTCCCCTTCTAGCGTGAATGCTT<br>CGCTAGGGGAGCGTGTGACCATCAC<br>ATGTAAAGCATCACGCGACATAAAT<br>AATTTCCTTTCCTGGTTTCATCAGAA<br>ACCGGGCAAGTCGCCTAAGACGCTG<br>ATTTACAGAGCAAATCGGTTGGTAG<br>ATGGAGTGCCAAGCAGATTCAGCGG<br>GAGCGGAAGTGGACAGGATTATAG<br>CTTCACTATTTCATCCCTGGAATACG<br>AGGACGTAGGTATCTATTATTGCCT<br>CCAGTATGGCGATCTTTACACATTT<br>GGTGGGGGGACTAAGCTGGAGATTA<br>AGAAGCCCACCACCACCCCTGCCCC<br>TAGACCTCCAACCCCAGCCCCTACA<br>ATCGCCAGCCAGCCCCTGAGCCTGA<br>GGCCCGAAGCCTGTAGACCTGCCGC<br>TGGCGGAGCCGTGCACACCAGAGGC<br>CTGGATTTCGCCTGCGACATCTACA<br>TCTGGGCCCCTCTGGCCGGCACCTG<br>TGGCGTGCTGCTGCTGAGCCTGGTC<br>ATCACCCTGTACTGCAACCACCGGA<br>ATAGGAGCAAGCGGAGCAGAGGCG<br>GCCACAGCGACTACATGAACATGAC<br>CCCCCGGAGGCCTGGCCCCACCCGG<br>AAGCACTACCAGCCCTACGCCCCTC<br>CAGGGACTTCGCCGCCTACCGGAG<br>CCGGGTGAAGTTCAGCCGGAGCGCC<br>GACGCCCCTGCCTACCAGCAGGGCC<br>AGAACCAGCTGTACAACGAGCTGAA<br>CCTGGGCCGGAGGGAGGAGTACGA<br>CGTGCTGGACAAGCGGAGAGGCCG<br>GGACCCTGAGATGGGCGGCAAGCCC<br>CGGAGAAAGAACCCTCAGGAGGGC<br>CTGTATAACGAACTGCAGAAAGACA<br>AGATGGCCGAGGCCTACAGCGAGAT<br>CGGCATGAAGGGCGAGCGGCGGAG<br>GGGCAAGGGCCACGACGGCCTGTAC<br>CAGGGCCTGAGCACCGCCACCAAGG<br>ATACCTACGACGCCCTGCACATGCA<br>GGCCCTGCCCCCAGA |

TABLE 11-continued

Exemplary Sequences

| | | | |
|---|---|---|---|
| MUC16-3 (vh-vl) scFv. CD8a (2x). CD28z | 47 | DVQLLESGPGLVRPS QSLSLTCSVTGYSIVS HYYWNWIRQFPGNK LEWMGYISSDGSNEY NPSLKNRISISLDTSK NQFFLKFDFVTTADT ATYFCVRGVDYWGQ GTTLTVSSGGGGSGG GGSGGGGSDIKMAQ SPSSVNASLGERVTIT CKASRDINNFLSWFH QKPGKSPKTLIYRAN RLVDGVPSRFSGSGS GQDYSFTISSLEYEDV GIYYCLQYGDLYTFG GGTKLEIKKPTTTPAP RPPTPAPTIASQPLSL RPEASRPAAGGAVHT RGLDFASDKPTTTPA PRPPTPAPTIASQPLSL RPEACRPAAGGAVH TRGLDFACDIYIWAP LAGTCGVLLLSLVITL YCNHRNRSKRSGG HSDYMNMTPRRPGP TRKHYQPYAPPRDFA AYRSRVKFSRSADAP AYQQGQNQLYNELN LGRREEYDVLDKRR GRDPEMGGKPRRKN PQEGLYNELQKDKM AEAYSEIGMKGERRR GKGHDGLYQGLSTA TKDTYDALHMQALP PR | 139 | GACGTGCAACTTCTGGAGAGCGGGC CAGGGCTAGTCAGGCCCTCCCAGTC GCTTTCACTGACTTGCAGTGTGACC GGTTACTCTATTGTGAGTCACTACTA TTGGAACTGGATTCGGCAGTTCCCA GGCAACAAACTGGAATGGATGGGG TACATATCTTCCGATGGCTCGAATG AATATAACCCATCATTGAAAAATCG TATTTCCATCAGTCTGGATACGAGT AAAAACCAGTTTTTCCTCAAATTCG ATTTCGTGACTACAGCAGATACTGC CACATACTTCTGTGTACGAGGTGTC GATTATTGGGGACAGGGCACAACGC TGACCGTAAGTTCTGGCGGAGGCGG AAGCGGAGGCGGAGGCTCCGGCGG AGGCGGAAGCGACATCAAGATGGC TCAGTCCCCTTCTAGCGTGAATGCTT CGCTAGGGGAGCGTGTGACCATCAC ATGTAAAGCATCACGCGACATAAAT AATTTCCTTTCCTGGTTTCATCAGAA ACCGGGCAAGTCGCCTAAGACGCTG ATTTACAGAGCAAATCGGTTGGTAG ATGGAGTGCCAAGCAGATTCAGCGG GAGCGGAAGTGGACAGGATTATAG CTTCACTATTTCATCCCTGGAATACG AGGACGTAGGTATCTATTATTGCCT CCAGTATGGCGATCTTTACACATTT GGTGGGGGGACTAAGCTGGAGATTA AGAAACCTACTACAACTCCTGCCCC CCGGCCTCCTACACCAGCTCCTACT ATCGCCTCCCAGCCACTCAGTCTCA GACCCGAGGCTTCTAGGCCAGCGGC CGGAGGCGCGGTCCACACCCGCGGG CTGGACTTTGCATCCGATAAGCCCA CCACCACCCCTGCCCCTAGACCTCC AACCCCAGCCCCTACAATCGCCAGC CAGCCCCTGAGCCTGAGGCCCGAAG CCTGTAGACCTGCCGCTGGCGGAGC CGTGCACACCAGAGGCCTGGATTTC GCCTGCGACATCTACATCTGGGCCC CTCTGGCCGGCACCTGTGGCGTGCT GCTGCTGAGCCTGGTCATCACCCTG TACTGCAACCACCGGAATAGGAGCA AGCGGAGCAGAGGCGGCCACAGCG ACTACATGAACATGACCCCCCGGAG GCCTGGCCCCACCCGGAAGCACTAC CAGCCCTACGCCCCTCCCAGGGACT TCGCCGCCTACCGGAGCCGGGTGAA GTTCAGCCGGAGCGCCGACGCCCCT GCCTACCAGCAGGGCCAGAACCAGC TGTACAACGAGCTGAACCTGGGCCG GAGGGAGGAGTACGACGTGCTGGA CAAGCGGAGAGGCCGGGACCCTGA GATGGGCGGCAAGCCCCGGAGAAA GAACCCTCAGGAGGGCCTGTATAAC GAACTGCAGAAAGACAAGATGGCC GAGGCCTACAGCGAGATCGGCATGA AGGGCGAGCGGCGGAGGGGCAAGG GCCACGACGGCCTGTACCAGGGCCT GAGCACCGCCACCAAGGATACCTAC GACGCCCTGCACATGCAGGCCCTGC CCCCCAGA |
| MUC16-3 (vh-vl) scFv. CD8a (3x). CD28z | 48 | DVQLLESGPGLVRPS QSLSLTCSVTGYSIVS HYYWNWIRQFPGNK LEWMGYISSDGSNEY NPSLKNRISISLDTSK NQFFLKFDFVTTADT ATYFCVRGVDYWGQ GTTLTVSSGGGGSGG GGSGGGGSDIKMAQ SPSSVNASLGERVTIT CKASRDINNFLSWFH QKPGKSPKTLIYRAN RLVDGVPSRFSGSGS GQDYSFTISSLEYEDV GIYYCLQYGDLYTFG | 140 | GACGTGCAACTTCTGGAGAGCGGGC CAGGGCTAGTCAGGCCCTCCCAGTC GCTTTCACTGACTTGCAGTGTGACC GGTTACTCTATTGTGAGTCACTACTA TTGGAACTGGATTCGGCAGTTCCCA GGCAACAAACTGGAATGGATGGGG TACATATCTTCCGATGGCTCGAATG AATATAACCCATCATTGAAAAATCG TATTTCCATCAGTCTGGATACGAGT AAAAACCAGTTTTTCCTCAAATTCG ATTTCGTGACTACAGCAGATACTGC CACATACTTCTGTGTACGAGGTGTC GATTATTGGGGACAGGGCACAACGC TGACCGTAAGTTCTGGCGGAGGCGG AAGCGGAGGCGGAGGCTCCGGCGG |

TABLE 11-continued

Exemplary Sequences

| | | | |
|---|---|---|---|
| | | GGTKLEIKKPTTTPAP | AGGCGGAAGCGACATCAAGATGGC |
| | | RPPTPAPTIASQPLSL | TCAGTCCCCTTCTAGCGTGAATGCTT |
| | | RPEASRPAAGGAVHT | CGCTAGGGGAGCGTGTGACCATCAC |
| | | RGLDFASDKPTTTPA | ATGTAAAGCATCACGCGACATAAAT |
| | | PRPPTPAPTIASQPLSL | AATTTCCTTTCCTGGTTTCATCAGAA |
| | | RPEASRPAAGGAVHT | ACCGGGCAAGTCGCCTAAGACGCTG |
| | | RGLDFASDKPTTTPA | ATTTACAGAGCAAATCGGTTGGTAG |
| | | PRPPTPAPTIASQPLSL | ATGGAGTGCCAAGCAGATTCAGCGG |
| | | RPEACRPAAGGAVH | GAGCGGAAGTGGACAGGATTATAG |
| | | TRGLDFACDIYIWAP | CTTCACTATTTCATCCCTGGAATACG |
| | | LAGTCGVLLLSLVITL | AGGACGTAGGTATCTATTATTGCCT |
| | | YCNHRNRSKRSRGG | CCAGTATGGCGATCTTTACACATTT |
| | | HSDYMNMTPRRPGP | GGTGGGGGACTAAGCTGGAGATTA |
| | | TRKHYQPYAPPRDFA | AGAAGCCTACCACCACCCCCGCACC |
| | | AYRSRVKFSRSADAP | TCGTCCTCCAACCCCTGCACCTACG |
| | | AYQQGQNQLYNELN | ATTGCCAGTCAGCCTCTTTCACTGCG |
| | | LGRREEYDVLDKRR | GCCTGAGGCCAGCAGACCAGCTGCC |
| | | GRDPEMGGKPRRKN | GGCGGTGCCGTCCATACAAGAGGAC |
| | | PQEGLYNELQKDKM | TGGACTTCGCGTCCGATAAACCTAC |
| | | AEAYSEIGMKGERRR | TACCACTCCAGCCCCAAGGCCCCCA |
| | | GKGHDGLYQGLSTA | ACCCCAGCACCGACTATCGCATCAC |
| | | TKDTYDALHMQALP | AGCCTTTGTCACTGCGTCCTGAAGC |
| | | PR | CAGCCGGCCAGCTGCAGGGGGGC |
| | | | CGTCCACACAAGGGGACTCGACTTT |
| | | | GCGAGTGATAAGCCCACCACCACCC |
| | | | CTGCCCCTAGACCTCCAACCCCAGC |
| | | | CCCTACAATCGCCAGCCAGCCCCTG |
| | | | AGCCTGAGGCCCGAAGCCTGTAGAC |
| | | | CTGCCGCTGGCGGAGCCGTGCACAC |
| | | | CAGAGGCCTGGATTTCGCCTGCGAC |
| | | | ATCTACATCTGGGCCCCTCTGGCCG |
| | | | GCACCTGTGGCGTGCTGCTGCTGAG |
| | | | CCTGGTCATCACCCTGTACTGCAAC |
| | | | CACCGGAATAGGAGCAAGCGGAGC |
| | | | AGAGGCGGCCACAGCGACTACATG |
| | | | AACATGACCCCCCGGAGGCCTGGCC |
| | | | CCACCCGGAAGCACTACCAGCCCTA |
| | | | CGCCCCTCCCAGGGACTTCGCCGCC |
| | | | TACCGGAGCCGGGTGAAGTTCAGCC |
| | | | GGAGCGCCGACGCCCCTGCCTACCA |
| | | | GCAGGGCCAGAACCAGCTGTACAAC |
| | | | GAGCTGAACCTGGGCCGGAGGGAG |
| | | | GAGTACGACGTGCTGGACAAGCGG |
| | | | AGAGGCCGGGACCCTGAGATGGGC |
| | | | GGCAAGCCCCGGAGAAAGAACCCT |
| | | | CAGGAGGGCCTGTATAACGAACTGC |
| | | | AGAAAGACAAGATGGCCGAGGCCT |
| | | | ACAGCGAGATCGGCATGAAGGGCG |
| | | | AGCGGCGGAGGGGCAAGGGCCACG |
| | | | ACGGCCTGTACCAGGGCCTGAGCAC |
| | | | CGCCACCAAGGATACCTACGACGCC |
| | | | CTGCACATGCAGGCCCTGCCCCCCA |
| | | | GA |
| MUC16-3 (vh-vl) scFv. CD8a. CD28. 4-1BB.z | 49 | DVQLLESGPGLVRPS | 141 GACGTGCAACTTCTGGAGAGCGGGC |
| | | QSLSLTCSVTGYSIVS | CAGGGCTAGTCAGGCCCTCCCAGTC |
| | | HYYWNWIRQFPGNK | GCTTTCACTGACTTGCAGTGTGACC |
| | | LEWMGYISSDGSNEY | GGTTACTCTATTGTGAGTCACTACTA |
| | | NPSLKNRISISLDTSK | TTGGAACTGGATTCGGCAGTTCCCA |
| | | NQFFLKFDFVTTADT | GGCAACAAACTGGAATGGATGGGG |
| | | ATYFCVRGVDYWGQ | TACATATCTTCCGATGGCTCGAATG |
| | | GTTLTVSSGGGGSGG | AATATAACCCATCATTGAAAAATCG |
| | | GGSGGGGSDIKMAQ | TATTTCCATCAGTCTGGATACGAGT |
| | | SPSSVNASLGERVTIT | AAAAACCAGTTTTTCCTCAAATTCG |
| | | CKASRDINNFLSWFH | ATTTCGTGACTACAGCAGATACTGC |
| | | QKPGKSPKTLIYRAN | CACATACTTCTGTGTACGAGGTGTC |
| | | RLVDGVPSRFSGSGS | GATTATTGGGGACAGGGCACAACGC |
| | | GQDYSFTISSLEYEDV | TGACCGTAAGTTCTGGCGGAGGCGG |
| | | GIYYCLQYGDLYTFG | AAGCGGAGGCGGAGGCTCAGGCGG |
| | | GGTKLEIKKPTTTPAP | AGGCGGAAGCGACATCAAGATGGC |
| | | RPPTPAPTIASQPLSL | TCAGTCCCCTTCTAGCGTGAATGCTT |
| | | RPEACRPAAGGAVH | CGCTAGGGGAGCGTGTGACCATCAC |
| | | TRGLDFACDIYIWAP | ATGTAAAGCATCACGCGACATAAAT |
| | | LAGTCGVLLLSLVITL | AATTTCCTTTCCTGGTTTCATCAGAA |
| | | YCNHRNRSKRSRGG | ACCGGGCAAGTCGCCTAAGACGCTG |
| | | HSDYMNMTPRRPGP | ATTTACAGAGCAAATCGGTTGGTAG |
| | | TRKHYQPYAPPRDFA | ATGGAGTGCCAAGCAGATTCAGCGG |
| | | AYRSKRGRKKLLYIF | GAGCGGAAGTGGACAGGATTATAG |

TABLE 11-continued

Exemplary Sequences

|  |  |  |
|---|---|---|
|  | KQPFMRPVQTTQEED | CTTCACTATTTCATCCCTGGAATACG |
|  | GCSCRFPEEEEGGCE | AGGACGTAGGTATCTATTATTGCCT |
|  | LRVKFSRSADAPAYQ | CCAGTATGGCGATCTTTACACATTT |
|  | QGQNQLYNELNLGR | GGTGGGGGGACTAAGCTGGAGATTA |
|  | REEYDVLDKRRGRD | AGAAGCCCACCACCACCCCTGCCCC |
|  | PEMGGKPRRKNPQE | TAGACCTCCAACCCCAGCCCCTACA |
|  | GLYNELQKDKMAEA | ATCGCCAGCCAGCCCCTGAGCCTGA |
|  | YSEIGMKGERRRGKG | GGCCCGAAGCCTGTAGACCTGCCGC |
|  | HDGLYQGLSTATKD | TGGCGGAGCCGTGCACACCAGAGGC |
|  | TYDALHMQALPPR | CTGGATTTCGCCTGCGACATCTACA |
|  |  | TCTGGGCCCCTCTGGCCGGCACCTG |
|  |  | TGGCGTGCTGCTGCTGAGCCTGGTC |
|  |  | ATCACCCTGTACTGCAACCACCGGA |
|  |  | ATAGGAGCAAGCGGAGCAGAGGCG |
|  |  | GCCACAGCGACTACATGAACATGAC |
|  |  | CCCCCGGAGGCCTGGCCCCACCCGG |
|  |  | AAGCACTACCAGCCCTACGCCCCTC |
|  |  | CCAGGGACTTCGCCGCCTACCGGAG |
|  |  | CAAGAGAGGCCGGAAGAAACTGCT |
|  |  | GTACATCTTCAAGCAGCCCTTCATG |
|  |  | CGGCCCGTGCAGACCACCCAGGAAG |
|  |  | AGGACGGCTGCAGCTGCCGGTTCCC |
|  |  | CGAGGAAGAGGAAGGCGGCTGCGA |
|  |  | ACTGCGGGTGAAGTTCAGCCGGAGC |
|  |  | GCCGACGCCCCTGCCTACCAGCAGG |
|  |  | GCCAGAACCAGCTGTACAACGAGCT |
|  |  | GAACCTGGGCCGGAGGGAGGAGTA |
|  |  | CGACGTGCTGGACAAGCGGAGAGG |
|  |  | CCGGGACCCTGAGATGGGCGGCAA |
|  |  | GCCCCGGAGAAAGAACCCTCAGGA |
|  |  | GGGCCTGTATAACGAACTGCAGAAA |
|  |  | GACAAGATGGCCGAGGCCTACAGC |
|  |  | GAGATCGGCATGAAGGGCGAGCGG |
|  |  | CGGAGGGGCAAGGGCCACGACGGC |
|  |  | CTGTACCAGGGCCTGAGCACCGCCA |
|  |  | CCAAGGATACCTACGACGCCCTGCA |
|  |  | CATGCAGGCCCTGCCCCCCAGA |
| MUC16-<br>3 (vh-vl)<br>scFv.<br>CD8a<br>(2x).<br>CD28.<br>4-1BB.z | 50 DVQLLESGPGLVRPS<br>QSLSLTCSVTGYSIVS<br>HYYWNWIRQFPGNK<br>LEWMGYISSDGSNEY<br>NPSLKNRISISLDTSK<br>NQFFLKFDFVTTADT<br>ATYFCVRGVDYWGQ<br>GTTLTVSSGGGGSGG<br>GGSGGGGSDIKMAQ<br>SPSSVNASLGERVTIT<br>CKASRDINNFLSWFH<br>QKPGKSPKTLIYRAN<br>RLVDGVPSRFSGSGS<br>GQDYSFTISSLEYEDV<br>GIYYCLQYGDLYTFG<br>GGTKLEIKKPTTTPAP<br>RPPTPAPTIASQPLSL<br>RPEASRPAAGGAVHT<br>RGLDFASDKPTTTPA<br>PRPPTPAPTIASQPLSL<br>RPEACRPAAGGAVH<br>TRGLDFACDIYIWAP<br>LAGTCGVLLLSLVITL<br>YCNHRNRSKRSRGG<br>HSDYMNMTPRRPGP<br>TRKHYQPYAPPRDFA<br>AYRSKRGRKKLLYIF<br>KQPFMRPVQTTQEED<br>GCSCRFPEEEEGGCE<br>LRVKFSRSADAPAYQ<br>QGQNQLYNELNLGR<br>REEYDVLDKRRGRD<br>PEMGGKPRRKNPQE<br>GLYNELQKDKMAEA<br>YSEIGMKGERRRGKG<br>HDGLYQGLSTATKD<br>TYDALHMQALPPR | 142 GACGTGCAACTTCTGGAGAGCGGGC<br>CAGGGCTAGTCAGGCCCTCCCAGTC<br>GCTTTCACTGACTTGCAGTGTGACC<br>GGTTACTCTATTGTGAGTCACTACTA<br>TTGGAACTGGATTCGGCAGTTCCCA<br>GGCAACAAACTGGAATGGATGGGG<br>TACATATCTTCCGATGGCTCGAATG<br>AATATAACCCATCATTGAAAAATCG<br>TATTTCCATCAGTCTGGATACGAGT<br>AAAAACCAGTTTTTCCTCAAATTCG<br>ATTTCGTGACTACAGCAGATACTGC<br>CACATACTTCTGTGTACGAGGTGTC<br>GATTATTGGGGACAGGGCACAACGC<br>TGACCGTAAGTTCTGGCGGAGGCGG<br>AAGCGGAGGCGGAGGCTCCGGCGG<br>AGGCGGAAGCGACATCAAGATGGC<br>TCAGTCCCCTTCTAGCGTGAATGCTT<br>CGCTAGGGGAGCGTGTGACCATCAC<br>ATGTAAAGCATCACGCGACATAAAT<br>AATTTCCTTTCCTGGTTTCATCAGAA<br>ACCGGGCAAGTCGCCTAAGACGCTG<br>ATTTACAGAGCAAATCGGTTGGTAG<br>ATGGAGTGCCAAGCAGATTCAGCGG<br>GAGCGGAAGTGGACAGGATTATAG<br>CTTCACTATTTCATCCCTGGAATACG<br>AGGACGTAGGTATCTATTATTGCCT<br>CCAGTATGGCGATCTTTACACATTT<br>GGTGGGGGGACTAAGCTGGAGATTA<br>AGAAACCTACTACAACTCCTGCCCC<br>CCGGCCTCCTACACCAGCTCCTACT<br>ATCGCCTCCCAGCCACTCAGTCTA<br>GACCCGAGGCTTCTAGGCCAGCGGC<br>CGGAGGCGCGGTCCACACCCGCGGG<br>CTGGACTTTGCATCCGATAAGCCCA<br>CCACCACCCCTGCCCCTAGACCTCC<br>AACCCCAGCCCCTACAATCGCCAGC<br>CAGCCCTGAGCCTGAGGCCCGAAG<br>CCTGTAGACCTGCCGCTGGCGGAGC<br>CGTGCACACCAGAGGCCTGGATTTC<br>GCCTGCGACATCTACATCTGGGCCC |

TABLE 11-continued

Exemplary Sequences

|  |  |  |
|---|---|---|
|  |  | CTCTGGCCGGCACCTGTGGCGTGCT |
|  |  | GCTGCTGAGCCTGGTCATCACCCTG |
|  |  | TACTGCAACCACCGGAATAGGAGCA |
|  |  | AGCGGAGCAGAGGCGGCCACAGCG |
|  |  | ACTACATGAACATGACCCCCCGGAG |
|  |  | GCCTGGCCCCACCCGGAAGCACTAC |
|  |  | CAGCCCTACGCCCCTCCCAGGGACT |
|  |  | TCGCCGCCTACCGGAGCAAGAGAGG |
|  |  | CCGGAAGAAACTGCTGTACATCTTC |
|  |  | AAGCAGCCCTTCATGCGGCCCGTGC |
|  |  | AGACCACCCAGGAAGAGGACGGCT |
|  |  | GCAGCTGCCGGTTCCCCGAGGAAGA |
|  |  | GGAAGGCGGCTGCGAACTG |
|  |  | CGGGTGAAGTTCAGCCGGAGCGCCG |
|  |  | ACGCCCCTGCCTACCAGCAGGGCCA |
|  |  | GAACCAGCTGTACAACGAGCTGAAC |
|  |  | CTGGGCCGGAGGGAGGAGTACGAC |
|  |  | GTGCTGGACAAGCGGAGAGGCCGG |
|  |  | GACCCTGAGATGGGCGGCAAGCCCC |
|  |  | GGAGAAAGAACCCTCAGGAGGGCC |
|  |  | TGTATAACGAACTGCAGAAAGACAA |
|  |  | GATGGCCGAGGCCTACAGCGAGATC |
|  |  | GGCATGAAGGGCGAGCGGCGGAGG |
|  |  | GGCAAGGGCCACGACGGCCTGTACC |
|  |  | AGGGCCTGAGCACCGCCACCAAGG |
|  |  | ATACCTACGACGCCCTGCACATGCA |
|  |  | GGCCCTGCCCCCAGA |
| MUC16-<br>3 (vh-vl)<br>scFv.<br>CD8a<br>(3x).<br>CD28.<br>4-1BB.z | 51 DVQLLESGPGLVRPS<br>QSLSLTCSVTGYSIVS<br>HYYWNWIRQFPGNK<br>LEWMGYISSDGSNEY<br>NPSLKNRISISLDTSK<br>NQFFLKFDFVTTADT<br>ATYFCVRGVDYWGQ<br>GTTLTVSSGGGGSGG<br>GGSGGGGSDIKMAQ<br>SPSSVNASLGERVTIT<br>CKASRDINNFLSWFH<br>QKPGKSPKTLIYRAN<br>RLVDGVPSRFSGSGS<br>GQDYSFTISSLEYEDV<br>GIYYCLQYGDLYTFG<br>GGTKLEIKKPTTTPAP<br>RPPTPAPTIASQPLSL<br>RPEASRPAAGGAVHT<br>RGLDFASDKPTTTPA<br>PRPPTPAPTIASQPLSL<br>RPEASRPAAGGAVHT<br>RGLDFASDKPTTTPA<br>PRPPTPAPTIASQPLSL<br>RPEACRPAAGGAVH<br>TRGLDFACDIYIWAP<br>LAGTCGVLLLSLVITL<br>YCNHRNRSKRSRGG<br>HSDYMNMTPRRPGP<br>TRKHYQPYAPPRDFA<br>AYRSKRGRKKLLYIF<br>KQPFMRPVQTTQEED<br>GCSCRFPEEEEGGCE<br>LRVKFSRSADAPAYQ<br>QGQNQLYNELNLGR<br>REEYDVLDKRRGRD<br>PEMGGKPRRKNPQE<br>GLYNELQKDKMAEA<br>YSEIGMKGERRRGKG<br>HDGLYQGLSTATKD<br>TYDALHMQALPPR | 143 GACGTGCAACTTCTGGAGAGCGGGC<br>CAGGGCTAGTCAGGCCCTCCCAGTC<br>GCTTTCACTGACTTGCAGTGTGACC<br>GGTTACTCTATTGTGAGTCACTACTA<br>TTGGAACTGGATTCGGCAGTTCCCA<br>GGCAACAAACTGGAATGGATGGGG<br>TACATATCTTCCGATGGCTCGAATG<br>AATATAACCCATCATTGAAAAATCG<br>TATTTCCATCAGTCTGGATACGAGT<br>AAAAACCAGTTTTTCCTCAAATTCG<br>ATTTCGTGACTACAGCAGATACTGC<br>CACATACTTCTGTGTACGAGGTGTC<br>GATTATTGGGGACAGGGCACAACGC<br>TGACCGTAAGTTCTGGCGGAGGCGG<br>AAGCGGAGGCGGAGGCTCCGGCGG<br>AGGCGGAAGCGACATCAAGATGGC<br>TCAGTCCCCTTCTAGCGTGAATGCTT<br>CGCTAGGGGAGCGTGTGACCATCAC<br>ATGTAAAGCATCACGCGACATAAAT<br>AATTTCCTTTCCTGGTTTCATCAGAA<br>ACCGGGCAAGTCGCCTAAGACGCTG<br>ATTTACAGAGCAAATCGGTTGGTAG<br>ATGGAGTGCCAAGCAGATTCAGCGG<br>GAGCGGAAGTGGACAGGATTATAG<br>CTTCACTATTTCATCCCTGGAATACG<br>AGGACGTAGGTATCTATTATTGCCT<br>CCAGTATGGCGATCTTTACACATTT<br>GGTGGGGGGACTAAGCTGGAGATTA<br>AGAAGCCTACCACCACCCCCGCACC<br>TCGTCCTCCAACCCCTGCACCTACG<br>ATTGCCAGTCAGCCTCTTTCACTGCG<br>GCCTGAGGCCAGCAGACCAGCTGCC<br>GGCGGTGCCGTCCATACAAGAGGAC<br>TGGACTTCGCGTCCGATAAACCTAC<br>TACCACTCCAGCCCAAGGCCCCCA<br>ACCCCAGCACCGACTATCGCATCAC<br>AGCCTTTGTCACTGCGTCCTGAAGC<br>CAGCCGGCCAGCTGCAGGGGGGC<br>CGTCCACACAAGGGGACTCGACTTT<br>GCGAGTGATAAGCCCACCACCACCC<br>CTGCCCCTAGACCTCCAACCCCAGC<br>CCCTACAATCGCCAGCCAGCCCCTG<br>AGCCTGAGGCCCGAAGCCTGTAGAC<br>CTGCCGCTGGCGGAGCCGTGCACAC<br>CAGAGGCCTGGATTTCGCCTGCGAC<br>ATCTACATCTGGGCCCCTCTGGCCG<br>GCACCTGTGGCGTGCTGCTGCTGAG<br>CCTGGTCATCACCCTGTACTGCAAC<br>CACCGGAAT<br>AGGAGCAAGCGGAGCAGAGGCGGC |

TABLE 11-continued

Exemplary Sequences

|  |  |  |
|---|---|---|
|  |  | CACAGCGACTACATGAACATGACCC |
|  |  | CCCGGAGGCCTGGCCCCACCCGGAA |
|  |  | GCACTACCAGCCCTACGCCCCTCCC |
|  |  | AGGGACTTCGCCGCCTACCGGAGCA |
|  |  | AGAGAGGCCGGAAGAAACTGCTGT |
|  |  | ACATCTTCAAGCAGCCCTTCATGCG |
|  |  | GCCCGTGCAGACCACCCAGGAAGA |
|  |  | GGACGGCTGCAGCTGCCGGTTCCCC |
|  |  | GAGGAAGAGGAAGGCGGCTGCGAA |
|  |  | CTGCGGGTGAAGTTCAGCCGGAGCG |
|  |  | CCGACGCCCCTGCCTACCAGCAGGG |
|  |  | CCAGAACCAGCTGTACAACGAGCTG |
|  |  | AACCTGGGCCGGAGGGAGGAGTAC |
|  |  | GACGTGCTGGACAAGCGGAGAGGC |
|  |  | CGGGACCCTGAGATGGGCGGCAAG |
|  |  | CCCCGGAGAAAGAACCCTCAGGAG |
|  |  | GGCCTGTATAACGAACTGCAGAAAG |
|  |  | ACAAGATGGCCGAGGCCTACAGCG |
|  |  | AGATCGGCATGAAGGGCGAGCGGC |
|  |  | GGAGGGGCAAGGGCCACGACGGCC |
|  |  | TGTACCAGGGCCTGAGCACCGCCAC |
|  |  | CAAGGATACCTACGACGCCCTGCAC |
|  |  | ATGCAGGCCCTGCCCCCCAGA |
| MUC16- 3 (vl-vh) scFv. CD8a. CD28z | 52 DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE YNPSLKNRISISLDTS KNQFFLKFDFVTTAD TATYFCVRGVDYWG QGTTLTVSSKPTTTP APRPPTPAPTIASQPL SLRPEACRPAAGGAV HTRGLDFACDIYIWA PLAGTCGVLLLSLVIT LYCNHRNRSKRSRG GHSDYMNMTPRRPG PTRKHYQPYAPPRDF AAYRSRVKFSRSADA PAYQQGQNQLYNEL NLGRREEYDVLDKR RGRDPEMGGKPRRK NPQEGLYNELQKDK MAEAYSEIGMKGER RRGKGHDGLYQGLS TATKDTYDALHMQA LPPR | 144 GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGA CTAAGCTGGAGATTAAGGGCGGAG GCGGAAGCGGAGGCGGAGGCTCCG GCGGAGGCGGAAGCGACGTGCAAC TTCTGGAGAGCGGGCCAGGGCTAGT CAGGCCCTCCCAGTCGCTTTCACTG ACTTGCAGTGTGACCGGTTACTCTA TTGTGAGTCACTACTATTGGAACTG GATTCGGCAGTTCCCAGGCAACAAA CTGGAATGGATGGGGTACATATCTT CCGATGGCTCGAATGAATATAACCC ATCATTGAAAAATCGTATTTCCATC AGTCTGGATACGAGTAAAAACCAGT TTTTCCTCAAATTCGATTTCGTGACT ACAGCAGATACTGCCACATACTTCT GTGTACGAGGTGTCGATTATTGGGG ACAGGGCACAACGCTGACCGTAAGT TCTAAGCCCACCACCACCCCTGCCC CTAGACCTCCAACCCCAGCCCCTAC AATCGCCAGCCAGCCCCTGAGCCTG AGGCCCGAAGCCTGTAGACCTGCCG CTGGCGGAGCCGTGCACACCAGAGG CCTGGATTTCGCCTGCGACATCTAC ATCTGGGCCCCTCTGGCCGGCACCT GTGGCGTGCTGCTGCTGAGCCTGGT CATCACCCTGTACTGCAACCACCGG AATAGGAGCAAGCGGAGCAGAGGC GGCCACAGCGACTACATGAACATGA CCCCCCGGAGGCCTGGCCCCACCCG GAAGCACTACCAGCCCTACGCCCCT CCCAGGGACTTCGCCGCCTACCGGA GCCGGGTGAAGTTCAGCCGGAGCGC CGACGCCCCTGCCTACCAGCAGGGC CAGAACCAGCTGTACAACGAGCTGA ACCTGGGCCGGAGGGAGGAGTACG ACGTGCTGGACAAGCGGAGAGGCC GGGACCCTGAGATGGGCGGCAAGC CCCGGAGAAAGAACCCTCAGGAGG GCCTGTATAACGAACTGCAGAAAGA CAAGATGGCCGAGGCCTACAGCGA GATCGGCATGAAGGGCGAGCGGCG GAGGGGCAAGGGCCACGACGGCCT GTACCAGGGCCTGAGCACCGCCACC |

TABLE 11-continued

Exemplary Sequences

```
                                AAGGATACCTACGACGCCCTGCACA
                                TGCAGGCCCTGCCCCCAGA
```

| MUC16-3 (vl-vh) scFv. CD8a (2x). CD28z | 53 | DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE YNPSLKNRISISLDTS KNQFFLKFDFVTTAD TATYFCVRGVDYWG QGTTLTVSSKPTTTP APRPPTPAPTIASQPL SLRPEASRPAAGGAV HTRGLDFASDKPTTT PAPRPPTPAPTIASQP LSLRPEACRPAAGGA VHTRGLDFACDIYIW APLAGTCGVLLLSLV ITLYCNHRNRSKRSR GGHSDYMNMTPRRP GPTRKHYQPYAPPRD FAAYRSRVKFSRSAD APAYQQGQNQLYNE LNLGRREEYDVLDK RRGRDPEMGGKPRR KNPQEGLYNELQKD KMAEAYSEIGMKGE RRRGKGHDGLYQGL STATKDTYDALHMQ ALPPR | 145 | GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGA CTAAGCTGGAGATTAAGGGCGGAG GCGGAAGCGGAGGCGGAGGCTCCG GCGGAGGCGGAAGCGACGTGCAAC TTCTGGAGAGCGGGCCAGGGCTAGT CAGGCCCTCCCAGTCGCTTTCACTG ACTTGCAGTGTGACCGGTTACTCTA TTTGTGAGTCACTACTATTGGAACTG GATTCGGCAGTTCCCAGGCAACAAA CTGGAATGGATGGGGTACATATCTT CCGATGGCTCGAATGAATATAACCC ATCATTGAAAAATCGTATTTCCATC AGTCTGGATACGAGTAAAAACCAGT TTTTCCTCAAATTCGATTTCGTGACT ACAGCAGATACTGCCACATACTTCT GTGTACGAGGTGTCGATTATTGGGG ACAGGGCACAACGCTGACCGTAAGT TCTAAACCTACTACAACTCCTGCCC CCCGGCCTCCTACACCAGCTCCTAC TATCGCCTCCCAGCCACTCAGTCTC AGACCCGAGGCTTCTAGGCCAGCGG CCGGAGGCGCGGTCCACACCCGCGG GCTGGACTTTGCATCCGATAAGCCC ACCACCACCCCTGCCCCTAGACCTC CAACCCCAGCCCCTACAATCGCCAG CCAGCCCCTGAGCCTGAGGCCCGAA GCCTGTAGACCTGCCGCTGGCGGAG CCGTGCACACCAGAGGCCTGGATTT CGCCTGCGACATCTACATCTGGGCC CCTCTGGCCGGCACCTGTGGCGTGC TGCTGCTGAGCCTGGTCATCACCCT GTACTGCAACCACCGGAATAGGAGC AAGCGGAGCAGAGGCGGCCACAGC GACTACATGAACATGACCCCCCGGA GGCCTGGCCCCACCCGGAAGCACTA CCAGCCCTACGCCCCTCCCAGGGAC TTCGCCGCCTACCGGAGCCGGGTGA AGTTCAGCCGGAGCGCCGACGCCCC TGCCTACCAGCAGGGCCAGAACCAG CTGTACAACGAGCTGAACCTGGGCC GGAGGGAGGAGTACGACGTGCTGG ACAAGCGGAGAGGCCGGGACCCTG AGATGGGCGGCAAGCCCCGGAGAA AGAACCCTCAGGAGGGCCTGTATAA CGAACTGCAGAAAGACAAGATGGC CGAGGCCTACAGCGAGATCGGCATG AAGGGCGAGCGGCGGAGGGGCAAG GGCCACGACGGCCTGTACCAGGGCC TGAGCACCGCCACCAAGGATACCTA CGACGCCCTGCACATGCAGGCCCTG CCCCCCAGA |
| MUC16-3 (vl-vh) scFv. CD8a (3x). CD28z | 54 | DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE | 146 | GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGA |

TABLE 11-continued

Exemplary Sequences

| | | | |
|---|---|---|---|
| | | YNPSLKNRISISLDTS KNQFFLKFDFVTTAD TATYFCVRGVDYWG QGTTLTVSSKPTTTP APRPPTPAPTIASQPL SLRPEASRPAAGGAV HTRGLDFASDKPTTT PAPRPPTPAPTIASQP LSLRPEASRPAAGGA VHTRGLDFASDKPTT TPAPRPPTPAPTIASQ PLSLRPEACRPAAGG AVHTRGLDFACDIYI WAPLAGTCGVLLLSL VITLYCNHRNRSKRS RGGHSDYMNMTPRR PGPTRKHYQPYAPPR DFAAYRSRVKFSRSA DAPAYQQGQNQLYN ELNLGRREEYDVLDK RRGRDPEMGGKPRR KNPQEGLYNELQKD KMAEAYSEIGMKGE RRRGKGHDGLYQGL STATKDTYDALHMQ ALPPR | | CTAAGCTGGAGATTAAGGGCGGAG GCGGAAGCGGAGGCGGAGGCTCCG GCGGAGGCGGAAGCGACGTGCAAC TTCTGGAGAGCGGGCCAGGGCTAGT CAGGCCCTCCCAGTCGCTTTCACTG ACTTGCAGTGTGACCGGTTACTCTA TTGTGAGTCACTACTATTGGAACTG GATTCGGCAGTTCCCAGGCAACAAA CTGGAATGGATGGGTACATATCTT CCGATGGCTCGAATGAATATAACCC ATCATTGAAAAATCGTATTTCCATC AGTCTGGATACGAGTAAAAACCAGT TTTTCCTCAAATTCGATTTCGTGACT ACAGCAGATACTGCCACATACTTCT GTGTACGAGGTGTCGATTATTGGGG ACAGGGCACAACGCTGACCGTAAGT TCTAAGCCTACCACCACCCCCGCAC CTCGTCCTCCAACCCCTGCACCTAC GATTGCCAGTCAGCCTCTTTCACTGC GGCCTGAGGCCAGCAGACCAGCTGC CGGCGGTGCCGTCCATACAAGAGGA CTGGACTTCGCGTCCGATAAACCTA CTACCACTCCAGCCCCAAGGCCCCC AACCCCAGCACCGACTATCGCATCA CAGCCTTTGTCACTGCGTCCTGAAG CCAGCCGGCCAGCTGCAGGGGGGG CCGTCCACACAAGGGGACTCGACTT TGCGAGTGATAAGCCCACCACCACC CCTGCCCCTAGACCTCCAACCCCAG CCCCTACAATCGCCAGCCAGCCCCT GAGCCTGAGGCCCGAAGCCTGTAGA CCTGCCGCTGGCGGAGCCGTGCACA CCAGAGGCCTGGATTTCGCCTGCGA CATCTACATCTGGGCCCCTCTGGCC GGCACCTGTGGCGTGCTGCTGCTGA GCCTGGTCATCACCCTGTACTGCAA CCACCGGAATAGGAGCAAGCGGAG CAGAGGCGGCCACAGCGACTACATG AACATGACCCCCGGAGGCCTGGCC CCACCCGGAAGCACTACCAGCCCTA CGCCCCTCCCAGGGACTTCGCCGCC TACCGGAGCCGGGTGAAGTTCAGCC GGAGCGCCGACGCCCCTGCCTACCA GCAGGGCCAGAACCAGCTGTACAAC GAGCTGAACCTGGGCCGGAGGGAG GAGTACGACGTGCTGGACAAGCGG AGAGGCCGGGACCCTGAGATGGGC GGCAAGCCCCGGAGAAAGAACCCT CAGGAGGGCCTGTATAACGAACTGC AGAAAGACAAGATGGCCGAGGCCT ACAGCGAGATCGGCATGAAGGGCG AGCGGCGGAGGGGCAAGGGCCACG ACGGCCTGTACCAGGGCCTGAGCAC CGCCACCAAGGATACCTACGACGCC CTGCACATGCAGGCCCTGCCCCCCA GA |
| MUC16- 3 (vl-vh) scFv. CD8a. CD28. 4-1BB.z | 55 | DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE YNPSLKNRISISLDTS KNQFFLKFDFVTTAD TATYFCVRGVDYWG QGTTLTVSSKPTTTP APRPPTPAPTIASQPL SLRPEACRPAAGGAV HTRGLDFACDIYIWA PLAGTCGVLLLSLVIT LYCNHRNRSKRSRG | 147 | GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGA AAGCAGATTCAGCGGGAGCGGAAG TGGACAGGATTATAGCTTCACTATT CTAAGCTGGAGATTAAGGGCGGAG GCGGAAGCGGAGGCGGAGGCTCCG GCGGAGGCGGAAGCGACGTGCAAC TTCTGGAGAGCGGGCCAGGGCTAGT CAGGCCCTCCCAGTCGCTTTCACTG ACTTGCAGTGTGACCGGTTACTCTA TTGTGAGTCACTACTATTGGAACTG GATTCGGCAGTTCCCAGGCAACAAA CTGGAATGGATGGGTACATATCTT |

TABLE 11-continued

Exemplary Sequences

| | | | |
|---|---|---|---|
| | GHSDYMNMTPRRPG | | CCGATGGCTCGAATGAATATAACCC |
| | PTRKHYQPYAPPRDF | | ATCATTGAAAAATCGTATTTCCATC |
| | AAYRSKRGRKKLLYI | | AGTCTGGATACGAGTAAAAACCAGT |
| | FKQPFMRPVQTTQEE | | TTTTCCTCAAATTCGATTTCGTGACT |
| | DGCSCRFPEEEEGGC | | ACAGCAGATACTGCCACATACTTCT |
| | ELRVKFSRSADAPAY | | GTGTACGAGGTGTCGATTATTGGGG |
| | QQGQNQLYNELNLG | | ACAGGGCACAACGCTGACCGTAAGT |
| | RREEYDVLDKRRGR | | TCTAAGCCCACCACCACCCCTGCCC |
| | DPEMGGKPRRKNPQ | | CTAGACCTCCAACCCCAGCCCCTAC |
| | EGLYNELQKDKMAE | | AATCGCCAGCCAGCCCCTGAGCCTG |
| | AYSEIGMKGERRRGK | | AGGCCCGAAGCCTGTAGACCTGCCG |
| | GHDGLYQGLSTATK | | CTGGCGGAGCCGTGCACACCAGAGG |
| | DTYDALHMQALPPR | | CCTGGATTTCGCCTGCGACATCTAC |
| | | | ATCTGGGCCCCTCTGGCCGGCACCT |
| | | | GTGGCGTGCTGCTGCTGAGCCTGGT |
| | | | CATCACCCTGTACTGCAACCACCGG |
| | | | AATAGGAGCAAGCGGAGCAGAGGC |
| | | | GGCCACAGCGACTACATGAACATGA |
| | | | CCCCCCGGAGGCCTGGCCCCACCCG |
| | | | GAAGCACTACCAGCCCTACGCCCCT |
| | | | CCCAGGGACTTCGCCGCCTACCGGA |
| | | | GCAAGAGAGGCCGGAAGAAACTGC |
| | | | TGTACATCTTCAAGCAGCCCTTCAT |
| | | | GCGGCCCGTGCAGACCACCCAGGAA |
| | | | GAGGACGGCTGCAGCTGCCGGTTCC |
| | | | CCGAGGAAGAGGAAGGCGGCTGCG |
| | | | AACTGCGGGTGAAGTTCAGCCGGAG |
| | | | CGCCGACGCCCCTGCCTACCAGCAG |
| | | | GGCCAGAACCAGCTGTACAACGAGC |
| | | | TGAACCTGGGCCGGAGGGAGGAGT |
| | | | ACGACGTGCTGGACAAGCGGAGAG |
| | | | GCCGGGACCCTGAGATGGGCGGCA |
| | | | AGCCCCGGAGAAAGAACCCTCAGG |
| | | | AGGGCCTGTATAACGAACTGCAGAA |
| | | | AGACAAGATGGCCGAGGCCTACAG |
| | | | CGAGATCGGCATGAAGGGCGAGCG |
| | | | GCGGAGGGGCAAGGGCCACGACGG |
| | | | CCTGTACCAGGGCCTGAGCACCGCC |
| | | | ACCAAGGATACCTACGACGCCCTGC |
| | | | ACATGCAGGCCCTGCCCCCCAGA |
| MUC16-3 (vl-vh) scFv. CD8a (2x). CD28. 4-1BB.z | 56 DIKMAQSPSSVNASL GERVTITCKASRDIN NFLSWFHQKPGKSPK TLIYRANRLVDGVPS RFSGSGSGQDYSFTIS SLEYEDVGIYYCLQY GDLYTFGGGTKLEIK GGGGSGGGGSGGGG SDVQLLESGPGLVRP SQSLSLTCSVTGYSIV SHYYWNWIRQFPGN KLEWMGYISSDGSNE YNPSLKNRISISLDTS KNQFFLKFDFVTTAD TATYFCVRGVDYWG QGTTLTVSSKPTTTP APRPPTPAPTIASQPL SLRPEASRPAAGGAV HTRGLDFASDKPTTT PAPRPPTPAPTIASQP LSLRPEACRPAAGGA VHTRGLDFACDIYIW APLAGTCGVLLLSLV ITLYCNHRNSKRSR GGHSDYMNMTPRRP GPTRKHYQPYAPPRD FAAYRSKRGRKKLL YIFKQPFMRPVQTTQ EEDGCSCRFPEEEEG CELRVKFSRSADAP AYQQGQNQLYNELN LGRREEYDVLDKRR GRDPEMGGKPRRKN PQEGLYNELQKDKM AEAYSEIGMKGERRR GKGHDGLYQGLSTA TKDTYDALHMQALP | 148 GACATCAAGATGGCTCAGTCCCCTT CTAGCGTGAATGCTTCGCTAGGGGA GCGTGTGACCATCACATGTAAAGCA TCACGCGACATAAATAATTTCCTTTC CTGGTTTCATCAGAAACCGGGCAAG TCGCCTAAGACGCTGATTTACAGAG CAAATCGGTTGGTAGATGGAGTGCC AAGCAGATTCAGCGGGAGCGGAAG TGGACAGGATTATAGCTTCACTATT TCATCCCTGGAATACGAGGACGTAG GTATCTATTATTGCCTCCAGTATGGC GATCTTTACACATTTGGTGGGGGGGA CTAAGCTGGAGATTAAGGGCGGAG GCGGAAGCGGAGGCGGAGGCTCCG GCGGAGGCGGAAGCGACGTGCAAC TTCTGGAGAGCGGGCCAGGGCTAGT CAGGCCCTCCCAGTCGCTTTCACTG ACTTGCAGTGTGACCGGTTACTCTA TTGTGAGTCACTACTATTGGAACTG GATTCGGCAGTTCCCAGGCAACAAA CTGGAATGGATGGGGTACATATCTT CCGATGGCTCGAATGAATATAACCC ATCATTGAAAAATCGTATTTCCATC AGTCTGGATACGAGTAAAAACCAGT TTTTCCTCAAATTCGATTTCGTGACT ACAGCAGATACTGCCACATACTTCT GTGTACGAGGTGTCGATTATTGGGG ACAGGGCACAACGCTGACCGTAAGT TCTAAACCTACTACAACTCCTGCCC CCCGGCCTCCTACACCAGCTCCTAC TATGCCTCCCAGCCACTCAGTCTC AGACCCGAGGCTTCTAGGCCAGCAG CCGGAGGCGCGGTCCACACCCGCGG GCTGGACTTTGCATCCGATAAGCCC ACCACCACCCCTGCCCCTAGACCTC CAACCCCAGCCCCTACAATCGCCAG CCAGCCCCTGAGCCTGAGGCCCGAA |

TABLE 11-continued

Exemplary Sequences

| | | |
|---|---|---|
| | PR | GCCTGTAGACCTGCCGCTGGCGGAG |
| | | CCGTGCACACCAGAGGCCTGGATTT |
| | | CGCCTGCGACATCTACATCTGGGCC |
| | | CCTCTGGCCGGCACCTGTGGCGTGC |
| | | TGCTGCTGAGCCTGGTCATCACCCT |
| | | GTACTGCAACCACCGGAATAGGAGC |
| | | AAGCGGAGCAGAGGCGGCCACAGC |
| | | GACTACATGAACATGACCCCCCGGA |
| | | GGCCTGGCCCCACCCGGAAGCACTA |
| | | CCAGCCCTACGCCCCTCCCAGGGAC |
| | | TTCGCCGCCTACCGGAGCAAGAGAG |
| | | GCCGGAAGAAACTGCTGTACATCTT |
| | | CAAGCAGCCCTTCATGCGGCCCGTG |
| | | CAGACCACCCAGGAAGAGGACGGC |
| | | TGCAGCTGCCGGTTCCCCGAGGAAG |
| | | AGGAAGGCGGCTGCGAACTGCGGG |
| | | TGAAGTTCAGCCGGAGCGCCGACGC |
| | | CCCTGCCTACCAGCAGGGCCAGAAC |
| | | CAGCTGTACAACGAGCTGAACCTGG |
| | | GCCGGAGGGAGGAGTACGACGTGC |
| | | TGGACAAGCGGAGAGGCCGGGACC |
| | | CTGAGATGGGCGGCAAGCCCCGGA |
| | | GAAAGAACCCTCAGGAGGGCCTGTA |
| | | TAACGAACTGCAGAAAGACAAGAT |
| | | GGCCGAGGCCTACAGCGAGATCGGC |
| | | ATGAAGGGCGAGCGGCGGAGGGGC |
| | | AAGGGCCACGGACGGCCTGTACCAGG |
| | | GCCTGAGCACCGCCACCAAGGATAC |
| | | CTACGACGCCCTGCACATGCAGGCC |
| | | CTGCCCCCCAGA |
| MUC16-<br>3 (vl-vh)<br>scFv.<br>CD8a<br>(3x).<br>CD28.<br>4-1BB.z | 57 DIKMAQSPSSVNASL<br>GERVTITCKASRDIN<br>NFLSWFHQKPGKSPK<br>TLIYRANRLVDGVPS<br>RFSGSGSGQDYSFTIS<br>SLEYEDVGIYYCLQY<br>GDLYTFGGGTKLEIK<br>GGGGSGGGGSGGGG<br>SDVQLLESGPGLVRP<br>SQSLSLTCSVTGYSIV<br>SHYYWNWIRQFPGN<br>KLEWMGYISSDGSNE<br>YNPSLKNRISISLDTS<br>KNQFFLKFDFVTTAD<br>TATYFCVRGVDYWG<br>QGTTLTVSSKPTTTP<br>APRPPTPAPTIASQPL<br>SLRPEASRPAAGGAV<br>HTRGLDFASDKPTTT<br>PAPRPPTPAPTIASQP<br>LSLRPEASRPAAGGA<br>VHTRGLDFASDKPTT<br>TPAPRPPTPAPTIASQ<br>PLSLRPEACRPAAGG<br>AVHTRGLDFACDIYI<br>WAPLAGTCGVLLLSL<br>VITLYCNHRNRSKRS<br>RGGHSDYMNMTPRR<br>PGPTRKHYQPYAPPR<br>DFAAYRSKRGRKKL<br>LYIFKQPFMRPVQTT<br>QEEDGCSCRFPEEEE<br>GGCELRVKFSRSADA<br>PAYQQGQNQLYNEL<br>NLGRREEYDVLDKR<br>RGRDPEMGGKPRRK<br>NPQEGLYNELQKDK<br>MAEAYSEIGMKGER<br>RRGKGHDGLYQGLS<br>TATKDTYDALHMQA<br>LPPR | 149 GACATCAAGATGGCTCAGTCCCCTT<br>CTAGCGTGAATGCTTCGCTAGGGGA<br>GCGTGTGACCATCACATGTAAAGCA<br>TCACGCGACATAAATAATTTCCTTTC<br>CTGGTTTCATCAGAAACCGGGCAAG<br>TCGCCTAAGACGCTGATTTACAGAG<br>CAAATCGGTTGGTAGATGGAGTGCC<br>AAGCAGATTCAGCGGGAGCGGAAG<br>TGGACAGGATTATAGCTTCACTATT<br>TCATCCCTGGAATACGAGGACGTAG<br>GTATCTATTATTGCCTCCAGTATGGC<br>GATCTTTACACATTTGGTGGGGGGA<br>CTAAGCTGGAGATTAAGGGCGGAG<br>GCGGAAGCGGAGGCGGAGGCTCCG<br>GCGGAGGCGGAAGCGACGTGCAAC<br>TTCTGGAGAGCGGGCCAGGGCTAGT<br>CAGGCCCTCCCAGTCGCTTTCACTG<br>ACTTGCAGTGTGACCGGTTACTCTA<br>TTGTGAGTCACTACTATTGGAACTG<br>GATTCGGCAGTTCCCAGGCAACAAA<br>CTGGAATGGATGGGGTACATATCTT<br>CCGATGGCTCGAATGAATATAACCC<br>ATCATTGAAAAATCGTATTTCCATC<br>AGTCTGGATACGAGTAAAAACCAGT<br>TTTTCCTCAAATTCGATTTCGTGACT<br>ACAGCAGATACTGCCACATACTTCT<br>GTGTACGAGGTGTCGATTATTGGGG<br>ACAGGGCACAACGCTGACCGTAAGT<br>TCTAAGCCTACCACCACCCCCCGCAC<br>CTCGTCCTCCAACCCCTGCACCTAC<br>GATTGCCAGTCAGCCTCTTTCACTGC<br>GGCCTGAGGCCAGCAGACCAGCTGC<br>CGGCGGTGCCGTCCATACAAGAGGA<br>CTGGACTTCGCGTCCGATAAACCTA<br>CTACCACTCCAGCCCCAAGGCCCCC<br>AACCCCAGCACCGACTATCGCATCA<br>CAGCCTTTGTCACTGCGTCCTGAAG<br>CCAGCCGGCCAGCTGCAGGGGGGG<br>CCGTCCACACAAGGGGACTCGACTT<br>TGCGAGTGATAAGCCCACCACCACC<br>CCTGCCCCTAGACCTCCAACCCCCAG<br>CCCCTACAATCGCCAGCCAGCCCCT<br>GAGCCTGAGGCCCGAAGCCTGTAGA<br>CCTGCCGCTGGCGGAGCCGTGCACA<br>CCAGAGGCCTGGATTTCGCCTGCGA<br>CATCTACATCTGGGCCCCTCTGGCC<br>GGCACCTGTGGCGTGCTGCTGCTGA |

TABLE 11-continued

| Exemplary Sequences |
|---|
| GCCTGGTCATCACCCTGTACTGCAA
CCACCGGAATAGGAGCAAGCGGAG
CAGAGGCGGCCACAGCGACTACATG
AACATGACCCCCGGAGGCCTGGCC
CCACCCGGAAGCACTACCAGCCCTA
CGCCCCTCCCAGGGACTTCGCCGCC
TACCGGAGCAAGAGAGGCCGGAAG
AAACTGCTGTACATCTTCAAGCAGC
CCTTCATGCGGCCCGTGCAGACCAC
CCAGGAAGAGGACGGCTGCAGCTG
CCGGTTCCCCGAGGAAGAGGAAGG
CGGCTGCGAACTGCGGGTGAAGTTC
AGCCGGAGCGCCGACGCCCCTGCCT
ACCAGCAGGGCCAGAACCAGCTGTA
CAACGAGCTGAACCTGGGCCGGAG
GGAGGAGTACGACGTGCTGGACAA
GCGGAGAGGCCGGGACCCTGAGAT
GGGCGGCAAGCCCCGGAGAAAGAA
CCCTCAGGAGGGCCTGTATAACGAA
CTGCAGAAAGACAAGATGGCCGAG
GCCTACAGCGAGATCGGCATGAAGG
GCGAGCGGCGGAGGGGCAAGGGCC
ACGACGGCCTGTACCAGGGCCTGAG
CACCGCCACCAAGGATACCTACGAC
GCCCTGCACATGCAGGCCCTGCCCC
CCAGA |

| SIGNAL PEPTIDES |||||
|---|---|---|---|---|
| GMCSF R alpha | 58 | MLLLVTSLLLCELPH PAFLLIP | 150 | ATGCTTCTCCTGGTGACAAGCCTTCT GCTCTGTGAGTTACCACACCCAGCA TTCCTCCTGATCCCA |
| Ig Kappa | 59 | MRLPAQLLGLLMLW VPGSSG | 151 | ATGAGGCTCCCTGCTCAGCTCCTGG GGCTGCTAATGCTCTGGGTCCCAGG ATCCAGTGGG |
| Immuno-globulin E | 60 | MDWTWILFLVAAAT RVHS | 152 | ATGGATTGGACCTGGATTCTGTTTCT GGTGGCCGCTGCCACAAGAGTGCAC AGC |
| CD8α | 61 | MALPVTALLLPLALL LHAARP | 153 | ATGGCGCTGCCCGTGACCGCCTTGC TCCTGCCGCTGGCCTTGCTGCTCCAC GCCGCCAGGCCG |
| TVB2 (T21A) | 62 | MGTSLLCWMALCLL GADHADA | 154 | ATGGGCACCAGCCTCCTCTGCTGGA TGGCCCTGTGTCTCCTGGGGGCAGA TCACGCAGATGCT |
| CD52 | 63 | MKRFLFLLLTISLLV MVQIQTGLS | 155 | ATGAAGCGCTTCCTCTTCCTCCTACT CACCATCAGCCTCCTGGTTATGGTA CAGATACAAACTGGACTCTCA |
| Low-affinity nerve growth factor receptor (LNGFR, TNFRSF 16) | 64 | MGAGATGRAMDGPR LLLLLLLGVSLGGA | 156 | ATGGGGGCAGGTGCCACCGGCCGCG CCATGGACGGGCCGCGCCTGCTGCT GTTGCTGCTTCTGGGGGTGTCCCTTG GAGGTGCC |

| KILL SWITCH |||||
|---|---|---|---|---|
| HER1t | 65 | RKVCNGIGIGEFKDS LSINATNIKHFKNCTS ISGDLHILPVAFRGDS FTHTPPLDPQELDILK TVKEITGFLLIQAWPE NRTDLHAFENLEIIRG RTKQHGQFSLAVVSL NITSLGLRSLKEISDG DVIISGNKNLCYANTI NWKKLFGTSGQKTKI ISNRGENSCKATGQV CHALCSPEGCWGPEP RDCVSCRNVSRGREC | 157 | CGCAAAGTGTGTAACGGAATAGGTA TTGGTGAATTTAAAGACTCACTCTC CATAAATGCTACGAATATTAAACAC TTCAAAAACTGCACCTCCATCAGTG GCGATCTCCACATCCTGCCGGTGGC ATTTAGGGGTGACTCCTTCACACAT ACTCCTCCTCTGGATCCACAGGAAC TGGATATTCTGAAAACCGTAAAGGA AATCACAGGGTTTTTGCTGATTCAG GCTTGGCCTGAAAACAGGACGGACC TCCATGCCTTTGAGAACCTAGAAAT CATACGCGGCAGGACCAAGCAACAT GGTCAGTTTTCTCTTGCAGTCGTCAG |

TABLE 11-continued

Exemplary Sequences

|  |  |  |  |
|---|---|---|---|
|  | VDKCNLLEGEPREFV<br>ENSECIQCHPECLPQA<br>MNITCTGRGPDNCIQ<br>CAHYIDGPHCVKTCP<br>AGVMGENNTLVWK<br>YADAGHVCHLCHPN<br>CTYGCTGPGLEGCPT<br>NGPKIPSIATGMVGA<br>LLLLLVVALGIGLFM |  | CCTGAACATAACATCCTTGGGATTA<br>CGCTCCCTCAAGGAGATAAGTGATG<br>GAGATGTGATAATTTCAGGAAACAA<br>AAATTTGTGCTATGCAAATACAATA<br>AACTGGAAAAAACTGTTTGGGACCT<br>CCGGTCAGAAAACCAAAATTATAAG<br>CAACAGAGGTGAAAACAGCTGCAA<br>GGCCACAGGCCAGGTCTGCCATGCC<br>TTGTGCTCCCCCGAGGGCTGCTGGG<br>GCCCGGAGCCCAGGGACTGCGTCTC<br>TTGCCGGAATGTCAGCCGAGGCAGG<br>GAATGCGTGGACAAGTGCAACCTTC<br>TGGAGGGTGAGCCAAGGGAGTTTGT<br>GGAGAACTCTGAGTGCATACAGTGC<br>CACCCAGAGTGCCTGCCTCAGGCCA<br>TGAACATCACCTGCACAGGACGGGG<br>ACCAGACAACTGTATCCAGTGTGCC<br>CACTACATTGACGGCCCCCACTGCG<br>TCAAGACCTGCCCGGCAGGAGTCAT<br>GGGAGAAAACAACACCCTGGTCTGG<br>AAGTACGCAGACGCCGGCCATGTGT<br>GCCACCTGTGCCATCCAAACTGCAC<br>CTACGGATGCACTGGGCCAGGTCTT<br>GAAGGCTGTCCAACGAATGGGCCTA<br>AGATCCCGTCCATCGCCACTGGGAT<br>GGTGGGGGCCCTCCTCTTGCTGCTG<br>GTGGTGGCCCTGGGGATCGGCCTCT<br>TCATG |
| HER1t-1 | 66 RKVCNGIGIGEFKDS<br>LSINATNIKHFKNCTS<br>ISGDLHILPVAFRGDS<br>FTHTPPLDPQELDILK<br>TVKEITGFLLIQAWPE<br>NRTDLHAFENLEIIRG<br>RTKQHGQFSLAVVSL<br>NITSLGLRSLKEISDG<br>DVIISGNKNLCYANTI<br>NWKKLFGTSGQKTKI<br>ISNRGENSCKATGQV<br>CHALCSPEGCWGPEP<br>RDCVSGGGGSGGGS<br>GGGGSGGGGSFWVL<br>VVVGGVLACYSLLV<br>TVAFIIFWVRSKRS | 158 | CGCAAAGTGTGTAACGGAATAGGTA<br>TTGGTGAATTTAAAGACTCACTCTC<br>CATAAATGCTACGAATATTAAACAC<br>TTCAAAAACTGCACCTCCATCAGTG<br>GCGATCTCCACATCCTGCCGGTGGC<br>ATTTAGGGGTGACTCCTTCACACAT<br>ACTCCTCCTCTGGATCCACAGGAAC<br>TGGATATTCTGAAAACCGTAAAGGA<br>AATCACAGGGTTTTTGCTGATTCAG<br>GCTTGGCCTGAAAACAGGACGGACC<br>TCCATGCCTTTGAGAACCTAGAAAT<br>CATACGCGGCAGGACCAAGCAACAT<br>GGTCAGTTTTCTCTTGCAGTCGTCAG<br>CCTGAACATAACATCCTTGGGATTA<br>CGCTCCCTCAAGGAGATAAGTGATG<br>GAGATGTGATAATTTCAGGAAACAA<br>AAATTTGTGCTATGCAAATACAATA<br>AACTGGAAAAAACTGTTTGGGACCT<br>CCGGTCAGAAAACCAAAATTATAAG<br>CAACAGAGGTGAAAACAGCTGCAA<br>GGCCACAGGCCAGGTCTGCCATGCC<br>TTGTGCTCCCCCGAGGGCTGCTGGG<br>GCCCGGAGCCCAGGGACTGCGTCTC<br>TGGTGGCGGTGGCTCGGGCGGTGGT<br>GGGTCGGGTGGCGGCGGATCTGGTG<br>GCGGTGGCTCGTTTTGGGTGCTGGT<br>GGTGGTTGGTGGAGTCCTGGCTTGC<br>TATAGCTTGCTAGTAACAGTGGCCT<br>TTATTATTTTCTGGGTGAGGAGTAA<br>GAGGAGC |
| FL CD20 | 67 MTTPRNSVNGTFPAE<br>PMKGPIAMQSGPKPL<br>FRRMSSLVGPTQSFF<br>MRESKTLGAVQIMN<br>GLFHIALGGLLMIPA<br>GIYAPICVTVWYPLW<br>GGIMYIISGSLLAATE<br>KNSRKCLVKGKMIM<br>NSLSLFAAISGMILSI<br>MDILNIKISHFLKMES<br>LNFIRAHTPYINIYNC<br>EPANPSEKNSPSTQY<br>CYSIQSLFLGILSVML<br>IFAFFQELVIAGIVEN<br>EWKRTCSRPKSNIVL<br>LSAEEKKEQTIEIKEE<br>VVGLTETSSQPKNEE<br>DIEIIPIQEEEEEETET | 159 | ATGACAACACCCAGAAATTCAGTAA<br>ATGGGACTTTCCCGGCAGAGCCAAT<br>GAAAGGCCCTATTGCTATGCAATCT<br>GGTCCAAAACCACTCTTCAGGAGGA<br>TGTCTTCACTGGTGGGCCCCACGCA<br>AAGCTTCTTCATGAGGGAATCTAAG<br>ACTTTGGGGGCTGTCCAGATTATGA<br>ATGGGCTCTTCCACATTGCCCTGGG<br>GGGTCTTCTGATGATCCCAGCAGGG<br>ATCTATGCACCCATCTGTGTGACTGT<br>GTGGTACCCTCTCTGGGGAGGCATT<br>ATGTATATTATTTCCGGATCACTCCT<br>GGCAGCAACGGAGAAAAACTCCAG<br>GAAGTGTTTGGTCAAAGGAAAAATG<br>ATAATGAATTCATTGAGCCTCTTTGC<br>TGCCATTTCTGGAATGATTCTTTCAA<br>TCATGGACATACTTAATATTAAAAT<br>TTCCCATTTTTTAAAAATGGAGAGT |

TABLE 11-continued

Exemplary Sequences

| | | | |
|---|---|---|---|
| | | NFPEPPQDQESSPIENDSSP | CTGAATTTTATTAGAGCTCACACACCATATATTAACATATACAACTGTGAACCAGCTAATCCCTCTGAGAAAAACTCCCCATCTACCCAATACTGTTACAGCATACAATCTCTGTTCTTGGGCATTTTGTCAGTGATGCTGATCTTTGCCTTCTTCCAGGAACTTGTAATAGCTGGCATCGTTGAGAATGAATGGAAAAGAACGTGCTCCAGACCCAAATCTAACATAGTTCTCCTGTCAGCAGAAGAAAAAAAAGAACAGACTATTGAAATAAAAGAAGAAGTGGTTGGGCTAACTGAAACATCTTCCCAACCAAGAATGAAGAAGACATTGAAATTATTCCAATCCAAGAAGAGGAAGAAGAAGAAACAGAGACGAACTTTCCAGAACCTCCCCAAGATCAGGAATCCTCACCAATAGAAAATGACAGCTCTCCT |
| CD20t-1 | 68 | MTTPRNSVNGTFPAEPMKGPIAMQSGPKPLFRRMSSLVGPTQSFFMRESKTLGAVQIMNGLFHIALGGLLMIPAGIYAPICVTVWYPLWGGIMYIISGSLLAATEKNSRKCLVKGKMIMNSLSLFAAISGMILSIMDILNIKISHFLKMESLNFIRAHTPYINIYNCEPANPSEKNSPSTQYCYSIQSLFLGILSVMLIFAFFQELVIAGIVENEWKRTCSRPKSNIVLLSAEEKKEQTIEIKEEVVGLTETSSQPKNEEDIE | 160 | ATGACCACACCACGGAACTCTGTGAATGGCACCTTCCCAGCAGAGCCAATGAAGGGACCAATCGCAATGCAGAGCGGACCCAAGCCTCTGTTTCGGAGAATGAGCTCCCTGGTGGGCCCAACCCAGTCCTTCTTTATGAGAGAGTCTAAGACACTGGGCGCCGTGCAGATCATGAACGGACTGTTCCACATCGCCCTGGGAGGACTGCTGATGATCCCAGCCGGCATCTACGCCCCTATCTGCGTGACCGTGTGGTACCCTCTGTGGGGCGGCATCATGTATATCATCTCCGGCTCTCTGCTGGCCGCCACAGAGAAGAACAGCAGGAAGTGTCTGGTGAAGGGCAAGATGATCATGAATAGCCTGTCCCTGTTTGCCGCCATCTCTGGCATGATCCTGAGCATCATGGACATCCTGAACATCAAGATCAGCCACTTCCTGAAGATGGAGAGCCTGAACTTCATCAGAGCCCACACCCCTTACATCAACATCTATAATTGCGAGCCTGCCAACCCATCCGAGAAGAATTCTCCAAGCACACAGTACTGTTATTCCATCCAGTCTCTGTTCCTGGGCATCCTGTCTGTGATGCTGATCTTTGCCTTCTTTCAGGAGCTGGTCATCGCCGGCATCGTGGAGAACGAGTGGAAGAGGACCTGCAGCCGCCCCAAGTCCAATATCGTGCTGCTGTCCGCCGAGGAGAAGAAGGAGCAGACAATCGAGATCAAGGAGGAGGTGGTGGGCCTGACCGAGACATCTAGCCAGCCTAAGAATGAGGAGGATATCGAG | mbIL-15

| | | | |
|---|---|---|---|
| mbIL15 | 69 | MDWTWILFLVAAATRVHSNWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMFINTSSGGGSGGGGSGGGGSGGGGSGGGGSLQITCPPPMSVEHADIWVKSYSLYSRERYICNSGFKRKAGTSSLTECVLNKATNVAHWTTPSLKCIRDPALVHQRPAPPSTVTTAGVTPQPESLSPSGKEPAASSPSSNNTAATTAAIVPGSQLMPSKSPSTGTTEISSHESSHGTPSQTTAKNWELTASASHQPPGVYPQGHSDTTVAISTSTVLLCGLSAVSLLACYLKSRQTPPL | 161 | ATGGATTGGACCTGGATTCTGTTTCTGGTGGCCGCTGCCACAAGAGTGCACAGCAACTGGGTGAATGTGATCAGCGACCTGAAGAAGATCGAGGATCTGATCCAGAGCATGCACATTGATGCCACCCTGTACACAGAATCTGATGTGCACCCTAGCTGTAAAGTGACCGCCATGAAGTGTTTTCTGCTGGAGCTGCAGGTGATTTCTCTGGAAAGCGGAGATGCCTCTATCCACGACACAGTGGAGAATCTGATCATCCTGGCCAACAATAGCCTGAGCAGCAATGGCAATGTGACAGAGTCTGGCTGTAAGGAGTGTGAGGAGCTGGAGGAGAAGAACATCAAGGAGTTTCTGCAGAGCTTTGTGCACATCGTGCAGATGTTCATCAATACAAGCTCTGGCGGAGGATCTGGAGGAGGCGGATCTGGAGGAGGAGGCAGTGGAGGCGGAGGATCTGGCGGAGGATCTGCAGGAGGATCTGCCCCTATGAGCGTGGAACATGCCCTCCTCCAATGTCTGTGGAGCACGCCGATATTTGGGTGAAGTCCTACAGCCTGTACAGCAGAGAGATACATCTGCAACAGCGGCTTTAAGAGAAAGGCCGGCACCTCTTCTCT |

TABLE 11-continued

Exemplary Sequences

|  |  |  |
|---|---|---|
|  | ASVEMEAMEALPVT<br>WGTSSRDEDLENCSH<br>HL | GACAGAGTGCGTGCTGAATAAGGCC<br>ACAAATGTGGCCCACTGGACAACAC<br>CTAGCCTGAAGTGCATTAGAGATCC<br>TGCCCTGGTCCACCAGAGGCCTGCC<br>CCTCCATCTACAGTGACAACAGCCG<br>GAGTGACACCTCAGCCTGAATCTCT<br>GAGCCCTTCTGGAAAAGAACCTGCC<br>GCCAGCTCTCCTAGCTCTAATAATA<br>CCGCCGCCACAACAGCCGCCATTGT<br>GCCTGGATCTCAGCTGATGCCTAGC<br>AAGTCTCCTAGCACAGGCACAACAG<br>AGATCAGCAGCCACGAATCTTCTCA<br>CGGAACACCTTCTCAGACCACCGCC<br>AAGAATTGGGAGCTGACAGCCTCTG<br>CCTCTCACCAGCCTCCAGGAGTGTA<br>TCCTCAGGGCCACTCTGATACAACA<br>GTGGCCATCAGCACATCTACAGTGC<br>TGCTGTGTGGACTGTCTGCCGTGTCT<br>CTGCTGGCCTGTTACCTGAAGTCTA<br>GACAGACACCTCCTCTGGCCTCTGT<br>GGGAGATGGAGGCCATGGAAGCCCT<br>GCCTGTGACATGGGGAACAAGCAGC<br>AGAGATGAGGACCTGGAGAATTGTT<br>CTCACCACCTG |
| IL-15 | 70 NWVNVISDLKKIEDL<br>IQSMHIDATLYTESD<br>VHPSCKVTAMKCFLL<br>ELQVISLESGDASIHD<br>TVENLIILANNSLSSN<br>GNVTESGCKECEELE<br>EKNIKEFLQSFVHIVQ<br>MFINTS | 162 AACTGGGTGAATGTGATCAGCGACC<br>TGAAGAAGATCGAGGATCTGATCCA<br>GAGCATGCACATTGATGCCACCCTG<br>TACACAGAATCTGATGTGCACCCTA<br>GCTGTAAAGTGACCGCCATGAAGTG<br>TTTTCTGCTGGAGCTGCAGGTGATTT<br>CTCTGGAAAGCGGAGATGCCTCTAT<br>CCACGACACAGTGGAGAATCTGATC<br>ATCCTGGCCAACAATAGCCTGAGCA<br>GCAATGGCAATGTGACAGAGTCTGG<br>CTGTAAGGAGTGTGAGGAGCTGGAG<br>GAGAAGAACATCAAGGAGTTTCTGC<br>AGAGCTTTGTGCACATCGTGCAGAT<br>GTTCATCAATACAAGC |
| IL-15Rα | 71 ITCPPPMSVEHADIW<br>VKSYSLYSRERYICN<br>SGFKRKAGTSSLTEC<br>VLNKATNVAHWTTP<br>SLKCIRDPALVHQRP<br>APPSTVTTAGVTPQP<br>ESLSPSGKEPAASSPS<br>SNNTAATTAAIVPGS<br>QLMPSKSPSTGTTEIS<br>SHESSHGTPSQTTAK<br>NWELTASASHQPPGV<br>YPQGHSDTTVAISTST<br>VLLCGLSAVSLLACY<br>LKSRQTPPLASVEME<br>AMEALPVTWGTSSR<br>DEDLENCSHHL | 163 ATTACATGCCCTCCTCCAATGTCTGT<br>GGAGCACGCCGATATTTGGGTGAAG<br>TCCTACAGCCTGTACAGCAGAGAGA<br>GATACATCTGCAACAGCGGCTTTAA<br>GAGAAAGGCCGGCACCTCTTCTCTG<br>ACAGAGTGCGTGCTGAATAAGGCCA<br>CAAATGTGGCCCACTGGACAACACC<br>TAGCCTGAAGTGCATTAGAGATCCT<br>GCCCTGGTCCACCAGAGGCCTGCCC<br>CTCCATCTACAGTGACAACAGCCGG<br>AGTGACACCTCAGCCTGAATCTCTG<br>AGCCCTTCTGGAAAAGAACCTGCCG<br>CCAGCTCTCCTAGCTCTAATAATAC<br>CGCCGCCACAACAGCCGCCATTGTG<br>CCTGGATCTCAGCTGATGCCTAGCA<br>AGTCTCCTAGCACAGGCACAACAGA<br>GATCAGCAGCCACGAATCTTCTCAC<br>GGAACACCTTCTCAGACCACCGCCA<br>AGAATTGGGAGCTGACAGCCTCTGC<br>CTCTCACCAGCCTCCAGGAGTGTAT<br>CCTCAGGGCCACTCTGATACAACAG<br>TGGCCATCAGCACATCTACAGTGCT<br>GCTGTGTGGACTGTCTGCCGTGTCTC<br>TGCTGGCCTGTTACCTGAAGTCTAG<br>ACAGACACCTCCTCTGGCCTCTGTG<br>GAGATGGAGGCCATGGAAGCCCTGC<br>CTGTGACATGGGGAACAAGCAGCA<br>GAGATGAGGACCTGGAGAATTGTTC<br>TCACCACCTG |

LINKERS

| T2A | 72 EGRGSLLTCGDVEEN<br>PGP | 164 GAGGGCAGAGGAAGTCTTCTAACATGC<br>GGTGACGTGGAGGAGAATCCCGGCCCT |
| Furin-<br>GSG-T2A | 73 RAKRGSGEGRGSLLT<br>CGDVEENPGP | 165 AGAGCTAAGAGGGGAAGCGGAGAGGG<br>CAGAGGAAGTCTGCTAACATGCGGTGA<br>CGTCGAGGAGAATCCTGGACCT |

TABLE 11-continued

Exemplary Sequences

| | | | |
|---|---|---|---|
| Furin-SGSG-T2A | 74 | RAKRSGSGEGRGSLLTCGDVEENPGP | 166 AGGGCCAAGAGGAGTGGCAGCGGCGAGGGCAGAGGAAGTCTTCTAACATGCGGTGACGTGGAGGAGAATCCCGGCCCT |
| Porcine teschovirus-1 2A region (P2A) | 75 | ATNFSLLKQAGDVEENPGP | 167 GCAACGAACTTCTCTCTCCTAAAACAGGCTGGTGATGTGGAGGAGAATCCTGGTCCA |
| GSG-p2a | 76 | GSGATNFSLLKQAGDVEENPGP | 168 GGAAGCGGAGCTACTAACTTCAGCCTGCTGAAGCAGGCTGGAGACGTGGAGGAGAACCCTGGACCT |
| fp2a | 77 | RAKRAPVKQGSGATNFSLLKQAGDVEENPGP | 169 CGTGCAAAGCGTGCACCGGTGAAACAGGGAAGCGGAGCTACTAACTTCAGCCTGCTGAAGCAGGCTGGAGACGTGGAGGAGAACCCTGGACCT |
| Equine rhinitis A virus 2A region (E2A | 78 | QCTNYALLKLAGDVESNPGP | 170 CAGTGTACTAATTATGCTCTCTTGAAATTGGCTGGAGATGTTGAGAGCAACCCTGGACCT |
| Foot-and-mouth disease virus 2A region (F2A) | 79 | VKQTLNFDLLKLAGDVESNPGP | 171 GTCAAACAGACCCTAAACTTTGATCTGCTAAAACTGGCCGGGGATGTGGAAAGTAATCCCGGCCCC |
| Linker | 80 | APVKQGSG | |
| Furinlink1 | 81 | RAKR | 172 CGTGCAAAGCGT |
| Fmdv | 82 | RAKRAPVKQTLNFDLLKLAGDVESNPGP | 173 AGAGCCAAGAGGGCACCGGTGAAACAGACTTTGAATTTTGACCTTCTGAAGTTGGCAGGAGACGTTGAGTCCAACCCTGGGCCC |
| (G4S)3 Linker | 83 | GGGGSGGGGSGGGGS | 174 GGTGGCGGTGGCTCGGGCGGTGGTGGGTCGGGTGGCGGCGGATCT |
| Whitlow Linker | 84 | GSTSGSGKPGSGEGSTKG | 175 GGCAGCACCTCCGGCAGCGGCAAGCCTGGCAGCGGCGAGGGCAGCACCAAGGGC |
| GSG linker | 85 | GSG | 176 GGAAGCGGA |
| SGSG linker | 86 | SGSG | 177 AGTGGCAGCGGC |

RTS-COMPONENTS

| | | | |
|---|---|---|---|
| VP16 activation domain | 87 | GPKKKRKVAPPTDVSLGDELHLDGEDVAMAHADALDDFDLDMLGDGDSPGPGFTPHDSAPYGALDMADFEFEQMFTDALGIDEYGG | 178 GGCCCCAAGAAGAAAAGGAAGGTGGCCCCCCCCACCGACGTGAGCCTGGGCGACGAGCTGCACCTGGACGGCGAGGACGTGGCCATGGCCCACGCCGACGCCCTGGACGACTTCGACCTGGACATGCTGGGCGACGGCGACAGCCCCGGCCCCGGCTTCACCCCCCACGACAGCGCCCCCTACGGCGCCCTGGACATGGCCGACTTCGAGTTCGAGCAGATGTTCACCGACGCCCTGGGCATCGACGAGTACGGCGGC |
| Retinoid x receptor (RxR) | 88 | EMPVDRILEAELAVEQKSDQGVEGPGGTGSGSSPNDPVTNICQAADKQLFTLVEWAKRIPHFSSLPLDDQVILLRAGWNELLIASFSHRSIDVRDGILLATGLHVHRNSAHSAGVGAIFDRVLTELVSKMRDMRMDKTELGCLRAIILFNPEVRGLKSAQEVEL | 179 GAGATGCCCGTGGACAGGATTCTGGAGGCCGAACTCGCCGTGGAGCAGAAAAGCGACCAGGGCGTGGAGGGCCCCGGCGGAACCGGCGGCAGCGGCAGCAGCCCCAACGACCCCGTGACCAACATCTGCCAGGCCGCCGACAAGCAGCTGTTCACCCTGGTGGAGTGGGCCAAGAGGATTCCCCACTTCAGCAGCCTGCCCCTGGACGACCAGGTGATCCTGCTGAGGGCCGGATGGAACGAGCTGCTGATCGCCAGCTTCAGCCACAGGAGCATCGACGTGAGGGACGGCATCCTGCT |

TABLE 11-continued

Exemplary Sequences

| | | |
|---|---|---|
| | LREKVYAALEEYTRT THPDEPGRFAKLLLR LPSLRSIGLKCLEHLF FFRLIGDVPIDTFLME MLESPSDS | GGCCACCGGCCTGCACGTCCATAGGAA CAGCGCCCACAGCGCCGGAGTGGGCGC CATCTTCGACAGGGTGCTGACCGAGCTG GTGAGCAAGATGAGGGACATGAGGATG GACAAGACCGAGCTGGGCTGCCTGAGG GCCATCATCCTGTTCAACCCCGAGGTGA GGGGCCTGAAAAGCGCCCAGGAGGTGG AGCTGCTGAGGGAGAAGGTGTACGCCG CCCTGGAGGAGTACACCAGGACCACCC ACCCCGACGAGCCCGGCAGATTCGCCA AGCTGCTGCTGAGGCTGCCCAGCCTGAG GAGCATCGGCCTGAAGTGCCTGGAGCA CCTGTTCTTCTTCAGGCTGATCGGCGAC GTGCCCATCGACACCTTCCTGATGGAGA TGCTGGAGAGCCCCAGCGACAGC |
| VP16-linker-RxR | 89 GPKKKRKVAPPTDVS LGDELHLDGEDVAM AHADALDDFDLDML GDGDSPGPGFTPHDS APYGALDMADFEFE QMFTDALGIDEYGGE FEMPVDRILEAELAV EQKSDQGVEGPGGT GGSGSSPNDPVTNIC QAADKQLFTLVEWA KRIPHFSSLPLDDQVI LLRAGWNELLIASFS HRSIDVRDGILLATGL HVHRNSAHSAGVGAI FDRVLTELVSKMRD MRMDKTELGCLRAII LFNPEVRGLKSAQEV ELLREKVYAALEEYT RTTHPDEPGRFAKLL LRLPSLRSIGLKCLEH LFFFRLIGDVPIDTFL MEMLESPSDS | 180 GGCCCCAAGAAGAAAAGGAAGGTGGCC CCCCCCACCGACGTGAGCCTGGGCGAC GAGCTGCACCTGGACGGCGAGGACGTG GCCATGGCCCACGCCGACGCCCTGGAC GACTTCGACCTGGACATGCTGGGCGAC GGCGACAGCCCCGGCCCCGGCTTCACC CCCCACGACAGCGCCCCCTACGGCGCC CTGGACATGGCCGACTTCGAGTTCGAGC AGATGTTCACCGACGCCCTGGGCATCGA CGAGTACGGCGGCGAATTCGAGATGCC CGTGGACAGGATTCTGGAGGCCGAACT CGCCGTGGAGCAGAAAAGCGACCAGGG CGTGGAGGGCCCCGGCGGAACCGGCGG CAGCGGCAGCAGCCCCAACGACCCCGT GACCAACATCTGCCAGGCCGCCGACAA GCAGCTGTTCACCCTGGTGGAGTGGGCC AAGAGGATTCCCCACTTCAGCAGCCTGC CCCTGGACGACCAGGTGATCCTGCTGAG GGCCGGATGGAACGAGCTGCTGATCGC CAGCTTCAGCCACAGGAGCATCGACGT GAGGGACGGCATCCTGCTGGCCACCGG CCTGCACGTCCATAGGAACAGCGCCCA CAGCGCCGGAGTGGGCGCCATCTTCGA CAGGGTGCTGACCGAGCTGGTGAGCAA GATGAGGGACATGAGGATGGACAAGAC CGAGCTGGGCTGCCTGAGGGCCATCATC CTGTTCAACCCCGAGGTGAGGGGCCTG AAAAGCGCCCAGGAGGTGGAGCTGCTG AGGGAGAAGGTGTACGCCGCCCTGGAG GAGTACACCAGGACCACCCACCCCGAC GAGCCCGGCAGATTCGCCAAGCTGCTG CTGAGGCTGCCCAGCCTGAGGAGCATC GGCCTGAAGTGCCTGGAGCACCTGTTCT TCTTCAGGCTGATCGGCGACGTGCCCAT CGACACCTTCCTGATGGAGATGCTGGAG AGCCCCAGCGACAGC |
| GAL4 DNA Binding Domain | 90 MKLLSSIEQACDICRL KKLKCSKEKPKCAK CLKNNWECRYSPKT KRSPLTRAHLTEVES RLERLEQLFLLIFPRE DLDMILKMDSLQDIK ALLTGLFVQDNVNK DAVTDRLASVETDM PLTLRQHRISATSSSE ESSNKGQRQLTVSPE F | 181 ATGAAGCTGCTGAGCAGCATCGAGCAG GCTTGCGACATCTGCAGGCTGAAGAAG CTGAAGTGCAGCAAGGAGAAGCCCAAG TGCGCCAAGTGCCTGAAGAACAACTGG GAGTGCAGATACAGCCCCAAGACCAAG AGGAGCCCCCTGACCAGGGCCCACCTG ACCGAGGTGGAGAGCAGGCTGGAGAGG CTGGAGCAGCTGTTCCTGCTGATCTTCC CCAGGGAGGACCTGGACATGATCCTGA AGATGGACAGCCTGCAAGACATCAAGG CCCTGCTGACCGGCCTGTTCGTGCAGGA CAACGTGAACAAGGACGCCGTGACCGA CAGGCTGGCCAGCGTGGAGACCGACAT GCCCCTGACCCTGAGGCAGCACAGGAT CAGCGCCACCAGCAGCAGCGAGGAGAG CAGCAACAAGGGCCAGAGGCAGCTGAC CGTGAGCCCCGAGTTT |
| Ecdysone Receptor Ligand Binding Domain-VY variant | 91 IRPECVVPETQCAMK RKEKKAQKEKDKLP VSTTTVDDHMPPIMQ CEPPPPPEAARIHEVP RFLSDKLLVTNRQKN IPQLTANQQFLIARLI WYQDGYEQPSDEDL | 182 ATCAGGCCCGAGTGCGTGGTGCCCG AGACCCAGTGCGCCATGAAAAGGA AGGAGAAGAAGGCCCAGAAGGAGA AGGACAAGCTGCCCGTGAGCACCAC CACCGTCGATGACCACATGCCCCCC ATCATGCAGTGCGAGCCCCCCCCCC CCGAGGCCGCCAGGATTCACGAGGT |

TABLE 11-continued

Exemplary Sequences

| | | | |
|---|---|---|---|
| (EcR) | KRITQTWQQADDEN<br>EESDTPFRQITEMTIL<br>TVQLIVEFAKGLPGF<br>AKISQPDQITLLKACS<br>SEVMMLRVARRYDA<br>ASDSILFANNQAYTR<br>DNYRKAGMAEVIED<br>LLHFCRCMYSMALD<br>NIHYALLTAVVIFSDR<br>PGLEQPQLVEEIQRY<br>YLNTLRIYILNQLSGS<br>ARSSVIYGKILSILSEL<br>RTLGMQNSNMCISLK<br>LKNRKLPPFLEEIWD<br>VADMSHTQPPPILESP<br>TNL | | CGTGCCCAGGTTCCTGAGCGACAAG<br>CTGCTGGTGACCAACAGGCAGAAGA<br>ACATCCCCCAGCTGACCGCCAACCA<br>GCAGTTCCTGATCGCCAGGCTGATC<br>TGGTATCAGGACGGCTACGAGCAGC<br>CCAGCGACGAGGACCTGAAAAGGA<br>TCACCCAGACCTGGCAGCAGGCCGA<br>CGACGAGAACGAGGAGAGCGACAC<br>CCCCTTCAGGCAGATCACCGAGATG<br>ACCATCCTGACCGTGCAGCTGATCG<br>TGGAGTTCGCCAAGGGCCTGCCCGG<br>ATTCGCCAAGATCAGCCAGCCCGAC<br>CAGATCACCCTGCTGAAGGCTTGCA<br>GCAGCGAGGTGATGATGCTGAGGGT<br>GGCCAGGAGGTACGACGCCGCCAG<br>CGACAGCATCCTGTTCGCCAACAAC<br>CAGGCTTACACCAGGGACAACTACA<br>GGAAGGCTGGCATGGCCGAGGTGAT<br>CGAGGACCTCCTGCACTTCTGCAGA<br>TGTATGTACAGCATGGCCCTGGACA<br>ACATCCACTACGCCCTGCTGACCGC<br>CGTGGTGATCTTCAGCGACAGGCCC<br>GGCCTGGAGCAGCCCCAGCTGGTGG<br>AGGAGATCCAGAGGTACTACCTGAA<br>CACCCTGAGGATCTACATCCTGAAC<br>CAGCTGAGCGGCAGCGCCAGGAGC<br>AGCGTGATCTACGGCAAGATCCTGA<br>GCATCCTGAGCGAGCTGAGGACCCT<br>GGGAATGCAGAACAGCAATATGTGT<br>ATCAGCCTGAAGCTGAAGAACAGG<br>AAGCTGCCCCCCTTCCTGGAGGAGA<br>TTTGGGACGTGGCCGACATGAGCCA<br>CACCCAGCCCCCCCCCATCCTGGAG<br>AGCCCCACCAACCTG |
| Ecdysone<br>Receptor<br>Ligand<br>Binding<br>Domain-<br>VY<br>variant<br>(EcR) | 92 | RPECVVPETQCAMK<br>RKEKKAQKEKDKLP<br>VSTTTVDDHMPPIMQ<br>CEPPPPEAARIHEVVP<br>RFLSDKLLVTNRQKN<br>IPQLTANQQFLIARLI<br>WYQDGYEQPSDEDL<br>KRITQTWQQADDEN<br>EESDTPFRQITEMTIL<br>TVQLIVEFAKGLPGF<br>AKISQPDQITLLKACS<br>SEVMMLRVARRYDA<br>ASDSILFANNQAYTR<br>DNYRKAGMAEVIED<br>LLHFCRCMYSMALD<br>NIHYALLTAVVIFSDR<br>PGLEQPQLVEEIQRY<br>YLNTLRIYILNQLSGS<br>ARSSVIYGKILSILSEL<br>RTLGMQNSNMCISLK<br>LKNRKLPPFLEEIWD<br>VADMSHTQPPPILESP<br>TNL | 183 CGGCCTGAGTGCGTAGTACCCGAGA<br>CTCAGTGCGCCATGAAGCGGAAAGA<br>GAAGAAAGCACAGAAGGAGAAGGA<br>CAAACTGCCTGTCAGCACGACGACG<br>GTGGACGACCACATGCCGCCCATTA<br>TGCAGTGTGAACCTCCACCTCCTGA<br>AGCAGCAAGGATTCACGAAGTGGTC<br>CCAAGGTTTCTCTCCGACAAGCTGT<br>TGGTGACAAACCGGCAGAAAACA<br>TCCCCCAGTTGACAGCCAACCAGCA<br>GTTCCTTATCGCCAGGCTCATCTGGT<br>ACCAGGACGGGTACGAGCAGCCTTC<br>TGATGAAGATTTGAAGAGGATTACG<br>CAGACGTGGCAGCAAGCGGACGAT<br>GAAAACGAAGAGTCGGACACTCCCT<br>TCCGCCAGATCACAGAGATGACTAT<br>CCTCACGGTCCAACTTATCGTGGAG<br>TTCGCGAAGGGATTGCCAGGGTTCG<br>CCAAGATCTCGCAGCCTGATCAAAT<br>TACGCTGCTTAAGGCTTGCTCAAGT<br>GAGGTAATGATGCTCCGAGTCGCGC<br>GACGATACGATGCGGCCTCAGACAG<br>TATTCTGTTCGCGAACAACCAAGCG<br>TACACTCGCGACAACTACCGCAAGG<br>CTGGCATGGCCGAGGTCATCGAGGA<br>TCTACTGCACTTCTGCCGGTGCATGT<br>ACTCTATGGCGTTGGACAACATCCA<br>TTACGCGCTGCTCACGGCTGTCGTC<br>ATCTTTTCTGACCGGCCAGGGTTGG<br>AGCAGCCGCAACTGGTGGAAGAGA<br>TCCAGCGGTACTACCTGAATACGCT<br>CCGCATCTATATCCTGAACCAGCTG<br>AGCGGGTCGGCGCGTTCGTCCGTCA<br>TATACGGCAAGATCCTCTCAATCCT<br>CTCTGAGCTACGCACGCTCGGCATG<br>CAAAACTCCAACATGTGCATCTCCC<br>TCAAGCTCAAGAACAGAAAGCTGCC<br>GCCTTTCCTCGAGGAGATCTGGGAT<br>GTGGCGGACATGTCGCACACCCAAC<br>CGCCGCCTATCCTCGAGTCCCCCAC<br>GAATCTCTAG |

TABLE 11-continued

Exemplary Sequences

| | | | |
|---|---|---|---|
| GAL4-Linker-EcR | 93 | MKLLSSIEQACDICRL KKLKCSKEKPKCAK CLKNNWECRYSPKT KRSPLTRAHLTEVES RLERLEQLFLLIFPRE DLDMILKMDSLQDIK ALLTGLFVQDNVNK DAVTDRLASVETDM PLTLRQHRISATSSSE ESSNKGQRQLTVSPE FPGIRPECVVPETQCA MKRKEKKAQKEKDK LPVSTTTVDDHMPPI MQCEPPPPEAARIHE VVPRFLSDKLLVTNR QKNIPQLTANQQFLI ARLIWYQDGYEQPSD EDLKRITQTWQQAD DENEESDTPFRQITE MTILTVQLIVEFAKG LPGFAKISQPDQITLL KACSSEVMMLRVAR RYDAASDSILFANNQ AYTRDNYRKAGMAE VIEDLLHFCRCMYSM ALDNIHYALLTAVVI FSDRPGLEQPQLVEEI QRYYLNTLRIYILNQ LSGSARSSVIYGKILSI LSELRTLGMQNSNM CISLKLKNRKLPPFLE EIWDVADMSHTQPPP ILESPTNL | 184 | ATGAAGCTACTGTCTTCTATCGAAC AAGCATGCGATATTTGCCGACTTAA AAAGCTCAAGTGCTCCAAAGAAAA ACCGAAGTGCGCCAAGTGTCTGAAG AACAACTGGGAGTGTCGCTACTCTC CCAAAACCAAAAGGTCTCCGCTGAC TAGGGCACATCTGACAGAAGTGGAA TCAAGGCTAGAAAGACTGGAACAG CTATTTCTACTGATTTTTCCTCGAGA AGACCTTGACATGATTTTGAAAATG GATTCTTTACAGGATATAAAAGCAT TGTTAACAGGATTATTTGTACAAGA TAATGTGAATAAAGATGCCGTCACA GATAGATTGGCTTCAGTGGAGACTG ATATGCCTCTAACATTGAGACGCCA TAGAATAAGTGCGACATCATCATCG GAAGAGAGTAGTAACAAAGGTCAA AGACAGTTGACTGTATCGCGGAAT TCCCGGGGATCCGGCCTGAGTGCGT AGTACCCGAGACTCAGTGCGCCATG AAGCGGAAAGAAGAAAAGCACAG AAGGAGAAGGACAAACTGCCTGTC AGCACGACGACGGTGGACGACCAC ATGCCGCCCATTATGCAGTGTGAAC CTCCACCTCCTGAAGCAGCAAGGAT TCACGAAGTGGTCCCAAGGTTTCTC TCCGACAAGCTGTTGGTGACAAACC GGCAGAAAACATCCCCCAGTTGAC AGCCAACCAGCAGTTCCTTATCGCC AGGCTCATCTGGTACCAGGACGGGT ACGAGCAGCCTTCTGATGAAGATTT GAAGAGGATTACGCAGACGTGGCA GCAAGCGGACGATGAAAACGAAGA GTCGGACACTCCCTTCCGCCAGATC ACAGAGATGACTATCCTCACGGTCC AACTTATCGTGGAGTTCGCGAAGGG ATTGCCAGGGTTCGCCAAGATCTCG CAGCCTGATCAAATTACGCTGCTTA AGGCTTGCTCAAGTGAGGTAATGAT GCTCCGAGTCGCGCGACGATACGAT GCGGCCTCAGACAGTATTCTGTTCG CGAACAACCAAGCGTACACTCGCGA CAACTACCGCAAGGCTGGCATGGCC GAGGTCATCGAGGATCTACTGCACT TCTGCCGGTGCATGTACTCTATGGC GTTGGACAACATCCATTACGCGCTG CTCACGGCTGTCGTCATCTTTTCTGA CCGGCCAGGGTTGGAGCAGCCGCAA CTGGTGGAAGAGATCCAGCGGTACT ACCTGAATACGCTCCGCATCTATAT CCTGAACCAGCTGAGCGGGTCGGCG CGTTCGTCCGTCATATACGGCAAGA TCCTCTCAATCCTCTCTGAGCTACGC ACGCTCGGCATGCAAAACTCCAACA TGTGCATCTCCCTCAAGCTCAAGAA CAGAAAGCTGCCGCCTTTCCTCGAG GAGATCTGGGATGTGGCGGACATGT CGCACACCCAACCGCCGCCTATCCT CGAGTCCCCCACGAATCTCTAG |
| GAL4-Linker-EcR | 94 | MKLLSSIEQACDICRL KKLKCSKEKPKCAK CLKNNWECRYSPKT KRSPLTRAHLTEVES RLERLEQLFLLIFPRE DLDMILKMDSLQDIK ALLTGLFVQDNVNK DAVTDRLASVETDM PLTLRQHRISATSSSE ESSNKGQRQLTVSPE FPGRPECVVPETQCA MKRKEKKAQKEKDK LPVSTTTVDDHMPPI MQCEPPPPEAARIHE VVPRFLSDKLLVTNR QKNIPQLTANQQFLI ARLIWYQDGYEQPSD EDLKRITQTWQQAD | 185 | ATGAAGCTGCTGAGCAGCATCGAGC AGGCTTGCGACATCTGCAGGCTGAA GAAGCTGAAGTGCAGCAAGGAGAA GCCCAAGTGCGCCAAGTGCCTGAAG AACAACTGGGAGTGCAGATACAGC CCAAGACCAAGAGGAGCCCCCTGAC CAGGGCCCACCTGACCGAGGTGGAG AGCAGGCTGGAGAGGCTGGAGCAG CTGTTCCTGCTGATCTTCCCCAGGGA GGACCTGGACATGATCCTGAAGATG GACAGCCTGCAAGACATCAAGGCCC TGCTGACCGGCCTGTTCGTGCAGGA CAACGTGAACAAGGACGCCGTGACC GACAGGCTGGCCAGCGTGGAGACC ATGCCCCTGACCCTGAGGCAGC ACAGGATCAGCGCCACCAGCAGCA GCGAGGAGAGCAGCAACAAGGGCC AGAGGCAGCTGACCGTGAGCCCCGA |

TABLE 11-continued

Exemplary Sequences

| | |
|---|---|
| DENEESDTPFRQITE | GTTTCCCGGGCGGCCTGAGTGCGTA |
| MTILTVQLIVEFAKG | GTACCCGAGACTCAGTGCGCCATGA |
| LPGFAKISQPDQITLL | AGCGGAAAGAGAAGAAAGCACAGA |
| KACSSEVMMLRVAR | AGGAGAAGGACAAACTGCCTGTCA |
| RYDAASDSILFANNQ | GCACGACGACGGTGGACGACCACAT |
| AYTRDNYRKAGMAE | GCCGCCCATTATGCAGTGTGAACCT |
| VIEDLLHFCRCMYSM | CCACCTCCTGAAGCAGCAAGGATTC |
| ALDNIHYALLTAVVI | ACGAAGTGGTCCCAAGGTTTCTCTC |
| FSDRPGLEQPQLVEEI | CGACAAGCTGTTGGTGACAAACCGG |
| QRYYLNTLRIYILNQ | CAGAAAAACATCCCCCAGTTGACAG |
| LSGSARSSVIYGKILSI | CCAACCAGCAGTTCCTTATCGCCAG |
| LSELRTLGMQNSNM | GCTCATCTGGTACCAGGACGGGTAC |
| CISLKLKNRKLPPFLE | GAGCAGCCTTCTGATGAAGATTTGA |
| EIWDVADMSHTQPPP | AGAGGATTACGCAGACGTGGCAGC |
| ILESPTNL | AAGCGGACGATGAAAACGAAGAGT |
| | CGGACACTCCCTTCCGCCAGATCAC |
| | AGAGATGACTATCCTCACGGTCCAA |
| | CTTATCGTGGAGTTCGCGAAGGGAT |
| | TGCCAGGGTTCGCCAAGATCTCGCA |
| | GCCTGATCAAATTACGCTGCTTAAG |
| | GCTTGCTCAAGTGAGGTAATGATGC |
| | TCCGAGTCGCGCGACGATACGATGC |
| | GGCCTCAGACAGTATTCTGTTCGCG |
| | AACAACCAAGCGTACACTCGCGACA |
| | ACTACCGCAAGGCTGGCATGGCCGA |
| | GGTCATCGAGGATCTACTGCACTTC |
| | TGCCGGTGCATGTACTCTATGGCGT |
| | TGGACAACATCCATTACGCGCTGCT |
| | CACGGCTGTCGTCATCTTTTCTGACC |
| | GGCCAGGGTTGGAGCAGCCGCAACT |
| | GGTGGAAGAGATCCAGCGGTACTAC |
| | CTGAATACGCTCCGCATCTATATCCT |
| | GAACCAGCTGAGCGGGTCGGCGCGT |
| | TCGTCCGTCATATACGGCAAGATCC |
| | TCTCAATCCTCTCTGAGCTACGCAC |
| | GCTCGGCATGCAAAACTCCAACATG |
| | TGCATCTCCCTCAAGCTCAAGAACA |
| | GAAAGCTGCCGCCTTTCCTCGAGGA |
| | GATCTGGGATGTGGCGGACATGTCG |
| | CACACCCAACCGCCGCCTATCCTCG |
| | AGTCCCCCACGAATCTCTAG |

| Name | SEQ ID NO | Nucleotide Sequence |
|---|---|---|
| Human EEF1A1 promoter variant | 186 | GAGCGTGCGTGAGGCTCCGGTGCCCGTCAGTGGGCAGAGC GCACATCGCCCACAGTCCCCGAGAAGTTGGGGGGAGGGGG TCGGCGATTGAACCGGTGCCTAGAGAAGGTGGCGCGGGGT AAACTGGGAAAGTGATGTCGTGTACTGGCTCCGCCTTTTTC CCGAGGGTGGGGGAGAACCGTATATAAGTGCAGTAGTCGC CGTGAACGTTCTTTTTCGCAACGGGTTTGCCGCCAGAACAC AG |
| 6 site GAL4-inducible proximal factor binding element (PFB) | 187 | ATTGTTCGGAGCAGTGCGGCGCGTTTAGCGGAGTACTGTCC TCCGATATTAATCGGGGCAGACTATTCCGGGGTTTACCGGC GCACTCTCGCCCGAACTTCACCGGCGGTCTTTCGTCCGTGC TTTATCGGGGCGGATCACTCCGAAC |
| Synthetic minimal promoter 1 [Inducible Promoter] | 188 | AGGTCTATATAAGCAGAGCTCGTTTAGTGAACCCTCATTCT GGAGACGGATCCCGAGCCGAGTGTTTTGACCTCCATAGAA |
| Synthetic 5' UTR based on RPL6 | 189 | CAGCCGCTAAATCCAAGGTAAGGTCAGAAGA |
| SV40e polyA | 190 | AACTTGTTTATTGCAGCTTATAATGGTTACAAATAAAGCAA TAGCATCACAAATTTCACAAATAAAGCATTTTTTTCACTGC ATTCTAGTTGTGGTTTGTCCAAACTCATCAATGTATCTTATC ATGTCTGG |

TABLE 11-continued

Exemplary Sequences

| | | |
|---|---|---|
| Bidirectional aCA polyA [bidirectional polyA] | 191 | ATCGATTAATCTAGCGGCCCTAGACGAGCAGACATGATAA GATACATTGATGAGTTTGGACAAACCACAACTAGAATGCA GTGAAAAAAATGCTTTATTTGTGAAATTTGTGATGCTATTG CTTTATTTGTAACCATTATAAGCTGCAATAAACAAGTTAAC AACAACAATTGCATTCATTTTATGTTTCAGGTTCAGGGGGA GATGTGGGAGGTTTTTTAAAGCAAGTAAAACCTCTACAAAT GTGGTAAAATCCGATAAGCGTACCTAGAGGC |
| 2xRbm3 IRES | 192 | ACTAGTTTTATAATTTCTTCTTCCAGAATTTCTGACATTTTA TAATTTCTTCTTCCAGAAGACTCACAACCTC |
| EMCV IRES | 193 | CCCCCTCTCCCTCCCCCCCCCCTAACGTTACTGGCCGAAGC CGCTTGGAATAAGGCCGGTGTGCGTTTGTCTATATGTTATT TTCCACCATATTGCCGTCTTTTGGCAATGTGAGGGCCCGGA AACCTGGCCCTGTCTTCTTGACGAGCATTCCTAGGGGTCTT TCCCCTCTCGCCAAAGGAATGCAAGGTCTGTTGAATGTCGT GAAGGAAGCAGTTCCTCTGGAAGCTTCTTGAAGACAAACA ACGTCTGTAGCGACCCTTTGCAGGCAGCGGAACCCCCCACC TGGCGACAGGTGCCTCTGCGGCCAAAAGCCACGTGTATAA GATACACCTGCAAAGGCGGCACAACCCCAGTGCCACGTTG TGAGTTGGATAGTTGTGGAAAGAGTCAAATGGCTCTCCTCA AGCGTATTCAACAAGGGGCTGAAGGATGCCCAGAAGGTAC CCCATTGTATGGGATCTGATCTGGGGCCTCGGTGCACATGC TTTACATGTGTTTAGTCGAGGTTAAAAAACGTCTAGGCCCC CCGAACCACGGGGACGTGGTTTTCCTTTGAAAAACACGATC |

What is claimed is:

1. An isolated nucleic acid encoding a chimeric antigen receptor (CAR), wherein the CAR comprises a polypeptide having the amino acid sequence of SEQ ID NO: 31.

2. The isolated nucleic acid of claim 1, further encoding a truncated epidermal growth factor receptor.

3. The isolated nucleic acid of claim 2, wherein the truncated epidermal growth factor receptor is HER1t and comprises a polypeptide having the amino acid sequence of SEQ ID NO: 65 or SEQ ID NO: 66.

4. A vector comprising a backbone and a nucleic acid encoding: (1) a truncated epidermal growth factor receptor comprising at least one of HER1t, HER1t-1, or a functional variant thereof; (2) a cytokine; and (3) a chimeric antigen receptor (CAR) comprising a polypeptide having the amino acid sequence of SEQ ID NO: 31.

5. The vector of claim 4, wherein the cytokine is IL-15 or IL-12.

6. The vector of claim 4, wherein the vector is a lentivirus vector, a retroviral vector, or a non-viral vector.

7. The vector of claim 5, wherein the IL-15 is membrane bound IL-15.

8. The vector of claim 7, wherein the membrane bound IL-15 comprises a nucleotide sequence that encodes a polypeptide having the amino acid sequence of SEQ ID NO: 69.

9. The vector of claim 4, further comprising a nucleotide sequence encoding a self-cleaving Thosea asigna virus (T2A) peptide.

10. An immune effector cell comprising the vector of claim 4.

11. The immune effector cell of claim 10, wherein the cell is a T cell, a Natural Killer (NK) cell, a cytotoxic T lymphocyte (CTL), or a regulatory T cell.

* * * * *

SEQUENCE LISTING

<160> NUMBER OF SEQ ID NOS: 205

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Gln Leu Ala Trp Tyr Gln Gln Lys Pro Gly Gln
            35                  40                  45

Ser Pro Glu Leu Leu Ile Tyr Trp Ala Ser Thr Arg Gln Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Val Lys
            100                 105                 110

Arg

<210> SEQ ID NO 2
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 2

Val Lys Leu Gln Glu Ser Gly Gly Phe Val Lys Pro Gly Gly Ser
1               5                   10                  15

Leu Lys Val Ser Cys Ala Ala Ser Gly Phe Thr Phe Ser Ser Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser
        115                 120

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Val Lys Leu Glu Glu Ser Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45
```

```
Thr Ile Ser Ser Ala Gly Gly Tyr Ile Phe Tyr Ser Asp Ser Val Gln
        50                  55                  60

Gly Arg Phe Thr Ile Ser Arg Asp Asn Ala Lys Asn Thr His Leu Gln
 65                  70                  75                  80

Met Gly Ser Leu Arg Ser Gly Asp Thr Ala Met Tyr Tyr Cys Ala Arg
                 85                  90                  95

Gln Gly Phe Gly Asn Tyr Gly Asp Tyr Tyr Ala Met Asp Tyr Trp Gly
            100                 105                 110

Gln Gly Thr Thr Val Thr Val Ser Ser
            115                 120
```

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asp Ile Lys Met Ala Gln Ser Pro Ser Ser Val Asn Ala Ser Leu Gly
 1                5                  10                  15

Glu Arg Val Thr Ile Thr Cys Lys Ala Ser Arg Asp Ile Asn Asn Phe
                 20                  25                  30

Leu Ser Trp Phe His Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Phe Thr Ile Ser Ser Leu Glu Tyr
 65                  70                  75                  80

Glu Asp Val Gly Ile Tyr Tyr Cys Leu Gln Tyr Gly Asp Leu Tyr Thr
                 85                  90                  95

Phe Gly Gly Gly Thr Lys Leu Glu Ile Lys
            100                 105
```

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Val Gln Leu Leu Glu Ser Gly Pro Gly Leu Val Arg Pro Ser Gln
 1                5                  10                  15

Ser Leu Ser Leu Thr Cys Ser Val Thr Gly Tyr Ser Ile Val Ser His
                 20                  25                  30

Tyr Tyr Trp Asn Trp Ile Arg Gln Phe Pro Gly Asn Lys Leu Glu Trp
            35                  40                  45

Met Gly Tyr Ile Ser Ser Asp Gly Ser Asn Glu Tyr Asn Pro Ser Leu
 50                  55                  60

Lys Asn Arg Ile Ser Ile Ser Leu Asp Thr Ser Lys Asn Gln Phe Phe
 65                  70                  75                  80

Leu Lys Phe Asp Phe Val Thr Thr Ala Asp Thr Ala Thr Tyr Phe Cys
                 85                  90                  95

Val Arg Gly Val Asp Tyr Trp Gly Gln Gly Thr Thr Leu Thr Val Ser
            100                 105                 110
```

Ser

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Ser Phe Leu Ser Val Ser Leu Gly
1               5                   10                  15

Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Leu Glu Ile Lys
            100                 105

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Tyr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                85                  90                  95

Ala Arg Trp Asp Gly Gly Leu Thr Tyr Trp Gly Gln Gly Thr Leu Val
            100                 105                 110

Thr Val Ser Ala
        115

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu
50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Gly Leu Thr Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu

```
                50                  55                  60
Lys Ser Arg Phe Thr Ile Ser Arg Asp Asn Ser Lys Asn Thr Phe Tyr
 65                  70                  75                  80

Leu Gln Met Asn Ser Leu Arg Ala Glu Asp Thr Ala Val Tyr Tyr Cys
                 85                  90                  95

Ala Arg Trp Asp Gly Gly Leu Thr Tyr Trp Gly Gln Gly Thr Leu Val
                100                 105                 110

Thr Val Ser Ser
        115

<210> SEQ ID NO 12
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Ala Ile Met Ser Ala Ser Leu Gly
  1               5                  10                  15

Glu Arg Val Thr Met Thr Cys Thr Ala Ser Ser Val Ser Ser Ser
                 20                  25                  30

Tyr Leu His Trp Tyr Gln Gln Lys Pro Gly Ser Ser Pro Lys Leu Trp
             35                  40                  45

Ile Tyr Ser Thr Ser Asn Leu Ala Ser Gly Val Pro Gly Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Tyr Thr Phe Gly Gly Gly Thr Lys Val Glu Ile Lys Arg
                100                 105

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Gln Gln Ser Gly Ala Glu Leu Val Lys Pro Gly Ala
  1               5                  10                  15

Ser Val Lys Leu Ser Cys Thr Ala Ser Gly Phe Asn Ile Lys Asp Thr
                 20                  25                  30

Tyr Met His Trp Val Lys Gln Arg Pro Glu Gln Gly Leu Glu Trp Ile
             35                  40                  45

Gly Arg Val Asp Pro Ala Asn Gly Asn Thr Lys Tyr Asp Pro Lys Phe
         50                  55                  60

Gln Gly Lys Ala Thr Leu Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Val Arg Asp Tyr Tyr Gly His Thr Tyr Gly Phe Ala Phe Cys Asp Gln
                100                 105                 110

Gly Thr Thr Leu Thr Val Ser Ala
```

<210> SEQ ID NO 14
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Tyr Thr Phe Gly Gln Gly Thr Lys Val Glu Ile Lys Arg
            100                 105

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

Gly Arg Val Asp Pro Ala Asn Gly Asn Thr Lys Tyr Asp Pro Lys Phe
    50                  55                  60

Gln Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Tyr Tyr Gly His Thr Tyr Gly Phe Ala Phe Trp Gly Gln
            100                 105                 110

Gly Thr Leu Val Thr Val Ser Ser
        115                 120

<210> SEQ ID NO 16
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp
            35                  40                  45

<210> SEQ ID NO 17
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
                20                  25                  30

Ala Gly Gly Ala Val His Thr Arg Gly Leu Asp Phe Ala Ser Asp Lys
            35                  40                  45

Pro Thr Thr Thr Pro Ala Pro Arg Pro Pro Thr Pro Ala Pro Thr Ile
        50                  55                  60

Ala Ser Gln Pro Leu Ser Leu Arg Pro Glu Ala Cys Arg Pro Ala Ala
65                  70                  75                  80

Gly Gly Ala Val His Thr Arg Gly Leu Asp Phe Ala Cys Asp
            85                  90

<210> SEQ ID NO 18
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
                20                  25                  30

Ala Gly Gly Ala Val His Thr Arg Gly Leu Asp Phe Ala Ser Asp Lys
            35                  40                  45

Pro Thr Thr Thr Pro Ala Pro Arg Pro Pro Thr Pro Ala Pro Thr Ile
        50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
            85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Cys Arg Pro Ala Ala Gly
            115                 120                 125

Gly Ala Val His Thr Arg Gly Leu Asp Phe Ala Cys Asp
        130                 135                 140

<210> SEQ ID NO 19

<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr Thr Pro Ala Pro Arg Pro Pro Thr Pro Ala Pro Thr Ile Ala Ser
1               5                   10                  15

Gln Pro Leu Ser Leu Arg Pro Glu Ala Ser Arg Pro Ala Ala Gly Gly
            20                  25                  30

Ala Val His Thr Arg Gly Leu Asp Phe Ala Ser Asp Lys Pro Thr Thr
        35                  40                  45

Thr Pro Ala Pro Arg Pro Pro Thr Pro Ala Pro Thr Ile Ala Ser Gln
    50                  55                  60

Pro Leu Ser Leu Arg Pro Glu Ala Ser Arg Pro Ala Ala Gly Gly Ala
65                  70                  75                  80

Val His Thr Arg Gly Leu Asp Phe Ala Ser Asp Lys Pro Thr Thr Thr
                85                  90                  95

Pro Ala Pro Arg Pro Pro Thr Pro Ala Pro Thr Ile Ala Ser Gln Pro
            100                 105                 110

Leu Ser Leu Arg Pro Glu Ala Ser Arg Pro Ala Ala Gly Gly Ala Val
        115                 120                 125

His Thr Arg Gly Leu Asp Phe Ala Ser Asp Lys Pro Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp
            180                 185

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 22
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Asp Gly Cys Ser Cys Arg Phe
            20                  25                  30

Pro Glu Glu Glu Glu Gly Gly Cys Glu Leu
        35                  40

<210> SEQ ID NO 23
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 25
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 27
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

```
Trp Ala Ser Thr Arg Gln Ser Gly Val Pro Asp Arg Phe Thr Gly Ser
            195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Asn His Arg Asn Lys Arg Gly Arg Lys Lys Leu Leu Tyr Ile Phe
                325                 330                 335

Lys Gln Pro Phe Met Arg Pro Val Gln Thr Thr Gln Glu Glu Asp Gly
            340                 345                 350

Cys Ser Cys Arg Phe Pro Glu Glu Glu Glu Gly Gly Cys Glu Leu Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475

<210> SEQ ID NO 28
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
```

```
                65                  70                  75                  80
            Gln Met Gly Ser Leu Arg Ser Gly Asp Thr Ala Met Tyr Tyr Cys Ala
                            85                  90                  95
            Arg Gln Gly Phe Gly Asn Tyr Gly Asp Tyr Tyr Ala Met Asp Tyr Trp
                            100                 105                 110
            Gly Gln Gly Thr Thr Val Thr Val Ser Ser Gly Gly Gly Gly Ser Gly
                            115                 120                 125
            Gly Gly Gly Ser Gly Gly Gly Ser Asp Ile Glu Leu Thr Gln Ser
            130                 135                 140
            Pro Ser Ser Leu Ala Val Ser Ala Gly Glu Lys Val Thr Met Ser Cys
            145                 150                 155                 160
            Lys Ser Ser Gln Ser Leu Leu Asn Ser Arg Thr Arg Lys Asn Gln Leu
                            165                 170                 175
            Ala Trp Tyr Gln Gln Lys Thr Gly Gln Ser Pro Glu Leu Leu Ile Tyr
                            180                 185                 190
            Trp Ala Ser Thr Arg Gln Ser Gly Val Pro Asp Arg Phe Thr Gly Ser
                            195                 200                 205
            Gly Ser Gly Thr Asp Phe Thr Leu Thr Ile Ser Ser Val Gln Ala Glu
                            210                 215                 220
            Asp Leu Ala Val Tyr Tyr Cys Gln Gln Ser Tyr Asn Leu Leu Thr Phe
            225                 230                 235                 240
            Gly Pro Gly Thr Lys Leu Glu Ile Lys Arg Lys Pro Thr Thr Thr Pro
                            245                 250                 255
            Ala Pro Arg Pro Pro Thr Pro Ala Pro Thr Ile Ala Ser Gln Pro Leu
                            260                 265                 270
            Ser Leu Arg Pro Glu Ala Ser Arg Pro Ala Ala Gly Gly Ala Val His
                            275                 280                 285
            Thr Arg Gly Leu Asp Phe Ala Ser Asp Lys Pro Thr Thr Thr Pro Ala
                            290                 295                 300
            Pro Arg Pro Pro Thr Pro Ala Pro Thr Ile Ala Ser Gln Pro Leu Ser
            305                 310                 315                 320
            Leu Arg Pro Glu Ala Cys Arg Pro Ala Ala Gly Gly Ala Val His Thr
                            325                 330                 335
            Arg Gly Leu Asp Phe Ala Cys Asp Ile Tyr Ile Trp Ala Pro Leu Ala
                            340                 345                 350
            Gly Thr Cys Gly Val Leu Leu Leu Ser Leu Val Ile Thr Leu Tyr Cys
                            355                 360                 365
            Asn His Arg Asn Lys Arg Gly Arg Lys Lys Leu Leu Tyr Ile Phe Lys
                            370                 375                 380
            Gln Pro Phe Met Arg Pro Val Gln Thr Thr Gln Glu Glu Asp Gly Cys
            385                 390                 395                 400
            Ser Cys Arg Phe Pro Glu Glu Glu Glu Gly Gly Cys Glu Leu Arg Val
                            405                 410                 415
            Lys Phe Ser Arg Ser Ala Asp Ala Pro Ala Tyr Gln Gln Gly Gln Asn
                            420                 425                 430
            Gln Leu Tyr Asn Glu Leu Asn Leu Gly Arg Arg Glu Glu Tyr Asp Val
                            435                 440                 445
            Leu Asp Lys Arg Arg Gly Arg Asp Pro Glu Met Gly Gly Lys Pro Arg
                            450                 455                 460
            Arg Lys Asn Pro Gln Glu Gly Leu Tyr Asn Glu Leu Gln Lys Asp Lys
            465                 470                 475                 480
            Met Ala Glu Ala Tyr Ser Glu Ile Gly Met Lys Gly Glu Arg Arg Arg
                            485                 490                 495
```

```
Gly Lys Gly His Asp Gly Leu Tyr Gln Gly Leu Ser Thr Ala Thr Lys
                500                 505                 510
Asp Thr Tyr Asp Ala Leu His Met Gln Ala Leu Pro Pro Arg
            515                 520                 525

<210> SEQ ID NO 29
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Val Lys Leu Glu Glu Ser Gly Gly Phe Val Lys Pro Gly Gly Ser
1               5                   10                  15

Leu Lys Ile Ser Cys Ala Ala Ser Gly Phe Thr Phe Arg Asn Tyr Ala
                20                  25                  30

Met Ser Trp Val Arg Leu Ser Pro Glu Met Arg Leu Glu Trp Val Ala
            35                  40                  45

Thr Ile Ser Ser Ala Gly Gly Tyr Ile Phe Tyr Ser Asp Ser Val Gln
        50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Ser Gly
            115                 120                 125

Gly Gly Ser Gly Gly Gly Ser Asp Ile Glu Leu Thr Gln Ser
        130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
        275                 280                 285

Thr Arg Gly Leu Asp Phe Ala Ser Asp Lys Pro Thr Thr Thr Pro Ala
            290                 295                 300

Pro Arg Pro Pro Thr Pro Ala Pro Thr Ile Ala Ser Gln Pro Leu Ser
305                 310                 315                 320

Leu Arg Pro Glu Ala Ser Arg Pro Ala Ala Gly Gly Ala Val His Thr
```

```
                    325                 330                 335
Arg Gly Leu Asp Phe Ala Ser Asp Lys Pro Thr Thr Thr Pro Ala Pro
                340                 345                 350
Arg Pro Pro Thr Pro Ala Pro Thr Ile Ala Ser Gln Pro Leu Ser Leu
            355                 360                 365
Arg Pro Glu Ala Cys Arg Pro Ala Ala Gly Gly Ala Val His Thr Arg
        370                 375                 380
Gly Leu Asp Phe Ala Cys Asp Ile Tyr Ile Trp Ala Pro Leu Ala Gly
385                 390                 395                 400
Thr Cys Gly Val Leu Leu Leu Ser Leu Val Ile Thr Leu Tyr Cys Asn
                405                 410                 415
His Arg Asn Lys Arg Gly Arg Lys Lys Leu Leu Tyr Ile Phe Lys Gln
                420                 425                 430
Pro Phe Met Arg Pro Val Gln Thr Thr Gln Glu Glu Asp Gly Cys Ser
            435                 440                 445
Cys Arg Phe Pro Glu Glu Glu Glu Gly Gly Cys Glu Leu Arg Val Lys
        450                 455                 460
Phe Ser Arg Ser Ala Asp Ala Pro Ala Tyr Gln Gln Gly Gln Asn Gln
465                 470                 475                 480
Leu Tyr Asn Glu Leu Asn Leu Gly Arg Arg Glu Glu Tyr Asp Val Leu
                485                 490                 495
Asp Lys Arg Arg Gly Arg Asp Pro Glu Met Gly Gly Lys Pro Arg Arg
                500                 505                 510
Lys Asn Pro Gln Glu Gly Leu Tyr Asn Glu Leu Gln Lys Asp Lys Met
            515                 520                 525
Ala Glu Ala Tyr Ser Glu Ile Gly Met Lys Gly Glu Arg Arg Arg Gly
        530                 535                 540
Lys Gly His Asp Gly Leu Tyr Gln Gly Leu Ser Thr Ala Thr Lys Asp
545                 550                 555                 560
Thr Tyr Asp Ala Leu His Met Gln Ala Leu Pro Pro Arg
                565                 570

<210> SEQ ID NO 30
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Leu Leu Leu Val Thr Ser Leu Leu Leu Cys Glu Leu Pro His Pro
1               5                   10                  15
Ala Phe Leu Leu Ile Pro Asp Ile Lys Met Ala Gln Ser Pro Ser Ser
                20                  25                  30
Val Asn Ala Ser Leu Gly Glu Arg Val Thr Ile Thr Cys Lys Ala Ser
            35                  40                  45
Arg Asp Ile Asn Asn Phe Leu Ser Trp Phe His Gln Lys Pro Gly Lys
        50                  55                  60
Ser Pro Lys Thr Leu Ile Tyr Arg Ala Asn Arg Leu Val Asp Gly Val
65                  70                  75                  80
Pro Ser Arg Phe Ser Gly Ser Gly Ser Gly Gln Asp Tyr Ser Phe Thr
                85                  90                  95
Ile Ser Ser Leu Glu Tyr Glu Asp Val Gly Ile Tyr Tyr Cys Leu Gln
                100                 105                 110
```

```
Tyr Gly Asp Leu Tyr Thr Phe Gly Gly Thr Lys Leu Glu Ile Lys
            115                 120                 125

Gly Gly Gly Gly Ser Gly Gly Gly Ser Gly Gly Gly Gly Ser Asp
130                 135                 140

Val Gln Leu Leu Glu Ser Gly Pro Gly Leu Val Arg Pro Ser Gln Ser
145                 150                 155                 160

Leu Ser Leu Thr Cys Ser Val Thr Gly Tyr Ser Ile Val Ser His Tyr
                165                 170                 175

Tyr Trp Asn Trp Ile Arg Gln Phe Pro Gly Asn Lys Leu Glu Trp Met
                180                 185                 190

Gly Tyr Ile Ser Ser Asp Gly Ser Asn Glu Tyr Asn Pro Ser Leu Lys
                195                 200                 205

Asn Arg Ile Ser Ile Ser Leu Asp Thr Ser Lys Asn Gln Phe Phe Leu
210                 215                 220

Lys Phe Asp Phe Val Thr Thr Ala Asp Thr Ala Thr Tyr Phe Cys Val
225                 230                 235                 240

Arg Gly Val Asp Tyr Trp Gly Gln Gly Thr Thr Leu Thr Val Ser Ser
                245                 250                 255

Lys Pro Thr Thr Thr Pro Ala Pro Arg Pro Pro Thr Pro Ala Pro Thr
                260                 265                 270

Ile Ala Ser Gln Pro Leu Ser Leu Arg Pro Glu Ala Cys Arg Pro Ala
                275                 280                 285

Ala Gly Gly Ala Val His Thr Arg Gly Leu Asp Phe Ala Cys Asp Ile
                290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Asn His Arg Asn Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
                355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 31
<211> LENGTH: 463
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 31

| Asp | Ile | Lys | Met | Ala | Gln | Ser | Pro | Ser | Ser | Val | Asn | Ala | Ser | Leu | Gly |
|---|---|---|---|---|---|---|---|---|---|---|---|---|---|---|---|
| 1 | | | | 5 | | | | | 10 | | | | | 15 | |

| Glu | Arg | Val | Thr | Ile | Thr | Cys | Lys | Ala | Ser | Arg | Asp | Ile | Asn | Asn | Phe |
|---|---|---|---|---|---|---|---|---|---|---|---|---|---|---|---|
| | | | 20 | | | | | 25 | | | | | 30 | | |

| Leu | Ser | Trp | Phe | His | Gln | Lys | Pro | Gly | Lys | Ser | Pro | Lys | Thr | Leu | Ile |
|---|---|---|---|---|---|---|---|---|---|---|---|---|---|---|---|
| | | | 35 | | | | | 40 | | | | | 45 | | |

| Tyr | Arg | Ala | Asn | Arg | Leu | Val | Asp | Gly | Val | Pro | Ser | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Gln | Asp | Tyr | Ser | Phe | Thr | Ile | Ser | Ser | Leu | Glu | Tyr |
|---|---|---|---|---|---|---|---|---|---|---|---|---|---|---|---|
| 65 | | | | | 70 | | | | | 75 | | | | | 80 |

| Glu | Asp | Val | Gly | Ile | Tyr | Tyr | Cys | Leu | Gln | Tyr | Gly | Asp | Leu | Tyr | Thr |
|---|---|---|---|---|---|---|---|---|---|---|---|---|---|---|---|
| | | | | 85 | | | | | 90 | | | | | 95 | |

| Phe | Gly | Gly | Gly | Thr | Lys | Leu | Glu | Ile | Lys | Gly | Gly | Gly | Gly | Ser | Gly |
|---|---|---|---|---|---|---|---|---|---|---|---|---|---|---|---|
| | | | | 100 | | | | | 105 | | | | | 110 | |

| Gly | Gly | Ser | Gly | Gly | Gly | Ser | Asp | Val | Gln | Leu | Leu | Glu | Ser |
|---|---|---|---|---|---|---|---|---|---|---|---|---|---|
| | | 115 | | | | | 120 | | | | | 125 | |

| Gly | Pro | Gly | Leu | Val | Arg | Pro | Ser | Gln | Ser | Leu | Ser | Leu | Thr | Cys | Ser |
|---|---|---|---|---|---|---|---|---|---|---|---|---|---|---|---|
| | 130 | | | | | 135 | | | | | 140 | | | | |

| Val | Thr | Gly | Tyr | Ser | Ile | Val | Ser | His | Tyr | Tyr | Trp | Asn | Trp | Ile | Arg |
|---|---|---|---|---|---|---|---|---|---|---|---|---|---|---|---|
| 145 | | | | | 150 | | | | | 155 | | | | | 160 |

| Gln | Phe | Pro | Gly | Asn | Lys | Leu | Glu | Trp | Met | Gly | Tyr | Ile | Ser | Ser | Asp |
|---|---|---|---|---|---|---|---|---|---|---|---|---|---|---|---|
| | | | | 165 | | | | | 170 | | | | | 175 | |

| Gly | Ser | Asn | Glu | Tyr | Asn | Pro | Ser | Leu | Lys | Asn | Arg | Ile | Ser | Ile | Ser |
|---|---|---|---|---|---|---|---|---|---|---|---|---|---|---|---|
| | | | 180 | | | | | 185 | | | | | 190 | | |

| Leu | Asp | Thr | Ser | Lys | Asn | Gln | Phe | Phe | Leu | Lys | Phe | Asp | Phe | Val | Thr |
|---|---|---|---|---|---|---|---|---|---|---|---|---|---|---|---|
| | | | 195 | | | | | 200 | | | | | 205 | | |

| Thr | Ala | Asp | Thr | Ala | Thr | Tyr | Phe | Cys | Val | Arg | Gly | Val | Asp | Tyr | Trp |
|---|---|---|---|---|---|---|---|---|---|---|---|---|---|---|---|
| | 210 | | | | | 215 | | | | | 220 | | | | |

| Gly | Gln | Gly | Thr | Thr | Leu | Thr | Val | Ser | Ser | Lys | Pro | Thr | Thr | Thr | Pro |
|---|---|---|---|---|---|---|---|---|---|---|---|---|---|---|---|
| 225 | | | | | 230 | | | | | 235 | | | | | 240 |

| Ala | Pro | Arg | Pro | Pro | Thr | Pro | Ala | Pro | Thr | Ile | Ala | Ser | Gln | Pro | Leu |
|---|---|---|---|---|---|---|---|---|---|---|---|---|---|---|---|
| | | | | 245 | | | | | 250 | | | | | 255 | |

| Ser | Leu | Arg | Pro | Glu | Ala | Cys | Arg | Pro | Ala | Ala | Gly | Gly | Ala | Val | His |
|---|---|---|---|---|---|---|---|---|---|---|---|---|---|---|---|
| | | | 260 | | | | | 265 | | | | | 270 | | |

| Thr | Arg | Gly | Leu | Asp | Phe | Ala | Cys | Asp | Ile | Tyr | Ile | Trp | Ala | Pro | Leu |
|---|---|---|---|---|---|---|---|---|---|---|---|---|---|---|---|
| | | 275 | | | | | 280 | | | | | 285 | | | |

| Ala | Gly | Thr | Cys | Gly | Val | Leu | Leu | Leu | Ser | Leu | Val | Ile | Thr | Leu | Tyr |
|---|---|---|---|---|---|---|---|---|---|---|---|---|---|---|---|
| | 290 | | | | | 295 | | | | | 300 | | | | |

| Cys | Asn | His | Arg | Asn | Lys | Arg | Gly | Arg | Lys | Lys | Leu | Leu | Tyr | Ile | Phe |
|---|---|---|---|---|---|---|---|---|---|---|---|---|---|---|---|
| 305 | | | | | 310 | | | | | 315 | | | | | 320 |

| Lys | Gln | Pro | Phe | Met | Arg | Pro | Val | Gln | Thr | Thr | Gln | Glu | Glu | Asp | Gly |
|---|---|---|---|---|---|---|---|---|---|---|---|---|---|---|---|
| | | | | 325 | | | | | 330 | | | | | 335 | |

| Cys | Ser | Cys | Arg | Phe | Pro | Glu | Glu | Glu | Gly | Gly | Cys | Glu | Leu | Arg |
|---|---|---|---|---|---|---|---|---|---|---|---|---|---|---|
| | | | 340 | | | | | 345 | | | | | 350 | |

| Val | Lys | Phe | Ser | Arg | Ser | Ala | Asp | Ala | Pro | Ala | Tyr | Gln | Gln | Gly | Gln |
|---|---|---|---|---|---|---|---|---|---|---|---|---|---|---|---|
| | | | 355 | | | | | 360 | | | | | 365 | | |

| Asn | Gln | Leu | Tyr | Asn | Glu | Leu | Asn | Leu | Gly | Arg | Arg | Glu | Glu | Tyr | Asp |
|---|---|---|---|---|---|---|---|---|---|---|---|---|---|---|---|
| | 370 | | | | | 375 | | | | | 380 | | | | |

| Val | Leu | Asp | Lys | Arg | Arg | Gly | Arg | Asp | Pro | Glu | Met | Gly | Gly | Lys | Pro |
|---|---|---|---|---|---|---|---|---|---|---|---|---|---|---|---|
| 385 | | | | | 390 | | | | | 395 | | | | | 400 |

```
Arg Arg Lys Asn Pro Gln Glu Gly Leu Tyr Asn Glu Leu Gln Lys Asp
            405                 410                 415

Lys Met Ala Glu Ala Tyr Ser Glu Ile Gly Met Lys Gly Glu Arg Arg
        420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 32
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Ser Gly
            100                 105                 110

Gly Gly Gly Ser Gly Gly Gly Ser Asp Val Gln Leu Leu Glu Ser
        115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
145                 150                 155                 160

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
            180                 185                 190

Leu Asp Thr Ser Lys Asn Gln Phe Phe Leu Lys Phe Asp Phe Val Thr
        195                 200                 205

Thr Ala Asp Thr Ala Thr Tyr Phe Cys Val Arg Gly Val Asp Tyr Trp
    210                 215                 220

Gly Gln Gly Thr Thr Leu Thr Val Ser Ser Lys Pro Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
        275                 280                 285

Pro Arg Pro Pro Thr Pro Ala Pro Thr Ile Ala Ser Gln Pro Leu Ser
    290                 295                 300
```

```
Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
            325                 330                 335

Gly Thr Cys Gly Val Leu Leu Leu Ser Leu Val Ile Thr Leu Tyr Cys
            340                 345                 350

Asn His Arg Asn Lys Arg Gly Arg Lys Lys Leu Leu Tyr Ile Phe Lys
            355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 33
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Asp Val Gln Leu Leu Glu Ser
        115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
```

```
            145                 150                 155                 160
        Gln Phe Pro Gly Asn Lys Leu Glu Trp Met Gly Tyr Ile Ser Ser Asp
                        165                 170                 175
        Gly Ser Asn Glu Tyr Asn Pro Ser Leu Lys Asn Arg Ile Ser Ile Ser
                        180                 185                 190
        Leu Asp Thr Ser Lys Asn Gln Phe Phe Leu Lys Phe Asp Phe Val Thr
                        195                 200                 205
        Thr Ala Asp Thr Ala Thr Tyr Phe Cys Val Arg Gly Val Asp Tyr Trp
                        210                 215                 220
        Gly Gln Gly Thr Thr Leu Thr Val Ser Ser Lys Pro Thr Thr Thr Pro
        225                 230                 235                 240
        Ala Pro Arg Pro Pro Thr Pro Ala Pro Thr Ile Ala Ser Gln Pro Leu
                        245                 250                 255
        Ser Leu Arg Pro Glu Ala Ser Arg Pro Ala Ala Gly Gly Ala Val His
                        260                 265                 270
        Thr Arg Gly Leu Asp Phe Ala Ser Asp Lys Pro Thr Thr Thr Pro Ala
                        275                 280                 285
        Pro Arg Pro Pro Thr Pro Ala Pro Thr Ile Ala Ser Gln Pro Leu Ser
                        290                 295                 300
        Leu Arg Pro Glu Ala Ser Arg Pro Ala Ala Gly Gly Ala Val His Thr
        305                 310                 315                 320
        Arg Gly Leu Asp Phe Ala Ser Asp Lys Pro Thr Thr Thr Pro Ala Pro
                        325                 330                 335
        Arg Pro Pro Thr Pro Ala Pro Thr Ile Ala Ser Gln Pro Leu Ser Leu
                        340                 345                 350
        Arg Pro Glu Ala Cys Arg Pro Ala Ala Gly Gly Ala Val His Thr Arg
                        355                 360                 365
        Gly Leu Asp Phe Ala Cys Asp Ile Tyr Ile Trp Ala Pro Leu Ala Gly
                        370                 375                 380
        Thr Cys Gly Val Leu Leu Leu Ser Leu Val Ile Thr Leu Tyr Cys Asn
        385                 390                 395                 400
        His Arg Asn Lys Arg Gly Arg Lys Lys Leu Leu Tyr Ile Phe Lys Gln
                        405                 410                 415
        Pro Phe Met Arg Pro Val Gln Thr Thr Gln Glu Asp Gly Cys Ser
                        420                 425                 430
        Cys Arg Phe Pro Glu Glu Glu Gly Gly Cys Glu Leu Arg Val Lys
                        435                 440                 445
        Phe Ser Arg Ser Ala Asp Ala Pro Ala Tyr Gln Gln Gly Gln Asn Gln
        450                 455                 460
        Leu Tyr Asn Glu Leu Asn Leu Gly Arg Arg Glu Glu Tyr Asp Val Leu
        465                 470                 475                 480
        Asp Lys Arg Arg Gly Arg Asp Pro Glu Met Gly Gly Lys Pro Arg Arg
                        485                 490                 495
        Lys Asn Pro Gln Glu Gly Leu Tyr Asn Glu Leu Gln Lys Asp Lys Met
                        500                 505                 510
        Ala Glu Ala Tyr Ser Glu Ile Gly Met Lys Gly Glu Arg Arg Arg Gly
                        515                 520                 525
        Lys Gly His Asp Gly Leu Tyr Gln Gly Leu Ser Thr Ala Thr Lys Asp
                        530                 535                 540
        Thr Tyr Asp Ala Leu His Met Gln Ala Leu Pro Pro Arg
        545                 550                 555

<210> SEQ ID NO 34
```

<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Lys Leu Glu Glu Ser Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Asn His Arg Asn Arg Ser Lys Arg Ser Arg Gly Gly His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn

```
            370                 375                 380

Gln Leu Tyr Asn Glu Leu Asn Leu Gly Arg Arg Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg
                435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 35
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
                20                  25                  30

Met Ser Trp Val Arg Leu Ser Pro Glu Met Arg Leu Glu Trp Val Ala
            35                  40                  45

Thr Ile Ser Ser Ala Gly Gly Tyr Ile Phe Tyr Ser Asp Ser Val Gln
        50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
                100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Glu Leu Thr Gln Ser
        130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255
```

```
Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
            275                 280                 285

Thr Arg Gly Leu Asp Phe Ala Ser Asp Lys Pro Thr Thr Thr Pro Ala
            290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Ile Tyr Ile Trp Ala Pro Leu Ala
            340                 345                 350

Gly Thr Cys Gly Val Leu Leu Leu Ser Leu Val Ile Thr Leu Tyr Cys
            355                 360                 365

Asn His Arg Asn Arg Ser Lys Arg Ser Arg Gly Gly His Ser Asp Tyr
            370                 375                 380

Met Asn Met Thr Pro Arg Arg Pro Gly Pro Thr Arg Lys His Tyr Gln
385                 390                 395                 400

Pro Tyr Ala Pro Pro Arg Asp Phe Ala Ala Tyr Arg Ser Arg Val Lys
                405                 410                 415

Phe Ser Arg Ser Ala Asp Ala Pro Ala Tyr Gln Gln Gly Gln Asn Gln
            420                 425                 430

Leu Tyr Asn Glu Leu Asn Leu Gly Arg Arg Glu Glu Tyr Asp Val Leu
            435                 440                 445

Asp Lys Arg Arg Gly Arg Asp Pro Glu Met Gly Gly Lys Pro Arg Arg
450                 455                 460

Lys Asn Pro Gln Glu Gly Leu Tyr Asn Glu Leu Gln Lys Asp Lys Met
465                 470                 475                 480

Ala Glu Ala Tyr Ser Glu Ile Gly Met Lys Gly Glu Arg Arg Arg Gly
                485                 490                 495

Lys Gly His Asp Gly Leu Tyr Gln Gly Leu Ser Thr Ala Thr Lys Asp
                500                 505                 510

Thr Tyr Asp Ala Leu His Met Gln Ala Leu Pro Pro Arg
            515                 520                 525

<210> SEQ ID NO 36
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95
```

```
Arg Gln Gly Phe Gly Asn Tyr Gly Asp Tyr Tyr Ala Met Asp Tyr Trp
                100                 105                 110
Gly Gln Gly Thr Thr Val Thr Val Ser Ser Gly Gly Gly Ser Gly
                115                 120                 125
Gly Gly Gly Ser Gly Gly Gly Ser Asp Ile Glu Leu Thr Gln Ser
    130                 135                 140
Pro Ser Ser Leu Ala Val Ser Ala Gly Glu Lys Val Thr Met Ser Cys
145                 150                 155                 160
Lys Ser Ser Gln Ser Leu Leu Asn Ser Arg Thr Arg Lys Asn Gln Leu
                165                 170                 175
Ala Trp Tyr Gln Gln Lys Thr Gly Gln Ser Pro Glu Leu Leu Ile Tyr
                180                 185                 190
Trp Ala Ser Thr Arg Gln Ser Gly Val Pro Asp Arg Phe Thr Gly Ser
                195                 200                 205
Gly Ser Gly Thr Asp Phe Thr Leu Thr Ile Ser Ser Val Gln Ala Glu
                210                 215                 220
Asp Leu Ala Val Tyr Tyr Cys Gln Gln Ser Tyr Asn Leu Leu Thr Phe
225                 230                 235                 240
Gly Pro Gly Thr Lys Leu Glu Ile Lys Arg Lys Pro Thr Thr Thr Pro
                245                 250                 255
Ala Pro Arg Pro Pro Thr Pro Ala Pro Thr Ile Ala Ser Gln Pro Leu
                260                 265                 270
Ser Leu Arg Pro Glu Ala Ser Arg Pro Ala Ala Gly Gly Ala Val His
                275                 280                 285
Thr Arg Gly Leu Asp Phe Ala Ser Asp Lys Pro Thr Thr Thr Pro Ala
                290                 295                 300
Pro Arg Pro Pro Thr Pro Ala Pro Thr Ile Ala Ser Gln Pro Leu Ser
305                 310                 315                 320
Leu Arg Pro Glu Ala Ser Arg Pro Ala Ala Gly Gly Ala Val His Thr
                325                 330                 335
Arg Gly Leu Asp Phe Ala Ser Asp Lys Pro Thr Thr Thr Pro Ala Pro
                340                 345                 350
Arg Pro Pro Thr Pro Ala Pro Thr Ile Ala Ser Gln Pro Leu Ser Leu
                355                 360                 365
Arg Pro Glu Ala Cys Arg Pro Ala Ala Gly Gly Ala Val His Thr Arg
                370                 375                 380
Gly Leu Asp Phe Ala Cys Asp Ile Tyr Ile Trp Ala Pro Leu Ala Gly
385                 390                 395                 400
Thr Cys Gly Val Leu Leu Leu Ser Leu Val Ile Thr Leu Tyr Cys Asn
                405                 410                 415
His Arg Asn Arg Ser Lys Arg Ser Arg Gly Gly His Ser Asp Tyr Met
                420                 425                 430
Asn Met Thr Pro Arg Arg Pro Gly Pro Thr Arg Lys His Tyr Gln Pro
                435                 440                 445
Tyr Ala Pro Pro Arg Asp Phe Ala Ala Tyr Arg Ser Arg Val Lys Phe
                450                 455                 460
Ser Arg Ser Ala Asp Ala Pro Ala Tyr Gln Gln Gly Gln Asn Gln Leu
465                 470                 475                 480
Tyr Asn Glu Leu Asn Leu Gly Arg Arg Glu Glu Tyr Asp Val Leu Asp
                485                 490                 495
Lys Arg Arg Gly Arg Asp Pro Glu Met Gly Gly Lys Pro Arg Arg Lys
                500                 505                 510
```

```
Asn Pro Gln Glu Gly Leu Tyr Asn Glu Leu Gln Lys Asp Lys Met Ala
            515                 520                 525

Glu Ala Tyr Ser Glu Ile Gly Met Lys Gly Arg Arg Arg Gly Lys
        530                 535                 540

Gly His Asp Gly Leu Tyr Gln Gly Leu Ser Thr Ala Thr Lys Asp Thr
545                 550                 555                 560

Tyr Asp Ala Leu His Met Gln Ala Leu Pro Pro Arg
                565                 570

<210> SEQ ID NO 37
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
        115                 120                 125

Gly Gly Ser Gly Gly Gly Gly Ser Asp Ile Glu Leu Thr Gln Ser
    130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300
```

```
Ala Gly Thr Cys Gly Val Leu Leu Leu Ser Leu Val Ile Thr Leu Tyr
305                 310                 315                 320

Cys Asn His Arg Asn Arg Ser Lys Arg Ser Arg Gly His Ser Asp
            325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Lys Arg
            355                 360                 365

Gly Arg Lys Lys Leu Leu Tyr Ile Phe Lys Gln Pro Phe Met Arg Pro
370                 375                 380

Val Gln Thr Thr Gln Glu Glu Asp Gly Cys Ser Cys Arg Phe Pro Glu
385                 390                 395                 400

Glu Glu Glu Gly Gly Cys Glu Leu Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly
            435                 440                 445

Arg Asp Pro Glu Met Gly Gly Lys Pro Arg Arg Lys Asn Pro Gln Glu
450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
            500                 505                 510

His Met Gln Ala Leu Pro Pro Arg
            515                 520

<210> SEQ ID NO 38
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
            35                  40                  45

Thr Ile Ser Ser Ala Gly Gly Tyr Ile Phe Tyr Ser Asp Ser Val Gln
50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
            85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Glu Leu Thr Gln Ser
```

```
            130                 135                 140
Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
                195                 200                 205

Gly Ser Gly Thr Asp Phe Thr Leu Thr Ile Ser Ser Val Gln Ala Glu
            210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
                275                 280                 285

Thr Arg Gly Leu Asp Phe Ala Ser Asp Lys Pro Thr Thr Thr Pro Ala
            290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Ile Tyr Ile Trp Ala Pro Leu Ala
            340                 345                 350

Gly Thr Cys Gly Val Leu Leu Leu Ser Leu Val Ile Thr Leu Tyr Cys
                355                 360                 365

Asn His Arg Asn Arg Ser Lys Arg Ser Arg Gly Gly His Ser Asp Tyr
            370                 375                 380

Met Asn Met Thr Pro Arg Arg Pro Gly Pro Thr Arg Lys His Tyr Gln
385                 390                 395                 400

Pro Tyr Ala Pro Pro Arg Asp Phe Ala Ala Tyr Arg Ser Lys Arg Gly
                405                 410                 415

Arg Lys Lys Leu Leu Tyr Ile Phe Lys Gln Pro Phe Met Arg Pro Val
            420                 425                 430

Gln Thr Thr Gln Glu Glu Asp Gly Cys Ser Cys Arg Phe Pro Glu Glu
                435                 440                 445

Glu Glu Gly Gly Cys Glu Leu Arg Val Lys Phe Ser Arg Ser Ala Asp
450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495

Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
                515                 520                 525

Ile Gly Met Lys Gly Glu Arg Arg Arg Gly Lys Gly His Asp Gly Leu
            530                 535                 540

Tyr Gln Gly Leu Ser Thr Ala Thr Lys Asp Thr Tyr Asp Ala Leu His
545                 550                 555                 560
```

```
Met Gln Ala Leu Pro Pro Arg
                565

<210> SEQ ID NO 39
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Ser Ser Leu Ala Val Ser Ala Gly Glu Lys Val Thr Met Ser Cys
145                 150                 155                 160

Lys Ser Ser Gln Ser Leu Leu Asn Ser Arg Thr Arg Lys Asn Gln Leu
                165                 170                 175

Ala Trp Tyr Gln Gln Lys Thr Gly Gln Ser Pro Glu Leu Leu Ile Tyr
            180                 185                 190

Trp Ala Ser Thr Arg Gln Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220

Asp Leu Ala Val Tyr Tyr Cys Gln Gln Ser Tyr Asn Leu Leu Thr Phe
225                 230                 235                 240

Gly Pro Gly Thr Lys Leu Glu Ile Lys Arg Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
        275                 280                 285

Thr Arg Gly Leu Asp Phe Ala Ser Asp Lys Pro Thr Thr Thr Pro Ala
    290                 295                 300

Pro Arg Pro Pro Thr Pro Ala Pro Thr Ile Ala Ser Gln Pro Leu Ser
305                 310                 315                 320

Leu Arg Pro Glu Ala Ser Arg Pro Ala Ala Gly Gly Ala Val His Thr
                325                 330                 335

Arg Gly Leu Asp Phe Ala Ser Asp Lys Pro Thr Thr Thr Pro Ala Pro
```

```
              340                 345                 350
Arg Pro Pro Thr Pro Ala Pro Thr Ile Ala Ser Gln Pro Leu Ser Leu
            355                 360                 365

Arg Pro Glu Ala Cys Arg Pro Ala Ala Gly Gly Ala Val His Thr Arg
        370                 375                 380

Gly Leu Asp Phe Ala Cys Asp Ile Tyr Ile Trp Ala Pro Leu Ala Gly
385                 390                 395                 400

Thr Cys Gly Val Leu Leu Ser Leu Val Ile Thr Leu Tyr Cys Asn
                405                 410                 415

His Arg Asn Arg Ser Lys Arg Ser Arg Gly Gly His Ser Asp Tyr Met
                420                 425                 430

Asn Met Thr Pro Arg Arg Pro Gly Pro Thr Arg Lys His Tyr Gln Pro
            435                 440                 445

Tyr Ala Pro Pro Arg Asp Phe Ala Ala Tyr Arg Ser Lys Arg Gly Arg
        450                 455                 460

Lys Lys Leu Leu Tyr Ile Phe Lys Gln Pro Phe Met Arg Pro Val Gln
465                 470                 475                 480

Thr Thr Gln Glu Glu Asp Gly Cys Ser Cys Arg Phe Pro Glu Glu Glu
                485                 490                 495

Glu Gly Gly Cys Glu Leu Arg Val Lys Phe Ser Arg Ser Ala Asp Ala
                500                 505                 510

Pro Ala Tyr Gln Gln Gly Gln Asn Gln Leu Tyr Asn Glu Leu Asn Leu
            515                 520                 525

Gly Arg Arg Glu Glu Tyr Asp Val Leu Asp Lys Arg Arg Gly Arg Asp
        530                 535                 540

Pro Glu Met Gly Gly Lys Pro Arg Arg Lys Asn Pro Gln Glu Gly Leu
545                 550                 555                 560

Tyr Asn Glu Leu Gln Lys Asp Lys Met Ala Glu Ala Tyr Ser Glu Ile
                565                 570                 575

Gly Met Lys Gly Glu Arg Arg Arg Gly Lys Gly His Asp Gly Leu Tyr
                580                 585                 590

Gln Gly Leu Ser Thr Ala Thr Lys Asp Thr Tyr Asp Ala Leu His Met
            595                 600                 605

Gln Ala Leu Pro Pro Arg
        610

<210> SEQ ID NO 40
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Glu Leu Thr Gln Ser Pro Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Gln Leu Ala Trp Tyr Gln Gln Lys Thr Gly Gln
            35                  40                  45

Ser Pro Glu Leu Leu Ile Tyr Trp Ala Ser Thr Arg Gln Ser Gly Val
        50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Gln Gln
                85                  90                  95
Ser Tyr Asn Leu Leu Thr Phe Gly Pro Gly Thr Lys Leu Glu Ile Lys
            100                 105                 110
Arg Gly Gly Gly Gly Ser Gly Gly Gly Ser Gly Gly Gly Gly Ser
        115                 120                 125
Val Lys Leu Glu Glu Ser Gly Gly Phe Val Lys Pro Gly Gly Ser
130                 135                 140
Leu Lys Ile Ser Cys Ala Ser Gly Phe Thr Phe Arg Asn Tyr Ala
145                 150                 155                 160
Met Ser Trp Val Arg Leu Ser Pro Glu Met Arg Leu Glu Trp Val Ala
                165                 170                 175
Thr Ile Ser Ser Ala Gly Gly Tyr Ile Phe Tyr Ser Asp Ser Val Gln
            180                 185                 190
Gly Arg Phe Thr Ile Ser Arg Asp Asn Ala Lys Asn Thr Leu His Leu
        195                 200                 205
Gln Met Gly Ser Leu Arg Ser Gly Asp Thr Ala Met Tyr Tyr Cys Ala
    210                 215                 220
Arg Gln Gly Phe Gly Asn Tyr Gly Asp Tyr Tyr Ala Met Asp Tyr Trp
225                 230                 235                 240
Gly Gln Gly Thr Thr Val Thr Val Ser Ser Lys Pro Thr Thr Thr Pro
                245                 250                 255
Ala Pro Arg Pro Pro Thr Pro Ala Pro Thr Ile Ala Ser Gln Pro Leu
            260                 265                 270
Ser Leu Arg Pro Glu Ala Cys Arg Pro Ala Ala Gly Gly Ala Val His
        275                 280                 285
Thr Arg Gly Leu Asp Phe Ala Cys Asp Ile Tyr Ile Trp Ala Pro Leu
290                 295                 300
Ala Gly Thr Cys Gly Val Leu Leu Leu Ser Leu Val Ile Thr Leu Tyr
305                 310                 315                 320
Cys Asn His Arg Asn Arg Ser Lys Arg Ser Arg Gly Gly His Ser Asp
                325                 330                 335
Tyr Met Asn Met Thr Pro Arg Arg Pro Gly Pro Thr Arg Lys His Tyr
            340                 345                 350
Gln Pro Tyr Ala Pro Pro Arg Asp Phe Ala Ala Tyr Arg Ser Arg Val
        355                 360                 365
Lys Phe Ser Arg Ser Ala Asp Ala Pro Ala Tyr Gln Gln Gly Gln Asn
370                 375                 380
Gln Leu Tyr Asn Glu Leu Asn Leu Gly Arg Arg Glu Glu Tyr Asp Val
385                 390                 395                 400
Leu Asp Lys Arg Arg Gly Arg Asp Pro Glu Met Gly Gly Lys Pro Arg
                405                 410                 415
Arg Lys Asn Pro Gln Glu Gly Leu Tyr Asn Glu Leu Gln Lys Asp Lys
            420                 425                 430
Met Ala Glu Ala Tyr Ser Glu Ile Gly Met Lys Gly Glu Arg Arg Arg
        435                 440                 445
Gly Lys Gly His Asp Gly Leu Tyr Gln Gly Leu Ser Thr Ala Thr Lys
450                 455                 460
Asp Thr Tyr Asp Ala Leu His Met Gln Ala Leu Pro Pro Arg
465                 470                 475

<210> SEQ ID NO 41
<211> LENGTH: 525
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 41

```
Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Val Lys Leu Glu Glu Ser Gly Gly Gly Phe Val Lys Pro Gly Gly Ser
    130                 135                 140

Leu Lys Ile Ser Cys Ala Ala Ser Gly Phe Thr Phe Arg Asn Tyr Ala
145                 150                 155                 160

Met Ser Trp Val Arg Leu Ser Pro Glu Met Arg Leu Glu Trp Val Ala
                165                 170                 175

Thr Ile Ser Ser Ala Gly Gly Tyr Ile Phe Tyr Ser Asp Ser Val Gln
            180                 185                 190

Gly Arg Phe Thr Ile Ser Arg Asp Asn Ala Lys Asn Thr Leu His Leu
        195                 200                 205

Gln Met Gly Ser Leu Arg Ser Gly Asp Thr Ala Met Tyr Tyr Cys Ala
    210                 215                 220

Arg Gln Gly Phe Gly Asn Tyr Gly Asp Tyr Tyr Ala Met Asp Tyr Trp
225                 230                 235                 240

Gly Gln Gly Thr Thr Val Thr Val Ser Ser Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
        275                 280                 285

Thr Arg Gly Leu Asp Phe Ala Ser Asp Lys Pro Thr Thr Thr Pro Ala
    290                 295                 300

Pro Arg Pro Pro Thr Pro Ala Pro Thr Ile Ala Ser Gln Pro Leu Ser
305                 310                 315                 320

Leu Arg Pro Glu Ala Cys Arg Pro Ala Ala Gly Gly Ala Val His Thr
                325                 330                 335

Arg Gly Leu Asp Phe Ala Cys Asp Ile Tyr Ile Trp Ala Pro Leu Ala
            340                 345                 350

Gly Thr Cys Gly Val Leu Leu Leu Ser Leu Val Ile Thr Leu Tyr Cys
        355                 360                 365

Asn His Arg Asn Arg Ser Lys Arg Ser Arg Gly Gly His Ser Asp Tyr
    370                 375                 380
```

```
Met Asn Met Thr Pro Arg Arg Pro Gly Pro Thr Arg Lys His Tyr Gln
385                 390                 395                 400

Pro Tyr Ala Pro Pro Arg Asp Phe Ala Ala Tyr Arg Ser Arg Val Lys
            405                 410                 415

Phe Ser Arg Ser Ala Asp Ala Pro Ala Tyr Gln Gln Gly Gln Asn Gln
            420                 425                 430

Leu Tyr Asn Glu Leu Asn Leu Gly Arg Arg Glu Glu Tyr Asp Val Leu
            435                 440                 445

Asp Lys Arg Arg Gly Arg Asp Pro Glu Met Gly Gly Lys Pro Arg Arg
    450                 455                 460

Lys Asn Pro Gln Glu Gly Leu Tyr Asn Glu Leu Gln Lys Asp Lys Met
465                 470                 475                 480

Ala Glu Ala Tyr Ser Glu Ile Gly Met Lys Gly Glu Arg Arg Arg Gly
            485                 490                 495

Lys Gly His Asp Gly Leu Tyr Gln Gly Leu Ser Thr Ala Thr Lys Asp
            500                 505                 510

Thr Tyr Asp Ala Leu His Met Gln Ala Leu Pro Pro Arg
            515                 520                 525

<210> SEQ ID NO 42
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Val Lys Leu Glu Glu Ser Gly Gly Gly Phe Val Lys Pro Gly Gly Ser
    130                 135                 140

Leu Lys Ile Ser Cys Ala Ala Ser Gly Phe Thr Phe Arg Asn Tyr Ala
145                 150                 155                 160

Met Ser Trp Val Arg Leu Ser Pro Glu Met Arg Leu Glu Trp Val Ala
                165                 170                 175

Thr Ile Ser Ser Ala Gly Gly Tyr Ile Phe Tyr Ser Asp Ser Val Gln
            180                 185                 190

Gly Arg Phe Thr Ile Ser Arg Asp Asn Ala Lys Asn Thr Leu His Leu
        195                 200                 205

Gln Met Gly Ser Leu Arg Ser Gly Asp Thr Ala Met Tyr Tyr Cys Ala
    210                 215                 220
```

```
Arg Gln Gly Phe Gly Asn Tyr Gly Asp Tyr Tyr Ala Met Asp Tyr Trp
225                 230                 235                 240

Gly Gln Gly Thr Thr Val Thr Val Ser Ser Arg Ser Lys Arg Ser Arg
            245                 250                 255

Gly Gly His Ser Asp Tyr Met Asn Met Thr Pro Arg Arg Pro Gly Pro
        260                 265                 270

Thr Arg Lys His Tyr Gln Pro Tyr Ala Pro Pro Arg Asp Phe Ala Ala
        275                 280                 285

Tyr Arg Ser Arg Val Lys Phe Ser Arg Ser Ala Asp Ala Pro Ala Tyr
290                 295                 300

Gln Gln Gly Gln Asn Gln Leu Tyr Asn Glu Leu Asn Leu Gly Arg Arg
305                 310                 315                 320

Glu Glu Tyr Asp Val Leu Asp Lys Arg Arg Gly Arg Asp Pro Glu Met
                325                 330                 335

Gly Gly Lys Pro Arg Arg Lys Asn Pro Gln Glu Gly Leu Tyr Asn Glu
            340                 345                 350

Leu Gln Lys Asp Lys Met Ala Glu Ala Tyr Ser Glu Ile Gly Met Lys
            355                 360                 365

Gly Glu Arg Arg Arg Gly Lys Gly His Asp Gly Leu Tyr Gln Gly Leu
370                 375                 380

Ser Thr Ala Thr Lys Asp Thr Tyr Asp Ala Leu His Met Gln Ala Leu
385                 390                 395                 400

Pro Pro Arg

<210> SEQ ID NO 43
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Val Lys Leu Glu Glu Ser Gly Gly Phe Val Lys Pro Gly Gly Ser
    130                 135                 140

Leu Lys Ile Ser Cys Ala Ala Ser Gly Phe Thr Phe Arg Asn Tyr Ala
145                 150                 155                 160

Met Ser Trp Val Arg Leu Ser Pro Glu Met Arg Leu Glu Trp Val Ala
                165                 170                 175
```

Thr Ile Ser Ser Ala Gly Gly Tyr Ile Phe Tyr Ser Asp Ser Val Gln
            180                 185                 190

Gly Arg Phe Thr Ile Ser Arg Asp Asn Ala Lys Asn Thr Leu His Leu
        195                 200                 205

Gln Met Gly Ser Leu Arg Ser Gly Asp Thr Ala Met Tyr Tyr Cys Ala
    210                 215                 220

Arg Gln Gly Phe Gly Asn Tyr Gly Asp Tyr Tyr Ala Met Asp Tyr Trp
225                 230                 235                 240

Gly Gln Gly Thr Thr Val Thr Val Ser Ser Arg Ser Lys Arg Ser Arg
                245                 250                 255

Gly Gly His Ser Asp Tyr Met Asn Met Thr Pro Arg Arg Pro Gly Pro
            260                 265                 270

Thr Arg Lys His Tyr Gln Pro Tyr Ala Pro Pro Arg Asp Phe Ala Ala
        275                 280                 285

Tyr Arg Ser Lys Arg Gly Arg Lys Lys Leu Leu Tyr Ile Phe Lys Gln
    290                 295                 300

Pro Phe Met Arg Pro Val Gln Thr Thr Gln Glu Glu Asp Gly Cys Ser
305                 310                 315                 320

Cys Arg Phe Pro Glu Glu Glu Glu Gly Gly Cys Glu Leu Arg Val Lys
                325                 330                 335

Phe Ser Arg Ser Ala Asp Ala Pro Ala Tyr Gln Gln Gly Gln Asn Gln
            340                 345                 350

Leu Tyr Asn Glu Leu Asn Leu Gly Arg Arg Glu Glu Tyr Asp Val Leu
        355                 360                 365

Asp Lys Arg Arg Gly Arg Asp Pro Glu Met Gly Gly Lys Pro Arg Arg
370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
                405                 410                 415

Lys Gly His Asp Gly Leu Tyr Gln Gly Leu Ser Thr Ala Thr Lys Asp
            420                 425                 430

Thr Tyr Asp Ala Leu His Met Gln Ala Leu Pro Pro Arg
        435                 440                 445

<210> SEQ ID NO 44
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln

-continued

```
                    85                  90                  95
Ser Tyr Asn Leu Leu Thr Phe Gly Pro Gly Thr Lys Leu Glu Ile Lys
                   100                 105                 110

Arg Gly Gly Gly Gly Ser Gly Gly Gly Ser Gly Gly Gly Gly Ser
                   115                 120                 125

Val Lys Leu Glu Glu Ser Gly Gly Gly Phe Val Lys Pro Gly Gly Ser
                   130                 135                 140

Leu Lys Ile Ser Cys Ala Ala Ser Gly Phe Thr Phe Arg Asn Tyr Ala
145                150                 155                 160

Met Ser Trp Val Arg Leu Ser Pro Glu Met Arg Leu Glu Trp Val Ala
                   165                 170                 175

Thr Ile Ser Ser Ala Gly Gly Tyr Ile Phe Tyr Ser Asp Ser Val Gln
                   180                 185                 190

Gly Arg Phe Thr Ile Ser Arg Asp Asn Ala Lys Asn Thr Leu His Leu
                   195                 200                 205

Gln Met Gly Ser Leu Arg Ser Gly Asp Thr Ala Met Tyr Tyr Cys Ala
                   210                 215                 220

Arg Gln Gly Phe Gly Asn Tyr Gly Asp Tyr Tyr Ala Met Asp Tyr Trp
225                230                 235                 240

Gly Gln Gly Thr Thr Val Thr Val Ser Ser Lys Pro Thr Thr Thr Pro
                   245                 250                 255

Ala Pro Arg Pro Pro Thr Pro Ala Pro Thr Ile Ala Ser Gln Pro Leu
                   260                 265                 270

Ser Leu Arg Pro Glu Ala Ser Arg Pro Ala Ala Gly Gly Ala Val His
                   275                 280                 285

Thr Arg Gly Leu Asp Phe Ala Ser Asp Lys Pro Thr Thr Thr Pro Ala
                   290                 295                 300

Pro Arg Pro Pro Thr Pro Ala Pro Thr Ile Ala Ser Gln Pro Leu Ser
305                310                 315                 320

Leu Arg Pro Glu Ala Cys Arg Pro Ala Ala Gly Gly Ala Val His Thr
                   325                 330                 335

Arg Gly Leu Asp Phe Ala Cys Asp Ile Tyr Ile Trp Ala Pro Leu Ala
                   340                 345                 350

Gly Thr Cys Gly Val Leu Leu Leu Ser Leu Val Ile Thr Leu Tyr Cys
                   355                 360                 365

Asn His Arg Asn Arg Ser Lys Arg Ser Arg Gly Gly His Ser Asp Tyr
                   370                 375                 380

Met Asn Met Thr Pro Arg Arg Pro Gly Pro Thr Arg Lys His Tyr Gln
385                390                 395                 400

Pro Tyr Ala Pro Pro Arg Asp Phe Ala Ala Tyr Arg Ser Lys Arg Gly
                   405                 410                 415

Arg Lys Lys Leu Leu Tyr Ile Phe Lys Gln Pro Phe Met Arg Pro Val
                   420                 425                 430

Gln Thr Thr Gln Glu Glu Asp Gly Cys Ser Cys Arg Phe Pro Glu Glu
                   435                 440                 445

Glu Glu Gly Gly Cys Glu Leu Arg Val Lys Phe Ser Arg Ser Ala Asp
                   450                 455                 460

Ala Pro Ala Tyr Gln Gln Gly Gln Asn Gln Leu Tyr Asn Glu Leu Asn
465                470                 475                 480

Leu Gly Arg Arg Glu Glu Tyr Asp Val Leu Asp Lys Arg Arg Gly Arg
                   485                 490                 495

Asp Pro Glu Met Gly Gly Lys Pro Arg Arg Lys Asn Pro Gln Glu Gly
                   500                 505                 510
```

```
Leu Tyr Asn Glu Leu Gln Lys Asp Lys Met Ala Glu Ala Tyr Ser Glu
            515                 520                 525

Ile Gly Met Lys Gly Glu Arg Arg Gly Lys Gly His Asp Gly Leu
        530                 535                 540

Tyr Gln Gly Leu Ser Thr Ala Thr Lys Asp Thr Tyr Asp Ala Leu His
545                 550                 555                 560

Met Gln Ala Leu Pro Pro Arg
                565

<210> SEQ ID NO 45
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Val Lys Leu Glu Glu Ser Gly Gly Gly Phe Val Lys Pro Gly Gly Ser
    130                 135                 140

Leu Lys Ile Ser Cys Ala Ala Ser Gly Phe Thr Phe Arg Asn Tyr Ala
145                 150                 155                 160

Met Ser Trp Val Arg Leu Ser Pro Glu Met Arg Leu Glu Trp Val Ala
                165                 170                 175

Thr Ile Ser Ser Ala Gly Gly Tyr Ile Phe Tyr Ser Asp Ser Val Gln
            180                 185                 190

Gly Arg Phe Thr Ile Ser Arg Asp Asn Ala Lys Asn Thr Leu His Leu
        195                 200                 205

Gln Met Gly Ser Leu Arg Ser Gly Asp Thr Ala Met Tyr Tyr Cys Ala
    210                 215                 220

Arg Gln Gly Phe Gly Asn Tyr Gly Asp Tyr Tyr Ala Met Asp Tyr Trp
225                 230                 235                 240

Gly Gln Gly Thr Thr Val Thr Val Ser Ser Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Ser Arg Pro Ala Ala Gly Gly Ala Val His
        275                 280                 285

Thr Arg Gly Leu Asp Phe Ala Ser Asp Lys Pro Thr Thr Thr Pro Ala
```

```
                290                 295                 300

Pro Arg Pro Pro Thr Pro Ala Pro Thr Ile Ala Ser Gln Pro Leu Ser
305                 310                 315                 320

Leu Arg Pro Glu Ala Ser Arg Pro Ala Ala Gly Gly Ala Val His Thr
                325                 330                 335

Arg Gly Leu Asp Phe Ala Ser Asp Lys Pro Thr Thr Pro Ala Pro
                340                 345                 350

Arg Pro Pro Thr Pro Ala Pro Thr Ile Ala Ser Gln Pro Leu Ser Leu
                355                 360                 365

Arg Pro Glu Ala Cys Arg Pro Ala Ala Gly Gly Ala Val His Thr Arg
                370                 375                 380

Gly Leu Asp Phe Ala Cys Asp Ile Tyr Ile Trp Ala Pro Leu Ala Gly
385                 390                 395                 400

Thr Cys Gly Val Leu Leu Leu Ser Leu Val Ile Thr Leu Tyr Cys Asn
                405                 410                 415

His Arg Asn Arg Ser Lys Arg Ser Arg Gly Gly His Ser Asp Tyr Met
                420                 425                 430

Asn Met Thr Pro Arg Arg Pro Gly Pro Thr Arg Lys His Tyr Gln Pro
                435                 440                 445

Tyr Ala Pro Pro Arg Asp Phe Ala Ala Tyr Arg Ser Lys Arg Gly Arg
                450                 455                 460

Lys Lys Leu Leu Tyr Ile Phe Lys Gln Pro Phe Met Arg Pro Val Gln
465                 470                 475                 480

Thr Thr Gln Glu Glu Asp Gly Cys Ser Cys Arg Phe Pro Glu Glu Glu
                485                 490                 495

Glu Gly Gly Cys Glu Leu Arg Val Lys Phe Ser Arg Ser Ala Asp Ala
                500                 505                 510

Pro Ala Tyr Gln Gln Gly Gln Asn Gln Leu Tyr Asn Glu Leu Asn Leu
                515                 520                 525

Gly Arg Arg Glu Glu Tyr Asp Val Leu Asp Lys Arg Arg Gly Arg Asp
                530                 535                 540

Pro Glu Met Gly Gly Lys Pro Arg Arg Lys Asn Pro Gln Glu Gly Leu
545                 550                 555                 560

Tyr Asn Glu Leu Gln Lys Asp Lys Met Ala Glu Ala Tyr Ser Glu Ile
                565                 570                 575

Gly Met Lys Gly Glu Arg Arg Arg Gly Lys Gly His Asp Gly Leu Tyr
                580                 585                 590

Gln Gly Leu Ser Thr Ala Thr Lys Asp Thr Tyr Asp Ala Leu His Met
                595                 600                 605

Gln Ala Leu Pro Pro Arg
                610

<210> SEQ ID NO 46
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
                20                  25                  30
```

```
Tyr Tyr Trp Asn Trp Ile Arg Gln Phe Pro Gly Asn Lys Leu Glu Trp
         35                  40                  45

Met Gly Tyr Ile Ser Ser Asp Gly Ser Asn Glu Tyr Asn Pro Ser Leu
 50                  55                  60

Lys Asn Arg Ile Ser Ile Ser Leu Asp Thr Ser Lys Asn Gln Phe Phe
 65                  70                  75                  80

Leu Lys Phe Asp Phe Val Thr Thr Ala Asp Thr Ala Thr Tyr Phe Cys
                 85                  90                  95

Val Arg Gly Val Asp Tyr Trp Gly Gln Gly Thr Leu Thr Val Ser
                100                 105                 110

Ser Gly Gly Gly Ser Gly Gly Gly Ser Gly Gly Gly Gly Ser
                115                 120                 125

Asp Ile Lys Met Ala Gln Ser Pro Ser Ser Val Asn Ala Ser Leu Gly
130                 135                 140

Glu Arg Val Thr Ile Thr Cys Lys Ala Ser Arg Asp Ile Asn Asn Phe
145                 150                 155                 160

Leu Ser Trp Phe His Gln Lys Pro Gly Lys Ser Pro Lys Thr Leu Ile
                165                 170                 175

Tyr Arg Ala Asn Arg Leu Val Asp Gly Val Pro Ser Arg Phe Ser Gly
                180                 185                 190

Ser Gly Ser Gly Gln Asp Tyr Ser Phe Thr Ile Ser Ser Leu Glu Tyr
                195                 200                 205

Glu Asp Val Gly Ile Tyr Tyr Cys Leu Gln Tyr Gly Asp Leu Tyr Thr
                210                 215                 220

Phe Gly Gly Gly Thr Lys Leu Glu Ile Lys Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Cys Arg Pro Ala Ala Gly Gly Ala Val His
                260                 265                 270

Thr Arg Gly Leu Asp Phe Ala Cys Asp Ile Tyr Ile Trp Ala Pro Leu
                275                 280                 285

Ala Gly Thr Cys Gly Val Leu Leu Leu Ser Leu Val Ile Thr Leu Tyr
290                 295                 300

Cys Asn His Arg Asn Arg Ser Lys Arg Ser Arg Gly Gly His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
                340                 345                 350

Lys Phe Ser Arg Ser Ala Asp Ala Pro Ala Tyr Gln Gln Gly Gln Asn
                355                 360                 365

Gln Leu Tyr Asn Glu Leu Asn Leu Gly Arg Arg Glu Glu Tyr Asp Val
                370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
                435                 440                 445

Asp Thr Tyr Asp Ala Leu His Met Gln Ala Leu Pro Pro Arg
```

<210> SEQ ID NO 47
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Glu Tyr Asn Pro Ser Leu
    50                  55                  60

Lys Asn Arg Ile Ser Ile Ser Leu Asp Thr Ser Lys Asn Gln Phe Phe
65                  70                  75                  80

Leu Lys Phe Asp Phe Val Thr Thr Ala Asp Thr Ala Thr Tyr Phe Cys
                85                  90                  95

Val Arg Gly Val Asp Tyr Trp Gly Gln Gly Thr Thr Leu Thr Val Ser
            100                 105                 110

Ser Gly Gly Gly Gly Ser Gly Gly Gly Ser Gly Gly Gly Gly Ser
        115                 120                 125

Asp Ile Lys Met Ala Gln Ser Pro Ser Ser Val Asn Ala Ser Leu Gly
130                 135                 140

Glu Arg Val Thr Ile Thr Cys Lys Ala Ser Arg Asp Ile Asn Asn Phe
145                 150                 155                 160

Leu Ser Trp Phe His Gln Lys Pro Gly Lys Ser Pro Lys Thr Leu Ile
                165                 170                 175

Tyr Arg Ala Asn Arg Leu Val Asp Gly Val Pro Ser Arg Phe Ser Gly
            180                 185                 190

Ser Gly Ser Gly Gln Asp Tyr Ser Phe Thr Ile Ser Ser Leu Glu Tyr
        195                 200                 205

Glu Asp Val Gly Ile Tyr Tyr Cys Leu Gln Tyr Gly Asp Leu Tyr Thr
    210                 215                 220

Phe Gly Gly Gly Thr Lys Leu Glu Ile Lys Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

```
Asn His Arg Asn Arg Ser Lys Arg Ser Arg Gly Gly His Ser Asp Tyr
            355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 48
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Glu Tyr Asn Pro Ser Leu
    50                  55                  60

Lys Asn Arg Ile Ser Ile Ser Leu Asp Thr Ser Lys Asn Gln Phe Phe
65                  70                  75                  80

Leu Lys Phe Asp Phe Val Thr Thr Ala Asp Thr Ala Thr Tyr Phe Cys
                85                  90                  95

Val Arg Gly Val Asp Tyr Trp Gly Gln Gly Thr Thr Leu Thr Val Ser
            100                 105                 110

Ser Gly Gly Gly Gly Ser Gly Gly Gly Gly Ser Gly Gly Gly Gly Ser
        115                 120                 125

Asp Ile Lys Met Ala Gln Ser Pro Ser Ser Val Asn Ala Ser Leu Gly
    130                 135                 140

Glu Arg Val Thr Ile Thr Cys Lys Ala Ser Arg Asp Ile Asn Asn Phe
145                 150                 155                 160

Leu Ser Trp Phe His Gln Lys Pro Gly Lys Ser Pro Lys Thr Leu Ile
                165                 170                 175

Tyr Arg Ala Asn Arg Leu Val Asp Gly Val Pro Ser Arg Phe Ser Gly
            180                 185                 190

Ser Gly Ser Gly Gln Asp Tyr Ser Phe Thr Ile Ser Ser Leu Glu Tyr
        195                 200                 205
```

Glu Asp Val Gly Ile Tyr Tyr Cys Leu Gln Tyr Gly Asp Leu Tyr Thr
    210                 215                 220

Phe Gly Gly Gly Thr Lys Leu Glu Ile Lys Lys Pro Thr Thr Thr Pro
225                 230                 235                 240

Ala Pro Arg Pro Pro Thr Pro Ala Pro Thr Ile Ala Ser Gln Pro Leu
            245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Ser Arg Pro Ala Ala Gly Gly Ala Val His Thr
305                 310                 315                 320

Arg Gly Leu Asp Phe Ala Ser Asp Lys Pro Thr Thr Thr Pro Ala Pro
            325                 330                 335

Arg Pro Pro Thr Pro Ala Pro Thr Ile Ala Ser Gln Pro Leu Ser Leu
            340                 345                 350

Arg Pro Glu Ala Cys Arg Pro Ala Ala Gly Gly Ala Val His Thr Arg
        355                 360                 365

Gly Leu Asp Phe Ala Cys Asp Ile Tyr Ile Trp Ala Pro Leu Ala Gly
    370                 375                 380

Thr Cys Gly Val Leu Leu Leu Ser Leu Val Ile Thr Leu Tyr Cys Asn
385                 390                 395                 400

His Arg Asn Arg Ser Lys Arg Ser Arg Gly Gly His Ser Asp Tyr Met
            405                 410                 415

Asn Met Thr Pro Arg Arg Pro Gly Pro Thr Arg Lys His Tyr Gln Pro
            420                 425                 430

Tyr Ala Pro Pro Arg Asp Phe Ala Ala Tyr Arg Ser Arg Val Lys Phe
        435                 440                 445

Ser Arg Ser Ala Asp Ala Pro Ala Tyr Gln Gln Gly Gln Asn Gln Leu
    450                 455                 460

Tyr Asn Glu Leu Asn Leu Gly Arg Arg Glu Glu Tyr Asp Val Leu Asp
465                 470                 475                 480

Lys Arg Arg Gly Arg Asp Pro Glu Met Gly Gly Lys Pro Arg Arg Lys
            485                 490                 495

Asn Pro Gln Glu Gly Leu Tyr Asn Glu Leu Gln Lys Asp Lys Met Ala
            500                 505                 510

Glu Ala Tyr Ser Glu Ile Gly Met Lys Gly Glu Arg Arg Arg Gly Lys
        515                 520                 525

Gly His Asp Gly Leu Tyr Gln Gly Leu Ser Thr Ala Thr Lys Asp Thr
    530                 535                 540

Tyr Asp Ala Leu His Met Gln Ala Leu Pro Pro Arg
545                 550                 555

<210> SEQ ID NO 49
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Val Gln Leu Leu Glu Ser Gly Pro Gly Leu Val Arg Pro Ser Gln

-continued

```
1               5                   10                  15
Ser Leu Ser Leu Thr Cys Ser Val Thr Gly Tyr Ser Ile Val Ser His
                20                  25                  30
Tyr Tyr Trp Asn Trp Ile Arg Gln Phe Pro Gly Asn Lys Leu Glu Trp
                35                  40                  45
Met Gly Tyr Ile Ser Ser Asp Gly Ser Asn Glu Tyr Asn Pro Ser Leu
                50                  55                  60
Lys Asn Arg Ile Ser Ile Ser Leu Asp Thr Ser Lys Asn Gln Phe Phe
65                  70                  75                  80
Leu Lys Phe Asp Phe Val Thr Thr Ala Asp Thr Ala Thr Tyr Phe Cys
                85                  90                  95
Val Arg Gly Val Asp Tyr Trp Gly Gln Gly Thr Thr Leu Thr Val Ser
                100                 105                 110
Ser Gly Gly Gly Gly Ser Gly Gly Gly Ser Gly Gly Gly Gly Ser
                115                 120                 125
Asp Ile Lys Met Ala Gln Ser Pro Ser Ser Val Asn Ala Ser Leu Gly
                130                 135                 140
Glu Arg Val Thr Ile Thr Cys Lys Ala Ser Arg Asp Ile Asn Asn Phe
145                 150                 155                 160
Leu Ser Trp Phe His Gln Lys Pro Gly Lys Ser Pro Lys Thr Leu Ile
                165                 170                 175
Tyr Arg Ala Asn Arg Leu Val Asp Gly Val Pro Ser Arg Phe Ser Gly
                180                 185                 190
Ser Gly Ser Gly Gln Asp Tyr Ser Phe Thr Ile Ser Ser Leu Glu Tyr
                195                 200                 205
Glu Asp Val Gly Ile Tyr Tyr Cys Leu Gln Tyr Gly Asp Leu Tyr Thr
210                 215                 220
Phe Gly Gly Gly Thr Lys Leu Glu Ile Lys Lys Pro Thr Thr Thr Pro
225                 230                 235                 240
Ala Pro Arg Pro Pro Thr Pro Ala Pro Thr Ile Ala Ser Gln Pro Leu
                245                 250                 255
Ser Leu Arg Pro Glu Ala Cys Arg Pro Ala Ala Gly Gly Ala Val His
                260                 265                 270
Thr Arg Gly Leu Asp Phe Ala Cys Asp Ile Tyr Ile Trp Ala Pro Leu
                275                 280                 285
Ala Gly Thr Cys Gly Val Leu Leu Leu Ser Leu Val Ile Thr Leu Tyr
                290                 295                 300
Cys Asn His Arg Asn Arg Ser Lys Arg Ser Arg Gly Gly His Ser Asp
305                 310                 315                 320
Tyr Met Asn Met Thr Pro Arg Arg Pro Gly Pro Thr Arg Lys His Tyr
                325                 330                 335
Gln Pro Tyr Ala Pro Pro Arg Asp Phe Ala Ala Tyr Arg Ser Lys Arg
                340                 345                 350
Gly Arg Lys Lys Leu Leu Tyr Ile Phe Lys Gln Pro Phe Met Arg Pro
                355                 360                 365
Val Gln Thr Thr Gln Glu Glu Asp Gly Cys Ser Cys Arg Phe Pro Glu
                370                 375                 380
Glu Glu Glu Gly Gly Cys Glu Leu Arg Val Lys Phe Ser Arg Ser Ala
385                 390                 395                 400
Asp Ala Pro Ala Tyr Gln Gln Gly Gln Asn Gln Leu Tyr Asn Glu Leu
                405                 410                 415
Asn Leu Gly Arg Arg Glu Glu Tyr Asp Val Leu Asp Lys Arg Arg Gly
                420                 425                 430
```

```
Arg Asp Pro Glu Met Gly Gly Lys Pro Arg Arg Lys Asn Pro Gln Glu
            435                 440                 445

Gly Leu Tyr Asn Glu Leu Gln Lys Asp Lys Met Ala Glu Ala Tyr Ser
        450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 50
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Glu Tyr Asn Pro Ser Leu
    50                  55                  60

Lys Asn Arg Ile Ser Ile Ser Leu Asp Thr Ser Lys Asn Gln Phe Phe
65                  70                  75                  80

Leu Lys Phe Asp Phe Val Thr Thr Ala Asp Thr Ala Thr Tyr Phe Cys
                85                  90                  95

Val Arg Gly Val Asp Tyr Trp Gly Gln Gly Thr Thr Leu Thr Val Ser
            100                 105                 110

Ser Gly Gly Gly Gly Ser Gly Gly Gly Gly Ser Gly Gly Gly Gly Ser
        115                 120                 125

Asp Ile Lys Met Ala Gln Ser Pro Ser Ser Val Asn Ala Ser Leu Gly
    130                 135                 140

Glu Arg Val Thr Ile Thr Cys Lys Ala Ser Arg Asp Ile Asn Asn Phe
145                 150                 155                 160

Leu Ser Trp Phe His Gln Lys Pro Gly Lys Ser Pro Lys Thr Leu Ile
                165                 170                 175

Tyr Arg Ala Asn Arg Leu Val Asp Gly Val Pro Ser Arg Phe Ser Gly
            180                 185                 190

Ser Gly Ser Gly Gln Asp Tyr Ser Phe Thr Ile Ser Ser Leu Glu Tyr
        195                 200                 205

Glu Asp Val Gly Ile Tyr Tyr Cys Leu Gln Tyr Gly Asp Leu Tyr Thr
    210                 215                 220

Phe Gly Gly Gly Thr Lys Leu Glu Ile Lys Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
```

```
            275                 280                 285
Pro Arg Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Asn His Arg Asn Arg Ser Lys Arg Ser Arg Gly Gly His Ser Asp Tyr
        355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
        435                 440                 445

Ala Pro Ala Tyr Gln Gln Gly Gln Asn Gln Leu Tyr Asn Glu Leu Asn
    450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu
            500                 505                 510

Ile Gly Met Lys Gly Glu Arg Arg Arg Gly Lys Gly His Asp Gly Leu
        515                 520                 525

Tyr Gln Gly Leu Ser Thr Ala Thr Lys Asp Thr Tyr Asp Ala Leu His
    530                 535                 540

Met Gln Ala Leu Pro Pro Arg
545                 550

<210> SEQ ID NO 51
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Glu Tyr Asn Pro Ser Leu
    50                  55                  60

Lys Asn Arg Ile Ser Ile Ser Leu Asp Thr Ser Lys Asn Gln Phe Phe
65                  70                  75                  80
```

```
Leu Lys Phe Asp Phe Val Thr Thr Ala Asp Thr Ala Thr Tyr Phe Cys
                85                  90                  95

Val Arg Gly Val Asp Tyr Trp Gly Gln Gly Thr Thr Leu Thr Val Ser
            100                 105                 110

Ser Gly Gly Gly Gly Ser Gly Gly Gly Gly Ser Gly Gly Gly Gly Ser
            115                 120                 125

Asp Ile Lys Met Ala Gln Ser Pro Ser Ser Val Asn Ala Ser Leu Gly
            130                 135                 140

Glu Arg Val Thr Ile Thr Cys Lys Ala Ser Arg Asp Ile Asn Asn Phe
145                 150                 155                 160

Leu Ser Trp Phe His Gln Lys Pro Gly Lys Ser Pro Lys Thr Leu Ile
                165                 170                 175

Tyr Arg Ala Asn Arg Leu Val Asp Gly Val Pro Ser Arg Phe Ser Gly
            180                 185                 190

Ser Gly Ser Gly Gln Asp Tyr Ser Phe Thr Ile Ser Ser Leu Glu Tyr
            195                 200                 205

Glu Asp Val Gly Ile Tyr Tyr Cys Leu Gln Tyr Gly Asp Leu Tyr Thr
210                 215                 220

Phe Gly Gly Gly Thr Lys Leu Glu Ile Lys Lys Pro Thr Thr Thr Pro
225                 230                 235                 240

Ala Pro Arg Pro Pro Thr Pro Ala Pro Thr Ile Ala Ser Gln Pro Leu
            245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
            275                 280                 285

Pro Arg Pro Pro Thr Pro Ala Pro Thr Ile Ala Ser Gln Pro Leu Ser
290                 295                 300

Leu Arg Pro Glu Ala Ser Arg Pro Ala Ala Gly Gly Ala Val His Thr
305                 310                 315                 320

Arg Gly Leu Asp Phe Ala Ser Asp Lys Pro Thr Thr Thr Pro Ala Pro
            325                 330                 335

Arg Pro Pro Thr Pro Ala Pro Thr Ile Ala Ser Gln Pro Leu Ser Leu
            340                 345                 350

Arg Pro Glu Ala Cys Arg Pro Ala Ala Gly Gly Ala Val His Thr Arg
            355                 360                 365

Gly Leu Asp Phe Ala Cys Asp Ile Tyr Ile Trp Ala Pro Leu Ala Gly
            370                 375                 380

Thr Cys Gly Val Leu Leu Leu Ser Leu Val Ile Thr Leu Tyr Cys Asn
385                 390                 395                 400

His Arg Asn Arg Ser Lys Arg Ser Arg Gly Gly His Ser Asp Tyr Met
            405                 410                 415

Asn Met Thr Pro Arg Arg Pro Gly Pro Thr Arg Lys His Tyr Gln Pro
            420                 425                 430

Tyr Ala Pro Pro Arg Asp Phe Ala Ala Tyr Arg Ser Lys Arg Gly Arg
            435                 440                 445

Lys Lys Leu Leu Tyr Ile Phe Lys Gln Pro Phe Met Arg Pro Val Gln
            450                 455                 460

Thr Thr Gln Glu Glu Asp Gly Cys Ser Cys Arg Phe Pro Glu Glu Glu
465                 470                 475                 480

Glu Gly Gly Cys Glu Leu Arg Val Lys Phe Ser Arg Ser Ala Asp Ala
            485                 490                 495

Pro Ala Tyr Gln Gln Gly Gln Asn Gln Leu Tyr Asn Glu Leu Asn Leu
```

```
                    500                 505                 510
Gly Arg Arg Glu Glu Tyr Asp Val Leu Asp Lys Arg Arg Gly Arg Asp
            515                 520                 525

Pro Glu Met Gly Gly Lys Pro Arg Arg Lys Asn Pro Gln Glu Gly Leu
    530                 535                 540

Tyr Asn Glu Leu Gln Lys Asp Lys Met Ala Glu Ala Tyr Ser Glu Ile
545                 550                 555                 560

Gly Met Lys Gly Glu Arg Arg Arg Gly Lys Gly His Asp Gly Leu Tyr
                565                 570                 575

Gln Gly Leu Ser Thr Ala Thr Lys Asp Thr Tyr Asp Ala Leu His Met
            580                 585                 590

Gln Ala Leu Pro Pro Arg
            595

<210> SEQ ID NO 52
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Ser Asp Val Gln Leu Leu Glu Ser
            115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
145                 150                 155                 160

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
            180                 185                 190

Leu Asp Thr Ser Lys Asn Gln Phe Phe Leu Lys Phe Asp Phe Val Thr
        195                 200                 205

Thr Ala Asp Thr Ala Thr Tyr Phe Cys Val Arg Gly Val Asp Tyr Trp
    210                 215                 220

Gly Gln Gly Thr Thr Leu Thr Val Ser Ser Lys Pro Thr Thr Thr Pro
225                 230                 235                 240

Ala Pro Arg Pro Pro Thr Pro Ala Pro Thr Ile Ala Ser Gln Pro Leu
                245                 250                 255
```

```
Ser Leu Arg Pro Glu Ala Cys Arg Pro Ala Ala Gly Ala Val His
            260                 265                 270

Thr Arg Gly Leu Asp Phe Ala Cys Asp Ile Tyr Ile Trp Ala Pro Leu
            275                 280                 285

Ala Gly Thr Cys Gly Val Leu Leu Leu Ser Leu Val Ile Thr Leu Tyr
            290                 295                 300

Cys Asn His Arg Asn Arg Ser Lys Arg Ser Arg Gly Gly His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
            355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
            435                 440                 445

Asp Thr Tyr Asp Ala Leu His Met Gln Ala Leu Pro Pro Arg
            450                 455                 460

<210> SEQ ID NO 53
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Ser Asp Val Gln Leu Leu Glu Ser
        115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
145                 150                 155                 160
```

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
            180                 185                 190

Leu Asp Thr Ser Lys Asn Gln Phe Phe Leu Lys Phe Asp Phe Val Thr
        195                 200                 205

Thr Ala Asp Thr Ala Thr Tyr Phe Cys Val Arg Gly Val Asp Tyr Trp
    210                 215                 220

Gly Gln Gly Thr Thr Leu Thr Val Ser Ser Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
                260                 265                 270

Thr Arg Gly Leu Asp Phe Ala Ser Asp Lys Pro Thr Thr Thr Pro Ala
            275                 280                 285

Pro Arg Pro Pro Thr Pro Ala Pro Thr Ile Ala Ser Gln Pro Leu Ser
290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
                340                 345                 350

Asn His Arg Asn Arg Ser Lys Arg Ser Arg Gly Gly His Ser Asp Tyr
                355                 360                 365

Met Asn Met Thr Pro Arg Arg Pro Gly Pro Thr Arg Lys His Tyr Gln
            370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 54
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Lys Met Ala Gln Ser Pro Ser Ser Val Asn Ala Ser Leu Gly

-continued

```
1               5                   10                  15
Glu Arg Val Thr Ile Thr Cys Lys Ala Ser Arg Asp Ile Asn Asn Phe
                20                  25                  30

Leu Ser Trp Phe His Gln Lys Pro Gly Lys Ser Pro Lys Thr Leu Ile
                35                  40                  45

Tyr Arg Ala Asn Arg Leu Val Asp Gly Val Pro Ser Arg Phe Ser Gly
                50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
                100                 105                 110

Gly Gly Gly Ser Gly Gly Gly Ser Asp Val Gln Leu Leu Glu Ser
                115                 120                 125

Gly Pro Gly Leu Val Arg Pro Ser Gln Ser Leu Ser Leu Thr Cys Ser
                130                 135                 140

Val Thr Gly Tyr Ser Ile Val Ser His Tyr Tyr Trp Asn Trp Ile Arg
145                 150                 155                 160

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
                180                 185                 190

Leu Asp Thr Ser Lys Asn Gln Phe Phe Leu Lys Phe Asp Phe Val Thr
                195                 200                 205

Thr Ala Asp Thr Ala Thr Tyr Phe Cys Val Arg Gly Val Asp Tyr Trp
210                 215                 220

Gly Gln Gly Thr Thr Leu Thr Val Ser Ser Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
                260                 265                 270

Thr Arg Gly Leu Asp Phe Ala Ser Asp Lys Pro Thr Thr Thr Pro Ala
                275                 280                 285

Pro Arg Pro Pro Thr Pro Ala Pro Thr Ile Ala Ser Gln Pro Leu Ser
                290                 295                 300

Leu Arg Pro Glu Ala Ser Arg Pro Ala Ala Gly Gly Ala Val His Thr
305                 310                 315                 320

Arg Gly Leu Asp Phe Ala Ser Asp Lys Pro Thr Thr Thr Pro Ala Pro
                325                 330                 335

Arg Pro Pro Thr Pro Ala Pro Thr Ile Ala Ser Gln Pro Leu Ser Leu
                340                 345                 350

Arg Pro Glu Ala Cys Arg Pro Ala Ala Gly Gly Ala Val His Thr Arg
                355                 360                 365

Gly Leu Asp Phe Ala Cys Asp Ile Tyr Ile Trp Ala Pro Leu Ala Gly
                370                 375                 380

Thr Cys Gly Val Leu Leu Leu Ser Leu Val Ile Thr Leu Tyr Cys Asn
385                 390                 395                 400

His Arg Asn Arg Ser Lys Arg Ser Arg Gly Gly His Ser Asp Tyr Met
                405                 410                 415

Asn Met Thr Pro Arg Arg Pro Gly Pro Thr Arg Lys His Tyr Gln Pro
                420                 425                 430
```

```
Tyr Ala Pro Pro Arg Asp Phe Ala Ala Tyr Arg Ser Arg Val Lys Phe
        435                 440                 445

Ser Arg Ser Ala Asp Ala Pro Ala Tyr Gln Gln Gly Gln Asn Gln Leu
    450                 455                 460

Tyr Asn Glu Leu Asn Leu Gly Arg Arg Glu Tyr Asp Val Leu Asp
465                 470                 475                 480

Lys Arg Arg Gly Arg Asp Pro Glu Met Gly Gly Lys Pro Arg Arg Lys
                485                 490                 495

Asn Pro Gln Glu Gly Leu Tyr Asn Glu Leu Gln Lys Asp Lys Met Ala
            500                 505                 510

Glu Ala Tyr Ser Glu Ile Gly Met Lys Gly Glu Arg Arg Arg Gly Lys
        515                 520                 525

Gly His Asp Gly Leu Tyr Gln Gly Leu Ser Thr Ala Thr Lys Asp Thr
    530                 535                 540

Tyr Asp Ala Leu His Met Gln Ala Leu Pro Pro Arg
545                 550                 555

<210> SEQ ID NO 55
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Asp Val Gln Leu Leu Glu Ser
        115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
145                 150                 155                 160

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
            180                 185                 190

Leu Asp Thr Ser Lys Asn Gln Phe Phe Leu Lys Phe Asp Phe Val Thr
        195                 200                 205

Thr Ala Asp Thr Ala Thr Tyr Phe Cys Val Arg Gly Val Asp Tyr Trp
    210                 215                 220

Gly Gln Gly Thr Thr Leu Thr Val Ser Ser Lys Pro Thr Thr Thr Pro
```

```
                225                 230                 235                 240
Ala Pro Arg Pro Thr Pro Ala Pro Thr Ile Ala Ser Gln Pro Leu
                245                 250                 255
Ser Leu Arg Pro Glu Ala Cys Arg Pro Ala Ala Gly Gly Ala Val His
                260                 265                 270
Thr Arg Gly Leu Asp Phe Ala Cys Asp Ile Tyr Ile Trp Ala Pro Leu
                275                 280                 285
Ala Gly Thr Cys Gly Val Leu Leu Ser Leu Val Ile Thr Leu Tyr
                290                 295                 300
Cys Asn His Arg Asn Arg Ser Lys Arg Ser Arg Gly Gly His Ser Asp
305                 310                 315                 320
Tyr Met Asn Met Thr Pro Arg Arg Pro Gly Pro Thr Arg Lys His Tyr
                    325                 330                 335
Gln Pro Tyr Ala Pro Pro Arg Asp Phe Ala Ala Tyr Arg Ser Lys Arg
                340                 345                 350
Gly Arg Lys Lys Leu Leu Tyr Ile Phe Lys Gln Pro Phe Met Arg Pro
                355                 360                 365
Val Gln Thr Thr Gln Glu Glu Asp Gly Cys Ser Cys Arg Phe Pro Glu
                370                 375                 380
Glu Glu Glu Gly Gly Cys Glu Leu Arg Val Lys Phe Ser Arg Ser Ala
385                 390                 395                 400
Asp Ala Pro Ala Tyr Gln Gln Gly Gln Asn Gln Leu Tyr Asn Glu Leu
                405                 410                 415
Asn Leu Gly Arg Arg Glu Glu Tyr Asp Val Leu Asp Lys Arg Arg Gly
                420                 425                 430
Arg Asp Pro Glu Met Gly Gly Lys Pro Arg Arg Lys Asn Pro Gln Glu
                435                 440                 445
Gly Leu Tyr Asn Glu Leu Gln Lys Asp Lys Met Ala Glu Ala Tyr Ser
                450                 455                 460
Glu Ile Gly Met Lys Gly Glu Arg Arg Arg Gly Lys Gly His Asp Gly
465                 470                 475                 480
Leu Tyr Gln Gly Leu Ser Thr Ala Thr Lys Asp Thr Tyr Asp Ala Leu
                485                 490                 495
His Met Gln Ala Leu Pro Pro Arg
                500

<210> SEQ ID NO 56
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Lys Met Ala Gln Ser Pro Ser Ser Val Asn Ala Ser Leu Gly
1               5                   10                  15
Glu Arg Val Thr Ile Thr Cys Lys Ala Ser Arg Asp Ile Asn Asn Phe
                20                  25                  30
Leu Ser Trp Phe His Gln Lys Pro Gly Lys Ser Pro Lys Thr Leu Ile
            35                  40                  45
Tyr Arg Ala Asn Arg Leu Val Asp Gly Val Pro Ser Arg Phe Ser Gly
        50                  55                  60
Ser Gly Ser Gly Gln Asp Tyr Ser Phe Thr Ile Ser Ser Leu Glu Tyr
65                  70                  75                  80
```

-continued

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Ser Asp Val Gln Leu Leu Glu Ser
        115                 120                 125

Gly Pro Gly Leu Val Arg Pro Ser Gln Ser Leu Ser Leu Thr Cys Ser
    130                 135                 140

Val Thr Gly Tyr Ser Ile Val Ser His Tyr Tyr Trp Asn Trp Ile Arg
145                 150                 155                 160

Gln Phe Pro Gly Asn Lys Leu Glu Trp Met Gly Tyr Ile Ser Ser Asp
                165                 170                 175

Gly Ser Asn Glu Tyr Asn Pro Ser Leu Lys Asn Arg Ile Ser Ile Ser
            180                 185                 190

Leu Asp Thr Ser Lys Asn Gln Phe Phe Leu Lys Phe Asp Phe Val Thr
        195                 200                 205

Thr Ala Asp Thr Ala Thr Tyr Phe Cys Val Arg Gly Val Asp Tyr Trp
    210                 215                 220

Gly Gln Gly Thr Thr Leu Thr Val Ser Ser Lys Pro Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Ser Arg Pro Ala Ala Gly Gly Ala Val His
            260                 265                 270

Thr Arg Gly Leu Asp Phe Ala Ser Asp Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Asn His Arg Asn Arg Ser Lys Arg Ser Arg Gly Gly His Ser Asp Tyr
        355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Arg Val Lys Phe Ser Arg Ser Ala Asp
        435                 440                 445

Ala Pro Ala Tyr Gln Gln Gly Gln Asn Gln Leu Tyr Asn Glu Leu Asn
    450                 455                 460

Leu Gly Arg Arg Glu Glu Tyr Asp Val Leu Asp Lys Arg Gly Arg
465                 470                 475                 480

Asp Pro Glu Met Gly Gly Lys Pro Arg Arg Lys Asn Pro Gln Glu Gly
                485                 490                 495

Leu Tyr Asn Glu Leu Gln Lys Asp Lys Met Ala Glu Ala Tyr Ser Glu

```
                500             505             510
Ile Gly Met Lys Gly Glu Arg Arg Gly Lys Gly His Asp Gly Leu
            515             520             525

Tyr Gln Gly Leu Ser Thr Ala Thr Lys Asp Thr Tyr Asp Ala Leu His
            530             535             540

Met Gln Ala Leu Pro Pro Arg
545             550
```

<210> SEQ ID NO 57
<211> LENGTH: 598
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Asp Ile Lys Met Ala Gln Ser Pro Ser Ser Val Asn Ala Ser Leu Gly
1               5               10              15

Glu Arg Val Thr Ile Thr Cys Lys Ala Ser Arg Asp Ile Asn Asn Phe
            20              25              30

Leu Ser Trp Phe His Gln Lys Pro Gly Lys Ser Pro Lys Thr Leu Ile
        35              40              45

Tyr Arg Ala Asn Arg Leu Val Asp Gly Val Pro Ser Arg Phe Ser Gly
    50              55              60

Ser Gly Ser Gly Gln Asp Tyr Ser Phe Thr Ile Ser Ser Leu Glu Tyr
65              70              75              80

Glu Asp Val Gly Ile Tyr Tyr Cys Leu Gln Tyr Gly Asp Leu Tyr Thr
                85              90              95

Phe Gly Gly Gly Thr Lys Leu Glu Ile Lys Gly Gly Gly Gly Ser Gly
            100             105             110

Gly Gly Gly Ser Gly Gly Gly Ser Asp Val Gln Leu Leu Glu Ser
        115             120             125

Gly Pro Gly Leu Val Arg Pro Ser Gln Ser Leu Ser Leu Thr Cys Ser
    130             135             140

Val Thr Gly Tyr Ser Ile Val Ser His Tyr Tyr Trp Asn Trp Ile Arg
145             150             155             160

Gln Phe Pro Gly Asn Lys Leu Glu Trp Met Gly Tyr Ile Ser Ser Asp
                165             170             175

Gly Ser Asn Glu Tyr Asn Pro Ser Leu Lys Asn Arg Ile Ser Ile Ser
            180             185             190

Leu Asp Thr Ser Lys Asn Gln Phe Phe Leu Lys Phe Asp Phe Val Thr
        195             200             205

Thr Ala Asp Thr Ala Thr Tyr Phe Cys Val Arg Gly Val Asp Tyr Trp
    210             215             220

Gly Gln Gly Thr Thr Leu Thr Val Ser Ser Lys Pro Thr Thr Pro
225             230             235             240

Ala Pro Arg Pro Pro Thr Pro Ala Pro Thr Ile Ala Ser Gln Pro Leu
                245             250             255

Ser Leu Arg Pro Glu Ala Ser Arg Pro Ala Ala Gly Gly Ala Val His
            260             265             270

Thr Arg Gly Leu Asp Phe Ala Ser Asp Lys Pro Thr Thr Thr Pro Ala
        275             280             285

Pro Arg Pro Pro Thr Pro Ala Pro Thr Ile Ala Ser Gln Pro Leu Ser
    290             295             300
```

```
Leu Arg Pro Glu Ala Ser Arg Pro Ala Ala Gly Gly Ala Val His Thr
305                 310                 315                 320

Arg Gly Leu Asp Phe Ala Ser Asp Lys Pro Thr Thr Thr Pro Ala Pro
            325                 330                 335

Arg Pro Pro Thr Pro Ala Pro Thr Ile Ala Ser Gln Pro Leu Ser Leu
            340                 345                 350

Arg Pro Glu Ala Cys Arg Pro Ala Ala Gly Gly Ala Val His Thr Arg
            355                 360                 365

Gly Leu Asp Phe Ala Cys Asp Ile Tyr Ile Trp Ala Pro Leu Ala Gly
        370                 375                 380

Thr Cys Gly Val Leu Leu Leu Ser Leu Val Ile Thr Leu Tyr Cys Asn
385                 390                 395                 400

His Arg Asn Arg Ser Lys Arg Ser Arg Gly Gly His Ser Asp Tyr Met
                405                 410                 415

Asn Met Thr Pro Arg Arg Pro Gly Pro Thr Arg Lys His Tyr Gln Pro
                420                 425                 430

Tyr Ala Pro Pro Arg Asp Phe Ala Ala Tyr Arg Ser Lys Arg Gly Arg
            435                 440                 445

Lys Lys Leu Leu Tyr Ile Phe Lys Gln Pro Phe Met Arg Pro Val Gln
450                 455                 460

Thr Thr Gln Glu Glu Asp Gly Cys Ser Cys Arg Phe Pro Glu Glu Glu
465                 470                 475                 480

Glu Gly Gly Cys Glu Leu Arg Val Lys Phe Ser Arg Ser Ala Asp Ala
                485                 490                 495

Pro Ala Tyr Gln Gln Gly Gln Asn Gln Leu Tyr Asn Glu Leu Asn Leu
            500                 505                 510

Gly Arg Arg Glu Glu Tyr Asp Val Leu Asp Lys Arg Gly Arg Asp
            515                 520                 525

Pro Glu Met Gly Gly Lys Pro Arg Arg Lys Asn Pro Gln Glu Gly Leu
530                 535                 540

Tyr Asn Glu Leu Gln Lys Asp Lys Met Ala Glu Ala Tyr Ser Glu Ile
545                 550                 555                 560

Gly Met Lys Gly Glu Arg Arg Arg Gly Lys Gly His Asp Gly Leu Tyr
                565                 570                 575

Gln Gly Leu Ser Thr Ala Thr Lys Asp Thr Tyr Asp Ala Leu His Met
            580                 585                 590

Gln Ala Leu Pro Pro Arg
        595

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 59
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 59

Met Arg Leu Pro Ala Gln Leu Leu Gly Leu Leu Met Leu Trp Val Pro
1               5                   10                  15

Gly Ser Ser Gly
            20

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Asp Trp Thr Trp Ile Leu Phe Leu Val Ala Ala Ala Thr Arg Val
1               5                   10                  15

His Ser

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Ala Leu Pro Val Thr Ala Leu Leu Leu Pro Leu Ala Leu Leu Leu
1               5                   10                  15

His Ala Ala Arg Pro
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Gly Thr Ser Leu Leu Cys Trp Met Ala Leu Cys Leu Leu Gly Ala
1               5                   10                  15

Asp His Ala Asp Ala
            20

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Lys Arg Phe Leu Phe Leu Leu Leu Thr Ile Ser Leu Leu Val Met
1               5                   10                  15

Val Gln Ile Gln Thr Gly Leu Ser
            20
```

-continued

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala
            20                  25

<210> SEQ ID NO 65
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
        290                 295                 300

Thr Asn Gly Pro Lys Ile Pro Ser Ile Ala Thr Gly Met Val Gly Ala
305                 310                 315                 320

Leu Leu Leu Leu Leu Val Ala Leu Gly Ile Gly Leu Phe Met
                325                 330                 335

<210> SEQ ID NO 66
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Ser Gly Gly Gly Ser Gly Gly
        195                 200                 205

Gly Gly Ser Phe Trp Val Leu Val Val Val Gly Gly Val Leu Ala Cys
    210                 215                 220

Tyr Ser Leu Leu Val Thr Val Ala Phe Ile Ile Phe Trp Val Arg Ser
225                 230                 235                 240

Lys Arg Ser

<210> SEQ ID NO 67
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 67

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 68
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45
```

```
Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu
            260

<210> SEQ ID NO 69
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Asp Trp Thr Trp Ile Leu Phe Leu Val Ala Ala Thr Arg Val
 1               5                  10                  15

His Ser Asn Trp Val Asn Val Ile Ser Asp Leu Lys Lys Ile Glu Asp
                20                  25                  30

Leu Ile Gln Ser Met His Ile Asp Ala Thr Leu Tyr Thr Glu Ser Asp
            35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
 65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Gly Gly Ser Gly Gly Gly Gly Ser Gly Gly
    130                 135                 140
```

Gly Gly Ser Gly Gly Gly Ser Gly Gly Gly Ser Leu Gln Ile Thr
145                 150                 155                 160

Cys Pro Pro Met Ser Val Glu His Ala Asp Ile Trp Val Lys Ser
            165                 170                 175

Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
            195                 200                 205

Thr Asn Val Ala His Trp Thr Thr Pro Ser Leu Lys Cys Ile Arg Asp
210                 215                 220

Pro Ala Leu Val His Gln Arg Pro Ala Pro Pro Ser Thr Val Thr Thr
225                 230                 235                 240

Ala Gly Val Thr Pro Gln Pro Glu Ser Leu Ser Pro Ser Gly Lys Glu
            245                 250                 255

Pro Ala Ala Ser Ser Pro Ser Ser Asn Asn Thr Ala Ala Thr Thr Ala
            260                 265                 270

Ala Ile Val Pro Gly Ser Gln Leu Met Pro Ser Lys Ser Pro Ser Thr
            275                 280                 285

Gly Thr Thr Glu Ile Ser Ser His Glu Ser Ser His Gly Thr Pro Ser
            290                 295                 300

Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Thr Val Ala Ile
            325                 330                 335

Ser Thr Ser Thr Val Leu Leu Cys Gly Leu Ser Ala Val Ser Leu Leu
            340                 345                 350

Ala Cys Tyr Leu Lys Ser Arg Gln Thr Pro Pro Leu Ala Ser Val Glu
            355                 360                 365

Met Glu Ala Met Glu Ala Leu Pro Val Thr Trp Gly Thr Ser Ser Arg
            370                 375                 380

Asp Glu Asp Leu Glu Asn Cys Ser His His Leu
385                 390                 395

<210> SEQ ID NO 70
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn

Thr Ser

<210> SEQ ID NO 71
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235

<210> SEQ ID NO 72
<211> LENGTH: 18
<212> TYPE: PRT
<213> ORGANISM: Thosea asigna virus

<400> SEQUENCE: 72

Glu Gly Arg Gly Ser Leu Leu Thr Cys Gly Asp Val Glu Glu Asn Pro
1               5                   10                  15

Gly Pro

<210> SEQ ID NO 73
<211> LENGTH: 25
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 73

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 74
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25

<210> SEQ ID NO 75
<211> LENGTH: 19
<212> TYPE: PRT
<213> ORGANISM: Porcine teschovirus 1

<400> SEQUENCE: 75

Ala Thr Asn Phe Ser Leu Leu Lys Gln Ala Gly Asp Val Glu Glu Asn
1               5                   10                  15

Pro Gly Pro

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 77
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Arg Ala Lys Arg Ala Pro Val Lys Gln Gly Ser Gly Ala Thr Asn Phe
1               5                   10                  15

Ser Leu Leu Lys Gln Ala Gly Asp Val Glu Glu Asn Pro Gly Pro
            20                  25                  30

<210> SEQ ID NO 78
<211> LENGTH: 20
<212> TYPE: PRT

```
<213> ORGANISM: Equine rhinitis A virus

<400> SEQUENCE: 78

Gln Cys Thr Asn Tyr Ala Leu Leu Lys Leu Ala Gly Asp Val Glu Ser
1               5                   10                  15

Asn Pro Gly Pro
            20

<210> SEQ ID NO 79
<211> LENGTH: 22
<212> TYPE: PRT
<213> ORGANISM: Foot-and-mouth disease virus

<400> SEQUENCE: 79

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Pro Val Lys Gln Gly Ser Gly
1               5

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ala Lys Arg
1

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ala Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Gly Gly Gly Gly Ser Gly Gly Gly Ser Gly Gly Gly Ser
1               5                   10                  15
```

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Gly Ser Thr Ser Gly Ser Gly Lys Pro Gly Ser Gly Glu Gly Ser Thr
1               5                   10                  15

Lys Gly
```

<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Gly Ser Gly
1
```

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Ser Gly Ser Gly
1
```

<210> SEQ ID NO 87
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
                20                  25                  30

Asp Ala Leu Asp Asp Phe Asp Leu Asp Met Leu Gly Asp Gly Asp Ser
            35                  40                  45

Pro Gly Pro Gly Phe Thr Pro His Asp Ser Ala Pro Tyr Gly Ala Leu
50                  55                  60

Asp Met Ala Asp Phe Glu Phe Glu Gln Met Phe Thr Asp Ala Leu Gly
65                  70                  75                  80

Ile Asp Glu Tyr Gly Gly
                85
```

<210> SEQ ID NO 88

```
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Met Pro Val Asp Arg Ile Leu Glu Ala Glu Leu Ala Val Glu Gln
1               5                   10                  15

Lys Ser Asp Gln Gly Val Glu Gly Pro Gly Thr Gly Gly Ser Gly
            20                  25                  30

Ser Ser Pro Asn Asp Pro Val Thr Asn Ile Cys Gln Ala Ala Asp Lys
        35                  40                  45

Gln Leu Phe Thr Leu Val Glu Trp Ala Lys Arg Ile Pro His Phe Ser
    50                  55                  60

Ser Leu Pro Leu Asp Asp Gln Val Ile Leu Leu Arg Ala Gly Trp Asn
65                  70                  75                  80

Glu Leu Leu Ile Ala Ser Phe Ser His Arg Ser Ile Asp Val Arg Asp
                85                  90                  95

Gly Ile Leu Leu Ala Thr Gly Leu His Val His Arg Asn Ser Ala His
            100                 105                 110

Ser Ala Gly Val Gly Ala Ile Phe Asp Arg Val Leu Thr Glu Leu Val
        115                 120                 125

Ser Lys Met Arg Asp Met Arg Met Asp Lys Thr Glu Leu Gly Cys Leu
    130                 135                 140

Arg Ala Ile Ile Leu Phe Asn Pro Glu Val Arg Gly Leu Lys Ser Ala
145                 150                 155                 160

Gln Glu Val Glu Leu Leu Arg Glu Lys Val Tyr Ala Ala Leu Glu Glu
                165                 170                 175

Tyr Thr Arg Thr Thr His Pro Asp Glu Pro Gly Arg Phe Ala Lys Leu
            180                 185                 190

Leu Leu Arg Leu Pro Ser Leu Arg Ser Ile Gly Leu Lys Cys Leu Glu
        195                 200                 205

His Leu Phe Phe Phe Arg Leu Ile Gly Asp Val Pro Ile Asp Thr Phe
    210                 215                 220

Leu Met Glu Met Leu Glu Ser Pro Ser Asp Ser
225                 230                 235

<210> SEQ ID NO 89
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80
```

Ile Asp Glu Tyr Gly Gly Glu Phe Glu Met Pro Val Asp Arg Ile Leu
            85                  90                  95

Glu Ala Glu Leu Ala Val Glu Gln Lys Ser Asp Gln Gly Val Glu Gly
            100                 105                 110

Pro Gly Gly Thr Gly Gly Ser Gly Ser Ser Pro Asn Asp Pro Val Thr
            115                 120                 125

Asn Ile Cys Gln Ala Ala Asp Lys Gln Leu Phe Thr Leu Val Glu Trp
130                 135                 140

Ala Lys Arg Ile Pro His Phe Ser Ser Leu Pro Leu Asp Asp Gln Val
145                 150                 155                 160

Ile Leu Leu Arg Ala Gly Trp Asn Glu Leu Ile Ala Ser Phe Ser
            165                 170                 175

His Arg Ser Ile Asp Val Arg Asp Gly Ile Leu Leu Ala Thr Gly Leu
            180                 185                 190

His Val His Arg Asn Ser Ala His Ser Ala Gly Val Gly Ala Ile Phe
            195                 200                 205

Asp Arg Val Leu Thr Glu Leu Val Ser Lys Met Arg Asp Met Arg Met
210                 215                 220

Asp Lys Thr Glu Leu Gly Cys Leu Arg Ala Ile Ile Leu Phe Asn Pro
225                 230                 235                 240

Glu Val Arg Gly Leu Lys Ser Ala Gln Glu Val Glu Leu Leu Arg Glu
            245                 250                 255

Lys Val Tyr Ala Ala Leu Glu Glu Tyr Thr Arg Thr Thr His Pro Asp
            260                 265                 270

Glu Pro Gly Arg Phe Ala Lys Leu Leu Leu Arg Leu Pro Ser Leu Arg
            275                 280                 285

Ser Ile Gly Leu Lys Cys Leu Glu His Leu Phe Phe Phe Arg Leu Ile
            290                 295                 300

Gly Asp Val Pro Ile Asp Thr Phe Leu Met Glu Met Leu Glu Ser Pro
305                 310                 315                 320

Ser Asp Ser

<210> SEQ ID NO 90
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
            50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
            85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe
145                 150

<210> SEQ ID NO 91
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ile Arg Pro Glu Cys Val Val Pro Glu Thr Gln Cys Ala Met Lys Arg
1               5                   10                  15

Lys Glu Lys Lys Ala Gln Lys Glu Lys Asp Lys Leu Pro Val Ser Thr
            20                  25                  30

Thr Thr Val Asp Asp His Met Pro Pro Ile Met Gln Cys Glu Pro Pro
        35                  40                  45

Pro Pro Glu Ala Ala Arg Ile His Glu Val Val Pro Arg Phe Leu Ser
    50                  55                  60

Asp Lys Leu Leu Val Thr Asn Arg Gln Lys Asn Ile Pro Gln Leu Thr
65                  70                  75                  80

Ala Asn Gln Gln Phe Leu Ile Ala Arg Leu Ile Trp Tyr Gln Asp Gly
                85                  90                  95

Tyr Glu Gln Pro Ser Asp Glu Asp Leu Lys Arg Ile Thr Gln Thr Trp
            100                 105                 110

Gln Gln Ala Asp Asp Glu Asn Glu Glu Ser Asp Thr Pro Phe Arg Gln
        115                 120                 125

Ile Thr Glu Met Thr Ile Leu Thr Val Gln Leu Ile Val Glu Phe Ala
    130                 135                 140

Lys Gly Leu Pro Gly Phe Ala Lys Ile Ser Gln Pro Asp Gln Ile Thr
145                 150                 155                 160

Leu Leu Lys Ala Cys Ser Ser Glu Val Met Met Leu Arg Val Ala Arg
                165                 170                 175

Arg Tyr Asp Ala Ala Ser Asp Ser Ile Leu Phe Ala Asn Asn Gln Ala
            180                 185                 190

Tyr Thr Arg Asp Asn Tyr Arg Lys Ala Gly Met Ala Glu Val Ile Glu
        195                 200                 205

Asp Leu Leu His Phe Cys Arg Cys Met Tyr Ser Met Ala Leu Asp Asn
    210                 215                 220

Ile His Tyr Ala Leu Leu Thr Ala Val Val Ile Phe Ser Asp Arg Pro
225                 230                 235                 240

Gly Leu Glu Gln Pro Gln Leu Val Glu Glu Ile Gln Arg Tyr Tyr Leu
                245                 250                 255

Asn Thr Leu Arg Ile Tyr Ile Leu Asn Gln Leu Ser Gly Ser Ala Arg
            260                 265                 270

Ser Ser Val Ile Tyr Gly Lys Ile Leu Ser Ile Leu Ser Glu Leu Arg
        275                 280                 285

Thr Leu Gly Met Gln Asn Ser Asn Met Cys Ile Ser Leu Lys Leu Lys
    290                 295                 300

Asn Arg Lys Leu Pro Pro Phe Leu Glu Glu Ile Trp Asp Val Ala Asp

Met Ser His Thr Gln Pro Pro Ile Leu Glu Ser Pro Thr Asn Leu
305                 310                 315                 320

Met Ser His Thr Gln Pro Pro Ile Leu Glu Ser Pro Thr Asn Leu
                325                 330                 335

<210> SEQ ID NO 92
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Arg Pro Glu Cys Val Val Pro Glu Thr Gln Cys Ala Met Lys Arg Lys
1               5                   10                  15

Glu Lys Lys Ala Gln Lys Glu Lys Asp Lys Leu Pro Val Ser Thr Thr
            20                  25                  30

Thr Val Asp Asp His Met Pro Pro Ile Met Gln Cys Glu Pro Pro Pro
        35                  40                  45

Pro Glu Ala Ala Arg Ile His Glu Val Val Pro Arg Phe Leu Ser Asp
    50                  55                  60

Lys Leu Leu Val Thr Asn Arg Gln Lys Asn Ile Pro Gln Leu Thr Ala
65                  70                  75                  80

Asn Gln Gln Phe Leu Ile Ala Arg Leu Ile Trp Tyr Gln Asp Gly Tyr
                85                  90                  95

Glu Gln Pro Ser Asp Glu Asp Leu Lys Arg Ile Thr Gln Thr Trp Gln
            100                 105                 110

Gln Ala Asp Asp Glu Asn Glu Glu Ser Asp Thr Pro Phe Arg Gln Ile
        115                 120                 125

Thr Glu Met Thr Ile Leu Thr Val Gln Leu Ile Val Glu Phe Ala Lys
    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                165                 170                 175

Tyr Asp Ala Ala Ser Asp Ser Ile Leu Phe Ala Asn Asn Gln Ala Tyr
            180                 185                 190

Thr Arg Asp Asn Tyr Arg Lys Ala Gly Met Ala Glu Val Ile Glu Asp
        195                 200                 205

Leu Leu His Phe Cys Arg Cys Met Tyr Ser Met Ala Leu Asp Asn Ile
    210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                245                 250                 255

Thr Leu Arg Ile Tyr Ile Leu Asn Gln Leu Ser Gly Ser Ala Arg Ser
            260                 265                 270

Ser Val Ile Tyr Gly Lys Ile Leu Ser Ile Leu Ser Glu Leu Arg Thr
        275                 280                 285

Leu Gly Met Gln Asn Ser Asn Met Cys Ile Ser Leu Lys Leu Lys Asn
    290                 295                 300

Arg Lys Leu Pro Pro Phe Leu Glu Glu Ile Trp Asp Val Ala Asp Met
305                 310                 315                 320

Ser His Thr Gln Pro Pro Ile Leu Glu Ser Pro Thr Asn Leu
                325                 330                 335

<210> SEQ ID NO 93
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Pro Glu Cys Val Val Pro
145                 150                 155                 160

Glu Thr Gln Cys Ala Met Lys Arg Lys Glu Lys Lys Ala Gln Lys Glu
                165                 170                 175

Lys Asp Lys Leu Pro Val Ser Thr Thr Thr Val Asp Asp His Met Pro
            180                 185                 190

Pro Ile Met Gln Cys Glu Pro Pro Pro Glu Ala Ala Arg Ile His
        195                 200                 205

Glu Val Val Pro Arg Phe Leu Ser Asp Lys Leu Leu Val Thr Asn Arg
    210                 215                 220

Gln Lys Asn Ile Pro Gln Leu Thr Ala Asn Gln Gln Phe Leu Ile Ala
225                 230                 235                 240

Arg Leu Ile Trp Tyr Gln Asp Gly Tyr Glu Gln Pro Ser Asp Glu Asp
                245                 250                 255

Leu Lys Arg Ile Thr Gln Thr Trp Gln Gln Ala Asp Asp Glu Asn Glu
            260                 265                 270

Glu Ser Asp Thr Pro Phe Arg Gln Ile Thr Glu Met Thr Ile Leu Thr
        275                 280                 285

Val Gln Leu Ile Val Glu Phe Ala Lys Gly Leu Pro Gly Phe Ala Lys
    290                 295                 300

Ile Ser Gln Pro Asp Gln Ile Thr Leu Leu Lys Ala Cys Ser Ser Glu
305                 310                 315                 320

Val Met Met Leu Arg Val Ala Arg Arg Tyr Asp Ala Ala Ser Asp Ser
                325                 330                 335

Ile Leu Phe Ala Asn Asn Gln Ala Tyr Thr Arg Asp Asn Tyr Arg Lys
            340                 345                 350

Ala Gly Met Ala Glu Val Ile Glu Asp Leu Leu His Phe Cys Arg Cys
        355                 360                 365
```

```
Met Tyr Ser Met Ala Leu Asp Asn Ile His Tyr Ala Leu Leu Thr Ala
            370                 375                 380

Val Val Ile Phe Ser Asp Arg Pro Gly Leu Glu Gln Pro Gln Leu Val
385                 390                 395                 400

Glu Glu Ile Gln Arg Tyr Tyr Leu Asn Thr Leu Arg Ile Tyr Ile Leu
                405                 410                 415

Asn Gln Leu Ser Gly Ser Ala Arg Ser Ser Val Ile Tyr Gly Lys Ile
                420                 425                 430

Leu Ser Ile Leu Ser Glu Leu Arg Thr Leu Gly Met Gln Asn Ser Asn
                435                 440                 445

Met Cys Ile Ser Leu Lys Leu Asn Arg Lys Leu Pro Pro Phe Leu
                450                 455                 460

Glu Glu Ile Trp Asp Val Ala Asp Met Ser His Thr Gln Pro Pro
465                 470                 475                 480

Ile Leu Glu Ser Pro Thr Asn Leu
                485

<210> SEQ ID NO 94
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
                35                  40                  45

Leu Thr Arg Ala His Leu Thr Glu Val Glu Ser Arg Leu Glu Arg Leu
            50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
130                 135                 140

Thr Val Ser Pro Glu Phe Pro Gly Arg Pro Glu Cys Val Val Pro Glu
145                 150                 155                 160

Thr Gln Cys Ala Met Lys Arg Lys Glu Lys Ala Gln Lys Glu Lys
                165                 170                 175

Asp Lys Leu Pro Val Ser Thr Thr Val Asp Asp His Met Pro Pro
                180                 185                 190

Ile Met Gln Cys Glu Pro Pro Pro Glu Ala Ala Arg Ile His Glu
            195                 200                 205

Val Val Pro Arg Phe Leu Ser Asp Lys Leu Leu Val Thr Asn Arg Gln
            210                 215                 220

Lys Asn Ile Pro Gln Leu Thr Ala Asn Gln Gln Phe Leu Ile Ala Arg
```

```
              225                 230                 235                 240
Leu Ile Trp Tyr Gln Asp Gly Tyr Glu Gln Pro Ser Asp Glu Asp Leu
                245                 250                 255

Lys Arg Ile Thr Gln Thr Trp Gln Gln Ala Asp Asp Glu Asn Glu Glu
                260                 265                 270

Ser Asp Thr Pro Phe Arg Gln Ile Thr Glu Met Thr Ile Leu Thr Val
                275                 280                 285

Gln Leu Ile Val Glu Phe Ala Lys Gly Leu Pro Gly Phe Ala Lys Ile
                290                 295                 300

Ser Gln Pro Asp Gln Ile Thr Leu Leu Lys Ala Cys Ser Ser Glu Val
305                 310                 315                 320

Met Met Leu Arg Val Ala Arg Arg Tyr Asp Ala Ala Ser Asp Ser Ile
                325                 330                 335

Leu Phe Ala Asn Asn Gln Ala Tyr Thr Arg Asp Asn Tyr Arg Lys Ala
                340                 345                 350

Gly Met Ala Glu Val Ile Glu Asp Leu Leu His Phe Cys Arg Cys Met
                355                 360                 365

Tyr Ser Met Ala Leu Asp Asn Ile His Tyr Ala Leu Leu Thr Ala Val
                370                 375                 380

Val Ile Phe Ser Asp Arg Pro Gly Leu Glu Gln Pro Gln Leu Val Glu
385                 390                 395                 400

Glu Ile Gln Arg Tyr Tyr Leu Asn Thr Leu Arg Ile Tyr Ile Leu Asn
                405                 410                 415

Gln Leu Ser Gly Ser Ala Arg Ser Ser Val Ile Tyr Gly Lys Ile Leu
                420                 425                 430

Ser Ile Leu Ser Glu Leu Arg Thr Leu Gly Met Gln Asn Ser Asn Met
                435                 440                 445

Cys Ile Ser Leu Lys Leu Lys Asn Arg Lys Leu Pro Pro Phe Leu Glu
                450                 455                 460

Glu Ile Trp Asp Val Ala Asp Met Ser His Thr Gln Pro Pro Ile
465                 470                 475                 480

Leu Glu Ser Pro Thr Asn Leu
                485

<210> SEQ ID NO 95
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gacatcgagc tgacacagag cccatctagc ctggctgtgt ctgccggcga gaaagtgacc      60
atgagctgca agagcagcca gagcctgctg aacagccgga ccagaaagaa tcagctggcc     120
tggtatcagc agaagcccgg ccaatctcct gagctgctga tctactgggc agcacaaga     180 cagagcggcg tgcccgatag attcacagga tctggcagcg gcaccgactt caccctgaca     240
atcagttctg tgcaggccga ggacctggcc gtgtactact gtcagcagag ctacaacctg     300
ctgaccttcg gacccggcac caagctggaa gtgaagaga                            339

<210> SEQ ID NO 96
<211> LENGTH: 366
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 96
gtgaagctgc aagagtccgg cggaggcttt gtgaagcctg gcggctctct gaaagtgtcc      60
tgtgccgcca gcggcttcac ctttagcagc tacgccatga gctgggtccg actgagccct    120
gagatgagac tggaatgggt cgccaccatc agtagcgcag gcggctacat cttctacagc    180
gactctgtgc agggcagatt caccatcagc cgggacaacg ccaagaacac cctgcacctc    240
cagatgggca gtctgagaag cggcgatacc gccatgtact actgcgccag acaaggcttc    300
ggcaactacg gcgactacta tgccatggat tactggggcc agggcaccac cgtgacagtc    360
tcttct                                                                366

<210> SEQ ID NO 97
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gacatcgagc tgacacagag cccatctagc ctggctgtgt ctgccggcga gaaagtgacc      60
atgagctgca gagcagcca gagcctgctg aacagccgga ccagaaagaa tcagctggcc    120
tggtatcagc agaaaaccgg acagagcccc gagctgctga tctactgggc cagcacaaga    180
cagagcggcg tgcccgatag attcacagga tctggcagcg gcaccgactt caccctgaca    240
atcagttctg tgcaggccga ggacctggcc gtgtactact gtcagcagag ctacaacctg    300
ctgaccttcg gacccggcac caagctggaa atcaagaga                            339

<210> SEQ ID NO 98
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gtgaagctgg aagagtccgg cggaggcttt gtgaagcctg gcggaagcct gaagatcagc      60
tgtgccgcca gcggcttcac cttcagaaac tacgccatga gctgggtccg actgagcccc    120
gagatgagac tggaatgggt cgccacaatc agcagcgcag gcggctacat cttctacagc    180
gatagcgtgc agggcagatt caccatcagc cgggacaacg ccaagaacac cctgcacctc    240
cagatgggca gtctgagatc tggcgacacc gccatgtact actgcgccag acaaggcttc    300
ggcaactacg gcgactacta tgccatggat tactggggcc agggcaccac cgtgacagtc    360
tcttct                                                                366

<210> SEQ ID NO 99
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gacatcaaga tggctcagtc cccttctagc gtgaatgctt cgctagggga gcgtgtgacc      60

```
atcacatgta aagcatcacg cgacataaat aatttccttt cctggtttca tcagaaaccg    120
ggcaagtcgc ctaagacgct gatttacaga gcaaatcggt tggtagatgg agtgccaagc    180
agattcagcg ggagcggaag tggacaggat tatagcttca ctatttcatc cctggaatac    240
gaggacgtag gtatctatta ttgcctccag tatggcgatc tttacacatt tggtgggggg    300
actaagctgg agattaag                                                  318

<210> SEQ ID NO 100
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gacgtgcaac ttctggagag cgggccaggg ctagtcaggc cctcccagtc gctttcactg     60
acttgcagtg tgaccggtta ctctattgtg agtcactact attggaactg gattcggcag    120
ttcccaggca acaaactgga atggatgggg tacatatctt ccgatggctc gaatgaatat    180
aacccatcat tgaaaaatcg tatttccatc agtctggata cgagtaaaaa ccagttttc    240 ctcaaattcg atttcgtgac tacagcagat actgccacat acttctgtgt acgaggtgtc    300
gattattggg gacagggcac aacgctgacc gtaagttct                           339

<210> SEQ ID NO 101
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gacatccaga tgacccagag cagcagcttc ctgagcgtgt cccttggcgg cagagtgacc     60
atcacctgta aagccagcga cctgatccac aactggctgg cctggtatca gcagaagcct    120
ggcaacgctc ccagactgct gattagcggc gccacctctc tggaaacagg cgtgccaagc    180
agattttccg gcagcggctc cggcaacgac tacacactgt ctattgccag cctgcagacc    240
gaggatgccg ccacctatta ctgccagcag tactggacca cccttttcac ctttggcagc    300
ggcaccaagc tggaaatcaa g                                              321

<210> SEQ ID NO 102
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gacgttcagc tgcaagagtc tggccctggc ctggtcaatc ctagccagag cctgagcctg     60
acatgtaccg tgaccggcta cagcatcacc aacgactacg cctggaactg gatcagacag    120
ttccccggca acaagctgga atggatgggc tacatcaact acagcggcta caccacctac    180
aatcccagcc tgaagtcccg gatctccatc accagagaca ccagcaagaa ccagttcttc    240
ctgcacctga acagcgtgac caccgaggat accgccacct actactgcgc tagatgggat    300
ggcggcctga catattgggg ccagggaaca ctggtcaccg tgtctgct                 348
```

<210> SEQ ID NO 103
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gacatccaga tgacccagag ccccagcagc ctgagcgcca gcgtgggcga cagggtgacc      60
atcacctgca aggccagcga cctgatccac aactggctgg cctggtacca gcagaagccc     120
ggcaaggccc ccaagctgct gatcagcggc gccaccagcc tggagaccgg cgtgcccagc     180
aggttcagcg gcagcggcag cggcaccgac ttcaccctga ccatcagcag cctgcagccc     240
gaggacttcg ccacctacta ctgccagcag tactggacca ccccttcac cttcggccag     300 ggcaccaagg tggagatcaa gagg                                            324

<210> SEQ ID NO 104
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gacatcgtgc tgacacagag ccctgccatc atgtctgcca gcctcggcga gcgagtgacc      60
atgacatgta cagccagcag cagcgtgtcc agcagctacc tgcattggta tcagcagaag     120
cccggcagca gccccaagct gtggatctac agcacaagca atctggccag cggcgtgcca     180
ggcagatttt ctggttctgg cagcggcacc agctacagcc tgacaatcag cagcatggaa     240
gccgaggatg ccgccaccta ctactgccac cagtaccaca aagccccta cacctttggc     300 ggaggcacca aggtggaaat caagcgg                                         327

<210> SEQ ID NO 105
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gaggttcagc tgcagcagtc tgcgccgaa cttgtgaaac ctggcgcctc tgtgaagctg       60
agctgtaccg ccagcggctt caacatcaag gacacctaca tgcactgggt caagcagagg     120
cctgagcagg gcctcgaatg gatcggaaga gtggatcccg ccaacggcaa caccaaatac     180
gaccccaagt tccagggcaa agccacactg accgccgaca cctctagcaa cacagcctac     240
ctgcagctgt ccagcctgac ctctgaagat accgccgtgt acttctgcgt gcgggactac     300
tacggccata cctacggctt cgccttctgc gaccaaggca aaccctgac agtgtctgct     360

<210> SEQ ID NO 106
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

| gacatccaga tgacacagag ccctagcagc ctgtctgcca gcgtgggaga cagagtgacc | 60 |
| atcacctgta cagccagcag cagcgtgtcc agcagctacc tgcattggta tcagcagaag | 120 |
| cccggcaagg cccctaagct gctgatctac agcaccagca atctggccag cggcgtgcca | 180 |
| agcagatttt ctggctctgg cagcggcacc gacttcaccc tgaccatatc tagcctgcag | 240 |
| cctgaggact cgccaccta ctactgccac cagtaccaca gaagccccta cacctttggc | 300 |
| cagggcacca aggtggaaat caagcgg | 327 |

<210> SEQ ID NO 107
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

| gaggtgcagc tggttgaatc tggcggagga ctggttcagc ctggcggatc tctgagactg | 60 |
| tcttgtgccg ccagcggctt caacatcaag gacacctaca tgcactgggt ccgacaggcc | 120 |
| cctggcaaag gacttgagtg ggttggaaga gtggaccccg ccaacggcaa caccaaatac | 180 |
| gaccccaagt tccagggcag attccaccatc agcgccgaca ccagcaagaa caccgcctac | 240 |
| ctgcagatga acagcctgag agccgaggac accgccgtgt actattgcgt gcgggattac | 300 |
| tacggccata cctacggctt cgccttttgg ggccagggca cactggttac cgttagctct | 360 |

<210> SEQ ID NO 108
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

| aagcccacca ccaccctgc ccctagacct ccaaccccag ccctacaat cgccagccag | 60 |
| cccctgagcc tgaggcccga agcctgtaga cctgccgctg gcggagccgt gcacaccaga | 120 |
| ggcctggatt tcgcctgcga c | 141 |

<210> SEQ ID NO 109
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

| aaacctacta caactcctgc ccccggcct cctacaccag ctcctactat cgcctcccag | 60 |
| ccactcagtc tcagacccga ggcttctagg ccagcggccg gaggcgcggt ccacacccgc | 120 |
| gggctggact ttgcatccga taagcccacc accaccctg ccctagacc tccaacccca | 180 |
| gcccctacaa tcgccagcca gcccctgagc ctgaggccca agcctgtag acctgccgct | 240 |
| ggcggagccg tgcacaccag aggcctggat ttcgcctgcg ac | 282 |

<210> SEQ ID NO 110
<211> LENGTH: 423
<212> TYPE: DNA

-continued

<213> ORGANISM: Artificial Sequence
<220> FEATURE:
<223> OTHER INFORMATION: Description of Artificial Sequence: Synthetic
      polynucleotide

<400> SEQUENCE: 110
aagcctacca ccaccccgc acctcgtcct ccaacccctg cacctacgat tgccagtcag    60
cctctttcac tgcggcctga ggccagcaga ccagctgccg gcggtgccgt ccatacaaga   120
ggactggact tcgcgtccga taaacctact accactccag ccccaaggcc cccaacccca   180
gcaccgacta tcgcatcaca gcctttgtca ctgcgtcctg aagccagccg ccagctgca   240 ggggggggccg tccacacaag gggactcgac tttgcgagtg ataagcccac caccacccct   300 gccccctagac ctccaacccc agccccctaca atcgccagcc agccctgag cctgaggccc   360 gaagcctgta gacctgccgc tggcggagcc gtgcacacca gaggcctgga tttcgcctgc   420
gac                                                                423

<210> SEQ ID NO 111
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
aagcctacca ccaccccgc acctcgtcct ccaacccctg cacctacgat tgccagtcag    60
cctctttcac tgcggcctga ggccagcaga ccagctgccg gcggtgccgt ccatacaaga   120
ggactggact tcgcgtccga taaacctact accactccag ccccaaggcc cccaacccca   180
gcaccgacta tcgcatcaca gcctttgtca ctgcgtcctg aagccagccg ccagctgca   240 ggggggggccg tccacacaag gggactcgac tttgcgagtg ataaacctac tacaactcct   300
gccccccggc ctcctacacc agctcctact atcgcctccc agccactcag tctcagaccc   360
gaggcttcta ggcagcggc cggaggcgcg gtccacaccc gcgggctgga ctttgcatcc   420
gataagccca ccaccacccc tgcccctaga cctccaaccc cagcccctac aatcgccagc   480
cagcccctga gcctgaggcc cgaagcctgt agacctgccg ctggcggagc cgtgcacacc   540
agaggcctgg atttcgcctg cgac                                         564

<210> SEQ ID NO 112
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atctacatct gggcccctct ggccggcacc tgtggcgtgc tgctgctgag cctggtcatc    60
accctgtact gcaaccaccg gaat                                          84

<210> SEQ ID NO 113
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
ttttgggtgc tggtggtggt tggtggagtc ctggcttgct atagcttgct agtaacagtg    60
gcctttatta ttttctgggt g                                              81

<210> SEQ ID NO 114
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
aagagaggcc ggaagaaact gctgtacatc ttcaagcagc ccttcatgcg gcccgtgcag    60
accacccagg aagaggacgg ctgcagctgc cggttccccg aggaagagga aggcggctgc   120
gaactg                                                              126

<210> SEQ ID NO 115
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
aggagcaagc ggagcagagg cggccacagc gactacatga acatgacccc ccggaggcct    60
ggccccaccc ggaagcacta ccagccctac gcccctccca gggacttcgc cgcctaccgg   120
agc                                                                 123

<210> SEQ ID NO 116
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctgtgcgcac gcccacgccg cagccccgcc caagaagatg gcaaagtcta catcaacatg    60
ccaggcaggg gc                                                        72

<210> SEQ ID NO 117
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tacttcctgg gccggctggt ccctcggggg cgaggggctg cggaggcagc gacccggaaa    60
cagcgtatca ctgagaccga gtcgccttat caggagctcc agggtcagag gtcggatgtc   120
tacagcgacc tcaacacaca gaggccgtat tacaaa                             156

<210> SEQ ID NO 118
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 118

```
cgggtgaagt tcagccggag cgccgacgcc cctgcctacc agcagggcca gaaccagctg    60
tacaacgagc tgaacctggg ccggagggag gagtacgacg tgctggacaa gcggagaggc   120
cgggaccctg agatgggcgg caagcccgg agaaagaacc ctcaggaggg cctgtataac   180
gaactgcaga agacaagat ggccgaggcc tacagcgaga tcggcatgaa gggcgagcgg   240
cggaggggca aggccacga cggcctgtac cagggcctga gcaccgccac caaggatacc   300
tacgacgccc tgcacatgca ggccctgccc ccaga                              336
```

<210> SEQ ID NO 119
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
gtgaagctgg aagagtccgg cggaggcttt gtgaagcctg gcggaagcct gaagatcagc    60
tgtgccgcca gcggcttcac cttcagaaac tacgccatga gctgggtccg actgagcccc   120
gagatgagac tggaatgggt cgccacaatc agcagcgcag cggctacat cttctacagc   180
gatagcgtgc aggcagatt caccatcagc cgggacaacg ccaagaacac cctgcacctc   240
cagatgggca gtctgagatc tggcgacacc gccatgtact actgcgccag acaaggcttc   300
ggcaactacg cgactacta tgccatggat tactggggcc agggcaccac cgtgacagtc   360
tcttctggtg gcggtggctc gggcggtggt gggtcgggtg gcggcggatc tgacatcgag   420
ctgacacaga gccatctag cctggctgtg tctgccggcg agaaagtgac catgagctgc   480
aagagcagcc agagcctgct gaacagccgg accagaaaga tcagctggc ctggtatcag   540
cagaaaaccg gacagagccc cgagctgctg atctactggg ccagcacaag acagagcggc   600
gtgcccgata gattcacagg atctggcagc ggcaccgact caccctgac aatcagttct   660
gtgcaggccg aggacctggc cgtgtactac tgtcagcaga gctacaacct gctgaccttc   720
ggacccggca ccaagctgga aatcaagaga agcccacca ccaccctgc ccctagacct   780
ccaaccccag cccctacaat cgccagccag cccctgagcc tgaggcccga agcctgtaga   840
cctgccgctg gcggagccgt gcacaccaga ggcctggatt cgcctgcga catctacatc   900
tgggcccctc tggccggcac ctgtggcgtg ctgctgctga gctggtcat caccctgtac   960
tgcaaccacc ggaataagag aggccggaag aaactgctgt acatcttcaa gcagcccttc  1020
atgcggcccg tgcagaccac ccaggaagag acggctgca gctgccggtt ccccgaggaa  1080
gaggaaggcg gctgcgaact gcgggtgaag ttcagccgga gcgccgacgc ccctgcctac  1140
cagcagggcc agaaccagct gtacaacgag ctgaacctgg ccggaggga ggagtacgac  1200
gtgctggaca gcggagaggg ccgggaccct gagatgggcg gcaagcccg gagaaagaac  1260
cctcaggagg gcctgtataa cgaactgcag aagacaaga tggccgaggc ctacagcgag  1320
atcggcatga gggcgagcg gcggaggggca aaggccacg acggcctgta ccagggcctg  1380
agcaccgcca ccaaggatac ctacgacgcc ctgcacatgc aggccctgcc cccaga      1437
```

<210> SEQ ID NO 120
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

| | | | | | |
|---|---|---|---|---|---|
| gtgaagctgg | aagagtccgg | cggaggcttt | gtgaagcctg | gcggaagcct | gaagatcagc | 60 |
| tgtgccgcca | gcggcttcac | cttcagaaac | tacgccatga | gctgggtccg | actgagcccc | 120 |
| gagatgagac | tggaatgggt | cgccacaatc | agcagcgcag | gcggctacat | cttctacagc | 180 |
| gatagcgtgc | agggcagatt | caccatcagc | cgggacaacg | ccaagaacac | cctgcacctc | 240 |
| cagatgggca | gtctgagatc | tggcgacacc | gccatgtact | actgcgccag | acaaggcttc | 300 |
| ggcaactacg | gcgactacta | tgccatggat | tactggggcc | agggcaccac | cgtgacagtc | 360 |
| tcttctggtg | gcggtggctc | gggcggtggt | gggtcgggtg | gcggcggatc | tgacatcgag | 420 |
| ctgacacaga | gcccatctag | cctggctgtg | tctgccggcg | agaaagtgac | catgagctgc | 480 |
| aagagcagcc | agagcctgct | gaacagccgg | accagaaaga | atcagctggc | ctggtatcag | 540 |
| cagaaaaccg | gacagagccc | cgagctgctg | atctactggg | ccagcacaag | acagagcggc | 600 |
| gtgcccgata | gattcacagg | atctggcagc | ggcaccgact | tcaccctgac | aatcagttct | 660 |
| gtgcaggccg | aggacctggc | cgtgtactac | tgtcagcaga | gctacaacct | gctgaccttc | 720 |
| ggacccggca | ccaagctgga | aatcaagaga | aaacctacta | caactcctgc | cccccggcct | 780 |
| cctacaccag | ctcctactat | cgcctcccag | ccactcagtc | tcagacccga | ggcttctagg | 840 |
| ccagcggccg | gaggcgcggt | ccacacccgc | gggctggact | ttgcatccga | taagcccacc | 900 |
| accaccctg | ccctagacc | tccaaccca | gcccctacaa | tcgccagcca | gcccctgagc | 960 |
| ctgaggcccg | aagcctgtag | acctgccgct | ggcggagccg | tgcacaccag | aggcctggat | 1020 |
| ttcgcctgcg | acatctacat | ctgggcccct | ctggccggca | cctgtggcgt | gctgctgctg | 1080 |
| agcctggtca | tcaccctgta | ctgcaaccac | cggaataaga | gaggccggaa | gaaactgctg | 1140 |
| tacatcttca | agcagccctt | catgcggccc | gtgcagacca | cccaggaaga | ggacggctgc | 1200 |
| agctgccggt | tccccgagga | agaggaaggc | ggctgcgaac | tgcgggtgaa | gttcagccgg | 1260 |
| agcgccgacg | cccctgccta | ccagcagggc | cagaaccagc | tgtacaacga | gctgaacctg | 1320 |
| ggccggaggg | aggagtacga | cgtgctggac | aagcggagag | gccgggaccc | tgagatgggc | 1380 |
| ggcaagcccc | ggagaaagaa | ccctcaggag | ggcctgtata | acgaactgca | gaaagacaag | 1440 |
| atggccgagg | cctacagcga | gatcggcatg | aagggcgagc | ggcggagggg | caagggccac | 1500 |
| gacggcctgt | accagggcct | gagcaccgcc | accaaggata | cctacgacgc | cctgcacatg | 1560 |
| caggccctgc | cccccaga | | | | | 1578 |

<210> SEQ ID NO 121
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

| | | | | | |
|---|---|---|---|---|---|
| gtgaagctgg | aagagtccgg | cggaggcttt | gtgaagcctg | gcggaagcct | gaagatcagc | 60 |
| tgtgccgcca | gcggcttcac | cttcagaaac | tacgccatga | gctgggtccg | actgagcccc | 120 |
| gagatgagac | tggaatgggt | cgccacaatc | agcagcgcag | gcggctacat | cttctacagc | 180 |
| gatagcgtgc | agggcagatt | caccatcagc | cgggacaacg | ccaagaacac | cctgcacctc | 240 |

| cagatgggca gtctgagatc tggcgacacc gccatgtact actgcgccag acaaggcttc | 300 |
| ggcaactacg gcgactacta tgccatggat tactggggcc agggcaccac cgtgacagtc | 360 |
| tcttctggtg gcggtggctc gggcggtggt gggtcgggtg gcggcggatc tgacatcgag | 420 |
| ctgacacaga gcccatctag cctggctgtg tctgccggcg agaaagtgac catgagctgc | 480 |
| aagagcagcc agagcctgct gaacagccgg accagaaaga atcagctggc ctggtatcag | 540 |
| cagaaaaccg gacagagccc cgagctgctg atctactggg ccagcacaag acagagcggc | 600 |
| gtgcccgata gattcacagg atctggcagc ggcaccgact tcaccctgac aatcagttct | 660 |
| gtgcaggccg aggacctggc cgtgtactac tgtcagcaga gctacaacct gctgaccttc | 720 |
| ggacccggca ccaagctgga aatcaagaga aagcctacca ccacccccgc acctcgtcct | 780 |
| ccaaccccctg cacctacgat tgccagtcag cctctttcac tgcggcctga ggccagcaga | 840 |
| ccagctgccg gcggtgccgt ccatacaaga ggactggact tcgcgtccga taaacctact | 900 |
| accactccag ccccaaggcc cccaacccca gcaccgacta tcgcatcaca gcctttgtca | 960 |
| ctgcgtcctg aagccagccg gccagctgca ggggggccg tccacacaag gggactcgac | 1020 |
| tttgcgagtg ataagcccac caccacccct gcccctagac ctccaacccc agccccctaca | 1080 |
| atcgccagcc agccctgag cctgaggccc gaagcctgta gacctgccgc tggcggagcc | 1140 |
| gtgcacacca gaggcctgga tttcgcctgc gacatctaca tctgggcccc tctggccggc | 1200 |
| acctgtggcg tgctgctgct gagcctggtc atcaccctgt actgcaacca ccggaataag | 1260 |
| agaggccgga gaaaactgct gtacatcttc aagcagccct tcatgcggcc cgtgcagacc | 1320 |
| acccaggaag aggacggctg cagctgccgg ttccccgagg aagaggaagg cggctgcgaa | 1380 |
| ctgcgggtga agttcagccg gagcgccgac gcccctgcct accagcaggg ccagaaccag | 1440 |
| ctgtacaacg agctgaacct gggccggagg gaggagtacg acgtgctgga caagcggaga | 1500 |
| ggccgggacc ctgagatggg cggcaagccc cggagaaaga accctcagga gggcctgtat | 1560 |
| aacgaactgc agaaagacaa gatggccgag gcctacagcg agatcggcat gaagggcgag | 1620 |
| cggcggaggg gcaagggcca cgacggcctg taccagggcc tgagcaccgc caccaaggat | 1680 |
| acctacgacg ccctgcacat gcaggccctg ccccccaga | 1719 |

<210> SEQ ID NO 122
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

| atgctgctgc tggtgaccag cctgctgctg tgtgagctgc ccaccccgc ctttctgctg | 60 |
| atccccgaca tcaagatggc tcagtccccct tctagcgtga atgcttcgct aggggagcgt | 120 |
| gtgaccatca catgtaaagc atcacgcgac ataaataatt tcctttcctg gtttcatcag | 180 |
| aaaccgggca agtcgcctaa gacgctgatt tacagagcaa atcggttggt agatggagtg | 240 |
| ccaagcagat tcagcgggag cggaagtgga caggattata gcttcactat ttcatccctg | 300 |
| gaatacgagg acgtaggtat ctattattgc ctccagtatg gcgatcttta cacatttggt | 360 |
| gggggggacta agctggagat taagggcgga ggcggaagcg gaggcggagg ctccggcgga | 420 |
| ggcggaagcg acgtgcaact tctgagagc gggccaggc tagtcaggcc ctcccagtcg | 480 |
| ctttcactga cttgcagtgt gaccggttac tctattgtga gtcactacta ttggaactgg | 540 |

| | | |
|---|---|---|
| attcggcagt tcccaggcaa caaactggaa tggatggggt acatatcttc cgatggctcg | 600 | |
| aatgaatata acccatcatt gaaaaatcgt atttccatca gtctggatac gagtaaaaac | 660 | |
| cagttttcc tcaaattcga tttcgtgact acagcagata ctgccacata cttctgtgta | 720 | |
| cgaggtgtcg attattgggg acagggcaca acgctgaccg taagttctaa gcccaccacc | 780 | |
| acccctgccc ctagacctcc aaccccagcc cctacaatcg ccagccagcc cctgagcctg | 840 | |
| aggcccgaag cctgtagacc tgccgctggc ggagccgtgc acaccagagg cctggatttc | 900 | |
| gcctgcgaca tctacatctg gcccctctg gccggcacct gtggcgtgct gctgctgagc | 960 | |
| ctggtcatca ccctgtactg caaccaccgg aataagagag gccggaagaa actgctgtac | 1020 | |
| atcttcaagc agcccttcat gcggcccgtg cagaccaccc aggaagagga cggctgcagc | 1080 | |
| tgccggttcc ccgaggaaga ggaaggcggc tgcgaactgc gggtgaagtt cagccggagc | 1140 | |
| gccgacgccc ctgcctacca gcagggccag aaccagctgt acaacgagct gaacctgggc | 1200 | |
| cggagggagg agtacgacgt gctggacaag cggagaggcc gggaccctga tgggcggc | 1260 | |
| aagccccgga gaaagaaccc tcaggagggc ctgtataacg aactgcagaa agacaagatg | 1320 | |
| gccgaggcct acagcgagat cggcatgaag ggcgagcggc ggaggggcaa gggccacgac | 1380 | |
| ggcctgtacc agggcctgag caccgccacc aaggatacct acgacgccct gcacatgcag | 1440 | |
| gccctgcccc ccaga | 1455 | |

<210> SEQ ID NO 123
<211> LENGTH: 1389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

| | | |
|---|---|---|
| gacatcaaga tggctcagtc cccttctagc gtgaatgctt cgctagggga gcgtgtgacc | 60 | |
| atcacatgta aagcatcacg cgacataaat aatttccttt cctggtttca tcagaaaccg | 120 | |
| ggcaagtcgc ctaagacgct gatttacaga gcaaatcggt tggtagatgg agtgccaagc | 180 | |
| agattcagcg ggagcggaag tggacaggat tatagcttca ctatttcatc cctggaatac | 240 | |
| gaggacgtag gtatctatta ttgcctccag tatggcgatc tttacacatt tggtgggggg | 300 | |
| actaagctgg agattaaggg cggaggcgga agcggaggcg gaggctccgg cggaggcgga | 360 | |
| agcgacgtgc aacttctgga gagcgggcca gggctagtca ggccctccca gtcgctttca | 420 | |
| ctgacttgca gtgtgaccgg ttactctatt gtgagtcact actattggaa ctggattcgg | 480 | |
| cagttcccag gcaacaaact ggaatggatg gggtacatat cttccgatgg ctcgaatgaa | 540 | |
| tataacccat cattgaaaaa tcgtatttcc atcagtctgg atacgagtaa aaaccagttt | 600 | |
| ttcctcaaat tcgatttcgt gactacagca gatactgcca catacttctg tgtacgaggt | 660 | |
| gtcgattatt ggggacaggg cacaacgctg accgtaagtt ctaagcccac caccaccct | 720 | |
| gcccctagac ctccaacccc agcccctaca atcgccagcc agcccctgag cctgaggccc | 780 | |
| gaagcctgta gacctgccgc tggcggagcc gtgcacacca gaggcctgga tttcgcctgc | 840 | |
| gacatctaca tctgggcccc tctggccggc acctgtggcg tgctgctgct gagcctggtc | 900 | |
| atcaccctgt actgcaacca ccggaataag agaggccgga gaaactgct gtacatcttc | 960 | |
| aagcagcccT tcatgcggcc cgtgcagacc acccaggaag gacggctg cagctgccgg | 1020 | |
| ttccccgagg aagaggaagg cggctgcgaa ctgcgggtga agttcagccg gagcgccgac | 1080 | |

```
gcccctgcct accagcaggg ccagaaccag ctgtacaacg agctgaacct gggccggagg      1140
gaggagtacg acgtgctgga caagcggaga ggccgggacc ctgagatggg cggcaagccc      1200
cggagaaaga accctcagga gggcctgtat aacgaactgc agaaagacaa gatggccgag      1260
gcctacagcg agatcggcat gaagggcgag cggcggaggg caagggcca cgacggcctg       1320 taccagggcc tgagcaccgc caccaaggat acctacgacg ccctgcacat gcaggccctg      1380
ccccccaga                                                              1389
```

<210> SEQ ID NO 124
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
gacatcaaga tggctcagtc cccttctagc gtgaatgctt cgctagggga gcgtgtgacc        60
atcacatgta agcatcacg cgacataaat aatttccttt cctggtttca tcagaaaccg        120
ggcaagtcgc ctaagacgct gatttacaga gcaaatcggt tggtagatgg agtgccaagc       180
agattcagcg ggagcggaag tggacaggat tatagcttca ctatttcatc cctggaatac      240
gaggacgtag gtatctatta ttgcctccag tatggcgatc tttacacatt tggtgggggg      300
actaagctgg agattaaggg cggaggcgga agcggaggcg gaggctccgg cggaggcgga      360
agcgacgtgc aacttctgga gagcgggcca gggctagtca ggccctccca gtcgctttca     420
ctgacttgca gtgtgaccgg ttactctatt gtgagtcact actattggaa ctggattcgg      480
cagttcccag caacaaaact ggaatggatg gggtacatat cttccgatgg ctcgaatgaa      540
tataacccat cattgaaaaa tcgtatttcc atcagtctgg atacgagtaa aaaccagttt      600
ttcctcaaat tcgatttcgt gactacagca gatactgcca catacttctg tgtacgaggt      660
gtcgattatt ggggacaggg cacaacgctg accgtaagtt ctaaacctac tacaactcct      720 gcccccccggc ctcctacacc agctcctact atcgcctccc agccactcag tctcagaccc      780
gaggcttcta ggccagcggc cggaggcgcg gtccacaccc gcgggctgga ctttgcatcc     840
gataagccca ccaccaccce tgcccctaga cctccaaccc cagcccctac aatcgccagc      900 cagccctga gcctgaggcc cgaagcctgt agacctgccg ctggcggagc cgtgcacacc      960
agaggcctgg atttcgcctg cgacatctac atctgggccc ctctggccgg cacctgtggc     1020
gtgctgctgc tgagcctggt catcaccctg tactgcaacc accggaataa gagaggccgg      1080
aagaaactgc tgtacatctt caagcagccc ttcatgcggc ccgtgcagac cacccaggaa      1140
gaggacggct gcagctgccg gttccccgag gaagaggaag cggctgcga actgcgggtg       1200 aagttcagcc ggagcgccga cgcccctgcc taccagcagg gccagaacca gctgtacaac      1260
gagctgaacc tgggccggag ggaggagtac gacgtgctgg acaagcggag aggccgggac      1320
cctgagatgg gcggcaagcc ccggagaaag aaccctcagg agggcctgta taacgaactg      1380
cagaaagaca gatggccga ggcctacagc gagatcggca tgaagggcga gcggcggagg       1440
ggcaagggcc acgacggcct gtaccagggc ctgagcaccg ccaccaagga tacctacgac      1500
gccctgcaca tgcaggccct gccccccaga                                      1530
```

<210> SEQ ID NO 125
<211> LENGTH: 1671
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 125

```
gacatcaaga tggctcagtc cccttctagc gtgaatgctt cgctagggga gcgtgtgacc      60
atcacatgta aagcatcacg cgacataaat aatttccttt cctggtttca tcagaaaccg     120
ggcaagtcgc ctaagacgct gatttacaga gcaaatcggt tggtagatgg agtgccaagc     180
agattcagcg ggagcggaag tggacaggat tatagcttca ctatttcatc cctggaatac     240
gaggacgtag gtatctatta ttgcctccag tatggcgatc tttacacatt tggtggggggg    300
actaagctgg agattaaggg cggaggcgga agcggaggcg gaggctccgg cggaggcgga     360
agcgacgtgc aacttctgga gagcgggcca gggctagtca ggccctccca gtcgctttca     420
ctgacttgca gtgtgaccgg ttactctatt gtgagtcact actattggaa ctggattcgg     480
cagttcccag gcaacaaact ggaatggatg gggtacatat cttccgatgg ctcgaatgaa     540
tataacccat cattgaaaaa tcgtatttcc atcagtctgg atacgagtaa aaaccagttt     600
ttcctcaaat tcgatttcgt gactacagca gatactgcca catacttctg tgtacgaggt     660
gtcgattatt ggggacaggg cacaacgctg accgtaagtt ctaagcctac caccaccccc     720
gcacctcgtc ctccaacccc tgcacctacg attgccagtc agcctctttc actgcggcct     780
gaggccagca gaccagctgc cggcggtgcc gtccatacaa gaggactgga cttcgcgtcc     840
gataaaccta ctaccactcc agccccaagg cccccaaccc cagcaccgac tatcgcatca     900
cagcctttgt cactgcgtcc tgaagccagc cggccagctg cagggggggc cgtccacaca     960
agggactcg actttgcgag tgataagccc accaccaccc ctgcccctag acctccaacc    1020
ccagccccta caatcgccag ccagcccctg agcctgaggc ccgaagcctg tagacctgcc    1080
gctggcggag ccgtgcacac cagaggcctg gatttcgcct gcgacatcta catctgggcc    1140
cctctggccg gcacctgtgg cgtgctgctg ctgagcctgg tcatcaccct gtactgcaac    1200
caccggaata agagaggccg gaagaaactg ctgtacatct tcaagcagcc cttcatgcgg    1260
cccgtgcaga ccacccagga agaggacggc tgcagctgcc ggttccccga ggaagaggaa    1320
ggcggctgcg aactgcgggt gaagttcagc cggagcgccg acgcccctgc ctaccagcag    1380
ggccagaacc agctgtacaa cgagctgaac ctgggccgga gggaggagta cgacgtgctg    1440
gacaagcgga gaggccggga ccctgagatg ggcggcaagc cccggagaaa gaaccctcag    1500
gagggcctgt ataacgaact gcagaaagac aagatggccg aggcctacag cgagatcggc    1560
atgaagggcg agcggcggag gggcaagggc cacgacggcc tgtaccaggg cctgagcacc    1620
gccaccaagg atacctacga cgccctgcac atgcaggccc tgcccccag a              1671
```

<210> SEQ ID NO 126
<211> LENGTH: 1434
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
gtgaagctgg aagagtccgg cggaggcttt gtgaagcctg gcggaagcct gaagatcagc      60
tgtgccgcca cgggcttcac cttcagaaac tacgccatga gctgggtccg actgagcccc     120
gagatgagac tggaatgggt cgccacaatc agcagcgcag gcggctacat cttctacagc     180
```

```
gatagcgtgc agggcagatt caccatcagc cgggacaacg ccaagaacac cctgcacctc    240
cagatgggca gtctgagatc tggcgacacc gccatgtact actgcgccag acaaggcttc    300
ggcaactacg gcgactacta tgccatggat tactggggcc agggcaccac cgtgacagtc    360
tcttctggtg gcggtggctc gggcggtggt gggtcgggtg gcggcggatc tgacatcgag    420
ctgacacaga gcccatctag cctggctgtg tctgccggcg agaaagtgac catgagctgc    480
aagagcagcc agagcctgct gaacagccgg accagaaaga atcagctggc ctggtatcag    540
cagaaaaccg acagagcccc gagctgctg atctactggg ccagcacaag acagagcggc    600
gtgcccgata gattcacagg atctggcagc ggcaccgact tcaccctgac aatcagttct    660
gtgcaggccg aggacctggc cgtgtactac tgtcagcaga gctacaacct gctgaccttc    720
ggacccggca ccaagctgga aatcaagaga aagcccacca ccacccctgc cctagacct     780 ccaaccccag cccctacaat cgccagccag cccctgagcc tgaggcccga agcctgtaga    840
cctgccgctg gcggagccgt gcacaccaga ggcctggatt cgcctgcga catctacatc     900 tgggcccctc tggccggcac ctgtggcgtg ctgctgctga gcctggtcat caccctgtac    960
tgcaaccacc ggaataggag caagcggagc agaggcggcc acagcgacta catgaacatg    1020 acccccgga ggcctggccc cacccggaag cactaccagc cctacgcccc tcccagggac     1080
ttcgccgcct accggagccg ggtgaagttc agccggagcg ccgacgcccc tgcctaccag    1140
cagggccaga ccagctgta caacgagctg aacctgggcc ggagggagga gtacgacgtg    1200
ctggacaagc ggagaggccg ggaccctgag atgggcggca gccccggag aaagaaccct     1260 caggagggcc tgtataacga actgcagaaa gacaagatgg ccgaggccta cagcgagatc    1320
ggcatgaagg gcgagcggcg gaggggcaag ggccacgacg gcctgtacca gggcctgagc    1380
accgccacca aggataccta cgacgccctg cacatgcagg ccctgccccc caga          1434
```

<210> SEQ ID NO 127
<211> LENGTH: 1575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
gtgaagctgg aagagtccgg cggaggcttt gtgaagcctg gcggaagcct gaagatcagc     60
tgtgccgcca gcggcttcac cttcagaaac tacgccatga gctgggtccg actgagcccc    120
gagatgagac tggaatgggt cgccacaatc agcagcgcag cggctacat cttctacagc     180 gatagcgtgc agggcagatt caccatcagc cgggacaacg ccaagaacac cctgcacctc    240
cagatgggca gtctgagatc tggcgacacc gccatgtact actgcgccag acaaggcttc    300
ggcaactacg gcgactacta tgccatggat tactggggcc agggcaccac cgtgacagtc    360
tcttctggtg gcggtggctc gggcggtggt gggtcgggtg gcggcggatc tgacatcgag    420
ctgacacaga gcccatctag cctggctgtg tctgccggcg agaaagtgac catgagctgc    480
aagagcagcc agagcctgct gaacagccgg accagaaaga atcagctggc ctggtatcag    540
cagaaaaccg acagagcccc gagctgctg atctactggg ccagcacaag acagagcggc    600
gtgcccgata gattcacagg atctggcagc ggcaccgact tcaccctgac aatcagttct    660
gtgcaggccg aggacctggc cgtgtactac tgtcagcaga gctacaacct gctgaccttc    720
ggacccggca ccaagctgga aatcaagaga aaacctacta caactcctgc ccccggcct    780
```

```
cctacaccag ctcctactat cgcctcccag ccactcagtc tcagacccga ggcttctagg    840
ccagcggccg gaggcgcggt ccacacccgc gggctggact ttgcatccga taagcccacc    900
accaccsctg cccctagacc tccaacccca gcccctacaa tcgccagcca gcccctgagc    960
ctgaggcccg aagcctgtag acctgccgct ggcggagccg tgcacaccag aggcctggat    1020
ttcgcctgcg acatctacat ctgggcccct ctggccggca cctgtggcgt gctgctgctg    1080
agcctggtca tcaccctgta ctgcaaccac cggaatagga gcaagcggag cagaggcggc    1140
cacagcgact acatgaacat gaccccccgg aggcctggcc ccacccggaa gcactaccag    1200
ccctacgccc ctcccaggga cttcgccgcc taccggagcc gggtgaagtt cagccggagc    1260
gccgacgccc ctgcctacca gcagggccag aaccagctgt acaacgagct gaacctgggc    1320
cggagggagg agtacgacgt gctggacaag cggagaggcc gggaccctga gatgggcggc    1380
aagccccgga gaaagaaccc tcaggagggc ctgtataacg aactgcagaa agacaagatg    1440
gccgaggcct acagcgagat cggcatgaag ggcgagcggc ggaggggcaa gggccacgac    1500
ggcctgtacc agggcctgag caccgccacc aaggatacct acgacgccct gcacatgcag    1560
gccctgcccc ccaga                                                     1575

<210> SEQ ID NO 128
<211> LENGTH: 1716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
gtgaagctgg aagagtccgg cggaggcttt gtgaagcctg gcggaagcct gaagatcagc    60
tgtgccgcca gcggcttcac cttcagaaac tacgccatga gctgggtccg actgagcccc    120
gagatgagac tggaatgggt cgccacaatc agcagcgcag cggctacat cttctacagc    180 gatagcgtgc agggcagatt caccatcagc cgggacaacg ccaagaacac cctgcacctc    240
cagatgggca gtctgagatc tggcgacacc gccatgtact actgcgccag acaaggcttc    300
ggcaactacg gcgactacta tgccatggat tactggggcc agggcaccac cgtgacagtc    360
tcttctggtg gcggtggctc gggcggtggt gggtcgggtg gcggcggatc tgacatcgag    420
ctgacacaga gcccatctag cctggctgtg tctgccggcg agaaagtgac catgagctgc    480
aagagcagcc agagcctgct gaacagccgg accagaaaga tcagctggc ctggtatcag    540 cagaaaaccg gacagagccc cgagctgctg atctactggg ccagcacaag acagagcggc    600
gtgcccgata gattcacagg atctggcagc ggcaccgact tcaccctgac aatcagttct    660
gtgcaggccg aggacctggc cgtgtactac tgtcagcaga gctacaacct gctgaccttc    720
ggacccggca ccaagctgga aatcaagaga aagcctacca ccacccccgc acctcgtcct    780 ccaaccccctg cacctacgat tgccagtcag cctctttcac tgcggcctga ggccagcaga    840
ccagctgccg gcggtgccgt ccatacaaga ggactggact tcgcgtccga taaacctact    900
accactccag ccccaaggcc cccaaccccca gcaccgacta tcgcatcaca gcctttgtca    960
ctgcgtcctg aagccagccg gccagctgca ggggggggccg tccacacaag gggactcgac    1020
tttgcgagtg ataagcccac caccaccccct gccctagac ctccaaccc agcccctaca    1080 atcgccagcc agccctgag cctgaggccc aagcctgta gacctgccgc tggcggagcc    1140
gtgcacacca gaggcctgga tttcgcctgc gacatctaca tctgggcccc tctggccggc    1200
```

```
acctgtggcg tgctgctgct gagcctggtc atcaccctgt actgcaacca ccggaatagg    1260
agcaagcgga gcagaggcgg ccacagcgac tacatgaaca tgaccccccg gaggcctggc    1320
cccacccgga agcactacca gccctacgcc cctcccaggg acttcgccgc ctaccggagc    1380
cgggtgaagt tcagccggag cgccgacgcc cctgcctacc agcagggcca gaaccagctg    1440
tacaacgagc tgaacctggg ccggagggag gagtacgacg tgctggacaa gcggagaggc    1500
cgggaccctg agatgggcgg caagcccgg agaaagaacc ctcaggaggg cctgtataac    1560
gaactgcaga aagacaagat ggccgaggcc tacagcgaga tcggcatgaa gggcgagcgg    1620
cggaggggca agggccacga cggcctgtac cagggcctga gcaccgccac caaggatacc    1680
tacgacgccc tgcacatgca ggccctgccc cccaga                              1716
```

<210> SEQ ID NO 129
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
gtgaagctgg aagagtccgg cggaggcttt gtgaagcctg gcggaagcct gaagatcagc     60
tgtgccgcca gcggcttcac cttcagaaac tacgccatga gctgggtccg actgagcccc    120
gagatgagac tggaatgggt cgccacaatc agcagcgcag cggctacat cttctacagc     180 gatagcgtgc agggcagatt caccatcagc cgggacaacg ccaagaacac cctgcacctc    240
cagatgggca gtctgagatc tggcgacacc gccatgtact actgcgccag acaaggcttc    300
ggcaactacg cgactacta tgccatggat tactggggcc agggcaccac cgtgacagtc    360
tcttctggtg gcggtggctc gggcggtggt gggtcgggtg gcggcggatc tgacatcgag    420
ctgacacaga gcccatctag cctggctgtg tctgccggcg agaaagtgac catgagctgc    480
aagagcagcc agagcctgct gaacagccgg accagaaaga tcagctggc ctggtatcag    540 cagaaaccg acagagccc cgagctgctg atctactggg ccagcacaag acagagcggc    600
gtgcccgata gattcacagg atctggcagc ggcaccgact tcaccctgac aatcagttct    660
gtgcaggccg aggacctggc cgtgtactac tgtcagcaga gctacaacct gctgaccttc    720
ggacccggca ccaagctgga aatcaagaga aagcccacca ccaccctgc ccctagacct    780 ccaaccccag cccctacaat cgccagccag cccctgagcc tgaggccgga agcctgtaga    840
cctgccgctg gcggagccgt gcacaccaga ggcctggatt tcgcctgcga catctacatc    900
tgggcccctc tggccggcac ctgtggcgtg ctgctgctga gcctggtcat caccctgtac    960
tgcaaccacc ggaataggag caagcggagc agaggcggcc acagcgacta catgaacatg   1020 acccccgga ggcctggcc cacccggaag cactaccagc cctacgcccc tcccagggac    1080
ttcgccgcct accggagcaa gagaggccgg aagaaactgc tgtacatctt caagcagccc    1140
ttcatgcggc ccgtgcagac cacccaggaa gaggacggct gcagctgccg gttccccgag    1200
gaagaggaag cggctgcga actgcgggtg aagttcagcc ggagcgccga cgcccctgcc    1260
taccagcagg gccagaacca gctgtacaac gagctgaacc tgggccggag ggaggagtac    1320
gacgtgctgg acaagcggag aggccgggac cctgagatgg gcggcaagcc cggagaaag    1380 aaccctcagg agggcctgta taacgaactg cagaaagaca gatggccga ggcctacagc    1440 gagatcggca tgaagggcga gcggcggagg ggcaagggcc acgacggcct gtaccagggc   1500
```

```
ctgagcaccg ccaccaagga tacctacgac gccctgcaca tgcaggccct gccccccaga    1560
```

<210> SEQ ID NO 130
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
gtgaagctgg aagagtccgg cggaggcttt gtgaagcctg gcggaagcct gaagatcagc      60
tgtgccgcca gcggcttcac cttcagaaac tacgccatga gctgggtccg actgagcccc     120
gagatgagac tggaatgggt cgccacaatc agcagcgcag gcggctacat cttctacagc     180
gatagcgtgc agggcagatt caccatcagc cgggacaacg ccaagaacac cctgcacctc     240
cagatgggca gtctgagatc tggcgacacc gccatgtact actgcgccag acaaggcttc     300
ggcaactacg gcgactacta tgccatggat tactggggcc agggcaccac cgtgacagtc     360
tcttctggtg gcggtggctc gggcggtggt gggtcgggtg gcggcggatc tgacatcgag     420
ctgacacaga gcccatctag cctggctgtg tctgccggcg agaaagtgac catgagctgc     480
aagagcagcc agagcctgct gaacagccgg accagaaaga tcagctggc ctggtatcag    540
cagaaaaccg gacagagccc cgagctgctg atctactggg ccagcacaag acagagcggc     600
gtgcccgata gattcacagg atctggcagc ggcaccgact tcaccctgac aatcagttct     660
gtgcaggccg aggacctggc cgtgtactac tgtcagcaga gctacaacct gctgaccttc     720
ggacccggca ccaagctgga aatcaagaga aaacctacta caactcctgc cccccggcct     780
cctacaccag ctcctactat cgcctcccag ccactcagtc tcagacccga ggcttctagg     840
ccagcggccg gaggcgcggt ccacacccgc gggctggact ttgcatccga taagcccacc     900
accaccctg cccctagacc tccaaccca gccctacaa cgccagcca gcccctgagc     960
ctgaggcccg aagcctgtag acctgccgct ggcggagccg tgcacaccag aggcctggat    1020
ttcgcctgcg acatctacat ctgggcccct ctggccggca cctgtggcgt gctgctgctg    1080
agcctggtca tcaccctgta ctgcaaccac cggaatagga gcaagcggag cagaggcggc    1140
cacagcgact acatgaacat gaccccccgg aggcctggcc ccaccccgaa gcactaccag    1200
ccctacgccc ctcccaggga cttcgccgcc taccggagca agagaggccg gaagaaactg    1260
ctgtacatct tcaagcagcc cttcatgcgg cccgtgcaga ccacccagga agaggacggc    1320
tgcagctgcc ggttccccga ggaagaggaa ggcggctgcg aactgcgggt gaagttcagc    1380
cggagcgccg acgcccctgc ctaccagcag ggccagaacc agctgtacaa cgagctgaac    1440
ctgggccgga gggaggagta cgacgtgctg gacaagcgga gggccggga ccctgagatg    1500
ggcggcaagc cccggagaaa gaaccctcag gagggcctgt ataacgaact gcagaaagac    1560
aagatggccg aggcctacag cgagatcggc atgaagggcg agcggcggag gggcaagggc    1620
cacgacggcc tgtaccaggg cctgagcacc gccaccaagg atacctacga cgccctgcac    1680
atgcaggccc tgccccccag a                                              1701
```

<210> SEQ ID NO 131
<211> LENGTH: 1842
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
gtgaagctgg aagagtccgg cggaggcttt gtgaagcctg gcggaagcct gaagatcagc      60
tgtgccgcca gcggcttcac cttcagaaac tacgccatga gctgggtccg actgagcccc     120
gagatgagac tggaatgggt cgccacaatc agcagcgcag gcggctacat cttctacagc     180
gatagcgtgc agggcagatt caccatcagc cgggacaacg ccaagaacac cctgcacctc     240
cagatgggca gtctgagatc tggcgacacc gccatgtact actgcgccag acaaggcttc     300
ggcaactacg cgactacta tgccatggat tactggggcc agggcaccac cgtgacagtc     360
tcttctggtg gcggtggctc gggcggtggt gggtcgggtg gcggcggatc tgacatcgag     420
ctgacacaga gcccatctag cctggctgtg tctgccggcg agaaagtgac catgagctgc     480
aagagcagcc agagcctgct gaacagccgg accagaaaga atcagctggc ctggtatcag     540
cagaaaaccg gacagagccc cgagctgctg atctactggg ccagcacaag acagagcggc     600
gtgcccgata gattcacagg atctggcagc ggcaccgact tcaccctgac aatcagttct     660
gtgcaggccg aggacctggc cgtgtactac tgtcagcaga gctacaacct gctgaccttc     720
ggaccccgca ccaagctgga aatcaagaga agcctacca ccaccccgc acctcgtcct      780
ccaaccctg cacctacgat tgccagtcag cctctttcac tgcggcctga ggccagcaga     840
ccagctgccg gcggtgccgt ccatacaaga ggactggact tcgcgtccga taaacctact     900
accactccag ccccaaggcc cccaacccca gcaccgacta tcgcatcaca gcctttgtca     960
ctgcgtcctg aagccagccg gccagctgca ggggggccg tccacacaag gggactcgac    1020
tttgcgagtg ataagcccac caccacccct gcccctagac ctccaacccc agcccctaca    1080
atcgccagcc agccctgag cctgaggcc gaagcctgta gacctgccgc tgcggagcc      1140
gtgcacacca gaggcctgga tttcgcctgc gacatctaca tctgggcccc tctggccggc    1200
acctgtggcg tgctgctgct gagcctggtc atcacctgt actgcaacca ccggaatagg    1260
agcaagcgga gcagaggcgg ccacagcgac tacatgaaca tgaccccccg gaggcctggc    1320
cccaccgga agcactacca gccctacgcc cctcccaggg acttcgccgc ctaccggagc    1380
aagagaggcc ggaagaaact gctgtacatc ttcaagcagc ccttcatgcg gcccgtgcag    1440
accacccagg aagaggacgg ctgcagctgc cggttccccg aggaagagga aggcggctgc    1500
gaactgcggg tgaagttcag ccggagcgcc gacgcccctg cctaccagca gggccagaac    1560
cagctgtaca acgagctgaa cctgggccgg agggaggagt acgacgtgct ggacaagcgg    1620
agaggccggg accctgagat gggcggcaag ccccggagaa agaaccctca ggagggcctg    1680
tataacgaac tgcagaaaga caagatggcc gaggcctaca gcgagatcgg catgaagggc    1740
gagcggcgga ggggcaaggg ccacgacggc ctgtaccagg gcctgagcac cgccaccaag    1800
gatacctacg acgccctgca catgcaggcc ctgccccca ga                       1842
```

<210> SEQ ID NO 132
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
gacatcgagc tgacacagag cccatctagc ctggctgtgt ctgccggcga gaaagtgacc      60
```

```
atgagctgca agagcagcca gagcctgctg aacagccgga ccagaaagaa tcagctggcc      120
tggtatcagc agaaaaccgg acagagcccc gagctgctga tctactgggc cagcacaaga      180
cagagcggcg tgcccgatag attcacagga tctggcagcg gcaccgactt caccctgaca      240
atcagttctg tgcaggccga ggacctggcc gtgtactact gtcagcagag ctacaacctg      300
ctgaccttcg gacccggcac caagctggaa atcaagagag gtggcggtgg ctcgggcggt      360
ggtgggtcgg gtggcggcgg atctgtgaag ctggaagagt ccggcggagg ctttgtgaag      420
cctggcggaa gcctgaagat cagctgtgcc gccagcggct tcaccttcag aaactacgcc      480
atgagctggg tccgactgag ccccgagatg agactggaat gggtcgccac aatcagcagc      540
gcaggcggct acatcttcta cagcgatagc gtgcagggca gattcaccat cagccgggac      600
aacgccaaga acaccctgca cctccagatg ggcagtctga gatctggcga caccgccatg      660
tactactgcg ccagacaagg cttcggcaac tacggcgact actatgccat ggattactgg      720
ggccagggca ccaccgtgac agtctcttct aagcccacca ccaccctgc ccctagacct      780 ccaacccag cccctacaat cgccagccag ccctgagcc tgaggccga agcctgtaga       840 cctgccgctg gcggagccgt gcacaccaga ggcctggatt cgcctgcga catctacatc       900 tgggcccctc tggccggcac ctgtggcgtg ctgctgctga cctggtcat cacctgtac       960 tgcaaccacc ggaataggag caagcggagc agaggcggcc acagcgacta catgaacatg     1020
accccccgga ggcctggccc cacccggaag cactaccagc cctacgcccc tccagggac     1080 ttcgccgcct accggagccg ggtgaagttc agccggagcg ccgacgcccc tgcctaccag     1140
cagggccaga accagctgta caacgagctg aacctgggcc ggagggagga gtacgacgtg     1200
ctggacaagc ggagaggccg ggaccctgag atgggcggca agcccggag aaagaaccct     1260 caggagggcc tgtataacga actgcagaaa gacaagatgg ccgaggccta cagcgagatc     1320
ggcatgaagg gcgagcggcg gaggggcaag ggccacgacg gcctgtacca gggcctgagc     1380
accgccacca aggataccta cgacgccctg cacatgcagg ccctgccccc caga           1434
```

<210> SEQ ID NO 133
<211> LENGTH: 1575
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 133

```
gacatcgagc tgacacagag cccatctagc ctggctgtgt ctgccggcga gaaagtgacc       60
atgagctgca agagcagcca gagcctgctg aacagccgga ccagaaagaa tcagctggcc      120
tggtatcagc agaaaaccgg acagagcccc gagctgctga tctactgggc cagcacaaga      180
cagagcggcg tgcccgatag attcacagga tctggcagcg gcaccgactt caccctgaca      240
atcagttctg tgcaggccga ggacctggcc gtgtactact gtcagcagag ctacaacctg      300
ctgaccttcg gacccggcac caagctggaa atcaagagag gtggcggtgg ctcgggcggt      360
ggtgggtcgg gtggcggcgg atctgtgaag ctggaagagt ccggcggagg ctttgtgaag      420
cctggcggaa gcctgaagat cagctgtgcc gccagcggct tcaccttcag aaactacgcc      480
atgagctggg tccgactgag ccccgagatg agactggaat gggtcgccac aatcagcagc      540
gcaggcggct acatcttcta cagcgatagc gtgcagggca gattcaccat cagccgggac      600
aacgccaaga acaccctgca cctccagatg ggcagtctga gatctggcga caccgccatg      660
```

| | |
|---|---|
| tactactgcg ccagacaagg cttcggcaac tacggcgact actatgccat ggattactgg | 720 |
| ggccagggca ccaccgtgac agtctcttct aaacctacta caactcctgc cccccggcct | 780 |
| cctacaccag ctcctactat cgcctcccag ccactcagtc tcagacccga ggcttctagg | 840 |
| ccagcggccg gaggcgcggt ccacaccgc gggctggact ttgcatccga taagcccacc | 900 |
| accacccctg cccctagacc tccaaccca gcccctacaa tcgccagcca gcccctgagc | 960 |
| ctgaggcccg aagcctgtag acctgccgct ggcggagccg tgcacaccag aggcctggat | 1020 |
| ttcgcctgcg acatctacat ctgggcccct ctggccggca cctgtggcgt gctgctgctg | 1080 |
| agcctggtca tcaccctgta ctgcaaccac cggaatagga gcaagcggag cagaggcggc | 1140 |
| cacagcgact acatgaacat gaccccccgg aggcctggcc ccacccggaa gcactaccag | 1200 |
| ccctacgccc ctcccaggga cttcgccgcc taccggagcc gggtgaagtt cagccggagc | 1260 |
| gccgacgccc ctgcctacca gcagggccag aaccagctgt acaacgagct gaacctgggc | 1320 |
| cggagggagg agtacgacgt gctggacaag cggagaggcc gggaccctga gatgggcggc | 1380 |
| aagccccgga gaaagaaccc tcaggagggc ctgtataacg aactgcagaa agacaagatg | 1440 |
| gccgaggcct acagcgagat cggcatgaag ggcgagcggc ggaggggcaa gggccacgac | 1500 |
| ggcctgtacc agggcctgag caccgccacc aaggatacct acgacgccct gcacatgcag | 1560 |
| gccctgcccc ccaga | 1575 |

<210> SEQ ID NO 134
<211> LENGTH: 1209
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

| | |
|---|---|
| gacatcgagc tgacacagag cccatctagc ctggctgtgt ctgccggcga gaaagtgacc | 60 |
| atgagctgca agagcagcca gagcctgctg aacagccgga ccagaaagaa tcagctggcc | 120 |
| tggtatcagc agaaaaccgg acagagcccc gagctgctga tctactgggc cagcacaaga | 180 |
| cagagcggcg tgcccgatag attcacagga tctggcagcg gcaccgactt caccctgaca | 240 |
| atcagttctg tgcaggccga ggacctggcc gtgtactact gtcagcagag ctacaacctg | 300 |
| ctgaccttcg gacccggcac caagctggaa atcaagagag tggcggtgg ctcgggcggt | 360 |
| ggtgggtcgg gtggcggcgg atctgtgaag ctggaagagt ccggcggagg ctttgtgaag | 420 |
| cctggcggaa gcctgaagat cagctgtgcc gccagcggct tcaccttcag aaactacgcc | 480 |
| atgagctggg tccgactgag ccccgagatg agactggaat gggtcgccac aatcagcagc | 540 |
| gcaggcggct acatcttcta cagcgatagc gtgcagggca gattcaccat cagccggac | 600 |
| aacgccaaga acaccctgca cctccagatg ggcagtctga gatctggcga caccgccatg | 660 |
| tactactgcg ccagacaagg cttcggcaac tacggcgact actatgccat ggattactgg | 720 |
| ggccagggca ccaccgtgac agtctcttct aggagcaagc ggagcagagg cggccacagc | 780 |
| gactacatga acatgacccc ccggaggcct ggccccaccc ggaagcacta ccagccctac | 840 |
| gcccctccca gggacttcgc cgcctaccgg agccgggtga agttcagccg gagcgccgac | 900 |
| gcccctgcct accagcaggg ccagaaccag ctgtacaacg agctgaacct gggccggagg | 960 |
| gaggagtacg acgtgctgga caagcggaga ggccgggacc tgagatgggc ggcaagccc | 1020 |
| cggagaaaga accctcagga gggcctgtat aacgaactgc agaaagacaa gatggccgag | 1080 |

| | |
|---|---|
| gcctacagcg agatcggcat gaagggcgag cggcggaggg gcaagggcca cgacggcctg | 1140 |
| taccagggcc tgagcaccgc caccaaggat acctacgacg ccctgcacat gcaggccctg | 1200 |
| cccccccaga | 1209 |

<210> SEQ ID NO 135
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

| | |
|---|---|
| gacatcgagc tgacacagag cccatctagc ctggctgtgt ctgccggcga gaaagtgacc | 60 |
| atgagctgca agagcagcca gagcctgctg aacagccgga ccagaaagaa tcagctggcc | 120 |
| tggtatcagc agaaaaccgg acagagcccc gagctgctga tctactgggc cagcacaaga | 180 |
| cagagcggcg tgcccgatag attcacagga tctggcagcg gcaccgactt caccctgaca | 240 |
| atcagttctg tgcaggccga ggacctggcc gtgtactact gtcagcagag ctacaacctg | 300 |
| ctgaccttcg gacccggcac caagctggaa atcaagagag tggcggtgg ctcgggcggt | 360 |
| ggtgggtcgg gtggcggcgg atctgtgaag ctggaagagt ccggcggagg ctttgtgaag | 420 |
| cctggcggaa gcctgaagat cagctgtgcc gccagcggct tcaccttcag aaactacgcc | 480 |
| atgagctggg tccgactgag ccccgagatg agactggaat gggtcgccac aatcagcagc | 540 |
| gcaggcggct acatcttcta cagcgatagc gtgcagggca gattcaccat cagccgggac | 600 |
| aacgccaaga cacccctgca cctccagatg ggcagtctga gatctggcga caccgccatg | 660 |
| tactactgcg ccagacaagg cttcggcaac tacggcgact actatgccat ggattactgg | 720 |
| ggccagggca ccaccgtgac agtctcttct aggagcaagc ggagcagagg cggccacagc | 780 |
| gactacatga acatgacccc ccggaggcct ggccccaccc ggaagcacta ccagccctac | 840 |
| gcccctccca gggacttcgc cgcctaccgg agcaagagag gccggaagaa actgctgtac | 900 |
| atcttcaagc agcccttcat gcggcccgtg cagaccaccc aggaagagga cggctgcagc | 960 |
| tgccggttcc ccgaggaaga ggaaggcggc tgcgaactgc gggtgaagtt cagccggagc | 1020 |
| gccgacgccc ctgcctacca gcagggccag aaccagctgt acaacgagct gaacctgggc | 1080 |
| cggagggagg agtacgacgt gctggacaag cggagaggcc gggaccctga tgggcggc | 1140 |
| aagccccgga gaaagaaccc tcaggagggc ctgtataacg aactgcagaa agacaagatg | 1200 |
| gccgaggcct acagcgagat cggcatgaag ggcgagcggc ggaggggcaa gggccacgac | 1260 |
| ggcctgtacc agggcctgag caccgccacc aaggatacct acgacgccct gcacatgcag | 1320 |
| gccctgcccc ccaga | 1335 |

<210> SEQ ID NO 136
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

| | |
|---|---|
| gacatcgagc tgacacagag cccatctagc ctggctgtgt ctgccggcga gaaagtgacc | 60 |
| atgagctgca agagcagcca gagcctgctg aacagccgga ccagaaagaa tcagctggcc | 120 |
| tggtatcagc agaaaaccgg acagagcccc gagctgctga tctactgggc cagcacaaga | 180 |

```
cagagcggcg tgcccgatag attcacagga tctggcagcg gcaccgactt caccctgaca      240
atcagttctg tgcaggccga ggacctggcc gtgtactact gtcagcagag ctacaacctg      300
ctgaccttcg gacccggcac caagctggaa atcaagagag gtggcggtgg ctcgggcggt      360
ggtgggtcgg gtggcggcgg atctgtgaag ctggaagagt ccggcggagg ctttgtgaag      420
cctggcggaa gcctgaagat cagctgtgcc gccagcggct tcaccttcag aaactacgcc      480
atgagctggg tccgactgag ccccgagatg agactggaat gggtcgccac aatcagcagc      540
gcaggcggct acatcttcta cagcgatagc gtgcagggca gattcaccat cagccgggac      600
aacgccaaga cacccctgca cctccagatg ggcagtctga gatctggcga caccgccatg      660
tactactgcg ccagacaagg cttcggcaac tacggcgact actatgccat ggattactgg      720
ggccagggca ccaccgtgac agtctcttct aaacctacta caactcctgc cccccggcct      780
cctacaccag ctcctactat cgcctcccag ccactcagtc tcagacccga ggcttctagg      840
ccagcggccg gaggcgcggt ccacaccgcg gggctggact ttgcatccga taagcccacc      900
accacccctg ccctagacc tccaacccca gcccctacaa tcgccagcca gcccctgagc      960
ctgaggccca agcctgtag acctgccgct ggcggagccg tgcacaccag aggcctggat     1020
ttcgcctgcg acatctacat ctgggcccct ctggccggca cctgtggcgt gctgctgctg     1080
agcctggtca tcaccctgta ctgcaaccac cggaatagga gcaagcggag cagaggcggc     1140
cacagcgact acatgaacat gaccccccgg aggcctggcc cacccggaa gcactaccag     1200 ccctacgccc ctcccaggga cttcgccgcc taccggagca agagaggccg gaagaaactg     1260
ctgtacatct tcaagcagcc cttcatgcgg cccgtgcaga ccacccagga agaggacggc     1320
tgcagctgcc ggttccccga ggaagaggaa ggcggctgcg aactgcgggt gaagttcagc     1380
cggagcgccg acgcccctgc ctaccagcag gccagaaacc agctgtacaa cgagctgaac     1440
ctgggccgga gggaggagta cgacgtgctg gacaagcgga gaggccggga ccctgagatg     1500
ggcggcaagc cccggagaaa gaaccctcag gagggcctgt ataacgaact gcagaaagac     1560
aagatggccg aggcctacag cgagatcggc atgaagggcg agcggcggag gggcaagggc     1620
cacgacggcc tgtaccaggg cctgagcacc gccaccaagg atacctacga cgccctgcac     1680
atgcaggccc tgccccccag a                                               1701

<210> SEQ ID NO 137
<211> LENGTH: 1842
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gacatcgagc tgacacagag cccatctagc ctggctgtgt ctgccggcga gaaagtgacc       60
atgagctgca gagcagcca gagcctgctg aacagccgga ccagaaagaa tcagctggcc      120
tggtatcagc agaaaaccgg acagagcccc gagctgctga tctactgggc cagcacaaga      180
cagagcggcg tgcccgatag attcacagga tctggcagcg gcaccgactt caccctgaca      240
atcagttctg tgcaggccga ggacctggcc gtgtactact gtcagcagag ctacaacctg      300
ctgaccttcg gacccggcac caagctggaa atcaagagag gtggcggtgg ctcgggcggt      360
ggtgggtcgg gtggcggcgg atctgtgaag ctggaagagt ccggcggagg ctttgtgaag      420
cctggcggaa gcctgaagat cagctgtgcc gccagcggct tcaccttcag aaactacgcc      480
```

```
atgagctggg tccgactgag ccccgagatg agactggaat gggtcgccac aatcagcagc       540
gcaggcggct acatcttcta cagcgatagc gtgcagggca gattcaccat cagccgggac       600
aacgccaaga acaccctgca cctccagatg ggcagtctga gatctggcga caccgccatg       660
tactactgcg ccagacaagg cttcggcaac tacggcgact actatgccat ggattactgg       720
ggccagggca ccaccgtgac agtctcttct aagcctacca ccacccccgc acctcgtcct       780 ccaaccctg cacctacgat tgccagtcag cctctttcac tgcggcctga ggccagcaga       840
ccagctgccg gcggtgccgt ccatacaaga ggactggact tcgcgtccga taaacctact       900
accactccag ccccaaggcc cccaacccca gcaccgacta tcgcatcaca gcctttgtca       960
ctgcgtcctg aagccagccg gccagctgca ggggggccg tccacacaag gggactcgac      1020
tttgcgagtg ataagcccac caccacccct gcccctagac tccaaccccc agcccctaca      1080
atcgccagcc agcccctgag cctgaggccc gaagcctgta gacctgccgc tggcggagcc      1140
gtgcacacca gaggcctgga tttcgcctgc gacatctaca tctgggcccc tctggccggc      1200
acctgtggcg tgctgctgct gagcctggtc atcaccctgt actgcaacca ccggaatagg      1260
agcaagcgga gcagaggcgg ccacagcgac tacatgaaca tgaccccccg gaggcctggc      1320
cccacccgga agcactacca gccctacgcc cctcccaggg acttcgccgc ctaccggagc      1380
aagagaggcc ggaagaaact gctgtacatc ttcaagcagc ccttcatgcg gcccgtgcag      1440
accacccagg aagaggacgg ctgcagctgc cggttccccg aggaagagga aggcggctgc      1500
gaactgcggg tgaagttcag ccggagcgcc gacgcccctg cctaccagca gggccagaac      1560
cagctgtaca acgagctgaa cctgggccgg agggaggagt acgacgtgct ggacaagcgg      1620
agaggccggg accctgagat gggcggcaag ccccggagaa agaaccctca ggagggcctg      1680
tataacgaac tgcagaaaga caagatggcc gaggcctaca gcgagatcgg catgaagggc      1740
gagcggcgga ggggcaaggg ccacgacggc ctgtaccagg gcctgagcac cgccaccaag      1800
gatacctacg acgccctgca catgcaggcc ctgccccca ga                         1842
```

<210> SEQ ID NO 138
<211> LENGTH: 1386
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 138

```
gacgtgcaac ttctggagag cgggccaggg ctagtcaggc cctcccagtc gctttcactg        60
acttgcagtg tgaccggtta ctctattgtg agtcactact attggaactg gattcggcag       120
ttcccaggca acaaactgga atggatgggg tacatatctt ccgatggctc gaatgaatat       180
aacccatcat tgaaaaatcg tatttccatc agtctggata cgagtaaaaa ccagttttc       240 ctcaaattcg atttcgtgac tacagcagat actgccacat acttctgtgt acgaggtgtc       300
gattattggg gacagggcac aacgctgacc gtaagttctg gcggaggcgg aagcggaggc       360
ggaggctccg gcggaggcgg aagcgacatc aagatggctc agtcccttc tagcgtgaat       420 gcttcgctag gggagcgtgt gaccatcaca tgtaaagcat cacgcgacat aaataatttc       480
ctttcctggt tcatcagaa accgggcaag tcgcctaaga cgctgattta cagagcaaat       540
cggttggtag atggagtgcc aagcagattc agcgggagcg gaagtggaca ggattatagc       600
ttcactattt catcccctgga atacgaggac gtaggtatct attattgcct ccagtatggc       660
```

```
gatctttaca catttggtgg ggggactaag ctggagatta agaagcccac caccacccct      720 gccccctagac ctccaacccc agcccctaca atcgccagcc agcccctgag cctgaggccc     780
gaagcctgta gacctgccgc tggcggagcc gtgcacacca gaggcctgga tttcgcctgc     840
gacatctaca tctgggcccc tctggccggc acctgtggcg tgctgctgct gagcctggtc     900
atcaccctgt actgcaacca ccggaatagg agcaagcgga gcagaggcgg ccacagcgac     960
tacatgaaca tgacccccccg gaggcctggc cccacccgga agcactacca gcctacgcc   1020 cctcccaggg acttcgccgc ctaccggagc cgggtgaagt tcagccggag cgccgacgcc   1080
cctgcctacc agcagggcca gaaccagctg tacaacgagc tgaacctggg ccggagggag   1140
gagtacgacg tgctggacaa gcggagaggc cgggaccctg agatgggcgg caagccccgg   1200
agaaagaacc ctcaggaggg cctgtataac gaactgcaga agacaagat ggccgaggcc    1260 tacagcgaga tcggcatgaa gggcgagcgg cggaggggca agggccacga cggcctgtac   1320
cagggcctga gcaccgccac caaggatacc tacgacgccc tgcacatgca ggccctgccc   1380
cccaga                                                             1386
```

<210> SEQ ID NO 139
<211> LENGTH: 1527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
gacgtgcaac ttctggagag cgggccaggg ctagtcaggc cctcccagtc gctttcactg      60
acttgcagtg tgaccggtta ctctattgtg agtcactact attggaactg gattcggcag    120
ttcccaggca acaaactgga atggatgggg tacatatctt ccgatggctc gaatgaatat    180
aacccatcat tgaaaaatcg tatttccatc agtctggata cgagtaaaaa ccagtttttc    240
ctcaaattcg atttcgtgac tacagcagat actgccacat acttctgtgt acgaggtgtc    300
gattattggg gacagggcac aacgctgacc gtaagttctg gcggaggcgg aagcggaggc    360
ggaggctccg gcggaggcgg aagcgacatc aagatggctc agtccccttc tagcgtgaat    420
gcttcgctag gggagcgtgt gaccatcaca tgtaaagcat cacgcgacat aaataatttc    480 cttttcctggt ttcatcagaa accgggcaag tcgcctaaga cgctgattta cagagcaaat    540
cggttggtag atggagtgcc aagcagattc agcgggagcg aagtggaca ggattatagc     600 ttcactattt catccctgga atacgaggac gtaggtatct attattgcct ccagtatggc    660
gatctttaca catttggtgg ggggactaag ctggagatta agaaacctac tacaactcct    720 gcccccccggc ctcctacacc agctcctact atcgcctccc agccactcag tctcagaccc    780
gaggcttcta ggccagcggc cggaggcgcg gtccacaccc gcgggctgga ctttgcatcc    840
gataagccca ccaccacccc tgcccctaga cctccaaccc cagcccctac aatcgccagc    900
cagcccctga gcctgaggcc cgaagcctgt agacctgccg ctggcggagc cgtgcacacc    960
agaggcctgg atttcgcctg cgacatctac atctgggccc ctctggccgg cacctgtggc   1020
gtgctgctgc tgagcctggt catcaccctg tactgcaacc accggaatag gagcaagcgg   1080
agcagaggcg gccacagcga ctacatgaac atgaccccccc ggaggcctgg ccccacccgg   1140
aagcactacc agcctacgc ccctcccagg gacttcgccg cctaccggag ccgggtgaag   1200
ttcagccgga gcgccgacgc ccctgcctac cagcagggcc agaaccagct gtacaacgag   1260
```

```
ctgaacctgg gccggaggga ggagtacgac gtgctggaca agcggagagg ccgggaccct    1320
gagatgggcg gcaagccccg gagaaagaac cctcaggagg gcctgtataa cgaactgcag    1380
aaagacaaga tggccgaggc ctacagcgag atcggcatga agggcgagcg gcggaggggc    1440
aagggccacg acggcctgta ccagggcctg agcaccgcca ccaaggatac ctacgacgcc    1500
ctgcacatgc aggccctgcc ccccaga                                        1527
```

<210> SEQ ID NO 140
<211> LENGTH: 1668
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
gacgtgcaac ttctggagag cgggccaggg ctagtcaggc cctcccagtc gctttcactg      60
acttgcagtg tgaccggtta ctctattgtg agtcactact attggaactg gattcggcag     120
ttcccaggca acaaactgga atggatgggg tacatatctt ccgatggctc gaatgaatat     180
aacccatcat tgaaaaatcg tatttccatc agtctggata cgagtaaaaa ccagttttc      240 ctcaaattcg atttcgtgac tacagcagat actgccacat acttctgtgt acgaggtgtc     300
gattattggg gacagggcac aacgctgacc gtaagttctg gcggaggcgg aagcggaggc     360
ggaggctccg gcggaggcgg aagcgacatc aagatggctc agtcccctcc tagcgtgaat     420
gcttcgctag gggagcgtgt gaccatcaca tgtaaagcat cacgcgacat aaataatttc     480 cttcctggt ttcatcagaa accgggcaag tcgcctaaga cgctgattta cagagcaaat     540
cggttggtag atggagtgcc aagcagattc agcgggagcg gaagtggaca ggattatagc     600
ttcactattt catccctgga atacgaggac gtaggtatct attattgcct ccagtatggc     660
gatctttaca catttggtgg ggggactaag ctggagatta agaagcctac caccaccccc     720
gcacctcgtc ctccaacccc tgcacctacg attgccagtc agcctctttc actgcggcct     780
gaggccagca gaccagctgc cggcggtgcc gtccatacaa gaggactgga cttcgcgtcc     840
gataaaccta ctaccactcc agccccaagg cccccaaccc cagcaccgac tatcgcatca     900
cagcctttgt cactgcgtcc tgaagccagc cggccagctg caggggggc cgtccacaca     960 agggactcg actttgcgag tgataagccc accaccaccc ctgcccctag acctccaacc    1020
ccagccccta caatcgccag ccagcccctg agcctgaggc ccgaagcctg tagacctgcc    1080
gctggcggag ccgtgcacac cagaggcctg gatttcgcct gcgacatcta catctgggcc    1140
cctctggccg gcacctgtgg cgtgctgctg ctgagcctgg tcatcacccct gtactgcaac    1200 caccggaata ggagcaagcg gagcagaggc ggccacagcg actacatgaa catgaccccc    1260
cggaggcctg cccccacccg gaagcactac cagccctacg cccctcccag ggacttcgcc    1320
gcctaccgga gccgggtgaa gttcagccgg agcgccgacg cccctgccta ccagcagggc    1380
cagaaccagc tgtacaacga gctgaacctg gccggagga aggagtacga cgtgctggac    1440
aagcggagag gccgggaccc tgagatgggc gcaagccccc ggagaaagaa ccctcaggag    1500
ggcctgtata cgaactgca gaaagacaag atggccgagg cctacagcga gatcggcatg    1560
aagggcgagc ggcggagggg ccaagggccac gacggcctgt accagggcct gagcaccgcc    1620
accaaggata cctacgacgc cctgcacatg caggccctgc ccccaga               1668
```

<210> SEQ ID NO 141
<211> LENGTH: 1512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

| | | | | | |
|---|---|---|---|---|---|
| gacgtgcaac | ttctggagag | cgggccaggg | ctagtcaggc | cctcccagtc | gctttcactg | 60 |
| acttgcagtg | tgaccggtta | ctctattgtg | agtcactact | attggaactg | gattcggcag | 120 |
| ttcccaggca | acaaactgga | atggatgggg | tacatatctt | ccgatggctc | gaatgaatat | 180 |
| aacccatcat | tgaaaaatcg | tatttccatc | agtctggata | cgagtaaaaa | ccagtttttc | 240 |
| ctcaaattcg | atttcgtgac | tacagcagat | actgccacat | acttctgtgt | acgaggtgtc | 300 |
| gattattggg | gacagggcac | aacgctgacc | gtaagttctg | gcggaggcgg | aagcggaggc | 360 |
| ggaggctccg | gcggaggcgg | aagcgacatc | aagatggctc | agtccccttc | tagcgtgaat | 420 |
| gcttcgctag | gggagcgtgt | gaccatcaca | tgtaaagcat | cacgcgacat | aaataatttc | 480 |
| ctttcctggt | ttcatcagaa | accgggcaag | tcgcctaaga | cgctgattta | cagagcaaat | 540 |
| cggttggtag | atggagtgcc | aagcagattc | agcgggagcg | gaagtggaca | ggattatagc | 600 |
| ttcactattt | catccctgga | atacgaggac | gtaggtatct | attattgcct | ccagtatggc | 660 |
| gatctttaca | catttggtgg | ggggactaag | ctggagatta | agaagcccac | caccacccct | 720 |
| gcccctagac | ctccaacccc | agccctaca | atcgccagcc | agccctgag | cctgaggccc | 780 |
| gaagcctgta | gacctgccgc | tggcggagcc | gtgcacacca | gaggcctgga | tttcgcctgc | 840 |
| gacatctaca | tctgggcccc | tctggccggc | acctgtggcg | tgctgctgct | gagcctggtc | 900 |
| atcaccctgt | actgcaacca | ccggaatagg | agcaagcgga | gcagaggcgg | ccacagcgac | 960 |
| tacatgaaca | tgacccccg | gaggcctggc | cccacccgga | agcactacca | gccctacgcc | 1020 |
| cctcccaggg | acttcgccgc | ctaccggagc | aagagaggcc | ggaagaaact | gctgtacatc | 1080 |
| ttcaagcagc | ccttcatgcg | gcccgtgcag | accacccagg | aagaggacgg | ctgcagctgc | 1140 |
| cggttccccg | aggaagagga | aggcggctgc | gaactgcggg | tgaagttcag | ccggagcgcc | 1200 |
| gacgcccctg | cctaccagca | gggccagaac | cagctgtaca | acgagctgaa | cctgggccgg | 1260 |
| agggaggagt | acgacgtgct | ggacaagcgg | agaggccggg | accctgagat | gggcggcaag | 1320 |
| ccccggagaa | agaaccctca | ggagggcctg | tataacgaac | tgcagaaaga | caagatggcc | 1380 |
| gaggcctaca | gcgagatcgg | catgaagggc | gagcggcgga | ggggcaaggg | ccacgacggc | 1440 |
| ctgtaccagg | gcctgagcac | cgccaccaag | gatacctacg | acgccctgca | catgcaggcc | 1500 |
| ctgccccca | ga | | | | | 1512 |

<210> SEQ ID NO 142
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

| | | | | | |
|---|---|---|---|---|---|
| gacgtgcaac | ttctggagag | cgggccaggg | ctagtcaggc | cctcccagtc | gctttcactg | 60 |
| acttgcagtg | tgaccggtta | ctctattgtg | agtcactact | attggaactg | gattcggcag | 120 |
| ttcccaggca | acaaactgga | atggatgggg | tacatatctt | ccgatggctc | gaatgaatat | 180 |

```
aacccatcat tgaaaaatcg tatttccatc agtctggata cgagtaaaaa ccagttttc      240 ctcaaattcg atttcgtgac tacagcagat actgccacat acttctgtgt acgaggtgtc     300
gattattggg gacagggcac aacgctgacc gtaagttctg gcggaggcgg aagcggaggc     360
ggaggctccg gcggaggcgg aagcgacatc aagatggctc agtcccctttc tagcgtgaat    420 gcttcgctag gggagcgtgt gaccatcaca tgtaaagcat cacgcgacat aaataatttc    480
ctttcctggt ttcatcagaa accgggcaag tcgcctaaga cgctgattta cagagcaaat    540
cggttggtag atggagtgcc aagcagattc agcgggagcg gaagtggaca ggattatagc    600
ttcactattt catccctgga atacgaggac gtaggtatct attattgcct ccagtatggc    660
gatctttaca catttggtgg ggggactaag ctggagatta agaaacctac tacaactcct    720
gccccccggc ctcctacacc agctcctact atcgcctccc agccactcag tctcagaccc    780
gaggcttcta ggccagcggc cggaggcgcg gtccacaccc gcgggctgga ctttgcatcc    840
gataagccca ccaccacccc tgcccctaga cctccaaccc cagcccctac aatcgccagc    900
cagcccctga gcctgaggcc cgaagcctgt agacctgccg ctggcggagc cgtgcacacc    960
agaggcctgg atttcgcctg cgacatctac atctgggccc ctctggccgg cacctgtggc    1020
gtgctgctgc tgagcctggt catcaccctg tactgcaacc accggaatag gagcaagcgg    1080
agcagaggcg ccacagcgga ctacatgaac atgacccccc ggaggcctgg ccccacccgg    1140
aagcactacc agcccacgcg ccctcccagg gacttcgccg cctaccggag caagagaggc    1200
cggaagaaac tgctgtacat cttcaagcag cccttcatgc ggcccgtgca gaccacccag    1260
gaagaggacg gctgcagctg ccggttcccc gaggaagagg aaggcggctg cgaactgcgg    1320
gtgaagttca gccggagcgc cgacgcccct gcctaccagc agggccagaa ccagctgtac    1380
aacgagctga acctgggccg gagggaggag tacgacgtgc tggacaagcg agaggccgg    1440 gaccctgaga tgggcggcaa gccccggaga aagaaccctc aggagggcct gtataacgaa    1500
ctgcagaaag acaagatggc cgaggcctac agcgagatcg gcatgaaggg cgagcggcgg    1560
aggggcaagg gccacgacgg cctgtaccag ggcctgagca ccgccaccaa ggatacctac    1620
gacgccctgc acatgcaggc cctgccccc aga                                   1653
```

<210> SEQ ID NO 143  
<211> LENGTH: 1794  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 143

```
gacgtgcaac ttctggagag cgggccaggg ctagtcaggc cctcccagtc gctttcactg      60
acttgcagtg tgaccggtta ctctattgtg agtcactact attggaactg gattcggcag    120
ttcccaggca acaaactgga atggatgggg tacatatctt ccgatggctc gaatgaatat    180
aacccatcat tgaaaaatcg tatttccatc agtctggata cgagtaaaaa ccagttttc     240 ctcaaattcg atttcgtgac tacagcagat actgccacat acttctgtgt acgaggtgtc    300
gattattggg gacagggcac aacgctgacc gtaagttctg gcggaggcgg aagcggaggc    360
ggaggctccg gcggaggcgg aagcgacatc aagatggctc agtcccctttc tagcgtgaat   420 gcttcgctag gggagcgtgt gaccatcaca tgtaaagcat cacgcgacat aaataatttc    480
ctttcctggt ttcatcagaa accgggcaag tcgcctaaga cgctgattta cagagcaaat    540
```

| | | | | |
|---|---|---|---|---|
| cggttggtag | atggagtgcc | aagcagattc | agcgggagcg | gaagtggaca ggattatagc | 600 |
| ttcactattt | catccctgga | atacgaggac | gtaggtatct | attattgcct ccagtatggc | 660 |
| gatctttaca | catttggtgg | ggggactaag | ctggagatta | agaagcctac caccaccccc | 720 |
| gcacctcgtc | ctccaacccc | tgcacctacg | attgccagtc | agcctctttc actgcggcct | 780 |
| gaggccagca | gaccagctgc | cggcggtgcc | gtccatacaa | gaggactgga cttcgcgtcc | 840 |
| gataaaccta | ctaccactcc | agccccaagg | ccccaaccc  | cagcaccgac tatcgcatca | 900 |
| cagcctttgt | cactgcgtcc | tgaagccagc | cggccagctg | caggggggc cgtccacaca | 960 |
| agggactcg  | actttgcgag | tgataagccc | accaccaccc | ctgcccctag acctccaacc | 1020 |
| ccagccccta | caatcgccag | ccagcccctg | agcctgaggc | ccgaagcctg tagacctgcc | 1080 |
| gctggcggag | ccgtgcacac | cagaggcctg | gatttcgcct | gcgacatcta catctgggcc | 1140 |
| cctctggccg | gcacctgtgg | cgtgctgctg | ctgagcctgg | tcatcaccct gtactgcaac | 1200 |
| caccggaata | ggagcaagcg | gagcagaggc | ggccacagcg | actacatgaa catgaccccc | 1260 |
| cggaggcctg | gccccacccg | gaagcactac | cagccctacg | cccctcccag ggacttcgcc | 1320 |
| gcctaccgga | gcaagagagg | ccggaagaaa | ctgctgtaca | tcttcaagca gcccttcatg | 1380 |
| cggcccgtgc | agaccaccca | ggaagaggac | ggctgcagct | gccggttccc cgaggaagag | 1440 |
| gaaggcggct | gcgaactgcg | ggtgaagttc | agccggagcg | ccgacgcccc tgcctaccag | 1500 |
| cagggccaga | accagctgta | caacgagctg | aacctgggcc | ggagggagga gtacgacgtg | 1560 |
| ctggacaagc | ggagaggccg | ggaccctgag | atgggcggca | agccccggag aaagaaccct | 1620 |
| caggagggcc | tgtataacga | actgcagaaa | gacaagatgg | ccgaggccta cagcgagatc | 1680 |
| ggcatgaagg | gcgagcggcg | gaggggcaag | ggccacgacg | gcctgtacca gggcctgagc | 1740 |
| accgccacca | aggataccta | cgacgccctg | cacatgcagg | ccctgccccc caga | 1794 |

<210> SEQ ID NO 144
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

| | | | | |
|---|---|---|---|---|
| gacatcaaga | tggctcagtc | cccttctagc | gtgaatgctt | cgctagggga gcgtgtgacc | 60 |
| atcacatgta | aagcatcacg | cgacataaat | aatttccttt | cctggtttca tcagaaaccg | 120 |
| ggcaagtcgc | ctaagacgct | gatttacaga | gcaaatcggt | tggtagatgg agtgccaagc | 180 |
| agattcagcg | ggagcggaag | tggacaggat | tatagcttca | ctatttcatc cctggaatac | 240 |
| gaggacgtag | gtatctatta | ttgcctccag | tatggcgatc | tttacacatt tggtgggggg | 300 |
| actaagctgg | agattaaggg | cggaggcgga | agcggaggcg | gaggctccgg cggaggcgga | 360 |
| agcgacgtgc | aacttctgga | gagcgggcca | gggctagtca | ggcctcccca gtcgctttca | 420 |
| ctgacttgca | gtgtgaccgg | ttactctatt | gtgagtcact | actattggaa ctggattcgg | 480 |
| cagttcccag | gcaacaaact | ggaatggatg | gggtacatat | cttccgatgg ctcgaatgaa | 540 |
| tataacccat | cattgaaaaa | tcgtatttcc | atcagtctgg | atacgagtaa aaaccagttt | 600 |
| ttcctcaaat | tcgatttcgt | gactacagca | gatactgcca | catacttctg tgtacgaggt | 660 |
| gtcgattatt | ggggacaggg | cacaacgctg | accgtaagtt | ctaagcccac caccacccct | 720 |
| gcccctagac | ctccaacccc | agcccctaca | atcgccagc  | agcccctgag cctgaggccc | 780 |

| | |
|---|---|
| gaagcctgta gacctgccgc tggcggagcc gtgcacacca gaggcctgga tttcgcctgc | 840 |
| gacatctaca tctgggcccc tctggccggc acctgtggcg tgctgctgct gagcctggtc | 900 |
| atcaccctgt actgcaacca ccggaatagg agcaagcgga gcagaggcgg ccacagcgac | 960 |
| tacatgaaca tgacccccg gaggcctggc cccacccgga agcactacca gccctacgcc | 1020 |
| cctcccaggg acttcgccgc ctaccggagc cgggtgaagt tcagccggag cgccgacgcc | 1080 |
| cctgcctacc agcagggcca gaaccagctg tacaacgagc tgaacctggg ccggagggag | 1140 |
| gagtacgacg tgctggacaa gcggagaggc cgggaccctg agatgggcgg caagccccgg | 1200 |
| agaaagaacc ctcaggaggg cctgtataac gaactgcaga agacaagat ggccgaggcc | 1260 |
| tacagcgaga tcggcatgaa gggcgagcgg cggaggggca agggccacga cggcctgtac | 1320 |
| cagggcctga gcaccgccac caaggatacc tacgacgccc tgcacatgca ggccctgccc | 1380 |
| cccaga | 1386 |

<210> SEQ ID NO 145
<211> LENGTH: 1527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

| | |
|---|---|
| gacatcaaga tggctcagtc cccttctagc gtgaatgctt cgctagggga gcgtgtgacc | 60 |
| atcacatgta agcatcacg cgacataaat aatttccttt cctggtttca tcagaaaccg | 120 |
| ggcaagtcgc ctaagacgct gatttacaga gcaaatcggt tggtagatgg agtgccaagc | 180 |
| agattcagcg ggagcggaag tggacaggat tatagcttca ctatttcatc cctggaatac | 240 |
| gaggacgtag gtatctatta ttgcctccag tatggcgatc tttacacatt tggtgggggg | 300 |
| actaagctgg agattaaggg cggaggcgga agcggaggcg gaggctccgg cggaggcgga | 360 |
| agcgacgtgc aacttctgga gagcgggcca gggctagtca ggccctccca gtcgctttca | 420 |
| ctgacttgca gtgtgaccgg ttactctatt gtgagtcact actattggaa ctggattcgg | 480 |
| cagttcccag gcaacaaact ggaatggatg gggtacatat cttccgatgg ctcgaatgaa | 540 |
| tataacccat cattgaaaaa tcgtatttcc atcagtctgg atacgagtaa aaaccagttt | 600 |
| ttcctcaaat tcgatttcgt gactacagca gatactgcca catacttctg tgtacgaggt | 660 |
| gtcgattatt ggggacaggg cacaacgctg accgtaagtt ctaaacctac tacaactcct | 720 |
| gcccccggc ctcctacacc agctcctact atcgcctccc agccactcag tctcagaccc | 780 |
| gaggcttcta ggccagcggc cggaggcgcg gtccacaccc gcgggctgga ctttgcatcc | 840 |
| gataagccca ccaccaccc tgcccctaga cctccaaccc cagcccctac aatcgccagc | 900 |
| cagcccctga gcctgaggcc cgaagcctgt agacctgccg ctggcggagc cgtgcacacc | 960 |
| agaggcctga tttcgcctg cgacatctac atctgggccc ctctggccgg cacctgtggc | 1020 |
| gtgctgctgc tgagcctggt catcaccctg tactgcaacc accggaatag gagcaagcgg | 1080 |
| agcagaggcg gccacagcga ctacatgaac atgaccccc ggaggcctgg ccccacccgg | 1140 |
| aagcactacc agccctacgc ccctcccagg gacttcgccg cctaccggag ccgggtgaag | 1200 |
| ttcagccgga gcgccgacgc ccctgcctac cagcagggcc agaaccagct gtacaacgag | 1260 |
| ctgaacctgg gccggaggga ggagtacgac gtgctggaca gcggagagg ccgggaccct | 1320 |
| gagatgggcg gcaagccccg gagaaagaac cctcaggagg gcctgtataa cgaactgcag | 1380 |

```
aaagacaaga tggccgaggc ctacagcgag atcggcatga agggcgagcg gcggaggggc    1440
aagggccacg acggcctgta ccagggcctg agcaccgcca ccaaggatac ctacgacgcc    1500
ctgcacatgc aggccctgcc ccccaga                                        1527

<210> SEQ ID NO 146
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gacatcaaga tggctcagtc cccttctagc gtgaatgctt cgctagggga gcgtgtgacc      60
atcacatgta aagcatcacg cgacataaat aatttccttt cctggtttca tcagaaaccg     120
ggcaagtcgc ctaagacgct gatttacaga gcaaatcggt tggtagatgg agtgccaagc     180
agattcagcg ggagcggaag tggacaggat tatagcttca ctatttcatc cctggaatac     240
gaggacgtag gtatctatta ttgcctccag tatggcgatc tttacacatt tggtggggg     300 actaagctgg agattaaggg cggaggcgga agcggaggcg gaggctccgg cggaggcgga     360
agcgacgtgc aacttctgga gagcgggcca gggctagtca ggccctccca gtcgctttca     420
ctgacttgca gtgtgaccgg ttactctatt gtgagtcact actattggaa ctggattcgg     480
cagttcccag gcaacaaact ggaatggatg gggtacatat cttccgatgg ctcgaatgaa     540
tataacccat cattgaaaaa tcgtatttcc atcagtctgg atacgagtaa aaaccagttt     600
ttcctcaaat tcgatttcgt gactacagca gatactgcca catacttctg tgtacgaggt     660
gtcgattatt ggggacaggg cacaacgctg accgtaagtt ctaagcctac caccacccc     720 gcacctcgtc ctccaacccc tgcacctacg attgccagtc agcctctttc actgcggcct     780
gaggccagca gaccagctgc cggcggtgcc gtccatacaa gaggactgga cttcgcgtcc     840
gataaaccta ctaccactcc agccccaagg ccccaacccc cagcaccgac tatcgcatca     900 cagccttttgt cactgcgtcc tgaagccagc cggccagctg cagggggggc cgtccacaca     960
aggggactcg actttgcgag tgataagccc accaccaccc ctgcccctag acctccaacc    1020
ccagccccta caatcgccag ccagcccctg agcctgaggc ccgaagcctg tagacctgcc    1080
gctggcggag ccgtgcacac cagaggcctg gatttcgcct cgacatcta catctgggcc    1140 cctctggccg gcacctgtgg cgtgctgctg ctgagcctgg tcatcaccct gtactgcaac    1200
caccggaata ggagcaagcg gagcagaggc ggccacagcg actacatgaa catgaccccc    1260
cggaggcctg gccccacccg gaagcactac cagccctacg cccctcccag ggacttcgcc    1320
gcctaccgga gccgggtgaa gttcagccgg agcgccgacg cccctgccta ccagcagggc    1380
cagaaccagc tgtacaacga gctgaacctg gccggaggg aggagtacga cgtgctggac    1440
aagcggagag gccgggaccc tgagatgggc ggcaagcccc ggagaaagaa ccctcaggag    1500
ggcctgtata cgaactgca gaaagacaag atggccgagg cctacagcga gatcggcatg    1560
aagggcgagc ggcggagggg caagggccac gacggcctgt accagggcct gagcaccgcc    1620
accaaggata cctacgacgc cctgcacatg caggccctgc ccccaga                 1668

<210> SEQ ID NO 147
<211> LENGTH: 1512
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 147

| | |
|---|---|
| gacatcaaga tggctcagtc cccttctagc gtgaatgctt cgctagggga gcgtgtgacc | 60 |
| atcacatgta aagcatcacg cgacataaat aatttccttt cctggtttca tcagaaaccg | 120 |
| ggcaagtcgc ctaagacgct gatttacaga gcaaatcggt tggtagatgg agtgccaagc | 180 |
| agattcagcg ggagcggaag tggacaggat tatagcttca ctatttcatc cctggaatac | 240 |
| gaggacgtag gtatctatta ttgcctccag tatggcgatc tttacacatt tggtgggggg | 300 |
| actaagctgg agattaaggg cggaggcgga agcggaggcg gaggctccgg cggaggcgga | 360 |
| agcgacgtgc aacttctgga gagcgggcca gggctagtca ggccctccca gtcgctttca | 420 |
| ctgacttgca gtgtgaccgg ttactctatt gtgagtcact actattggaa ctggattcgg | 480 |
| cagttcccag gcaacaaact ggaatggatg gggtacatat cttccgatgg ctcgaatgaa | 540 |
| tataacccat cattgaaaaa tcgtatttcc atcagtctgg atacgagtaa aaaccagttt | 600 |
| ttcctcaaat tcgatttcgt gactacagca gatactgcca catacttctg tgtacgaggt | 660 |
| gtcgattatt ggggacaggg cacaacgctg accgtaagtt ctaagcccac caccacccct | 720 |
| gcccctagac ctccaacccc agcccctaca atcgccagcc agcccctgag cctgaggccc | 780 |
| gaagcctgta gacctgccgc tggcggagcc gtgcacacca gaggcctgga tttcgcctgc | 840 |
| gacatctaca tctgggcccc tctggccggc acctgtggcg tgctgctgct gagcctggtc | 900 |
| atcaccctgt actgcaacca ccggaatagg agcaagcgga gcagaggcgg ccacagcgac | 960 |
| tacatgaaca tgacccccg gaggcctggc cccacccgga agcactacca gccctacgcc | 1020 |
| cctcccaggg acttcgccgc ctaccggagc aagagaggcc ggaagaaact gctgtacatc | 1080 |
| ttcaagcagc ccttcatgcg gcccgtgcag accacccagg aagaggacgg ctgcagctgc | 1140 |
| cggttccccg aggaagagga aggcggctgc gaactgcggg tgaagttcag ccggagcgcc | 1200 |
| gacgcccctg cctaccagca gggccagaac cagctgtaca acgagctgaa cctgggccgg | 1260 |
| agggaggagt acgacgtgct ggacaagcgg agaggccggg accctgagat gggcggcaag | 1320 |
| ccccggagaa agaaccctca ggagggcctg tataacgaac tgcagaaaga caagatggcc | 1380 |
| gaggcctaca gcgagatcgg catgaagggc gagcggcgga ggggcaaggg ccacgacggc | 1440 |
| ctgtaccagg gcctgagcac cgccaccaag gatacctacg acgccctgca catgcaggcc | 1500 |
| ctgccccca ga | 1512 |

<210> SEQ ID NO 148
<211> LENGTH: 1653
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 148

| | |
|---|---|
| gacatcaaga tggctcagtc cccttctagc gtgaatgctt cgctagggga gcgtgtgacc | 60 |
| atcacatgta aagcatcacg cgacataaat aatttccttt cctggtttca tcagaaaccg | 120 |
| ggcaagtcgc ctaagacgct gatttacaga gcaaatcggt tggtagatgg agtgccaagc | 180 |
| agattcagcg ggagcggaag tggacaggat tatagcttca ctatttcatc cctggaatac | 240 |
| gaggacgtag gtatctatta ttgcctccag tatggcgatc tttacacatt tggtgggggg | 300 |
| actaagctgg agattaaggg cggaggcgga agcggaggcg gaggctccgg cggaggcgga | 360 |

```
agcgacgtgc aacttctgga gagcgggcca gggctagtca ggccctccca gtcgctttca    420
ctgacttgca gtgtgaccgg ttactctatt gtgagtcact actattggaa ctggattcgg    480
cagttcccag gcaacaaact ggaatggatg gggtacatat cttccgatgg ctcgaatgaa    540
tataacccat cattgaaaaa tcgtatttcc atcagtctgg atacgagtaa aaaccagttt    600
ttcctcaaat tcgatttcgt gactacagca gatactgcca catacttctg tgtacgaggt    660
gtcgattatt ggggacaggg cacaacgctg accgtaagtt ctaaacctac tacaactcct    720 gcccccccggc ctcctacacc agctcctact atcgcctccc agccactcag tctcagaccc    780
gaggcttcta ggccagcggc cggaggcgcg tccacacccc gcgggctgga ctttgcatcc    840
gataagccca ccaccacccc tgcccctaga cctccaaccc cagcccctac aatcgccagc    900
cagcccctga gcctgaggcc cgaagcctgt agacctgccg ctggcggagc cgtgcacacc    960
agaggcctgg atttcgcctg cgacatctac atctgggccc ctctggccgg cacctgtggc    1020
gtgctgctgc tgagcctggt catcaccctg tactgcaacc accggaatag gagcaagcgg    1080
agcagaggcg gccacagcga ctacatgaac atgacccccc ggaggcctgg ccccacccgg    1140
aagcactacc agccctacgc ccctcccagg gacttcgccg cctaccggag caagagaggc    1200
cggaagaaac tgctgtacat cttcaagcag cccttcatgc ggcccgtgca gaccacccag    1260
gaagaggacg gctgcagctg ccggttcccc gaggaagagg aaggcggctg cgaactgcgg    1320
gtgaagttca gccggagcgc cgacgcccct gcctaccagc agggccagaa ccagctgtac    1380
aacgagctga actgggccg gagggaggag tacgacgtgc tggacaagcg agaggccgg    1440 gaccctgaga tgggcggcaa gccccggaga aagaaccctc aggagggcct gtataacgaa    1500
ctgcagaaag acaagatggc cgaggcctac agcgagatcg gcatgaaggg cgagcggcgg    1560
aggggcaagg gccacgacgg cctgtaccag ggcctgagca ccgccaccaa ggatacctac    1620
gacgccctgc acatgcaggc cctgccccccc aga    1653
```

<210> SEQ ID NO 149  
<211> LENGTH: 1794  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 149

```
gacatcaaga tggctcagtc cccttctagc gtgaatgctt cgctagggga gcgtgtgacc     60
atcacatgta aagcatcacg cgacataaat aatttccttt cctggtttca tcagaaaccg    120
ggcaagtcgc ctaagacgct gatttacaga gcaaatcggt tggtagatgg agtgccaagc    180
agattcagcg ggagcggaag tggacaggat tatagcttca ctatttcatc cctggaatac    240
gaggacgtag gtatctatta ttgcctccag tatggcgatc tttacacatt tggtgggggg    300
actaagctgg agattaaggg cggaggcgga agcggaggcg gaggctccgg cggaggcgga    360
agcgacgtgc aacttctgga gagcgggcca gggctagtca ggccctccca gtcgctttca    420
ctgacttgca gtgtgaccgg ttactctatt gtgagtcact actattggaa ctggattcgg    480
cagttcccag gcaacaaact ggaatggatg gggtacatat cttccgatgg ctcgaatgaa    540
tataacccat cattgaaaaa tcgtatttcc atcagtctgg atacgagtaa aaaccagttt    600
ttcctcaaat tcgatttcgt gactacagca gatactgcca catacttctg tgtacgaggt    660
gtcgattatt ggggacaggg cacaacgctg accgtaagtt ctaagcctac caccaccccc    720
```

```
gcacctcgtc ctccaacccc tgcacctacg attgccagtc agcctctttc actgcggcct    780
gaggccagca gaccagctgc cggcggtgcc gtccatacaa gaggactgga cttcgcgtcc    840
gataaaccta ctaccactcc agccccaagg cccccaaccc cagcaccgac tatcgcatca    900
cagcctttgt cactgcgtcc tgaagccagc cggccagctg caggggggc cgtccacaca     960 aggggactcg actttgcgag tgataagccc accaccaccc ctgcccctag acctccaacc   1020
ccagccccta caatcgccag ccagcccctg agcctgaggc ccgaagcctg tagacctgcc   1080
gctggcggag ccgtgcacac cagaggcctg gatttcgcct gcgacatcta catctgggcc   1140
cctctggccg gcacctgtgg cgtgctgctg ctgagcctgg tcatcaccct gtactgcaac   1200
caccggaata ggagcaagcg gagcagaggc ggccacagcg actacatgaa catgaccccc   1260
cggaggcctg gccccacccg gaagcactac cagccctacg cccctcccag ggacttcgcc   1320
gcctaccgga gcaagagagg ccggaagaaa ctgctgtaca tcttcaagca gcccttcatg   1380
cggcccgtgc agaccaccca ggaagaggac ggctgcagct gccggttccc cgaggaagag   1440
gaaggcggct gcgaactgcg ggtgaagttc agccggagcg ccgacgcccc tgcctaccag   1500
cagggccaga accagctgta caacgagctg aacctgggcc ggagggagga gtacgacgtg   1560
ctggacaagc ggagaggccg ggaccctgag atgggcggca agccccggag aaagaaccct   1620
caggagggcc tgtataacga actgcagaaa gacaagatgg ccgaggccta cagcgagatc   1680
ggcatgaagg gcgagcggcg gaggggcaag ggccacgacg gcctgtacca gggcctgagc   1740
accgccacca aggataccta cgacgccctg cacatgcagg ccctgccccc caga          1794
```

<210> SEQ ID NO 150
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150

```
atgcttctcc tggtgacaag ccttctgctc tgtgagttac cacacccagc attcctcctg     60
atccca                                                                66
```

<210> SEQ ID NO 151
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151

```
atgaggctcc ctgctcagct cctggggctg ctaatgctct gggtcccagg atccagtggg     60
```

<210> SEQ ID NO 152
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152

```
atggattgga cctggattct gtttctggtg gccgctgcca caagagtgca cagc            54
```

```
<210> SEQ ID NO 153
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
atggcgctgc cgtgaccgc cttgctcctg ccgctggcct tgctgctcca cgccgccagg    60
ccg                                                                63

<210> SEQ ID NO 154
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atgggcacca gcctcctctg ctggatggcc ctgtgtctcc tgggggcaga tcacgcagat    60
gct                                                                63

<210> SEQ ID NO 155
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atgaagcgct tcctcttcct cctactcacc atcagcctcc tggttatggt acagatacaa    60
actggactct ca                                                      72

<210> SEQ ID NO 156
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
atgggggcag gtgccaccgg ccgcgccatg gacgggccgc gcctgctgct gttgctgctt    60
ctgggggtgt cccttggagg tgcc                                         84

<210> SEQ ID NO 157
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
cgcaaagtgt gtaacggaat aggtattggt gaatttaaag actcactctc cataaatgct    60
acgaatatta aacacttcaa aaactgcacc tccatcagtg gcgatctcca catcctgccg   120
gtggcattta gggtgactc cttcacacat actcctcctc tggatccaca ggaactggat   180
attctgaaaa ccgtaaagga aatcacaggg tttttgctga ttcaggcttg gcctgaaaac   240
aggacggacc tccatgcctt tgagaaccta gaaatcatac gcggcaggac caagcaacat   300
```

```
ggtcagttttt ctcttgcagt cgtcagcctg aacataacat ccttgggatt acgctccctc    360
aaggagataa gtgatggaga tgtgataatt tcaggaaaca aaaatttgtg ctatgcaaat    420
acaataaact ggaaaaaact gtttgggacc tccggtcaga aaccaaaat tataagcaac     480 agaggtgaaa acagctgcaa ggccacaggc caggtctgcc atgccttgtg ctcccccgag    540
ggctgctggg gcccggagcc cagggactgc gtctcttgcc ggaatgtcag ccgaggcagg    600
gaatgcgtgg acaagtgcaa ccttctggag ggtgagccaa gggagtttgt ggagaactct    660
gagtgcatac agtgccaccc agagtgcctg cctcaggcca tgaacatcac ctgcacagga    720
cggggaccag acaactgtat ccagtgtgcc cactacattg acggccccca ctgcgtcaag    780
acctgcccgg caggagtcat gggagaaaac aacaccctgg tctggaagta cgcagacgcc    840
ggccatgtgt gccacctgtg ccatccaaac tgcacctacg gatgcactgg gccaggtctt    900
gaaggctgtc caacgaatgg gcctaagatc ccgtccatcg ccactgggat ggtggggggcc    960 ctcctcttgc tgctggtggt ggccctgggg atcggcctct tcatg                    1005

<210> SEQ ID NO 158
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
cgcaaagtgt gtaacggaat aggtattggt gaatttaaag actcactctc cataaatgct     60
acgaatatta aacacttcaa aaactgcacc tccatcagtg gcgatctcca catcctgccg    120
gtggcattta ggggtgactc cttcacacat actcctcctc tggatccaca ggaactggat    180
attctgaaaa ccgtaaagga atcacaggg tttttgctga ttcaggcttg gcctgaaaac    240
aggacggacc tccatgcctt tgagaaccta gaaatcatac gcggcaggac caagcaacat    300 ggtcagttttt ctcttgcagt cgtcagcctg aacataacat ccttgggatt acgctccctc    360
aaggagataa gtgatggaga tgtgataatt tcaggaaaca aaaatttgtg ctatgcaaat    420
acaataaact ggaaaaaact gtttgggacc tccggtcaga aaccaaaat tataagcaac     480 agaggtgaaa acagctgcaa ggccacaggc caggtctgcc atgccttgtg ctcccccgag    540
ggctgctggg gcccggagcc cagggactgc gtctctggtg gcggtggctc gggcggtggt    600
gggtcgggtg gcggcggatc tggtggcggt ggctcgtttt gggtgctggt ggtggttggt    660
ggagtcctgg cttgctatag cttgctagta acagtggcct ttattatttt ctgggtgagg    720
agtaagagga gc                                                        732

<210> SEQ ID NO 159
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
atgacaacac ccagaaattc agtaaatggg actttccccgg cagagccaat gaaaggccct    60
attgctatgc aatctggtcc aaaaccactc ttcaggagga tgtcttcact ggtgggcccc    120
acgcaaagct tcttcatgag ggaatctaag actttggggg ctgtccagat tatgaatggg    180
```

```
ctcttccaca ttgccctggg gggtcttctg atgatcccag cagggatcta tgcacccatc    240
tgtgtgactg tgtggtaccc tctctgggga ggcattatgt atattatttc cggatcactc    300
ctggcagcaa cggagaaaaa ctccaggaag tgtttggtca aggaaaaat gataatgaat     360 tcattgagcc tctttgctgc catttctgga atgattcttt caatcatgga catacttaat    420
attaaaattt cccatttttt aaaaatggag agtctgaatt ttattagagc tcacacacca    480
tatattaaca tatacaactg tgaaccagct aatccctctg agaaaaactc cccatctacc    540
caatactgtt acagcataca atctctgttc ttgggcattt tgtcagtgat gctgatcttt    600
gccttcttcc aggaacttgt aatagctggc atcgttgaga atgaatggaa agaacgtgc     660 tccagaccca atctaacat agttctcctg tcagcagaag aaaaaaaaga acagactatt     720
gaaataaaag aagaagtggt tgggctaact gaaacatctt cccaaccaaa gaatgaagaa    780
gacattgaaa ttattccaat ccaagaagag gaagaagaag aaacagagac gaactttcca    840
gaacctcccc aagatcagga atcctcacca atagaaaatg acagctctcc t             891
```

```
<210> SEQ ID NO 160
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
atgaccacac cacggaactc tgtgaatggc accttcccag cagagccaat gaagggacca     60
atcgcaatgc agagcggacc caagcctctg tttcggagaa tgagctccct ggtgggccca    120
acccagtcct tctttatgag agagtctaag acactgggcg ccgtgcagat catgaacgga    180
ctgttccaca tcgccctggg aggactgctg atgatcccag ccggcatcta cgcccctatc    240
tgcgtgaccg tgtggtaccc tctgtggggc ggcatcatgt atatcatctc cggctctctg    300
ctggccgcca cagagaagaa cagcaggaag tgtctggtga agggcaagat gatcatgaat    360
agcctgtccc tgtttgccgc catctctggc atgatcctga gcatcatgga catcctgaac    420
atcaagatca gccacttcct gaagatggag agcctgaact tcatcagagc ccacacccct    480
tacatcaaca tctataattg cgagcctgcc aacccatccg agaagaattc tccaagcaca    540
cagtactgtt attccatcca gtctctgttc ctgggcatcc tgtctgtgat gctgatcttt    600
gccttctttc aggagctggt catcgccggc atcgtggaga acgagtggaa gaggacctgc    660
agccgcccca gtccaatat cgtgctgctg tccgccgagg agaagaagga gcagacaatc    720
gagatcaagg aggaggtggt gggcctgacc gagacatcta gccagcctaa gaatgaggag    780
gatatcgag                                                             789
```

```
<210> SEQ ID NO 161
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
atggattgga cctggattct gtttctggtg gccgctgcca caagagtgca cagcaactgg     60
gtgaatgtga tcagcgacct gaagaagatc gaggatctga tccagagcat gcacattgat    120 gccacccctgt acacagaatc tgatgtgcac cctagctgta aagtgaccgc catgaagtgt    180
```

```
tttctgctgg agctgcaggt gatttctctg gaaagcggag atgcctctat ccacgacaca     240
gtggagaatc tgatcatcct ggccaacaat agcctgagca gcaatggcaa tgtgacagag     300
tctggctgta aggagtgtga ggagctggag gagaagaaca tcaaggagtt tctgcagagc     360
tttgtgcaca tcgtgcagat gttcatcaat acaagctctg cggaggatc tggaggaggc      420 ggatctggag gaggaggcag tggaggcgga ggatctggcg gaggatctct gcagattaca    480
tgccctcctc aatgtctgt ggagcacgcc gatatttggg tgaagtccta cagcctgtac      540
agcagagaga gatacatctg caacagcggc tttaagagaa aggccggcac ctcttctctg     600
acagagtgcg tgctgaataa ggccacaaat gtggcccact ggacaacacc tagcctgaag     660
tgcattagag atcctgccct ggtccaccag aggcctgccc ctccatctac agtgacaaca     720
gccggagtga cacctcagcc tgaatctctg agcccttctg gaaaagaacc tgccgccagc     780
tctcctagct ctaataatac cgccgccaca acagccgcca ttgtgcctgg atctcagctg     840
atgcctagca gtctcctag cacaggcaca acagagatca gcagccacga atcttctcac      900
ggaacacctt ctcagaccac cgccaagaat tgggagctga cagcctctgc ctctcaccag     960
cctccaggag tgtatcctca gggccactct gatacaacag tggccatcag cacatctaca    1020
gtgctgctgt gtggactgtc tgccgtgtct ctgctggcct gttacctgaa gtctagacag    1080
acacctcctc tggcctctgt ggagatggag gccatggaag ccctgcctgt gacatgggga    1140
acaagcagca gagatgagga cctggagaat tgttctcacc acctg                    1185

<210> SEQ ID NO 162
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
aactgggtga atgtgatcag cgacctgaag aagatcgagg atctgatcca gagcatgcac     60
attgatgcca ccctgtacac agaatctgat gtgcaccca gctgtaaagt gaccgccatg      120
aagtgttttc tgctggagct gcaggtgatt tctctggaaa gcggagatgc ctctatccac     180
gacacagtgg agaatctgat catcctggcc aacaatagcc tgagcagcaa tggcaatgtg     240
acagagtctg gctgtaagga gtgtgaggag ctggaggaga gaacatcaa ggagtttctg      300 cagagctttg tgcacatcgt gcagatgttc atcaatacaa gc                       342

<210> SEQ ID NO 163
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
attacatgcc ctcctccaat gtctgtggag cacgccgata tttgggtgaa gtcctacagc     60
ctgtacagca gagagagata catctgcaac agcggctttta agagaaaggc cggcacctct    120
tctctgacag agtgcgtgct gaataaggcc acaaatgtgg cccactggac aacacctagc    180
ctgaagtgca ttagagatcc tgccctggtc caccagaggc tgcccctcc atctacagtg      240 acaacagccg gagtgacacc tcagcctgaa tctctgagcc cttctggaaa agaacctgcc    300
```

```
gccagctctc ctagctctaa taataccgcc gccacaacag ccgccattgt gcctggatct      360
cagctgatgc ctagcaagtc tcctagcaca ggcacaacag agatcagcag ccacgaatct      420
tctcacggaa caccttctca gaccaccgcc aagaattggg agctgacagc ctctgcctct      480
caccagcctc caggagtgta tcctcagggc cactctgata caacagtggc catcagcaca      540
tctacagtgc tgctgtgtgg actgtctgcc gtgtctctgc tggcctgtta cctgaagtct      600
agacagacac ctcctctggc ctctgtggag atggaggcca tggaagccct gcctgtgaca      660
tggggaacaa gcagcagaga tgaggacctg gagaattgtt ctcaccacct g              711
```

<210> SEQ ID NO 164
<211> LENGTH: 54
<212> TYPE: DNA
<213> ORGANISM: Thosea asigna virus

<400> SEQUENCE: 164

```
gagggcagag gaagtcttct aacatgcggt gacgtggagg agaatcccgg ccct            54
```

<210> SEQ ID NO 165
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
agagctaaga ggggaagcgg agagggcaga ggaagtctgc taacatgcgg tgacgtcgag      60
gagaatcctg gacct                                                        75
```

<210> SEQ ID NO 166
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166

```
agggccaaga ggagtggcag cggcgagggc agaggaagtc ttctaacatg cggtgacgtg      60
gaggagaatc ccggccct                                                     78
```

<210> SEQ ID NO 167
<211> LENGTH: 57
<212> TYPE: DNA
<213> ORGANISM: Porcine teschovirus 1

<400> SEQUENCE: 167

```
gcaacgaact tctctctcct aaaacaggct ggtgatgtgg aggagaatcc tggtcca         57
```

<210> SEQ ID NO 168
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
ggaagcggag ctactaactt cagcctgctg aagcaggctg agacgtgga ggagaaccct       60 ggacct                                                                  66
```

<210> SEQ ID NO 169
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
cgtgcaaagc gtgcaccggt gaaacaggga agcggagcta ctaacttcag cctgctgaag    60
caggctggag acgtggagga gaaccctgga cct    93

<210> SEQ ID NO 170
<211> LENGTH: 60
<212> TYPE: DNA
<213> ORGANISM: Equine rhinitis A virus

<400> SEQUENCE: 170
cagtgtacta attatgctct cttgaaattg gctggagatg ttgagagcaa ccctggacct    60

<210> SEQ ID NO 171
<211> LENGTH: 66
<212> TYPE: DNA
<213> ORGANISM: Foot-and-mouth disease virus

<400> SEQUENCE: 171
gtcaaacaga ccctaaactt tgatctgcta aaactggccg gggatgtgga aagtaatccc    60
ggcccc    66

<210> SEQ ID NO 172
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
cgtgcaaagc gt    12

<210> SEQ ID NO 173
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
agagccaaga gggcaccggt gaaacagact ttgaattttg accttctgaa gttggcagga    60
gacgttgagt ccaaccctgg gccc    84

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
ggtggcggtg gctcgggcgg tggtgggtcg ggtggcggcg gatct    45

```
<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggcagcacct ccggcagcgg caagcctggc agcggcgagg cagcaccaa gggc          54

<210> SEQ ID NO 176
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176 ggaagcgga                                                            9

<210> SEQ ID NO 177
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
agtggcagcg gc                                                       12

<210> SEQ ID NO 178
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
ggccccaaga agaaaaggaa ggtggccccc cccaccgacg tgagcctggg cgacgagctg     60
cacctggacg gcgaggacgt ggccatggcc cacgccgacg ccctggacga cttcgacctg    120
gacatgctgg gcgacggcga cagccccggc cccggcttca cccccacga cagcgccccc     180 tacggcgccc tggacatggc cgacttcgag ttcgagcaga tgttcaccga cgccctgggc    240
atcgacgagt acggcggc                                                 258

<210> SEQ ID NO 179
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
gagatgcccg tggacaggat tctggaggcc gaactcgccg tggagcagaa aagcgaccag     60
ggcgtggagg gccccggcgg aaccggcggc agcggcagca gccccaacga ccccgtgacc    120
aacatctgcc aggccgccga caagcagctg ttcaccctgg tggagtgggc caagaggatt    180
ccccacttca gcagcctgcc cctggacgac caggtgatcc tgctgagggc cggatggaac    240
gagctgctga tcgccagctt cagccacagg agcatcgacg tgagggacgg catcctgctg    300
```

```
gccaccggcc tgcacgtcca taggaacagc gcccacagcg ccggagtggg cgccatcttc      360
gacagggtgc tgaccgagct ggtgagcaag atgaggcaca tgaggatgga caagaccgag      420
ctgggctgcc tgagggccat catcctgttc aaccccgagg tgaggggcct gaaaagcgcc      480
caggaggtgg agctgctgag ggagaaggtg tacgccgccc tggaggagta caccaggacc      540
acccaccccg acgagcccgg cagattcgcc aagctgctgc tgaggctgcc cagcctgagg      600
agcatcggcc tgaagtgcct ggagcacctg ttcttcttca ggctgatcgg cgacgtgccc      660
atcgacacct tcctgatgga gatgctggag agccccagcg acagc                     705

<210> SEQ ID NO 180
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
ggccccaaga agaaaaggaa ggtggccccc cccaccgacg tgagcctggg cgacgagctg      60
cacctggacg gcgaggacgt ggccatggcc cacgccgacg ccctggacga cttcgacctg      120
gacatgctgg gcgacggcga cagccccggc cccggcttca ccccccacga cagcgccccc      180
tacgccgccc tggacatggc cgacttcgag ttcgagcaga tgttcaccga cgccctgggc      240
atcgacgagt acggcggcga attcgagatg cccgtggaca ggattctgga ggccgaactc      300
gccgtggagc agaaaagcga ccagggcgtg gagggccccg gcggaaccgg cggcagcggc      360
agcagcccca cgaccccgt gaccaacatc tgccaggccg ccgacaagca gctgttcacc      420
ctggtggagt gggccaagag gattccccac ttcagcagcc tgccccttgga cgaccaggtg      480 atcctgctga gggccggatg gaacgagctg ctgatcgcca gcttcagcca caggagcatc      540
gacgtgaggg acggcatcct gctggccacc ggcctgcacg tccataggaa cagcgcccac      600
agcgccggag tgggcgccat cttcgacagg gtgctgaccg agctggtgag caagatgagg      660
gacatgagga tggacaagac cgagctgggc tgcctgaggg ccatcatcct gttcaacccc      720
gaggtgaggg gcctgaaaag cgcccaggag gtggagctgc tgagggagaa ggtgtacgcc      780
gccctggagg agtacaccag gaccacccac cccgacgagc ccggcagatt cgccaagctg      840
ctgctgaggc tgcccagcct gaggagcatc ggcctgaagt gcctggagca cctgttcttc      900
ttcaggctga tcggcgacgt gcccatcgac accttcctga tggagatgct ggagagcccc      960
agcgacagc                                                              969

<210> SEQ ID NO 181
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
atgaagctgc tgagcagcat cgagcaggct tgcgacatct gcaggctgaa gaagctgaag      60
tgcagcaagg agaagcccaa gtgcgccaag tgcctgaaga caactgggga gtgcagatac      120
agccccaaga ccaagaggag cccccctgacc agggcccacc tgaccgaggt ggagagcagg      180
ctggagaggc tggagcagct gttcctgctg atcttccccc gggaggacct ggacatgatc      240
```

| | |
|---|---|
| ctgaagatgg acagcctgca agacatcaag gccctgctga ccggcctgtt cgtgcaggac | 300 |
| aacgtgaaca aggacgccgt gaccgacagg ctggccagcg tggagaccga catgcccctg | 360 |
| accctgaggc agcacaggat cagcgccacc agcagcagcg aggagagcag caacaagggc | 420 |
| cagaggcagc tgaccgtgag ccccgagttt | 450 |

<210> SEQ ID NO 182
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

| | |
|---|---|
| atcaggcccg agtgcgtggt gcccgagacc cagtgcgcca tgaaaaggaa ggagaagaag | 60 |
| gcccagaagg agaaggacaa gctgcccgtg agcaccacca ccgtcgatga ccacatgccc | 120 |
| cccatcatgc agtgcgagcc ccccccccc gaggccgcca ggattcacga ggtcgtgccc | 180 |
| aggttcctga gcgacaagct gctggtgacc aacaggcaga agaacatccc ccagctgacc | 240 |
| gccaaccagc agttcctgat cgccaggctg atctggtatc aggacggcta cgagcagccc | 300 |
| agcgacgagg acctgaaaag gatcacccag acctggcagc aggccgacga cgagaacgag | 360 |
| gagagcgaca ccccttcag gcagatcacc gagatgacca tcctgaccgt gcagctgatc | 420 |
| gtggagttcg ccaagggcct gcccggattc gccaagatca gccagcccga ccagatcacc | 480 |
| ctgctgaagg cttgcagcag cgaggtgatg atgctgaggg tggccaggag gtacgacgcc | 540 |
| gccagcgaca gcatcctgtt cgccaacaac caggcttaca ccagggacaa ctacaggaag | 600 |
| gctggcatgg ccgaggtgat cgaggacctc ctgcacttct gcagatgtat gtacagcatg | 660 |
| gccctggaca acatccacta cgccctgctg accgccgtgg tgatcttcag cgacaggccc | 720 |
| ggcctggagc agccccagct ggtggaggag atccagaggt actacctgaa cacccctgagg | 780 |
| atctacatcc tgaaccagct gagcggcagc gccaggagca gcgtgatcta cggcaagatc | 840 |
| ctgagcatcc tgagcgagct gaggaccctg ggaatgcaga acagcaatat gtgtatcagc | 900 |
| ctgaagctga gaacaggaa gctgcccccc ttcctggagg agattgggaa cgtggccgac | 960 |
| atgagccaca cccagccccc ccccatcctg gagagcccca ccaacctg | 1008 |

<210> SEQ ID NO 183
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

| | |
|---|---|
| cggcctgagt gcgtagtacc cgagactcag tgcgccatga gcggaaaga gaagaaagca | 60 |
| cagaaggaga aggacaaact gcctgtcagc acgacgacgg tggacgacca catgccgccc | 120 |
| attatgcagt gtgaacctcc acctcctgaa gcagcaagga ttcacgaagt ggtcccaagg | 180 |
| tttctctccg acaagctgtt ggtgacaaac cggcagaaaa acatcccca gttgacagcc | 240 |
| aaccagcagt tccttatcgc caggctcatc tggtaccagg acgggtacga gcagccttct | 300 |
| gatgaagatt tgaagaggat tacgcagacg tggcagcaag cggacgatga aaacgaagag | 360 |
| tcggacactc ccttccgcca gatcacagag atgactatcc tcacggtcca acttatcgtg | 420 |
| gagttcgcga agggattgcc agggttcgcc aagatctcgc agcctgatca aattacgctg | 480 |

```
cttaaggctt gctcaagtga ggtaatgatg ctccgagtcg cgcgacgata cgatgcggcc    540
tcagacagta ttctgttcgc gaacaaccaa gcgtacactc gcgacaacta ccgcaaggct    600
ggcatggccg aggtcatcga ggatctactg cacttctgcc ggtgcatgta ctctatggcg    660
ttggacaaca tccattacgc gctgctcacg gctgtcgtca tcttttctga ccggccaggg    720
ttggagcagc cgcaactggt ggaagagatc cagcggtact acctgaatac gctccgcatc    780
tatatcctga accagctgag cgggtcggcc gttcgtccg tcatatacgg caagatcctc     840
tcaatcctct ctgagctacg cacgctcggc atgcaaaact ccaacatgtg catctccctc    900
aagctcaaga cagaaagct gccgcctttc ctcgaggaga tctgggatgt ggcggacatg     960
tcgcacaccc aaccgccgcc tatcctcgag tcccccacga atctctag               1008
```

<210> SEQ ID NO 184
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184

```
atgaagctac tgtcttctat cgaacaagca tgcgatattt gccgacttaa aaagctcaag     60
tgctccaaag aaaaccgaa gtgcgccaag tgtctgaaga caactggga gtgtcgctac      120 tctcccaaaa ccaaaaggtc tccgctgact agggcacatc tgacagaagt ggaatcaagg    180
ctagaaagac tggaacagct atttctactg attttttcctc gagaagacct tgacatgatt   240
ttgaaaatgg attctttaca ggatataaaa gcattgttaa caggattatt tgtacaagat    300
aatgtgaata aagatgccgt cacagataga ttggcttcag tggagactga tatgcctcta    360
acattgagac agcatagaat aagtgcgaca tcatcatcgg aagagagtag taacaaaggt    420
caaagacagt tgactgtatc gccggaattc ccggggatcc ggcctgagtg cgtagtaccc    480
gagactcagt gcgccatgaa gcggaaagag aagaaagcac agaaggagaa ggacaaactg    540
cctgtcagca cgacgacggt ggacgaccac atgccgccca ttatgcagtg tgaacctcca    600
cctcctgaag cagcaaggat tcacgaagtg gtcccaaggt ttctctccga caagctgttg    660
gtgacaaacc ggcagaaaaa catcccccag ttgacagcca accagcagtt ccttatcgcc    720
aggctcatct ggtaccagga cgggtacgag cagccttctg atgaagattt gaagaggatt    780
acgcagacgt ggcagcaagc ggacgatgaa acgaagagt cggacactcc cttccgccag     840
atcacagaga tgactatcct cacggtccaa cttatcgtgg agttcgcgaa gggattgcca    900
gggttcgcca agatctcgca gcctgatcaa attacgctgc ttaaggcttg ctcaagtgag    960
gtaatgatgc tccgagtcgc gcgacgatac gatgcggcct cagacagtat tctgttcgcg   1020
aacaaccaag cgtacactcg cgacaactac cgcaaggctg gcatggccga ggtcatcgag    1080
gatctactgc acttctgccg gtgcatgtac tctatgcgct tggacaacat ccattacgcg   1140
ctgctcacgg ctgtcgtcat cttttctgac cggccagggt tggagcagcc gcaactggtg    1200
gaagagatcc agcggtacta cctgaatacg ctccgcatct atatcctgaa ccagctgagc    1260
gggtcggcgc gttcgtccgt catatacggc aagatcctct caatcctctc tgagctacgc    1320
acgctcggca tgcaaaactc caacatgtgc atctccctca agctcaagaa cagaaagctg    1380
ccgcctttcc tcgaggagat ctgggatgtg gcggacatgt cgcacaccca accgccgcct    1440
atcctcgagt cccccacgaa tctctag                                        1467
```

<210> SEQ ID NO 185
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185

| | | |
|---|---|---|
| atgaagctgc tgagcagcat cgagcaggct tgcgacatct gcaggctgaa gaagctgaag | 60 |
| tgcagcaagg agaagcccaa gtgcgccaag tgcctgaaga caactggga gtgcagatac | 120 |
| agccccaaga ccaagaggag cccctgacc agggcccacc tgaccgaggt ggagagcagg | 180 |
| ctggagaggc tggagcagct gttcctgctg atcttcccca gggaggacct ggacatgatc | 240 |
| ctgaagatgg acagcctgca agacatcaag gccctgctga ccggcctgtt cgtgcaggac | 300 |
| aacgtgaaca aggacgccgt gaccgacagg ctggccagcg tggagaccga catgcccctg | 360 |
| accctgaggc agcacaggat cagcgccacc agcagcagcg aggagagcag caacaagggc | 420 |
| cagaggcagc tgaccgtgag ccccgagttt ccgggcggc ctgagtgcgt agtacccgag | 480 |
| actcagtgcg ccatgaagcg gaaagagaag aaagcacaga aggagaagga caaactgcct | 540 |
| gtcagcacga cgacggtgga cgaccacatg ccgcccatta tgcagtgtga acctccacct | 600 |
| cctgaagcag caaggattca cgaagtggtc ccaaggtttc tctccgacaa gctgttggtg | 660 |
| acaaaccggc agaaaaacat cccccagttg acagccaacc agcagttcct tatcgccagg | 720 |
| ctcatctggt accaggacgg gtacgagcag ccttctgatg aagatttgaa gaggattacg | 780 |
| cagacgtggc agcaagcgga cgatgaaaac gaagagtcgg acactcccctt ccgccagatc | 840 |
| acagagatga ctatcctcac ggtccaactt atcgtggagt tcgcgaaggg attgccaggg | 900 |
| ttcgccaaga tctcgcagcc tgatcaaatt acgctgctta aggcttgctc aagtgaggta | 960 |
| atgatgctcc gagtcgcgcg acgatacgat gcggcctcag acagtattct gttcgcgaac | 1020 |
| aaccaagcgt acactcgcga caactaccgc aaggctggca tggccgaggt catcgaggat | 1080 |
| ctactgcact tctgccggtg catgtactct atggcgttgg acaacatcca ttacgcgctg | 1140 |
| ctcacggctg tcgtcatctt ttctgaccgg ccagggttgg agcagccgca actggtggaa | 1200 |
| gagatccagc ggtactacct gaatacgctc cgcatctata tcctgaacca gctgagcggg | 1260 |
| tcggcgcgtt cgtccgtcat atacggcaag atcctctcaa tcctctctga gctacgcacg | 1320 |
| ctcggcatgc aaaactccaa catgtgcatc tccctcaagc tcaagaacag aaagctgccg | 1380 |
| cctttcctcg aggagatctg ggatgtggcg gacatgtcgc acacccaacc gccgcctatc | 1440 |
| ctcgagtccc ccacgaatct ctag | 1464 |

<210> SEQ ID NO 186
<211> LENGTH: 244
<212> TYPE: DNA
<213> ORGANISM: Homo sapiens

<400> SEQUENCE: 186

| | | |
|---|---|---|
| gagcgtgcgt gaggctccgg tgcccgtcag tgggcagagc gcacatcgcc cacagtcccc | 60 |
| gagaagttgg ggggaggggg tcggcgattg aaccggtgcc tagagaaggt ggcgcggggt | 120 |
| aaactgggaa agtgatgtcg tgtactggct ccgccttttt cccgagggtg ggggagaacc | 180 |
| gtatataagt gcagtagtcg ccgtgaacgt tcttttcgc aacgggtttg ccgccagaac | 240 |
| acag | 244 |

<210> SEQ ID NO 187
<211> LENGTH: 148
<212> TYPE: DNA
<213> ORGANISM: Unknown
<220> FEATURE:
<223> OTHER INFORMATION: Description of Unknown:
      6 site GAL4-inducible proximal factor binding
      element (PFB) sequence

<400> SEQUENCE: 187
attgttcgga gcagtgcggc gcgtttagcg gagtactgtc ctccgatatt aatcggggca      60
gactattccg gggtttaccg gcgcactctc gcccgaactt caccggcggt ctttcgtccg     120
tgctttatcg gggcggatca ctccgaac                                        148

<210> SEQ ID NO 188
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aggtctatat aagcagagct cgtttagtga accctcattc tggagacgga tcccgagccg      60
agtgttttga cctccataga a                                                81

<210> SEQ ID NO 189
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cagccgctaa atccaaggta aggtcagaag a                                     31

<210> SEQ ID NO 190
<211> LENGTH: 132
<212> TYPE: DNA
<213> ORGANISM: Simian virus 40

<400> SEQUENCE: 190
aacttgttta ttgcagctta taatggttac aaataaagca atagcatcac aaatttcaca      60
aataaagcat ttttttcact gcattctagt tgtggtttgt ccaaactcat caatgtatct     120
tatcatgtct gg                                                         132

<210> SEQ ID NO 191
<211> LENGTH: 275
<212> TYPE: DNA
<213> ORGANISM: Unknown
<220> FEATURE:
<223> OTHER INFORMATION: Description of Unknown:
      Bidirectional aCA polyA [bidirectional polyA]
      sequence

<400> SEQUENCE: 191
atcgattaat ctagcggccc tagacgagca gacatgataa gatacattga tgagtttgga      60
caaaccacaa ctagaatgca gtgaaaaaaa tgctttattt gtgaaatttg tgatgctatt     120
gctttatttg taaccattat aagctgcaat aaacaagtta acaacaacaa ttgcattcat     180

```
tttatgtttc aggttcaggg ggagatgtgg gaggtttttt aaagcaagta aaacctctac    240
aaatgtggta aaatccgata agcgtaccta gaggc                              275
```

<210> SEQ ID NO 192
<211> LENGTH: 73
<212> TYPE: DNA
<213> ORGANISM: Unknown
<220> FEATURE:
<223> OTHER INFORMATION: Description of Unknown:
    2xRbm3 IRES sequence

<400> SEQUENCE: 192

```
actagtttta taatttcttc ttccagaatt tctgacattt tataatttct tcttccagaa     60
gactcacaac ctc                                                       73
```

<210> SEQ ID NO 193
<211> LENGTH: 570
<212> TYPE: DNA
<213> ORGANISM: Unknown
<220> FEATURE:
<223> OTHER INFORMATION: Description of Unknown:
    EMCV IRES sequence

<400> SEQUENCE: 193

```
cccctctcc ctccccccc cctaacgtta ctggccgaag ccgcttggaa taaggccggt      60
gtgcgtttgt ctatatgtta ttttccacca tattgccgtc ttttggcaat gtgagggccc   120
ggaaacctgg ccctgtcttc ttgacgagca ttcctagggg tctttcccct ctcgccaaag   180
gaatgcaagg tctgttgaat gtcgtgaagg aagcagttcc tctggaagct tcttgaagac   240
aaacaacgtc tgtagcgacc ctttgcaggc agcggaaccc cccacctggc gacaggtgcc   300
tctgcggcca aaagccacgt gtataagata cacctgcaaa ggcggcacaa ccccagtgcc   360
acgttgtgag ttggatagtt gtggaaagag tcaaatggct ctcctcaagc gtattcaaca   420
aggggctgaa ggatgcccag aaggtacccc attgtatggg atctgatctg gggcctcggt   480
gcacatgctt tacatgtgtt tagtcgaggt taaaaaacgt ctaggccccc cgaaccacgg   540
ggacgtggtt ttcctttgaa aaacacgatc                                    570
```

<210> SEQ ID NO 194
<211> LENGTH: 348
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 194

```
gaggtgcagc tggtggagag cggcggcggc ctggtgcagc ccggcggcag cctgaggctg     60
agctgcgccg ccagcggcta cagcatcacc aacgactacg cctggaactg ggtgaggcag   120
gcccccggca agggcctgga gtgggtgggc tacatcaact acagcggcta caccacctac   180
aaccccagcc tgaagagcag gttcaccatc agcagggaca cagcaagaa caccctgtac   240 ctgcagatga acagcctgag ggccgaggac accgccgtgt actactgcgc caggtgggac   300
ggcggcctga cctactgggg ccagggcacc ctggtgaccg tgagcagc                348
```

<210> SEQ ID NO 195
<211> LENGTH: 348
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 195

```
gaggtgcagc tggtggagag cggcggcggc ctggtgcagc ccggcggcag cctgaggctg    60
agctgcgccg ccagcggcta cagcatcacc aacgactacg cctggaactg ggtgaggcag   120
gcccccggca agggcctgga gtgggtgggc tacatcaact acagcggcta caccacctac   180
aaccccagcc tgaagagcag gttcaccatc agcagggaca cagcaagaa caccttctac    240
ctgcagatga acagcctgag ggccgaggac accgccgtgt actactgcgc caggtgggac   300
ggcggcctga cctactgggg ccagggcacc ctggtgaccg tgagcagc                348
```

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Ser Lys Tyr Gly Pro Pro Cys Pro Pro Cys Pro
1               5                   10

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Gly Gly Gly Ser
1               5

<210> SEQ ID NO 198
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This sequence may encompass 0-15 "Gly Ser Gly"
      repeating units

<400> SEQUENCE: 198

Gly Ser Gly Gly Ser Gly Gly Ser Gly Gly Ser Gly Gly Ser Gly Gly
1               5                   10                  15
Ser Gly Gly Ser Gly Gly Ser Gly Gly Ser Gly Gly Ser Gly Gly Ser
            20                  25                  30
Gly Gly Ser Gly Gly Ser Gly Gly Ser Gly Gly Ser Gly
        35                  40                  45

<210> SEQ ID NO 199
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MISC_FEATURE
<222> LOCATION: (1)..(60)
<223> OTHER INFORMATION: This sequence may encompass 0-15 "Ser Gly Ser
      Gly" repeating units

<400> SEQUENCE: 199

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly Ser Gly
            20                  25                  30

Ser Gly Ser Gly Ser Gly Ser Gly Ser Gly Ser Gly Ser Gly Ser Gly
        35                  40                  45

Ser Gly Ser Gly Ser Gly Ser Gly Ser Gly Ser Gly
    50                  55                  60

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Gly Gly Gly Ser Gly Gly Gly Gly Ser Gly Gly Gly Gly Ser Gly
1               5                   10                  15

Gly Gly Gly Ser
            20

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 201

Asp Xaa Glu Xaa Asn Pro Gly Pro
1               5

<210> SEQ ID NO 202
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(26)
<223> OTHER INFORMATION: This region may encompass 2-5 "Glu Ala Ala Ala
      Lys" repeating units

<400> SEQUENCE: 202

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```

```
<210> SEQ ID NO 203
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 0-15 "Gly Ser"
      repeating units

<400> SEQUENCE: 203

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 0-15 "Ser Gly"
      repeating units

<400> SEQUENCE: 204

Ser Gly Ser Gly Ser Gly Ser Gly Ser Gly Ser Gly Ser Gly Ser Gly
1               5                   10                  15

Ser Gly Ser Gly Ser Gly Ser Gly Ser Gly Ser Gly Ser Gly
            20                  25                  30

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Pro Val Lys Gln
1               5
```